US012492263B2

(12) United States Patent
Chen et al.

(10) Patent No.: US 12,492,263 B2
(45) Date of Patent: Dec. 9, 2025

(54) ANTI-HER2 ANTIBODIES AND IMMUNOCONJUGATES

(71) Applicant: Genentech, Inc., South San Francisco, CA (US)

(72) Inventors: Xiaocheng Chen, Burlingame, CA (US); Mark Dennis, San Carlos, CA (US); Jagath Reddy Junutula, Fremont, CA (US); Gail Lewis Phillips, San Carlos, CA (US); Thomas Harden Pillow, San Francisco, CA (US); Mark X. Sliwkowski, San Carlos, CA (US)

(73) Assignee: Genentech, Inc., South San Francisco, CA (US)

( * ) Notice: Subject to any disclaimer, the term of this patent is extended or adjusted under 35 U.S.C. 154(b) by 645 days.

(21) Appl. No.: 17/720,717

(22) Filed: Apr. 14, 2022

(65) Prior Publication Data

US 2023/0041134 A1 Feb. 9, 2023

Related U.S. Application Data

(60) Continuation of application No. 16/721,525, filed on Dec. 19, 2019, now abandoned, which is a division of application No. 16/170,819, filed on Oct. 25, 2018, now Pat. No. 10,556,966, which is a division of application No. 15/296,454, filed on Oct. 18, 2016, now Pat. No. 10,179,820, which is a division of application No. 14/851,001, filed on Sep. 11, 2015, now Pat. No. 9,518,118.

(60) Provisional application No. 62/049,594, filed on Sep. 12, 2014.

(51) Int. Cl.

| | |
|---|---|
| ***C07K 16/32*** | (2006.01) |
| ***A61K 31/5517*** | (2006.01) |
| ***A61K 31/675*** | (2006.01) |
| ***A61K 31/704*** | (2006.01) |
| ***A61K 39/395*** | (2006.01) |
| ***A61K 47/68*** | (2017.01) |
| ***A61K 49/00*** | (2006.01) |
| ***C07K 16/28*** | (2006.01) |
| ***C07K 16/30*** | (2006.01) |
| ***G01N 33/574*** | (2006.01) |

(52) U.S. Cl.

CPC .......... *C07K 16/32* (2013.01); *A61K 31/5517* (2013.01); *A61K 31/675* (2013.01); *A61K 31/704* (2013.01); *A61K 39/3955* (2013.01); *A61K 47/68* (2017.08); *A61K 47/6809* (2017.08); *A61K 47/6849* (2017.08); *A61K 47/6855* (2017.08); *A61K 47/6863* (2017.08); *A61K 49/00* (2013.01); *C07K 16/2863* (2013.01); *C07K 16/3015* (2013.01); *G01N 33/57415* (2013.01); *G01N 33/57446* (2013.01); *G01N 33/57492* (2013.01); *C07K 2317/24* (2013.01); *C07K 2317/34* (2013.01); *C07K 2317/51* (2013.01); *C07K 2317/515* (2013.01); *C07K 2317/56* (2013.01); *C07K 2317/565* (2013.01); *C07K 2317/73* (2013.01); *C07K 2317/92* (2013.01); *G01N 2333/82* (2013.01)

(58) Field of Classification Search

CPC ................ C07K 16/32; C07K 16/2863; C07K 16/3015; A61K 31/5517; A61K 31/675; A61K 31/704; A61K 39/3955; A61K 47/68; A61K 47/6809; A61K 47/6849; A61K 47/6855; A61K 47/6863; A61K 49/00; G01N 33/57415; G01N 33/57446

See application file for complete search history.

(56) References Cited

U.S. PATENT DOCUMENTS

| | | | |
|---|---|---|---|
| 4,427,588 | A | 1/1984 | Kaneko et al. |
| 5,660,856 | A | 8/1997 | Adler-Moore et al. |
| 6,660,856 | B2 | 12/2003 | Wang |
| 6,949,245 | B1 | 9/2005 | Sliwkowski |
| 6,984,494 | B2 | 1/2006 | Ralph |
| 7,041,292 | B1 | 5/2006 | Sliwkowski |
| 7,049,311 | B1 | 5/2006 | Thurston et al. |
| 7,129,254 | B2 | 10/2006 | Berger et al. |
| 7,265,105 | B2 | 9/2007 | Thurston et al. |
| 7,449,184 | B2 | 11/2008 | Allison et al. |
| 7,498,298 | B2 | 3/2009 | Doronina et al. |
| 7,521,541 | B2 | 4/2009 | Eigenbrot et al. |
| 7,855,275 | B2 | 12/2010 | Eigenbrot et al. |
| 7,993,834 | B2 | 8/2011 | Mass |
| 8,034,808 | B2 | 10/2011 | DeLavault et al. |
| 8,309,300 | B2 | 11/2012 | Junutula et al. |
| 8,372,396 | B2 | 2/2013 | Andya et al. |
| 8,481,042 | B2 | 7/2013 | Commercon et al. |

(Continued)

FOREIGN PATENT DOCUMENTS

| | | |
|---|---|---|
| CN | 101023100 | 8/2007 |
| EP | 1 413 582 B1 | 3/2006 |

(Continued)

OTHER PUBLICATIONS

Antonow et al., "Synthesis of a novel C2-aryl pyrrolo[2,1-c][1,4]benzodiazepine-5, 11-dione library: effect of C2-aryl substitution on cytotoxicity and non-covalent DNA binding" Bioorg Med Chem. 15(8):3041-53 (Apr. 15, 2007).

(Continued)

*Primary Examiner* — Nelson B Moseley, II
(74) *Attorney, Agent, or Firm* — McNeill PLLC

(57) ABSTRACT

The invention provides anti-HER2 antibodies and immunoconjugates and methods of using the same.

15 Claims, 22 Drawing Sheets

Specification includes a Sequence Listing.

(56) References Cited

U.S. PATENT DOCUMENTS

| | | | |
|---|---|---|---|
| 8,487,092 | B2 | 7/2013 | Howard et al. |
| 8,592,576 | B2 | 11/2013 | Howard et al. |
| 8,691,232 | B2 | 4/2014 | Derynck et al. |
| 8,765,740 | B2 | 7/2014 | Li et al. |
| 8,802,667 | B2 | 8/2014 | Li et al. |
| 8,809,320 | B2 | 8/2014 | Li et al. |
| 9,000,130 | B2 | 4/2015 | Bhakta et al. |
| 9,518,118 | B2 * | 12/2016 | Chen .................. A61K 39/3955 |
| 10,179,820 | B2 * | 1/2019 | Chen ................ G01N 33/57492 |
| 10,314,846 | B2 * | 6/2019 | Chen ................ A61K 47/68035 |
| 10,556,966 | B2 * | 2/2020 | Chen .................... A61K 31/675 |
| 2002/0141993 | A1 | 10/2002 | Ashkenazi et al. |
| 2005/0208043 | A1 | 9/2005 | Adams et al. |
| 2005/0244417 | A1 | 11/2005 | Ashkenazi et al. |
| 2007/0092940 | A1 | 4/2007 | Eigenbrot et al. |
| 2008/0112957 | A1 | 5/2008 | Fendly et al. |
| 2009/0175865 | A1 | 7/2009 | Eigenbrot et al. |
| 2010/0003766 | A1 | 1/2010 | Eigenbrot et al. |
| 2010/0111856 | A1 | 5/2010 | Gill et al. |
| 2011/0033460 | A1 | 2/2011 | Fendly et al. |
| 2011/0137017 | A1 | 6/2011 | Eigenbrot et al. |
| 2011/0256157 | A1 | 10/2011 | Howard et al. |
| 2011/0301334 | A1 | 12/2011 | Bhakta et al. |
| 2013/0028917 | A1 | 1/2013 | Howard et al. |
| 2013/0195845 | A1 | 8/2013 | Fendly et al. |
| 2013/0266595 | A1 | 10/2013 | Flygare et al. |
| 2014/0111298 | A1 | 4/2014 | Chiang et al. |
| 2014/0120118 | A1 | 5/2014 | Howard |
| 2014/0288280 | A1 | 9/2014 | Bhakta et al. |
| 2015/0017094 | A1 | 1/2015 | Gill et al. |
| 2015/0017188 | A1 | 1/2015 | Eigenbrot, Jr. et al. |
| 2015/0111298 | A1 | 4/2015 | Lattemann et al. |
| 2015/0209444 | A1 | 7/2015 | Chari et al. |
| 2015/0344482 | A1 | 12/2015 | Howard |
| 2016/0074527 | A1 | 3/2016 | Flygare et al. |
| 2016/0096893 | A1 | 4/2016 | Chen et al. |
| 2016/0130358 | A1 | 5/2016 | Bhakta et al. |
| 2016/0310611 | A1 | 10/2016 | Flygare et al. |
| 2017/0095570 | A1 | 4/2017 | Dragovich et al. |
| 2017/0274092 | A1 | 9/2017 | Chen et al. |
| 2018/0185486 | A1 | 7/2018 | Dragovich et al. |

FOREIGN PATENT DOCUMENTS

| | | | |
|---|---|---|---|
| EP | 2 540 745 | A1 | 1/2013 |
| WO | WO 1998/17797 | A1 | 4/1998 |
| WO | WO 2000/012507 | A2 | 3/2000 |
| WO | WO 2004/087717 | A1 | 10/2004 |
| WO | WO 2005/023814 | A1 | 3/2005 |
| WO | WO 2005/085251 | A1 | 9/2005 |
| WO | WO 2006/034488 | A2 | 3/2006 |
| WO | WO 2006033700 | A2 | 3/2006 |
| WO | WO 2007/085930 | A1 | 8/2007 |
| WO | WO 2010/043877 | A1 | 4/2010 |
| WO | WO 2010/091150 | A1 | 8/2010 |
| WO | WO 2011/056983 | A1 | 5/2011 |
| WO | WO 2011/130598 | A1 | 10/2011 |
| WO | WO 2011/130613 | A1 | 10/2011 |
| WO | WO 2011/130616 | A1 | 10/2011 |
| WO | WO 2011/156328 | A1 | 12/2011 |
| WO | WO 2012/014147 | A1 | 2/2012 |
| WO | WO 2012/112708 | A1 | 8/2012 |
| WO | WO 2013/041606 | A1 | 3/2013 |
| WO | WO 2013/053873 | A1 | 4/2013 |
| WO | WO 2013/055987 | A1 | 4/2013 |
| WO | WO 2013/055990 | A1 | 4/2013 |
| WO | WO 2013/055993 | A1 | 4/2013 |
| WO | WO 2013/177481 | A1 | 11/2013 |
| WO | WO 2014/011518 | A1 | 1/2014 |
| WO | WO 2014/057072 | A1 | 4/2014 |
| WO | WO 2014/057113 | A1 | 4/2014 |
| WO | WO 2014/057114 | A1 | 4/2014 |
| WO | WO 2014/057115 | A1 | 4/2014 |
| WO | WO 2014/057117 | A1 | 4/2014 |
| WO | WO 2014/057118 | A1 | 4/2014 |
| WO | WO 2014/057119 | A1 | 4/2014 |
| WO | WO 2014/057120 | A1 | 4/2014 |
| WO | WO 2014/057122 | A1 | 4/2014 |
| WO | WO 2014/096365 | A1 | 6/2014 |
| WO | WO 2014/096368 | A1 | 6/2014 |
| WO | WO 2014/130879 | A2 | 8/2014 |
| WO | WO 2015/095124 | A1 | 6/2015 |
| WO | WO 2016/040723 | A1 | 3/2016 |
| WO | WO 2016/040856 | A2 | 3/2016 |
| WO | WO 2016/044396 | A1 | 3/2016 |
| WO | WO 2016/044560 | A1 | 3/2016 |

OTHER PUBLICATIONS

Antonow et al., "Synthesis of DNA-interactive pyrrolo[2,1-c][1,4]benzodiazepines (PBDs)" Chem Rev. 111(4):2815-64 ( 2011).

Arima et al., "Studies on tomaymycin, a new antibiotic. I. Isolation and properties of tomaymycin" J Antibiot (Tokyo) 25(8):437-44 (Aug. 1972).

Baselga et al., "Recombinant Humanized Anti-HER2 Antibody (Herceptin ™) Enhances the Antitumor Activity of Paclitaxel and Doxorubicin against HER2/neu Overexpressing Human Breast Cancer Xenografts" Cancer Res. 58:2825-2831 (Jul. 1, 1998).

Bookman et al., "Evaluation of Monoclonal Humanized Anti-HER2 Antibody, Trastuzumab, in Patients with Recurrent or Refractory Ovarian or Primary Peritoneal Carcinoma With Overexpression of HER2: A Phase II Trial of the Gynecologic Oncology Group" Journal of Clinical Oncology 21(2):283-290 (Jan. 15, 2003).

Bose et al., "New approaches to pyrrolo[2,1-c][1,4]benzodiazepines: synthesis, DNA-binding and cytotoxicity of DC-81" Tetrahedron 48(4):751-8 ( 1992).

Fendly et al., "Characterization of murine monoclonal antibodies reactive to either the human epidermal growth factor receptor or HER2/neu gene product" Cancer Res 50:1550-1558 (Mar. 1, 1990).

Gregson et al., "Linker Length Modulates DNA Cross-Linking Reactivity and Cytotoxic Potency of C8/C8' Ether-Linked C2-exo-Unsaturated Pyrrolo[2,1-c][1,4]benzodiazepine (PBD) Dimers" J. Med. Chem. 47(5):1161-74 ( 2004).

Gregson, et al., "Design, Synthesis, and Evaluation of a Novel Pyrrolobenzodiazepine DNA-Interactive Agent with Highly Efficient Cross-Linking Ability and Potent Cytotoxicity", J Med Chem 44, 737-748 (2001).

Gregson, et al., "Synthesis of a novel C2/C2'-exo unsaturated pyrrolobenzodiazepine cross-linking agent with remarkable DNA binding affinity and cytotoxicity", Chem Commun, 797-798 (1999).

Grimm et al., "Reaction Safety: An Improved Procedure for the Preparation of 1,3,4,12a-Tetrahydro-11H-[1,4]-oxanio[3,4-c][1,4]benzodiazepine-6,12-dione with Iron in Acetic Acid" Organic Process Research And Development 7(6):1067-70 (Nov. 1, 2003).

Hara et al., "DC 102, a new glycosidic pyrrolo(1,4)benzodiazepine antibiotic produced by *Streptomyces* sp" J Antibiot (Tokyo) 41(5):702-4 (May 1988).

Hochlowski et al., "Abbeymycin, a new anthramycin-type antibiotic produced by a streptomycete" J Antibiot (Tokyo) 40(2):145-8 (Feb. 1987).

Howard et al., "Synthesis of a novel C2/C2'-aryl-substituted pyrrolo[2,1-c][1,4]benzodiazepine dimer prodrug with improved water solubility and reduced DNA reaction rate" Bioorg Med Chem Lett 19(22):6463-6466 ( 2009).

Hurley et al., "Covalent Binding of Antitumor Antibiotics in the Minor Groove of DNA. Mechanism of Action of CC-1065 and the Pyrrolo(1,4)benzodiazepines" Acc Chem Res 19:230-237 ( 1986).

International Search Report and Written Opinion for PCT Application PCT/US2015/049549, filed Sep. 11, 2015, pp. 14 (mailed Dec. 16, 2015).

ISR and Written Opinion for PCT/EP2013/077705 (10 pages).

ISR and Written Opinion for PCT/US2013/042566 (11 pages).

ISR and Written Opinion for PCT/US2015/049549 (12 pages).

ISR and Written Opinion for PCT/US2016/054858 (13 pages).

Itoh et al., "Sibanomicin, a new pyrrolo[1,4]benzodiazepine antitumor antibiotic produced by a *Micromonospora* sp" J Antibiot (Tokyo) 41(9):1281-4 ( 1988).

(56) References Cited

OTHER PUBLICATIONS

Kamal et al., "Design, synthesis, and evaluation of mixed imine-amine pyrrolobenzodiazepine dimers with efficient DNA binding affinity and potent cytotoxicity" Bioorg Med Chem. 12(20):5427-36 (2004).
Kamal et al., "Design, synthesis, and evaluation of new noncross-linking pyrrolobenzodiazepine dimers with efficient DNA binding ability and potent antitumor activity" J Med Chem. 45(21):4679-88 (2002).
Kamal et al., "Pyrrolo[2,1-c][1,4]benzodiazepine-beta-glucuronide prodrugs with a potential for selective therapy of solid tumors by PMT and ADEPT strategies" Bioorg Med Chem Lett. 18(13):3769-73 (Jul. 1, 2008).
Kaneko, et al., "A new and mild method for the reduction of secondary amides to carbinolamine ethers and imines: a conversion of oxotomaymycin to tomaymycin", Tetrahedron Letters 24(47), 5165-5168 (1983).
Kaneko, et al., "Bicyclic and tricyclic analogues of anthramycin", Journal of Medicinal Chemistry 28(3), 388-392 (1985).
Kang, et al. "Synthesis of a novel C2-aryl substituted 1,2-unsaturated pyrrolobenzodiazepine", Chemical Communications 14, 1688-1698 (2003).
Kohn, Mechanism of Action of Antimicrobial and Antitumor Agents "Anthramycin" New York:Springer-Verlag,:3-11 (1975).
Konishi et al., "Chicamycin, a new antitumor antibiotic. II. Structure determination of chicamycins A and B" J Antibiot (Tokyo) 37(3):200-6 (Mar. 1984).
Kunimoto et al., "Mazethramycin, a new member of anthramycin group antibiotics" J. Antibiotics 33(6):665-7 (Jun. 1980).
Langley et al., "A versatile and efficient synthesis of carbinolamine-containing pyrrolo[1,4]benzodiazepines via the cyclization of N-(2-aminobenzoyl)pyrrolidine-2-carboxaldehyde diethyl thioacetals: total synthesis of prothracarcin" J. Org. Chem. 52(1):91-97 ( 1987).
Leber et al., "A revised structure of sibiromycin" J. Am. Chem. Soc. 110:2992-93 ( 1988).
Leimgruber et al., "Isolation and characterization of anthramycin, a new antitumor antibiotic" J Am Chem Soc 87(24):5791-5793 (1965).
Leimgruber et al., "The structure of anthramycin" J Am Chem Soc 87(24):5793-5795 (1965).
Martin et al., "Sequence-selective interaction of the minor-groove interstrand cross-linking agent SJG-136 with naked and cellular DNA: footprinting and enzyme inhibition studies" Biochemistry 44(11):4135-47 (Mar. 22, 2005).
Scheer JM et al., "Reorienting the Fab Domains of Trastuzumab Results in Potent HER2 Activators," PLoS One, vol. 7, No. 12, e51817, 13 pages (2012).
Shimizu et al., "Prothracarcin, a novel antitumor antibiotic" J. Antibiotics 8:972-8 (Aug. 1982).
Takeuchi et al., "Neothramycins A and B, new antitumor antibiotics" J Antibiot (Tokyo) 29(1):93-6 (1976).
Thurston et al., "Synthesis of DNA-Interactive Pyrrolo[2,1-c][1,4]benzodiazepines" Chem Rev 94:433-465 ( 1994).
Thurston et al., "The molecular recognition of DNA" Chem. Brit. 26(8):767-72 (Aug. 1990).
Tsunakawa et al., "Porothramycin, a new antibiotic of the anthramycin group: production, isolation, structure and biological activity" J Antibiot (Tokyo) 41(10):1366-73 (Oct. 1988).

* cited by examiner 1 2 3 4 5 6 7 8 9 10

Scheme 1

10 11 12 13 14 58b 66d 67d

Scheme 2

51a 57a 57b 66a 66b 66c 66d

1 Cmp 66d 2 3

4

*FIG. 12A*: thio-hu7C2-HC-A118C-disulfide-PBD and thio-hu7C2-LC-K149C-disulfide-PBD
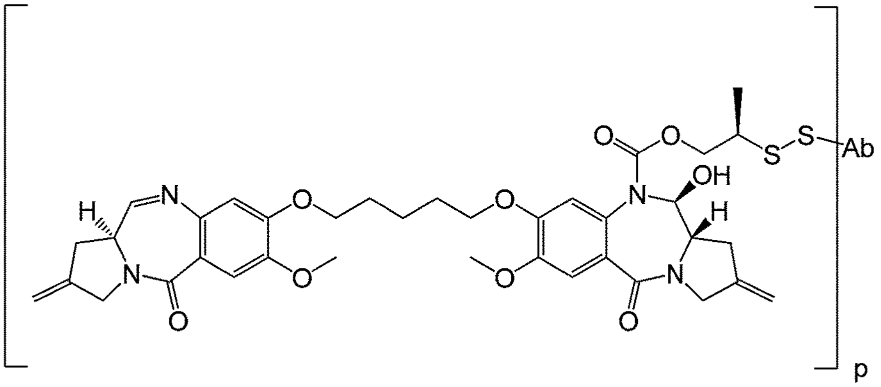
*FIG. 12B*: thio-hu7C2-LC-K149C-CBI dimer
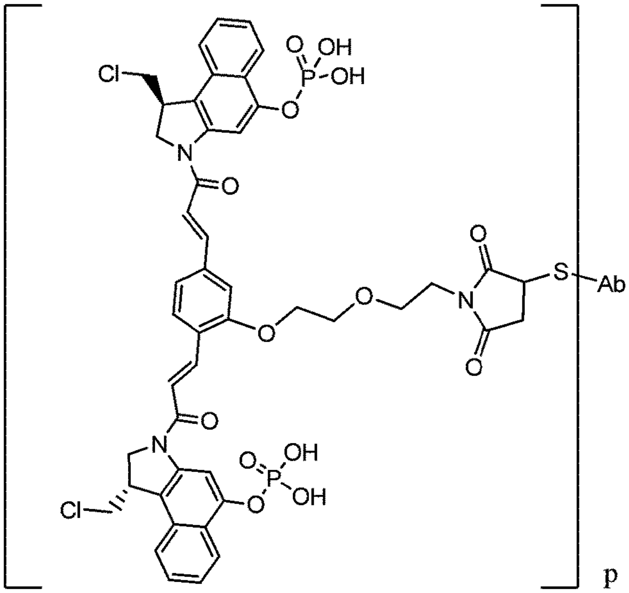
*FIG. 12C*: thio-hu7C2-LC-K149C-disulfide-CBI-PBD
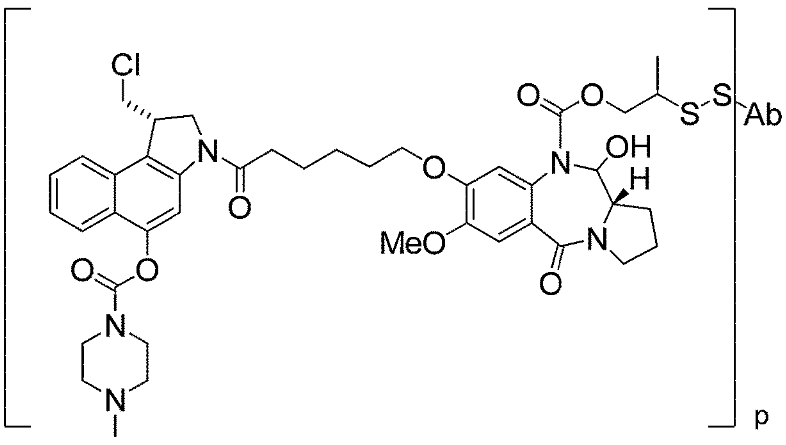

*FIG. 12D*: thio-hu7C2-LC-K149C-disulfide-PNU
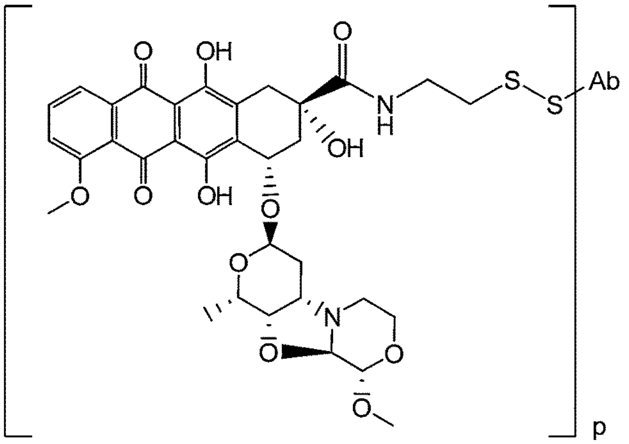
*FIG. 12E*: thio-hu7C2-HC-A118C-maleimide-PNU and thio-hu7C2-LC-K149C-maleimide-PNU
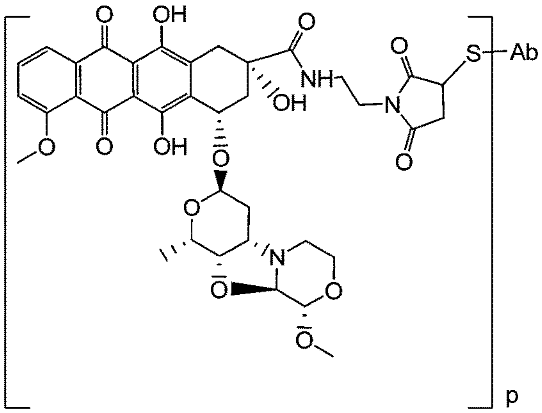
*FIG. 12F*: thio-hu7C2-LC-K149C-disulfide-CBI-PBD (phosphate)
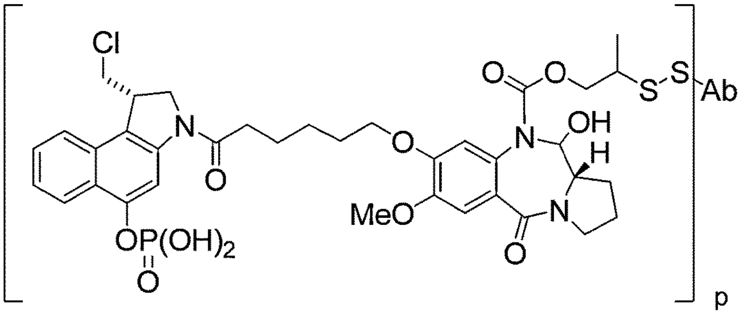

Amino Acid Sequence for Pertuzumab Light Chain 1 10 20 30 40 50 60

DIQMTQSPSSLSASVGDRVTITCKASQDVSIGVAWYQQKPGKAPKLLIYSASYRYTGVPS 70 80 90 100 110 120

RFSGSGSGTDFTLTISSLQPEDFATYYCQQYYIYPYTFGQGTKVEIKRTVAAPSVFIFPP 130 140 150 160 170 180

SDEQLKSGTASVVCLLNNFYPREAKVQWKVDNALQSGNSQESVTEQDSKDSTYSLSSTLT 190 200 210

LSKADYEKHKVYACEVTHQGLSSPVTKSFNRGEC SEQ ID NO: 32

*FIG. 13A*

Amino Acid Sequence for Pertuzumab Heavy Chain 1 10 20 30 40 50 60

EVQLVESGGGLVQPGGSLRLSCAASGFTFTDYTMDWVRQAPGKGLEWVADVNPNSGGSIY

70 80 90 100 110 120

NQRFKGRFTLSVDRSKNTLYLQMNSLRAEDTAVYYCARNLGPSFYFDYWGQGTLVTVSSA 130 140 150 160 170 180

STKGPSVFPLAPSSKSTSGGTAALGCLVKDYFPEPVTVSWNSGALTSGVHTFPAVLQSSG 190 200 210 220 230 240

LYSLSSVVTVPSSSLGTQTYICNVNHKPSNTKVDKKVEPKSCDKTHTCPPCPAPELLGGP 250 260 270 280 290 300 *

SVFLFPPKPKDTLMISRTPEVTCVVVDVSHEDPEVKFNWYVDGVEVHNAKTKPREEQYNS 310 320 330 340 350 360

TYRVVSVLTVLHQDWLNGKEYKCKVSNKALPAPIEKTISKAKGQPREPQVYTLPPSREEM 370 380 390 400 410 420

TKNQVSLTCLVKGFYPSDIAVEWESNGQPENNYKTTPPVLDSDGSFFLYSKLTVDKSRWQ 430 440 448

QGNVFSCSVMHEALHNHYTQKSLSLSPG SEQ ID NO: 31

*FIG. 13B*

Pertuzumab Variant Light Chain

```
1                                                           15                                                          30                                                          45
V H S D I Q M T Q S P S S L S A S V G D R V T I T C K A S Q D V S I G V A W Y Q Q K P G K

46                                                          60                                                          75                                                          90
A P K L L I Y S A S Y R Y T G V P S R F S G S G S G T D F T L T I S S L Q P E D F A T Y Y

91                                                          105                                                         120                                                         135
C Q Q Y Y I Y P Y T F G Q G T K V E I K R T V A A P S V F I F P P S D E Q L K S G T A S V

136                                                         150                                                         165                                                         180
V C L L N N F Y P R E A K V Q W K V D N A L Q S G N S Q E S V T E Q D S K D S T Y S L S S

181                                                         195                                                         210                       217
T L T L S K A D Y E K H K V Y A C E V T H Q G L S S P V T K S F N R G E C   SEQ ID NO: 34
```

*FIG. 14A*

Pertuzumab Variant Heavy Chain

```
1                                         15                                        30                                        45
E V Q L V E S G G G L V Q P G G S L R L S C A A S G F T F T D Y T M D W V R Q A P G K G L

46                                        60                                        75                                        90
E W V A D V N P N S G G S I Y N Q R F K G R F T L S V D R S K N T L Y L Q M N S L R A E D

91                                        105                                       120                                       135
T A V Y Y C A R N L G P S F Y F D Y W G Q G T L V T V S S A S T K G P S V F P L A P S S K

136                                       150                                       165                                       180
S T S G G T A A L G C L V K D Y F P E P V T V S W N S G A L T S G V H T F P A V L Q S S G

181                                       195                                       210                                       225
L Y S L S S V V T V P S S S L G T Q T Y I C N V N H K P S N T K V D K K V E P K S C D K T

226                                       240                                       255                                       270
H T C P P C P A P E L L G G P S V F L F P P K P K D T L M I S R T P E V T C V V V D V S H

271                                       285                                       300                                       315
E D P E V K F N W Y V D G V E V H N A K T K P R E E Q Y N S T Y R V V S V L T V L H Q D W

316                                       330                                       345                                       360
L N G K E Y K C K V S N K A L P A P I E K T I S K A K G Q P R E P Q V Y T L P P S R E E M

361                                       375                                       390                                       405
T K N Q V S L T C L V K G F Y P S D I A V E W E S N G Q P E N N Y K T T P P V L D S D G S

406                                       420                                       435                                   449
F F L Y S K L T V D K S R W Q Q G N V F S C S V M H E A L H N H Y T Q K S L S L S P G K
```

SEQ ID NO: 33

*FIG. 14B*

Trastuzmab Light Chain

```
1                                           15                                          30                                          45
D I Q M T Q S P S S L S A S V G D R V T I T C R A S Q D V N T A V A W Y Q Q K P G K A P K
46                                          60                                          75                                          90
L L I Y S A S F L Y S G V P S R F S G S R S G T D F T L T I S S L Q P E D F A T Y Y C Q Q
91                                          105                                         120                                         135
H Y T T P P T F G Q G T K V E I K R T V A A P S V F I F P P S D E Q L K S G T A S V V C L
136                                         150                                         165                                         180
L N N F Y P R E A K V Q W K V D N A L Q S G N S Q E S V T E Q D S K D S T Y S L S S T L T
181                                         195                                         210          214
L S K A D Y E K H K V Y A C E V T H Q G L S S P V T K S F N R G E C
```

SEQ ID NO: 30

FIG. 15A

Trastuzmab Heavy Chain 1 15 30 45
E V Q L V E S G G G L V Q P G G S L R L S C A A S G F N I K D T Y I H W V R Q A P G K G L 46 60 75 90
E W V A R I Y P T N G Y T R Y A D S V K G R F T I S A D T S K N T A Y L Q M N S L R A E D 91 105 120 135
T A V Y Y C S R W G G D G F Y A M D Y W G Q G T L V T V S S A S T K G P S V F P L A P S S 136 150 165 180
K S T S G G T A A L G C L V K D Y F P E P V T V S W N S G A L T S G V H T F P A V L Q S S 181 195 210 225
G L Y S L S S V V T V P S S S L G T Q T Y I C N V N H K P S N T K V D K K V E P K S C D K 226 240 255 270
T H T C P P C P A P E L L G G P S V F L F P P K P K D T L M I S R T P E V T C V V V D V S 271 285 300 315
H E D P E V K F N W Y V D G V E V H N A K T K P R E E Q Y N S T Y R V V S V L T V L H Q D 316 330 345 360
W L N G K E Y K C K V S N K A L P A P I E K T I S K A K G Q P R E P Q V Y T L P P S R E E 361 375 390 405
M T K N Q V S L T C L V K G F Y P S D I A V E W E S N G Q P E N N Y K T T P P V L D S D G 406 420 435 449
S F F L Y S K L T V D K S R W Q Q G N V F S C S V M H E A L H N H Y T Q K S L S L S P G

SEQ ID NO: 29

FIG. 15B

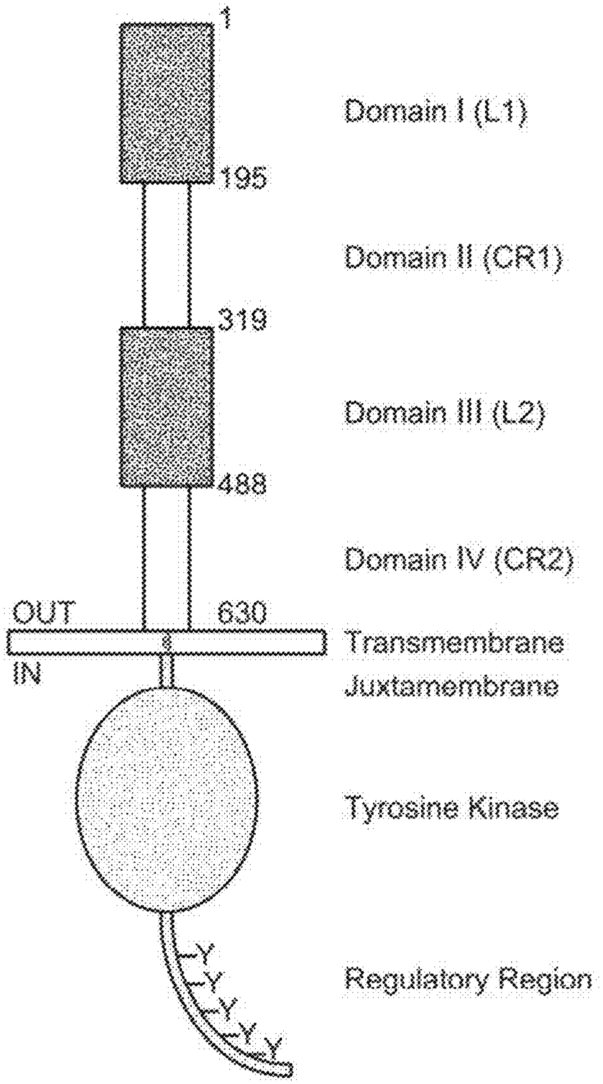

TQVCTGTDMKLRLPASPETHLDMLRHLYQGCQVVQGNLELTYLPTNASLSFLQDIQEVQGYV
LIAHNQVRQVPLQRLRIVRGTQLFEDNYALAVLDNGDPLNNTTPVTGASPGGLRELQLRSLT
EILKGGVLIQRNPQLCYQDTILWKDIFHKNNQLALTLIDTNRSRACHPCSPMCKGSRCWGES
SEDCQSLTR SEQ ID NO: 35

TVCAGGCARCKGPLPTDCCHEQCAAGCTGPKHSDCLACLHFNHSGICELHCPALVTYNTDTF
ESMPNPEGRYTFGASCVTACPYNYLSTDVGSCTLVCPLHNQEVTAEDGTQRCEKCSKPCARV
SEQ ID NO: 36

CYGLGMEHLREVRAVTSANIQEFAGCKKIFGSLAFLPESFDGDPASNTAPLQPEQLQVFETLE
EITGYLYISAWPDSLPDLSVFQNLQVIRGRILHNGAYSLTLQGLGISWLGLRSLRELGSGLAL
IHHNTHLCFVHTVPWDQLFRNPHQALLHTANRPEDECVGEGLA SEQ ID NO: 37

CHQLCARGHCWGPGPTQCVNCSQFLRGQECVEECRVLQGLPREYVNARHCLPCHPECQPQNGS
VTCFGPEADQCVACAHYKDPPFCVARCPSGVKPDLSYMPIWKFPDEEGACQPCPINCTHSCVD
LDDKGCPAEQRASPLT SEQ ID NO: 38

*FIG. 16*

ANTI-HER2 ANTIBODIES AND IMMUNOCONJUGATES

CROSS-REFERENCE TO RELATED APPLICATIONS

The present application is a continuation of U.S. application Ser. No. 16/721,525, filed Dec. 19, 2019, which is a divisional of U.S. application Ser. No. 16/170,819, filed Oct. 25, 2018, now U.S. Pat. No. 10,556,966, which is a divisional of US application Ser. No. 15/296,454, filed Oct. 18, 2016, now U.S. Pat. No. 10,179,820, which is a divisional of U.S. application Ser. No. 14/851,001, filed Sep. 11, 2015, now U.S. Pat. No. 9,518,118, which claims the benefit of priority of U.S. Provisional Application No. 62/049,594, filed Sep. 12, 2014, each of which is incorporated by reference herein in its entirety for any purpose.

SEQUENCE LISTING

The present application is filed with a Sequence Listing in electronic format. The Sequence Listing is provided as a file entitled "2022-04-12_01146-0037-04US_Sequence_Listing_ST25.txt" created on Apr. 12, 2022, which is 74.5 KB in size. The information in the electronic format of the sequence listing is incorporated herein by reference in its entirety.

FIELD

The present invention relates to anti-HER2 antibodies and immunoconjugates and methods of using the same.

BACKGROUND

Breast cancer is a highly significant cause of morbidity and mortality worldwide. There are over 1.3 million cases of breast cancer diagnosed globally each year with more than 450,000 deaths related to the disease (Jemal A, Bray F, Center M, et al. Global cancer statistics. CA Cancer J Clin, 2011; 61(2):69-90).

The HER2 (ErbB2) receptor tyrosine kinase is a member of the epidermal growth factor receptor (EGFR) family of transmembrane receptors. Overexpression of HER2 is observed in approximately 20% of human breast cancers and is implicated in the aggressive growth and poor clinical outcomes associated with these tumors (Slamon et al (1987) Science 235:177-182). HER2 protein overexpression can be determined using an immunohistochemistry based assessment of fixed tumor blocks (Press M F, et al (1993) Cancer Res 53:4960-70).

Trastuzumab (CAS 180288-69-1, HERCEPTIN®, huMAb4D5-8, rhuMAb HER2, Genentech) is a recombinant DNA-derived, IgG1 kappa, monoclonal antibody that is a humanized version of a murine anti-HER2 antibody (4D5) that selectively binds with high affinity in a cell-based assay (Kd=5 nM) to the extracellular domain of HER2 (U.S. Pat. Nos. 5,677,171; 5,821,337; 6,054,297; 6,165,464; 6,339,142; 6,407,213; 6,639,055; 6,719,971; 6,800,738; 7,074,404; Coussens et al (1985) Science 230:1132-9; Slamon et al (1989) Science 244:707-12; Slamon et al (2001) New Engl. J. Med. 344:783-792). Trastuzumab has been shown, in both in vitro assays and in animals, to inhibit the proliferation of human tumor cells that overexpress HER2 (Hudziak et al (1989) Mol Cell Biol 9:1165-72; Lewis et al (1993) Cancer Immunol Immunother; 37:255-63; Baselga et al (1998) Cancer Res. 58:2825-2831). Trastuzumab is a mediator of antibody-dependent cellular cytotoxicity, ADCC (Lewis et al (1993) Cancer Immunol Immunother 37(4): 255-263; Hotaling et al (1996) [abstract]. Proc. Annual Meeting Am Assoc Cancer Res; 37:471; Pegram M D, et al (1997) [abstract]. Proc Am Assoc Cancer Res; 38:602; Sliwkowski et al (1999) Seminars in Oncology 26(4), Suppl 12:60-70; Yarden Y. and Sliwkowski, M. (2001) Nature Reviews: Molecular Cell Biology, Macmillan Magazines, Ltd., Vol. 2:127-137).

HERCEPTIN® was approved in 1998 for the treatment of patients with HER2-overexpressing metastatic breast cancers (Baselga et al, (1996) J. Clin. Oncol. 14:737-744) that have received extensive prior anti-cancer therapy, and has since been used in over 300,000 patients (Slamon D J, et al. N Engl J Med 2001; 344:783-92; Vogel C L, et al. J Clin Oncol 2002; 20:719-26; Marty M, et al. J Clin Oncol 2005; 23:4265-74; Romond E H, et al. T N Engl J Med 2005; 353:1673-84; Piccart-Gebhart M J, et al. N Engl J Med 2005; 353:1659-72; Slamon D, et al. [abstract]. Breast Cancer Res Treat 2006, 100 (Suppl 1): 52). In 2006, the FDA approved HERCEPTIN® (trastuzumab, Genentech Inc.) as part of a treatment regimen containing doxorubicin, cyclophosphamide and paclitaxel for the adjuvant treatment of patients with HER2-positive, node-positive breast cancer.

Trastuzumab-MCC-DM1 (T-DM1, trastuzumab emtansine, ado-trastuzumab emtansine, KADCYLA®), a novel antibody-drug conjugate (ADC) for the treatment of HER2-positive breast cancer, is composed of the cytotoxic agent DM1 (a thiol-containing maytansinoid anti-microtubule agent) conjugated to trastuzumab at lysine side chains via an MCC linker, with an average drug load (drug to antibody ratio) of about 3.5. After binding to HER2 expressed on tumor cells, T-DM1 undergoes receptor-mediated internalization, resulting in intracellular release of cytotoxic catabolites containing DM1 and subsequent cell death.

The U.S. Food and Drug Administration approved ado-trastuzumab emtansine, marketed under the tradename KADCYLA®, on Feb. 22, 2013 for the treatment of patients with HER2-positive, metastatic breast cancer who previously received treatment with trastuzumab and a taxane.

Pertuzumab (also known as recombinant humanized monoclonal antibody 2C4, rhuMAb 2C4, PERJETA®, Genentech, Inc, South San Francisco) represents the first in a new class of agents known as HER dimerization inhibitors (HDI) and functions to inhibit the ability of HER2 to form active heterodimers or homodimers with other HER receptors (such as EGFR/HER1, HER2, HER3 and HER4). See, for example, Harari and Yarden Oncogene 19:6102-14 (2000); Yarden and Sliwkowski. Nat Rev Mol Cell Biol 2:127-37 (2001); Sliwkowski Nat Struct Biol 10:158-9 (2003); Cho et al. Nature 421:756-60 (2003); and Malik et al. Pro Am Soc Cancer Res 44:176-7 (2003) Pertuzumab blockade of the formation of HER2-HER 3 heterodimers in tumor cells has been demonstrated to inhibit critical cell signaling, which results in reduced tumor proliferation and survival (Agus et al. Cancer Cell 2:127-37 (2002)).

Pertuzumab has been evaluated in Phase II studies in combination with trastuzumab in patients with HER2-positive metastatic breast cancer who have previously received trastuzumab for metastatic disease. One study, conducted by the National cancer Institute (NCI), enrolled 11 patients with previously treated HER2-positive metastatic breast cancer. Two out of the 11 patients exhibited a partial response (PR)(Baselga et al., J Clin Oncol 2007 ASCO Annual Meeting Proceedings; 25:18 S (June 20 Supplement): 1004. The results of a Phase II neoadjuvant study evaluating the effect of a novel combination regimen of pertuzumab and trastuzumab plus chemotherapy (Docetaxel) in women with early-stage HER2-positive breast cancer, presented at the CTRC-AACR San Antonio Breast Cancer Symposium (SABCS), Dec. 8-12, 2010, showed that the two HER2 antibodies plus Docetaxel given in the neoadjuvant setting prior to surgery significantly improved the rate of complete tumor disappearance (pathological complete response rate, pCR, of 45.8 percent) in the breast by more than half compared to trastuzumab plus Docetaxel (pCR of 29.0 percent), p=0.014.

Pertuzumab, marketed under the tradename PERJETA®, was approved in 2012 for the treatment of patients with advanced or late-stage (metastatic) HER2-positive breast cancer. HER2-positive breast cancers have increased amounts of the HER2 protein that contributes to cancer cell growth and survival.

On Sep. 30, 2013, the U.S. Food and Drug Administration granted accelerated approval to PERJETA® (pertuzumab) as part of a complete treatment regimen for patients with early stage breast cancer (EBC) before surgery (neoadjuvant setting). PERJETA® is the first FDA-approved drug for the neoadjuvant treatment of breast cancer.

There is a need in the art for additional safe and effective agents that target HER2 for treatment of HER2-associated conditions, such as breast cancer, for use in monotherapy and combination therapy. The invention fulfills that need and provides other benefits.

SUMMARY

The invention provides anti-HER2 antibodies and immunoconjugates and methods of using the same.

In some embodiments, an isolated antibody that binds to HER2 is provided, wherein the antibody comprises (a) HVR-H1 comprising the amino acid sequence of SEQ ID NO:15; (b) HVR-H2 comprising the amino acid sequence of SEQ ID NO:16; (c) HVR-H3 comprising the amino acid sequence of SEQ ID NO:17; (d) HVR-L1 comprising the amino acid sequence of SEQ ID NO:12; (e) HVR-L2 comprising the amino acid sequence of SEQ ID NO:13; and (f) HVR-L3 comprising the amino acid sequence of SEQ ID NO:14. In some embodiments, the antibody comprises a heavy chain variable region comprising the sequence of SEQ ID NO: 11 and a light chain variable region comprising the sequence of SEQ ID NO: 10. In some embodiments, the antibody is a monoclonal antibody. In some embodiments, the antibody is a humanized or chimeric antibody. In some embodiments, the antibody is an antibody fragment that binds HER2.

In some embodiments, HER2 is human HER2 comprising amino acids 23 to 1255 of SEQ ID NO: 1. In some embodiments, the antibody binds to extracellular domain I of HER2. In some embodiments, extracellular domain I of HER2 has the sequence of SEQ ID NO: 35. In some embodiments, the antibody binds to loop 163-189 and loop 185-189 of extracellular domain I (e.g., a first loop defined by amino acids 163-189 and a second loop defined by amino acids 185-189 of extracellular domain I). In some embodiments, the antibody contacts His171, Ser186, Ser187 and Glu188 of extracellular domain I.

In some embodiments, the antibody is an IgG1, IgG2a or IgG2b antibody. In some embodiments, the antibody comprises at least one mutation in the heavy chain constant region selected from A118C and S400C. In some embodiments, the antibody comprises at least one mutation in the light chain constant region selected from K149C and V205C.

In some embodiments, the antibody comprises:

a) a heavy chain comprising the sequence of SEQ ID NO: 19 and a light chain comprising the sequence of SEQ ID NO: 18; or b) a heavy chain comprising the sequence of SEQ ID NO: 19 and a light chain comprising the sequence of SEQ ID NO: 23; or c) a heavy chain comprising the sequence of SEQ ID NO: 24 and a light chain comprising the sequence of SEQ ID NO: 18.

In some embodiments, the antibody comprises the heavy chain constant region of SEQ ID NO: 28. In some embodiments, the antibody comprises the light chain constant region of SEQ ID NO: 25.

In some embodiments, an isolated antibody that binds to HER2 is provided, wherein the antibody comprises a heavy chain comprising the sequence of SEQ ID NO: 19 and a light chain comprising the sequence of SEQ ID NO: 23. In some embodiments, an isolated antibody that binds to HER2 is provided, wherein the antibody comprises a heavy chain comprising the sequence of SEQ ID NO: 24 and a light chain comprising the sequence of SEQ ID NO: 18.

In some embodiments, an isolated nucleic acid is provided, which encodes an antibody described herein. In some embodiments, a host cell comprising the nucleic acid is provided. In some embodiments, a method of producing an antibody is provided, comprising culturing the host cell so that the antibody is produced.

In some embodiments, an immunoconjugate is provided, which comprises an antibody described herein and a cytotoxic agent. In some embodiments, the immunoconjugate has the formula Ab-(L-D)p, wherein:

a) Ab is the antibody;

b) L is a linker;

c) D is a cytotoxic agent; and d) p ranges from 1-8.

In some embodiments, the cytotoxic agent is selected from an auristatin, a maytansinoid, a calicheamicin, a pyrrolobenzodiazepine, a nemorubicin derivative, and a 1-(chloromethyl)-2,3-dihydro-1H-benzo[e]indole (CBI).

In some embodiments, an immunoconjugate is provided, wherein D is a pyrrolobenzodiazepine of Formula A:

A

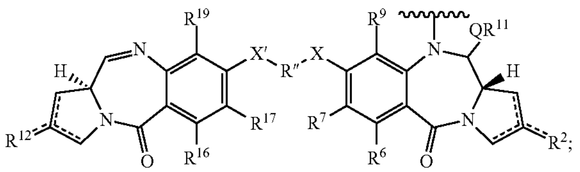

wherein the dotted lines indicate the optional presence of a double bond between C1 and C2 or C2 and C3;

$R^2$ is independently selected from H, OH, =O, =$CH_2$, CN, R, OR, =CH—$R^D$, =$C(R^D)_2$, O—$SO_2$—R, $CO_2R$ and COR, and optionally further selected from halo or dihalo, wherein $R^D$ is independently selected from R, $CO_2R$, COR, CHO, $CO_2H$, and halo;

$R^6$ and $R^9$ are independently selected from H, R, OH, OR, SH, SR, $NH_2$, NHR, NRR', $NO_2$, $Me_3Sn$ and halo;

$R^7$ is independently selected from H, R, OH, OR, SH, SR, $NH_2$, NHR, NRR', $NO_2$, $Me_3Sn$ and halo;

Q is independently selected from O, S and NH;

$R^{11}$ is either H, or R or, where Q is O, $SO_3M$, where M is a metal cation;

R and R' are each independently selected from optionally substituted $C_{1-8}$ alkyl, $C_{3-8}$ heterocyclyl and $C_{5-20}$ aryl groups, and optionally in relation to the group NRR', R and R' together with the nitrogen atom to which they are attached form an optionally substituted 4-, 5-, 6- or 7-membered heterocyclic ring;

$R^{12}$, $R^{16}$, $R^{19}$ and $R^{17}$ are as defined for $R^2$, $R^6$, $R^9$ and $R^7$ respectively;

R" is a $C_{3-12}$ alkylene group, which chain may be interrupted by one or more heteroatoms and/or aromatic rings that are optionally substituted; and X and X' are independently selected from O, S and N(H).

In some embodiments, D has the structure:

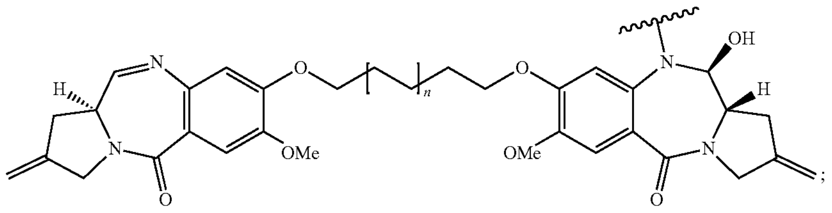

wherein n is 0 or 1.

In some embodiments, an immunoconjugate is provided, wherein D is a nemorubicin derivative. In some embodiments, D has a structure selected from:

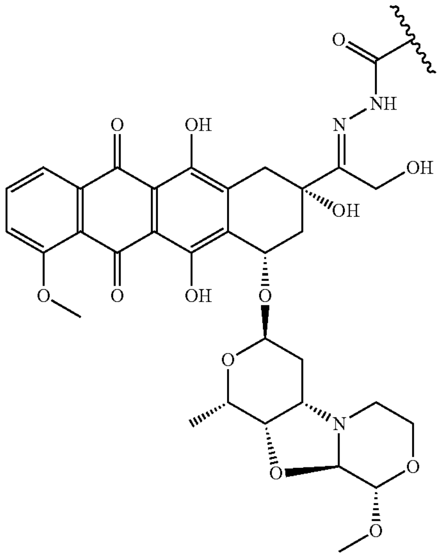

, and

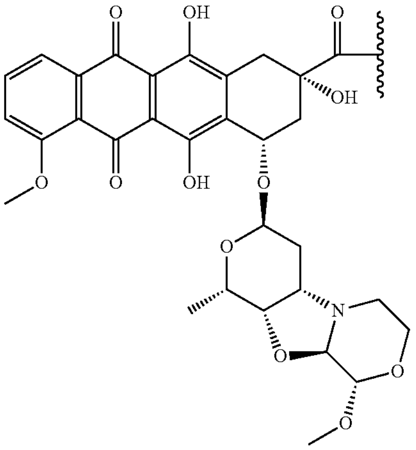

In some embodiments, an immunoconjugate is provided, wherein D comprises a 1-(chloromethyl)-2,3-dihydro-1H-benzo[e]indole (CBI). In some embodiments, D has the formula:

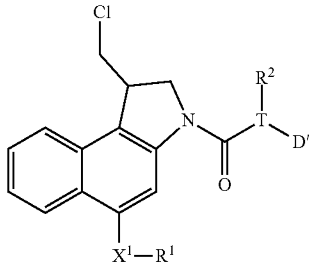

where $R^1$ is selected from H, $P(O)_3H_2$, $C(O)NR^aR^b$, or a bond to L;

$R^2$ is selected from H, $P(O)_3H_2$, $C(O)NR^aR^b$, or a bond to L;

$R^a$ and $R^b$ are independently selected from H and $C_1$-$C_6$ alkyl optionally substituted with one or more F, or $R^a$ and $R^b$ form a five or six membered heterocyclyl group;

T is a tether group selected from $C_3$-$C_{12}$ alkylene, Y, ($C_1$-$C_6$ alkylene)-Y—($C_1$-$C_6$ alkylene), ($C_1$-$C_6$ alkylene)-Y—($C_1$-$C_6$ alkylene)-Y—($C_1$-$C_6$ alkylene), ($C_2$-$C_6$ alkenylene)-Y—($C_2$-$C_6$ alkenylene), and ($C_2$-$C_6$ alkynylene)-Y—($C_2$-$C_6$ alkynylene);

where Y is independently selected from O, S, $NR^1$, aryl, and heteroaryl;

where alkylene, alkenylene, aryl, and heteroaryl are independently and optionally substituted with F, OH, O($C_1$-$C_6$ alkyl), $NH_2$, $NHCH_3$, $N(CH_3)_2$, $OP(O)_3H_2$, and $C_1$-$C_6$ alkyl, where alkyl is optionally substituted with one or more F;

or alkylene, alkenylene, aryl, and heteroaryl are independently and optionally substituted with a bond to L;

D' is a drug moiety selected from:

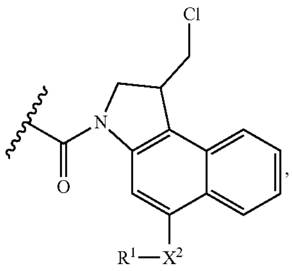

,

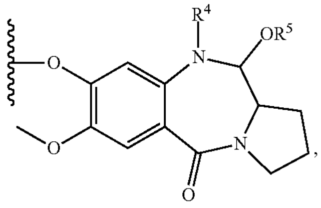

, and

-continued

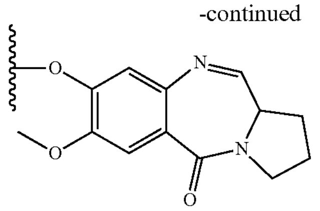

where the wavy line indicates the site of attachment to T;

$X^1$ and $X^2$ are independently selected from O and $NR^3$, where $R^3$ is selected from H and $C_1$-$C_6$ alkyl optionally substituted with one or more F;

$R^4$ is H, $CO_2R$, or a bond to a linker (L), where R is $C_1$-$C_6$ alkyl or benzyl; and $R^5$ is H or $C_1$-$C_6$ alkyl.

In some embodiments, D has a structure selected from:

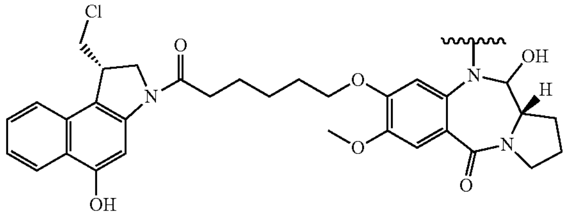

;

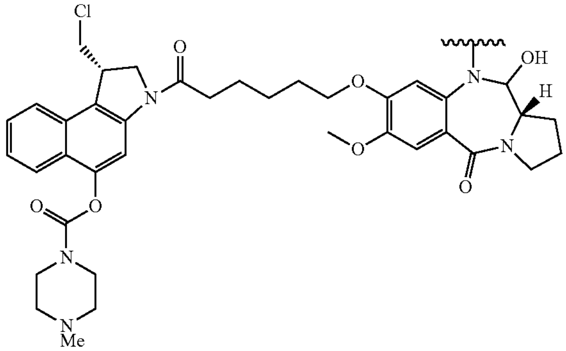

;

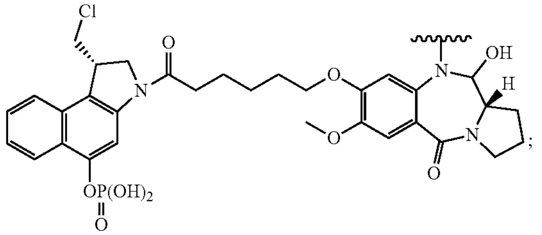

; and

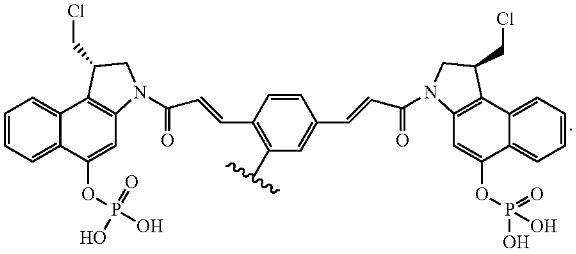

.

In some embodiments, an immunoconjugate is provided, wherein the linker is cleavable by a protease. In some embodiments, the linker is acid-labile. In some embodiments, the linker comprises hydrazone. In some embodiments, the linker comprises a disulfide.

In some embodiments, an immunoconjugate is provided, wherein the immunoconjugate comprises a structure selected from:

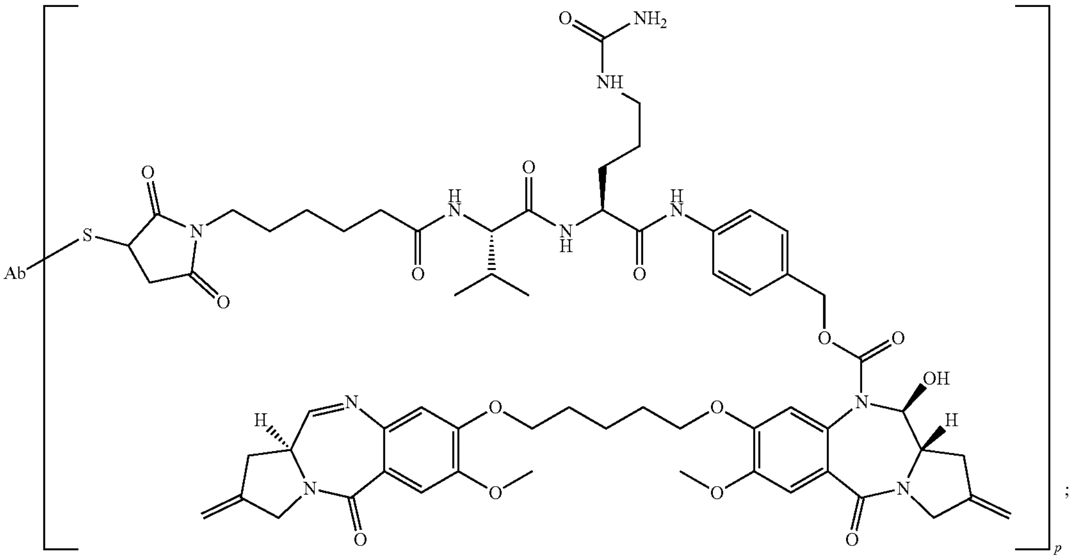
;
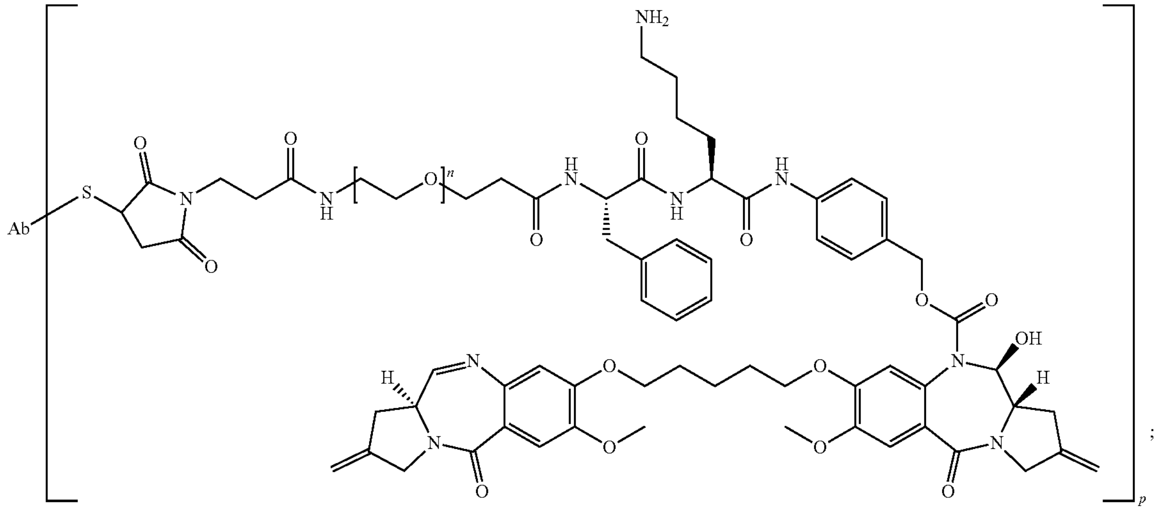
; and
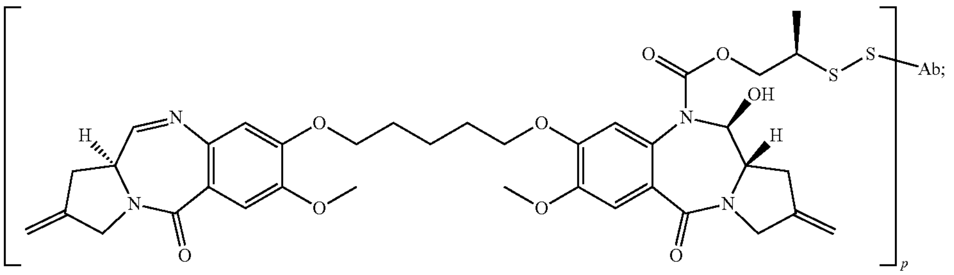
wherein Ab is an antibody described herein.

In some embodiments, an immunoconjugate is provided, wherein the immunoconjugate comprises a structure selected from:
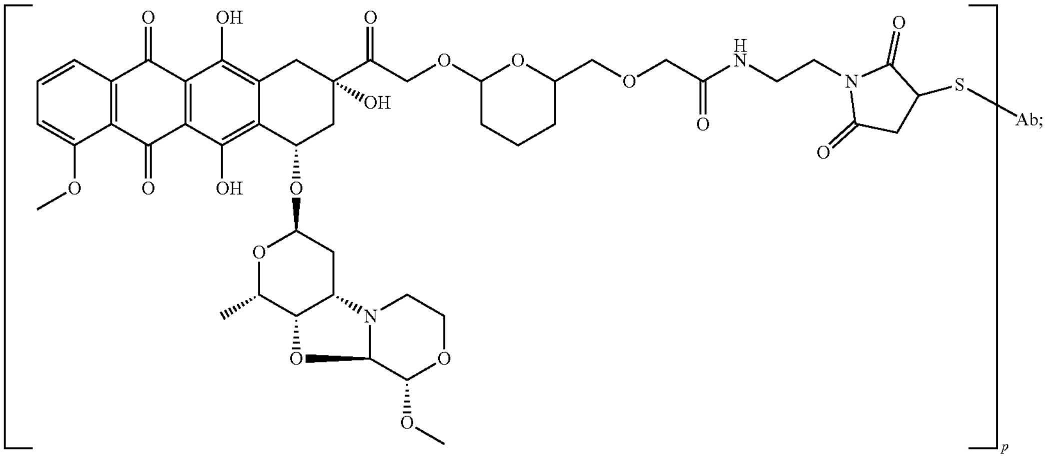
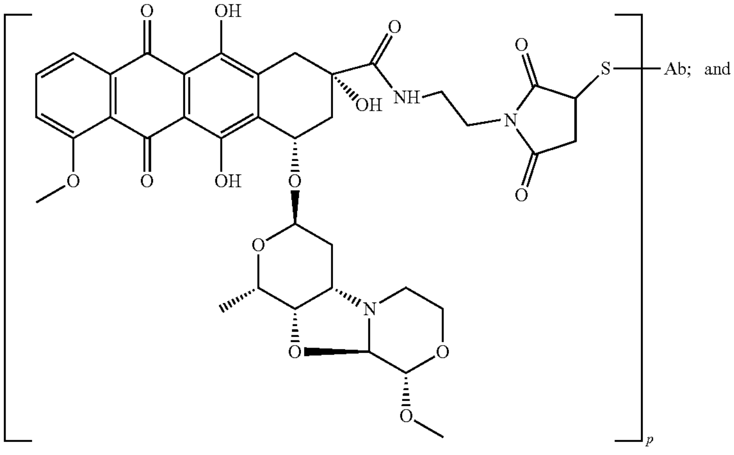
and
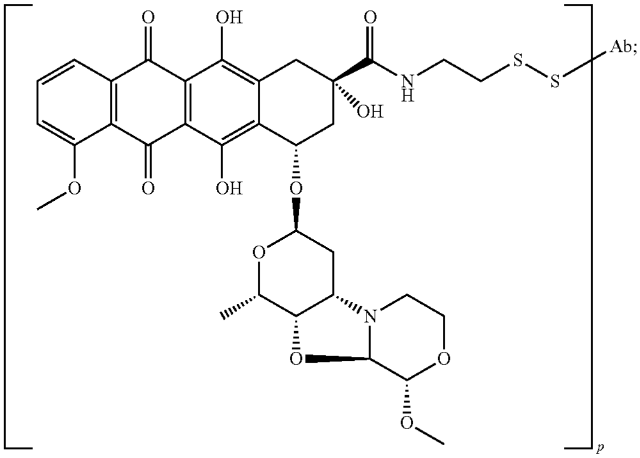
wherein Ab is an antibody described herein.

In some embodiments, an immunoconjugate is provided, wherein the immunoconjugate comprises a structure selected from:
14
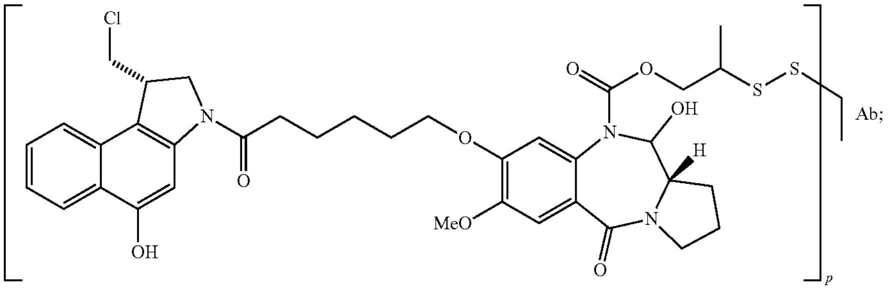
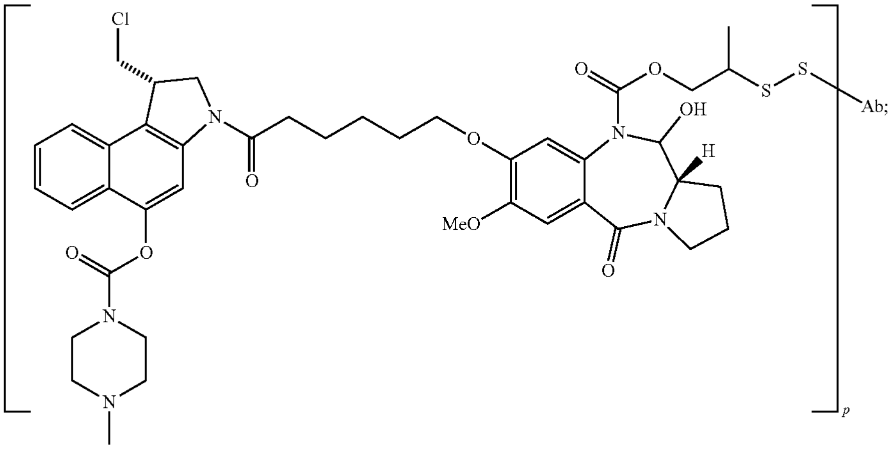
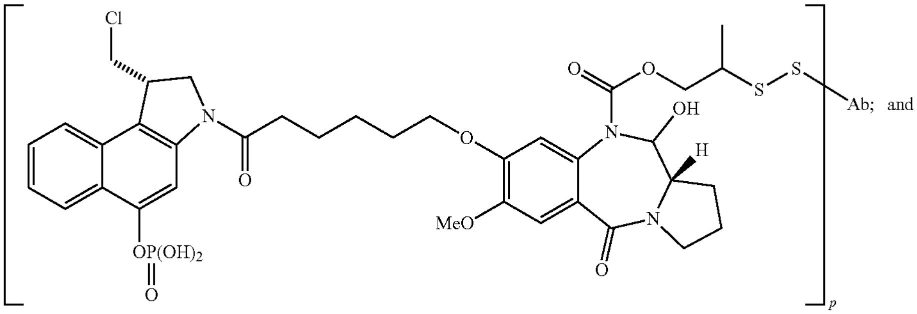
and -continued

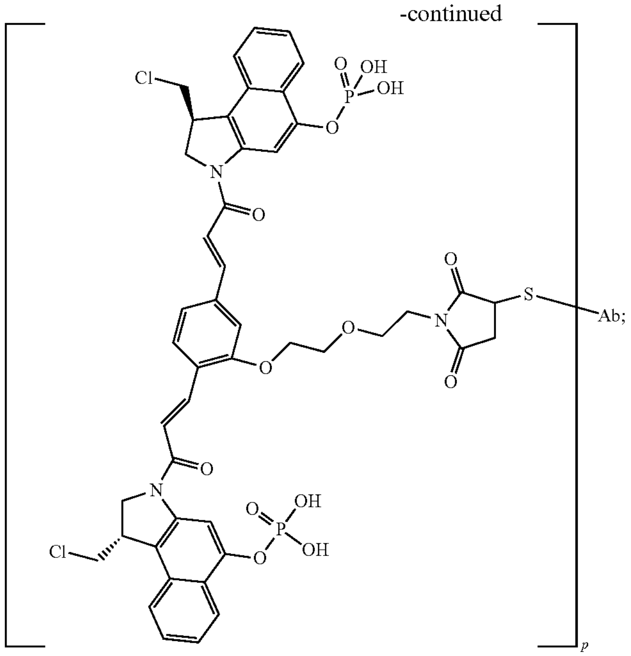

wherein Ab is an antibody described herein.

In any of the immunoconjugates described herein, p may range from 1.3-2, 1.4-2, 1.5-2, or 2-5.

In some embodiments, a pharmaceutical formulation is provided, comprising an immunoconjugate described herein and a pharmaceutically acceptable carrier. In some embodiments, the pharmaceutical formulation further comprises an additional therapeutic agent. In some embodiments, the additional therapeutic agent is an antibody or immunoconjugate that binds to HER2. In some embodiments, the additional therapeutic agent is (i) an antibody or immunoconjugate that binds to domain II of HER2, and/or (ii) an antibody or immunoconjugate that binds to domain IV or HER2. In some embodiments, the additional therapeutic agent is (i) an antibody or immunoconjugate that binds to epitope 2C4, and/or (ii) an antibody or immunoconjugate that binds to epitope 4D5. In some embodiments, the additional therapeutic agent is selected from trastuzumab, trastuzumab-MCC-DM1 (T-DM1), and pertuzumab. In some embodiments, the pharmaceutical formulation further comprises (1) trastuzumab or T-DM1, and (2) pertuzumab.

In some embodiments, methods of treating an individual having a HER2-positive cancer are provided. In some embodiments, a method comprises administering to the individual an effective amount of an immunoconjugate described herein, or a pharmaceutical composition described herein. In some embodiments, the HER2-positive cancer is breast cancer or gastric cancer. In some embodiments, the HER2-positive breast cancer is early-stage breast cancer. In some embodiments, the HER2-positive breast cancer is metastatic breast cancer. In some embodiments, the HER2-positive cancer is recurrent cancer. In some embodiments, the recurrent cancer is locally recurrent cancer. In some embodiments, the HER2-positive cancer is advanced cancer. In some embodiments, the HER2-positive cancer is non-resectable. In some embodiments, the method further comprises administering an additional therapeutic agent to the individual.

In some embodiments, a method of treating an individual having a HER2-positive cancer comprises administering to the individual an effective amount of an immunoconjugate described herein and at least one additional therapeutic agent to the individual. In some embodiments, the additional therapeutic agent is an antibody or immunoconjugate that binds to HER2. In some embodiments, the additional therapeutic agent is (i) an antibody or immunoconjugate that binds to domain II of HER2, and/or (ii) an antibody or immunoconjugate that binds to domain IV or HER2. In some embodiments, the additional therapeutic agent is (i) an antibody or immunoconjugate that binds to epitope 2C4, and/or (ii) an antibody or immunoconjugate that binds to epitope 4D5. In some embodiments, the additional therapeutic agent is selected from trastuzumab, trastuzumab-MCC-DM1 (T-DM1), and pertuzumab. In some embodiments, the additional therapeutic agents are (1) trastuzumab or T-DM1, and (2) pertuzumab. In some embodiments, the HER2-positive cancer is breast cancer or gastric cancer. In some embodiments, the HER2-positive breast cancer is early-stage breast cancer. In some embodiments, the HER2-positive breast cancer is metastatic breast cancer. In some embodiments, the HER2-positive cancer is recurrent cancer. In some embodiments, the recurrent cancer is locally recurrent cancer. In some embodiments, the HER2-positive cancer is advanced cancer. In some embodiments, the HER2-positive cancer is non-resectable.

In some embodiments, a method of treating an individual having a HER2-positive cancer comprises:

a) subjecting the individual to neoadjuvant treatment with an immunoconjugate described herein or a pharmaceutical formulation described herein,
b) removing the cancer by definitive surgery, and
c) subjecting the individual to adjuvant treatment with an immunoconjugate described herein or a pharmaceutical formulation described herein.

In some embodiments, the HER2-positive cancer is breast cancer or gastric cancer.

In some embodiments, methods of inhibiting proliferation of a HER2-positive cell are provided. In some embodiments a method comprises exposing the cell to an immunoconjugate described herein under conditions permissive for binding of the immunoconjugate to HER2 on the surface of the cell, thereby inhibiting proliferation of the cell. In some embodiments, the cell is a breast cancer cell of a gastric cancer cell.

In some embodiments, an antibody described herein conjugated to a label is provided. In some embodiments, the label is a positron emitter. In some embodiments, the positron emitter is $^{89}Zr$.

In some embodiments, methods of detecting human HER2 in a biological sample are provided. In some embodiments, a method comprises contacting the biological sample with an anti-HER2 antibody described herein under conditions permissive for binding of the anti-HER2 antibody to a naturally occurring human HER2, and detecting whether a complex is formed between the anti-HER2 antibody and a naturally occurring human HER2 in the biological sample. In some embodiments, the biological sample is a breast cancer or gastric cancer sample.

In some embodiments, methods for detecting a HER2-positive cancer in a subject are provided. In some embodiments, a method comprises (i) administering a labeled anti-HER2 antibody to a subject having or suspected of having a HER2-positive cancer, wherein the labeled anti-HER2 antibody comprises an anti-HER2 antibody described herein, and (ii) detecting the labeled anti-HER2 antibody in the subject, wherein detection of the labeled anti-HER2 antibody indicates a HER2-positive cancer in the subject. In some embodiments, the labeled anti-HER2 antibody comprises an anti-HER2 antibody conjugated to a positron emitter. In some embodiments, the positron emitter is $^{89}Zr$.

BRIEF DESCRIPTION OF THE FIGURES

FIGS. 12A-F show the structures for certain antibody-drug conjugates used in the examples herein.

FIGS. 13A-B show the pertuzumab main species antibody light chain (A) and heavy chain (B) amino acid sequences.

FIGS. 14A-B show exemplary pertuzumab variant species antibody light chain (A) and heavy chain (B) amino acid sequences.

FIGS. 15A-B show the trastuzumab antibody light chain (A) and heavy chain (B) amino acid sequences.

FIG. 16 shows a schematic of the Her2 receptor and the sequences for domains I to IV.

DETAILED DESCRIPTION

Figure 1:
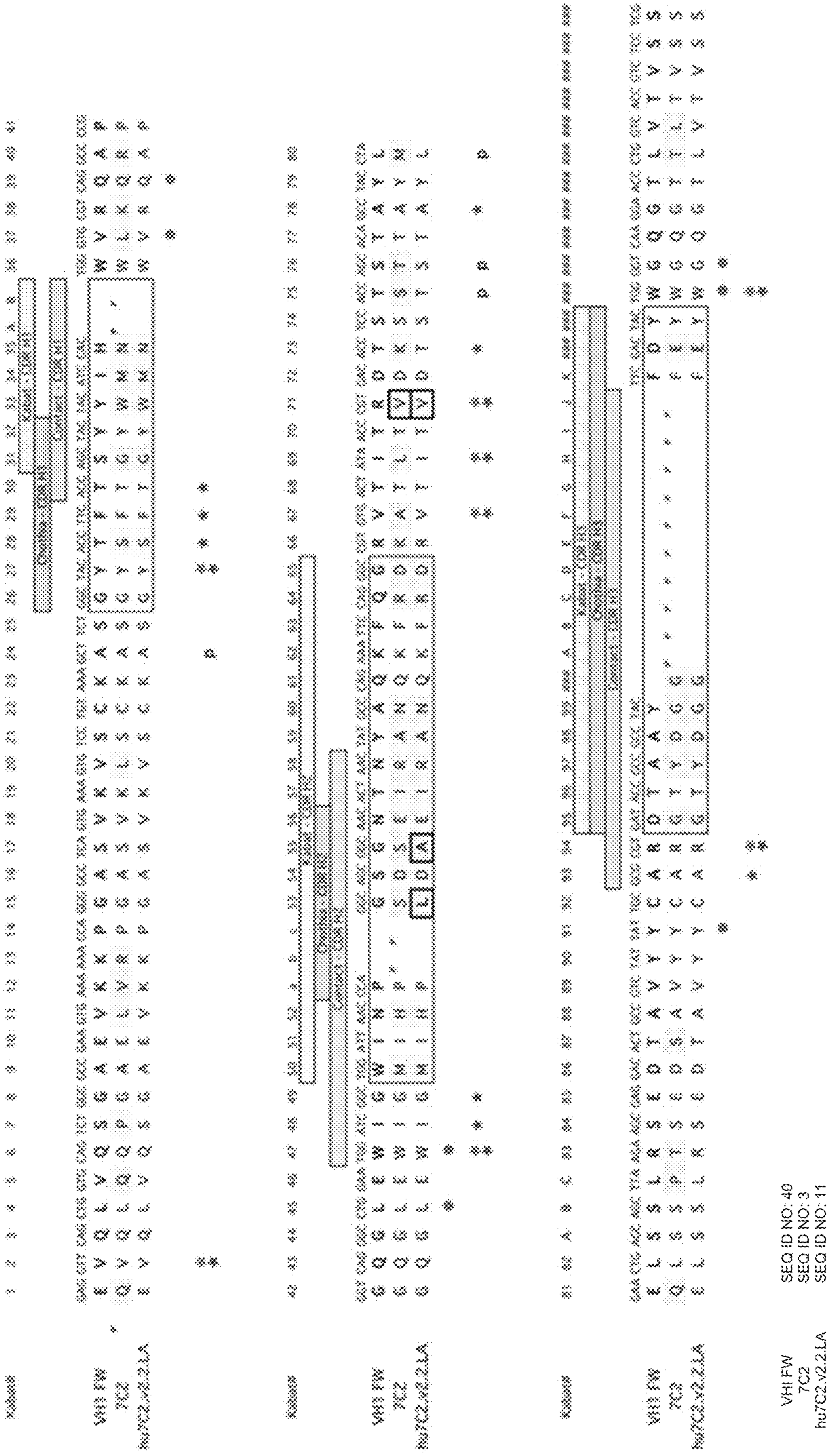
FIG. 1 shows an alignment of the human VH subgroup I ($VH_I$) consensus sequence and heavy chain variable region sequences of murine 7C2. B9 ("7C2") and humanized 7C2.v2.2. LA, as described in Example 1.

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described.

All references cited throughout the disclosure are expressly incorporated by reference herein in their entirety. In the event that one or more of the incorporated literature, patents, and similar materials differs from or contradicts this application, including but not limited to defined terms, term usage, described techniques, or the like, this application controls.

I. DEFINITIONS

The words "comprise," "comprising," "include," "including," and "includes" when used in this specification and claims are intended to specify the presence of stated features, integers, components, or steps, but they do not preclude the presence or addition of one or more other features, integers, components, steps, or groups thereof.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-HER2 antibody" and "an antibody that binds to HER2" refer to an antibody that is capable of binding HER2 with sufficient affinity such that the antibody is useful as a diagnostic and/or therapeutic agent in targeting HER2. In one embodiment, the extent of binding of an anti-HER2 antibody to an unrelated, non-HER2 protein is less than about 10% of the binding of the antibody to HER2 as measured, e.g., by a radioimmunoassay (RIA). In certain embodiments, an antibody that binds to HER2 has a dissociation constant (Kd) of ≤1 μM, ≤100 nM, ≤10 nM, ≤5 nm, ≤4 nM, ≤3 nM, ≤2 nM, ≤1 nM, ≤0.1 nM, ≤0.01 nM, or ≤0.001 nM (e.g., $10^{-8}$ M or less, e.g. from $10^{-8}$ M to $10^{-13}$ M, e.g., from $10^{-9}$ M to $10^{-13}$ M). In certain embodiments, an anti-HER2 antibody binds to an epitope of HER2 that is conserved among HER2 from different species.

The term "antibody" is used herein in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody and that binds the antigen to which the intact antibody binds. Examples of antibody fragments include but are not limited to Fv, Fab, Fab', Fab'-SH, $F(ab')_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The terms "cancer" and "cancerous" refer to or describe the physiological condition in mammals that is typically characterized by unregulated cell growth/proliferation. Examples of cancer include, but are not limited to, carcinoma, lymphoma, blastoma, sarcoma, and leukemia. In some embodiments, the cancer is breast cancer or gastric cancer. In some embodiments, a cancer is any HER2-positive cancer.

A "HER2-positive" cancer comprises cancer cells which have higher than normal levels of HER2. Examples of HER2-positive cancer include HER2-positive breast cancer and HER2-positive gastric cancer. Optionally, HER2-positive cancer has an immunohistochemistry (IHC) score of 2+ or 3+ and/or an in situ hybridization (ISH) amplification ratio ≥2.0.

The term "early stage breast cancer (EBC)" or "early breast cancer" is used herein to refer to breast cancer that has not spread beyond the breast or the axillary lymph nodes. This includes ductal carcinoma in situ and stage I, stage IIA, stage IIB, and stage IIIA breast cancers.

Reference to a tumor or cancer as a "Stage 0," "Stage I," "Stage II," "Stage III," or "Stage IV", and various sub-stages within this classification, indicates classification of the tumor or cancer using the Overall Stage Grouping or Roman Numeral Staging methods known in the art. Although the actual stage of the cancer is dependent on the type of cancer, in general, a Stage 0 cancer is an in situ lesion, a Stage I cancer is small localized tumor, a Stage II and III cancer is a local advanced tumor which exhibits involvement of the local lymph nodes, and a Stage IV cancer represents metastatic cancer. The specific stages for each type of tumor is known to the skilled clinician.

The term "metastatic breast cancer" means the state of breast cancer where the cancer cells are transmitted from the original site to one or more sites elsewhere in the body, by the blood vessels or lymphatics, to form one or more secondary tumors in one or more organs besides the breast.

An "advanced" cancer is one which has spread outside the site or organ of origin, either by local invasion or metastasis. Accordingly, the term "advanced" cancer includes both locally advanced and metastatic disease.

A "recurrent" cancer is one which has regrown, either at the initial site or at a distant site, after a response to initial therapy, such as surgery.

A "locally recurrent" cancer is cancer that returns after treatment in the same place as a previously treated cancer.

An "operable" or "resectable" cancer is cancer which is confined to the primary organ and suitable for surgery (resection).

A "non-resectable" or "unresectable" cancer is not able to be removed (resected) by surgery.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result. The effective amount of the drug for treating cancer may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. The effective amount may extend progression free survival (e.g. as measured by Response Evaluation Criteria for Solid Tumors, RECIST, or CA-125 changes), result in an objective response (including a partial response, PR, or complete response, CR), increase overall survival time, and/or improve one or more symptoms of cancer (e.g. as assessed by FOSI).

The term "epitope" refers to the particular site on an antigen molecule to which an antibody binds.

The "epitope 4D5" or "4D5 epitope" or "4D5" is the region in the extracellular domain of HER2 to which the antibody 4D5 (ATCC CRL 10463) and trastuzumab bind. This epitope is close to the transmembrane domain of HER2, and within domain IV of HER2. To screen for antibodies which bind to the 4D5 epitope, a routine cross-blocking assay such as that described in Antibodies, A Laboratory Manual, Cold Spring Harbor Laboratory, Ed Harlow and David Lane (1988), can be performed. Alternatively, epitope mapping can be performed to assess whether the antibody binds to the 4D5 epitope of HER2 (e.g. any one or more residues in the region from about residue 550 to about residue 610, inclusive, of HER2 (SEQ ID NO: 39).

The "epitope 2C4" or "2C4 epitope" is the region in the extracellular domain of HER2 to which the antibody 2C4 binds. In order to screen for antibodies which bind to the 2C4 epitope, a routine cross-blocking assay such as that described in Antibodies, A Laboratory Manual, Cold Spring Harbor Laboratory, Ed Harlow and David Lane (1988), can be performed. Alternatively, epitope mapping can be performed to assess whether the antibody binds to the 2C4 epitope of HER2. Epitope 2C4 comprises residues from domain II in the extracellular domain of HER2. The 2C4 antibody and pertuzumab bind to the extracellular domain of HER2 at the junction of domains I, II and III (Franklin et al. *Cancer Cell* 5:317-328 (2004)).

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest,* 5th Ed. Public Health Service, National Institutes of Health, Bethesda, MD, 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The term "glycosylated forms of HER2" refers to naturally occurring forms of HER2 that are post-translationally modified by the addition of carbohydrate residues.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda MD (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest,* 5th Ed. Public Health Service, National Institutes of Health, Bethesda, MD (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or α-CDRs. Exemplary α-CDRs (a-CDR-L1, α-CDR-L2, α-CDR-L3, α-CDR-H1, α-CDR-H2, and α-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

A "patient" or "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the patient, individual, or subject is a human. In some embodiments, the patient may be a "cancer patient," i.e. one who is suffering or at risk for suffering from one or more symptoms of cancer, in particular gastric or breast cancer.

A "patient population" refers to a group of cancer patients. Such populations can be used to demonstrate statistically significant efficacy and/or safety of a drug.

A "relapsed" patient is one who has signs or symptoms of cancer after remission. Optionally, the patient has relapsed after adjuvant or neoadjuvant therapy.

A cancer or biological sample which "displays HER expression, amplification, or activation" is one which, in a diagnostic test, expresses (including overexpresses) a HER receptor, has amplified HER gene, and/or otherwise demonstrates activation or phosphorylation of a HER receptor.

"Neoadjuvant therapy" or "preoperative therapy" herein refers to therapy given prior to surgery. The goal of neoadjuvant therapy is to provide immediate systemic treatment, potentially eradicating micrometastases that would otherwise proliferate if the standard sequence of surgery followed by systemic therapy were followed. Neoadjuvant therapy may also help to reduce tumor size thereby allowing complete resection of initially unresectable tumors or preserving portions of the organ and its functions. Furthermore, neoadjuvant therapy permits an in vivo assessment of drug efficacy, which may guide the choice of subsequent treatments.

"Adjuvant therapy" herein refers to therapy given after definitive surgery, where no evidence of residual disease can be detected, so as to reduce the risk of disease recurrence. The goal of adjuvant therapy is to prevent recurrence of the cancer, and therefore to reduce the chance of cancer-related death. Adjuvant therapy herein specifically excludes neoadjuvant therapy.

"Definitive surgery" is used as that term is used within the medical community. Definitive surgery includes, for example, procedures, surgical or otherwise, that result in removal or resection of the tumor, including those that result in the removal or resection of all grossly visible tumor. Definitive surgery includes, for example, complete or curative resection or complete gross resection of the tumor. Definitive surgery includes procedures that occur in one or more stages, and includes, for example, multi-stage surgical procedures where one or more surgical or other procedures are performed prior to resection of the tumor. Definitive surgery includes procedures to remove or resect the tumor including involved organs, parts of organs and tissues, as well as surrounding organs, such as lymph nodes, parts of organs, or tissues. Removal may be incomplete such that tumor cells might remain even though undetected.

"Survival" refers to the patient remaining alive, and includes disease free survival (DFS), progression free survival (PFS) and overall survival (OS). Survival can be estimated by the Kaplan-Meier method, and any differences in survival are computed using the stratified log-rank test.

"Progression-Free Survival" (PFS) is the time from the first day of treatment to documented disease progression (including isolated CNS progression) or death from any cause on study, whichever occurs first.

"Disease free survival (DFS)" refers to the patient remaining alive, without return of the cancer, for a defined period of time such as about 1 year, about 2 years, about 3 years, about 4 years, about 5 years, about 10 years, etc., from initiation of treatment or from initial diagnosis. In one aspect of the invention, DFS is analyzed according to the intent-to-treat principle, i.e., patients are evaluated on the basis of their assigned therapy. The events used in the analysis of DFS can include local, regional and distant recurrence of cancer, occurrence of secondary cancer, and death from any cause in patients without a prior event (e.g., breast cancer recurrence or second primary cancer).

"Overall survival" refers to the patient remaining alive for a defined period of time, such as about 1 year, about 2 years, about 3 years, about 4 years, about 5 years, about 10 years, etc., from initiation of treatment or from initial diagnosis. In the studies underlying the invention the event used for survival analysis was death from any cause.

By "extending survival" is meant increasing DFS and/or OS in a treated patient relative to an untreated patient, or relative to a control treatment protocol. Survival is monitored for at least about six months, or at least about 1 year, or at least about 2 years, or at least about 3 years, or at least about 4 years, or at least about 5 years, or at least about 10 years, etc., following the initiation of treatment or following the initial diagnosis.

By "monotherapy" is meant a therapeutic regimen that includes only a single therapeutic agent for the treatment of the cancer or tumor during the course of the treatment period.

By "maintenance therapy" is meant a therapeutic regimen that is given to reduce the likelihood of disease recurrence or progression. Maintenance therapy can be provided for any length of time, including extended time periods up to the life-span of the subject. Maintenance therapy can be provided after initial therapy or in conjunction with initial or additional therapies. Dosages used for maintenance therapy can vary and can include diminished dosages as compared to dosages used for other types of therapy.

As defined herein, the terms "trastuzumab", "HERCEPTIN®" and "huMAb4D5-8" are used interchangeably. Such antibody preferably comprises the light and heavy chain amino acid sequences shown in SEQ ID NO: 30 and SEQ ID NO. 29, respectively.

For the purposes herein, "pertuzumab", "PERJETA®" and "rhuMAb 2C4", are used interchangeably. Such antibody comprises a main species antibody having the light and heavy chain amino acid sequences in SEQ ID NOs: 32 and 31, respectively (FIGS. 13A and B). In some embodiments, pertuzumab comprises a variant species antibody with an amino-terminal leader extension, e.g., comprising a light chain amino acid sequence of SEQ ID NO: 34, and a heavy chain amino acid sequence of SEQ ID NO: 33. The antibody is optionally produced by recombinant Chinese Hamster Ovary (CHO) cells.

As defined herein, the terms "T-DM1," "trastuzumab-MCC-DM1," "ado-trastuzumab emtansine," "trastuzumab emtansine," and "KADCYLA®" are used interchangeably, and refer to trastuzumab linked through the linker moiety MCC to the maytansinoid drug moiety DM1, including all mixtures of variously loaded and attached antibody-drug conjugates where 1, 2, 3, 4, 5, 6, 7, and 8 drug moieties are covalently attached to the antibody trastuzumab (U.S. Pat. Nos. 7,097,840; 8,337,856; US 2005/0276812; US 2005/0166993).

An "isolated antibody" is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated nucleic acid" refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-HER2 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "HER2," as used herein, refers to any native, mature HER2 which results from processing of a HER2 precursor protein in a cell. The term includes HER2 from any vertebrate source, including mammals such as primates (e.g. humans and cynomolgus monkeys) and rodents (e.g., mice and rats), unless otherwise indicated. The term also includes naturally occurring variants of HER2, e.g., splice variants or allelic variants. The amino acid sequence of an exemplary human HER2 precursor protein, with signal sequence (with signal sequence, amino acids 1-22) is shown in SEQ ID NO: 1. The amino acid sequence of an exemplary mature human HER2 is amino acids 23-1255 of SEQ ID NO: 1.

The term "HER2-positive cell" refers to a cell that expresses HER2 on its surface.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and $CH_3$). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

A "vial" is a container suitable for holding a liquid or lyophilized preparation. In one embodiment, the vial is a single-use vial, e.g. a 20-cc single-use vial with a stopper.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

By "co-administering" is meant intravenously administering two (or more) drugs during the same administration, rather than sequential infusions of the two or more drugs. Generally, this will involve combining the two (or more) drugs into the same IV bag prior to co-administration thereof.

A drug that is administered "concurrently" with one or more other drugs is administered during the same treatment cycle, on the same day of treatment as the one or more other drugs, and, optionally, at the same time as the one or more other drugs. For instance, for cancer therapies given every 3 weeks, the concurrently administered drugs are each administered on day-1 of a 3-week cycle.

A "chemotherapy" is use of a chemotherapeutic agent useful in the treatment of cancer.

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Examples of chemotherapeutic agents include: anthracyclines, such as epirubicin or doxorubicin (ADRIAMYCIN®), cyclophosphamide (CYTOXAN®, NEOSAR®), anthracycline and cyclophosphamide in combination ("AC"); a taxane, e.g., docetaxel (TAXOTERE®) or paclitaxel (TAXOL®), 5-FU (fluorouracil, 5-fluorouracil, CAS No. 51-21-8), lapatinib (TYKERB®), capecitabine (XELODA®), gemcitabine (GEMZAR®, Lilly), PD-0325901 (CAS No. 391210-10-9, Pfizer), cisplatin (cis-diaminedichloroplatinum(II), CAS No. 15663-27-1), carboplatin (CAS No. 41575-94-4), temozolomide (4-methyl-5-oxo-2,3,4,6,8-pentaazabicyclo[4.3.0]nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethyl-ethanamine, NOLVADEX®, ISTUBAL®, VALODEX®).

More examples of chemotherapeutic agents include: oxaliplatin (ELOXATIN®, Sanofi), bortezomib (VELCADE®, Millennium Pharm), sutent (SUNITINIB®, SU11248, Pfizer), letrozole (FEMARA®, Novartis), imatinib mesylate (GLEEVEC®, Novartis), XL-518 (MEK inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gammalI, calicheamicin omegaI1 (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, OR); razoxane; rhizoxin; sizofiran; spirogermanium; tenuazonic acid; triaziquone; 2,2',2"-trichlorotriethylamine; trichothecenes (T-2 toxin, verracurin A, roridin A and anguidine); urethan; vindesine; dacarbazine; mannomustine; mitobronitol; mitolactol; pipobroman; gacytosine; arabinoside (Ara-C); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; ibandronate; CPT-11; topoisomerase inhibitor RFS 2000; difluoromethylornithine (DMFO); retinoids such as retinoic acid; and pharmaceutically acceptable salts, acids and derivatives of any of the above.

A "fixed" or "flat" dose of a therapeutic agent herein refers to a dose that is administered to a human patient without regard for the weight (WT) or body surface area (BSA) of the patient. The fixed or flat dose is therefore not provided as a mg/kg dose or a mg/m2 dose, but rather as an absolute amount of the therapeutic agent.

A "loading" dose herein generally comprises an initial dose of a therapeutic agent administered to a patient, and is followed by one or more maintenance dose(s) thereof. Generally, a single loading dose is administered, but multiple loading doses are contemplated herein. Usually, the amount of loading dose(s) administered exceeds the amount of the maintenance dose(s) administered and/or the loading dose(s) are administered more frequently than the maintenance dose(s), so as to achieve the desired steady-state concentration of the therapeutic agent earlier than can be achieved with the maintenance dose(s).

A "maintenance" dose herein refers to one or more doses of a therapeutic agent administered to the patient over a treatment period. Usually, the maintenance doses are administered at spaced treatment intervals, such as approximately every week, approximately every 2 weeks, approximately every 3 weeks, or approximately every 4 weeks, preferably every 3 weeks.

"Infusion" or "infusing" refers to the introduction of a drug-containing solution into the body through a vein for therapeutic purposes. Generally, this is achieved via an intravenous (IV) bag.

An "intravenous bag" or "IV bag" is a bag that can hold a solution which can be administered via the vein of a patient. In one embodiment, the solution is a saline solution (e.g. about 0.9% or about 0.45% NaCl). Optionally, the IV bag is formed from polyolefin or polyvinyl chloride.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology,* $6^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

"Alkyl" is $C_1$-$C_{18}$ hydrocarbon containing normal, secondary, tertiary or cyclic carbon atoms. Examples are methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)$ $CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$.

The term "$C_1$-$C_8$ alkyl," as used herein refers to a straight chain or branched, saturated or unsaturated hydrocarbon having from 1 to 8 carbon atoms. Representative "$C_1$-$C_8$ alkyl" groups include, but are not limited to, -methyl, -ethyl, -n-propyl, -n-butyl, -n-pentyl, -n-hexyl, -n-heptyl, -n-octyl, -n-nonyl and -n-decyl; while branched $C_1$-$C_8$ alkyls include, but are not limited to, -isopropyl, -sec-butyl, -isobutyl, -tert-butyl, -isopentyl, 2-methylbutyl, unsaturated $C_1$-$C_8$ alkyls include, but are not limited to, -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, 1-hexyl, 2-hexyl, 3-hexyl, -acetylenyl, -propynyl, -1-butynyl, -2-butynyl, -1-pentynyl, -2-pentynyl, -3-methyl-1 butynyl. A $C_1$-$C_8$ alkyl group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N$(R')_2$—NHC(O)R', —$SO_3$R', —S$(O)_2$R', —S(O)R', —OH, -halogen, —$N_3$, —$NH_2$, —NH(R'), —N$(R')_2$ and —CN; where each R' is independently selected from H, —$C_1$-$C_8$ alkyl and aryl.

The term "$C_1$-$C_{12}$ alkyl," as used herein refers to a straight chain or branched, saturated or unsaturated hydrocarbon having from 1 to 12 carbon atoms. A $C_1$-$C_{12}$ alkyl group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N$(R')_2$—NHC(O)R', —$SO_3$R', —S$(O)_2$R', —S(O)R', —OH, -halogen, —$N_3$, —$NH_2$, —NH(R'), —N$(R')_2$ and —CN; where each R' is independently selected from H, —$C_1$-$C_8$ alkyl and aryl.

The term "$C_1$-$C_6$ alkyl," as used herein refers to a straight chain or branched, saturated or unsaturated hydrocarbon having from 1 to 6 carbon atoms. Representative "$C_1$-$C_6$ alkyl" groups include, but are not limited to, -methyl, -ethyl, -n-propyl, -n-butyl, -n-pentyl, -and n-hexyl; while branched $C_1$-$C_6$ alkyls include, but are not limited to, -isopropyl, -sec-butyl, -isobutyl, -tert-butyl, -isopentyl, and 2-methylbutyl; unsaturated $C_1$-$C_6$ alkyls include, but are not limited to, -vinyl, -allyl, -1-butenyl, -2-butenyl, and -isobutylenyl, -1-pentenyl, -2-pentenyl, -3-methyl-1-butenyl, -2-methyl-2-butenyl, -2,3-dimethyl-2-butenyl, 1-hexyl, 2-hexyl, and 3-hexyl. A $C_1$-$C_6$ alkyl group can be unsubstituted or substituted with one or more groups, as described above for $C_1$-$C_8$ alkyl group.

The term "$C_1$-$C_4$ alkyl," as used herein refers to a straight chain or branched, saturated or unsaturated hydrocarbon having from 1 to 4 carbon atoms. Representative "$C_1$-$C_4$ alkyl" groups include, but are not limited to, -methyl, -ethyl, -n-propyl, -n-butyl; while branched $C_1$-$C_4$ alkyls include, but are not limited to, -isopropyl, -sec-butyl, -isobutyl, -tert-butyl; unsaturated $C_1$-$C_4$ alkyls include, but are not limited to, -vinyl, -allyl, -1-butenyl, -2-butenyl, and -isobutylenyl. A $C_1$-$C_4$ alkyl group can be unsubstituted or substituted with one or more groups, as described above for $C_1$-$C_8$ alkyl group.

"Alkoxy" is an alkyl group singly bonded to an oxygen. Exemplary alkoxy groups include, but are not limited to, methoxy (—$OCH_3$) and ethoxy (—$OCH_2CH_3$). A "$C_1$-$C_5$ alkoxy" is an alkoxy group with 1 to 5 carbon atoms. Alkoxy groups may can be unsubstituted or substituted with one or more groups, as described above for alkyl groups.

"Alkenyl" is $C_2$-$C_{18}$ hydrocarbon containing normal, secondary, tertiary or cyclic carbon atoms with at least one site of unsaturation, i.e. a carbon-carbon, $sp^2$ double bond. Examples include, but are not limited to: ethylene or vinyl (—$CH{=}CH_2$), allyl (—$CH_2CH{=}CH_2$), cyclopentenyl (—$C_5H_7$), and 5-hexenyl (—$CH_2CH_2CH_2CH_2CH{=}CH_2$). A "$C_2$-$C_8$ alkenyl" is a hydrocarbon containing 2 to 8 normal, secondary, tertiary or cyclic carbon atoms with at least one site of unsaturation, i.e. a carbon-carbon, $sp^2$ double bond.

"Alkynyl" is $C_2$-$C_{18}$ hydrocarbon containing normal, secondary, tertiary or cyclic carbon atoms with at least one site of unsaturation, i.e. a carbon-carbon, sp triple bond. Examples include, but are not limited to: acetylenic (—$C{\equiv}CH$) and propargyl (—$CH_2C{\equiv}CH$). A "$C_2$-$C_8$ alkynyl" is a hydrocarbon containing 2 to 8 normal, secondary, tertiary or cyclic carbon atoms with at least one site of unsaturation, i.e. a carbon-carbon, sp triple bond.

"Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to: methylene (—$CH_2$—) 1,2-ethyl (—$CH_2CH_2$—), 1,3-propyl (—$CH_2CH_2CH_2$—), 1,4-butyl (—$CH_2CH_2CH_2CH_2$—), and the like.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to: 1,2-ethylene (—$CH{=}CH$—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to: acetylene (—$C{\equiv}C$—), propargyl (—$CH_2C{\equiv}C$—), and 4-pentynyl (—$CH_2CH_2CH_2C{\equiv}C$—).

"Aryl" refers to a carbocyclic aromatic group. Examples of aryl groups include, but are not limited to, phenyl, naphthyl and anthracenyl. A carbocyclic aromatic group or a heterocyclic aromatic group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N$(R')_2$—NHC(O)R', —S$(O)_2$R', —S(O)R', —OH, -halogen, —$N_3$, —$NH_2$, —NH(R'), —N$(R')_2$ and —CN; wherein each R' is independently selected from H, —$C_1$-$C_8$ alkyl and aryl.

A "$C_5$-$C_{20}$ aryl" is an aryl group with 5 to 20 carbon atoms in the carbocyclic aromatic rings. Examples of $C_5$-$C_{20}$ aryl groups include, but are not limited to, phenyl, naphthyl and anthracenyl. A $C_5$-$C_{20}$ aryl group can be substituted or unsubstituted as described above for aryl groups. A "$C_5$-$C_{14}$ aryl" is an aryl group with 5 to 14 carbon atoms in the carbocyclic aromatic rings. Examples of $C_5$-$C_{14}$ aryl groups include, but are not limited to, phenyl, naphthyl and anthracenyl. A $C_5$-$C_{14}$ aryl group can be substituted or unsubstituted as described above for aryl groups.

An "arylene" is an aryl group which has two covalent bonds and can be in the ortho, meta, or para configurations as shown in the following structures:

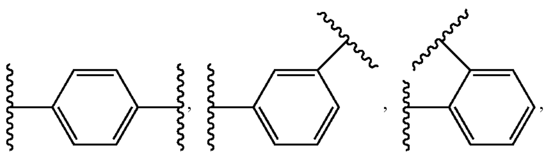

in which the phenyl group can be unsubstituted or substituted with up to four groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N$(R')_2$—NHC(O)R', —$S(O)_2$R', —S(O)R', —OH, -halogen, —$N_3$, —$NH_2$, —NH(R'), —$N(R')_2$ and —CN; wherein each R' is independently selected from H, —$C_1$-$C_8$ alkyl and aryl.

"Arylalkyl" refers to an acyclic alkyl radical in which one of the hydrogen atoms bonded to a carbon atom, typically a terminal or $sp^3$ carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group comprises 6 to 20 carbon atoms, e.g. the alkyl moiety, including alkanyl, alkenyl or alkynyl groups, of the arylalkyl group is 1 to 6 carbon atoms and the aryl moiety is 5 to 14 carbon atoms.

"Heteroarylalkyl" refers to an acyclic alkyl radical in which one of the hydrogen atoms bonded to a carbon atom, typically a terminal or $sp^3$ carbon atom, is replaced with a heteroaryl radical. Typical heteroarylalkyl groups include, but are not limited to, 2-benzimidazolylmethyl, 2-furylethyl, and the like. The heteroarylalkyl group comprises 6 to 20 carbon atoms, e.g. the alkyl moiety, including alkanyl, alkenyl or alkynyl groups, of the heteroarylalkyl group is 1 to 6 carbon atoms and the heteroaryl moiety is 5 to 14 carbon atoms and 1 to 3 heteroatoms selected from N, O, P, and S. The heteroaryl moiety of the heteroarylalkyl group may be a monocycle having 3 to 7 ring members (2 to 6 carbon atoms or a bicycle having 7 to 10 ring members (4 to 9 carbon atoms and 1 to 3 heteroatoms selected from N, O, P, and S), for example: a bicyclo[4.5], [5.5], [5.6], or [6,6] system.

"Substituted alkyl," "substituted aryl," and "substituted arylalkyl" mean alkyl, aryl, and arylalkyl respectively, in which one or more hydrogen atoms are each independently replaced with a substituent. Typical substituents include, but are not limited to, —X, —R, —$O^-$, —OR, —SR, —$S^-$, —$NR_2$, —$NR_3$, =NR, —$CX_3$, —CN, —OCN, —SCN, —N=C=O, —NCS, —NO, —$NO_2$, =$N_2$, —$N_3$, NC(=O)R, —C(=O)R, —C(=O)$NR_2$, —$SO_3^-$, —$SO_3$H, —S(=O)$_2$R, —OS(=O)$_2$OR, —S(=O)$_2$NR, —S(=O)R, —OP(=O)$(OR)_2$, —P(=O)$(OR)_2$, —$PO^-_3$, —$PO_3H_2$, —C(=O)R, —C(=O)X, —C(=S)R, —$CO_2$R, —$CO_2^-$, —C(=S)OR, —C(=O)SR, —C(=S)SR, —C(=O)$NR_2$, —C(=S)$NR_2$, —C(=NR)$NR_2$, where each X is independently a halogen: F, Cl, Br, or I; and each R is independently —H, $C_2$-$C_{18}$ alkyl, $C_6$-$C_{20}$ aryl, $C_3$-$C_{14}$ heterocycle, protecting group or prodrug moiety. Alkylene, alkenylene, and alkynylene groups as described above may also be similarly substituted.

"Heteroaryl" and "heterocycle" refer to a ring system in which one or more ring atoms is a heteroatom, e.g. nitrogen, oxygen, and sulfur. The heterocycle radical comprises 3 to 20 carbon atoms and 1 to 3 heteroatoms selected from N, O, P, and S. A heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo[4.5], [5.5], [5.6], or [6,6] system.

Exemplary heterocycles are described, e.g., in Paquette, Leo A., "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* (1960) 82:5566.

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetidyl, 1-pyrrolyl, 1-imidazolyl, 1-pyrazolyl, and 1-piperidinyl.

A "$C_3$-$C_8$ heterocycle" refers to an aromatic or non-aromatic $C_3$-$C_8$ carbocycle in which one to four of the ring carbon atoms are independently replaced with a heteroatom from the group consisting of O, S and N. Representative examples of a $C_3$-$C_8$ heterocycle include, but are not limited to, benzofuranyl, benzothiophene, indolyl, benzopyrazolyl, coumarinyl, isoquinolinyl, pyrrolyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl and tetrazolyl. A $C_3$-$C_8$ heterocycle can be unsubstituted or substituted with up to seven groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N$(R')_2$—NHC(O)R', —S$(O)_2$R', —S(O)R', —OH, -halogen, —$N_3$, —$NH_2$, —NH(R'), —N$(R')_2$ and —CN; wherein each R' is independently selected from H, —$C_1$-$C_8$ alkyl and aryl.

"$C_3$-$C_8$ heterocyclo" refers to a $C_3$-$C_8$ heterocycle group defined above wherein one of the heterocycle group's hydrogen atoms is replaced with a bond. A $C_3$-$C_8$ heterocyclo can be unsubstituted or substituted with up to six groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N$(R')_2$—NHC(O)R', —S$(O)_2$R', —S(O)R', —OH, -halogen, —$N_3$, —$NH_2$, —NH(R'), —N$(R')_2$ and —CN; wherein each R' is independently selected from H, —$C_1$-$C_8$ alkyl and aryl.

A "$C_3$-$C_{20}$ heterocycle" refers to an aromatic or non-aromatic $C_3$-$C_8$ carbocycle in which one to four of the ring carbon atoms are independently replaced with a heteroatom from the group consisting of O, S and N. A $C_3$-$C_{20}$ heterocycle can be unsubstituted or substituted with up to seven groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N$(R')_2$—NHC(O)R', —S$(O)_2$R', —S(O)R', —OH, -halogen, —$N_3$, —$NH_2$, —NH (R'), —N$(R')_2$ and —CN; wherein each R' is independently selected from H, —$C_1$-$C_8$ alkyl and aryl.

"$C_3$-$C_{20}$ heterocyclo" refers to a $C_3$-$C_{20}$ heterocycle group defined above wherein one of the heterocycle group's hydrogen atoms is replaced with a bond.

"Carbocycle" means a saturated or unsaturated ring having 3 to 7 carbon atoms as a monocycle or 7 to 12 carbon atoms as a bicycle. Monocyclic carbocycles have 3 to 6 ring atoms, still more typically 5 or 6 ring atoms. Bicyclic carbocycles have 7 to 12 ring atoms, e.g. arranged as a bicyclo[4.5], [5.5], [5.6] or [6,6] system, or 9 or 10 ring atoms arranged as a bicyclo[5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cycloheptyl, and cyclooctyl.

A "$C_3$-$C_8$ carbocycle" is a 3-, 4-, 5-, 6-, 7- or 8-membered saturated or unsaturated non-aromatic carbocyclic ring. Representative $C_3$-$C_8$ carbocycles include, but are not limited to, -cyclopropyl, -cyclobutyl, -cyclopentyl, -cyclopentadienyl, -cyclohexyl, -cyclohexenyl, -1,3-cyclohexadienyl, -1,4-cyclohexadienyl, -cycloheptyl, -1,3-cycloheptadienyl, -1,3,5-cycloheptatrienyl, -cyclooctyl, and -cyclooctadienyl. A $C_3$-$C_8$ carbocycle group can be unsubstituted or substituted with one or more groups including, but not limited to, —$C_1$-$C_8$ alkyl, —O—($C_1$-$C_8$ alkyl), -aryl, —C(O)R', —OC (O)R', —C(O)OR', —C(O)$NH_2$, —C(O)NHR', —C(O)N $(R')_2$—NHC(O)R', —S$(O)_2$R', —S(O)R', —OH, -halogen, —$N_3$, —$NH_2$, —NH(R'), —N$(R')_2$ and —CN; where each R' is independently selected from H, —$C_1$-$C_8$ alkyl and aryl.

A "$C_3$-$C_8$ carbocyclo" refers to a $C_3$-$C_8$ carbocycle group defined above wherein one of the carbocycle groups' hydrogen atoms is replaced with a bond.

"Linker" refers to a chemical moiety comprising a covalent bond or a chain of atoms that covalently attaches an antibody to a drug moiety. In various embodiments, linkers include a divalent radical such as an alkyldiyl, an aryldiyl, a heteroaryldiyl, moieties such as: —$(CR_2)_n$O$(CR_2)_n$—, repeating units of alkyloxy (e.g. polyethylenoxy, PEG, polymethyleneoxy) and alkylamino (e.g. polyethyleneamino, Jeffamine™); and diacid ester and amides including succinate, succinamide, diglycolate, malonate, and caproamide. In various embodiments, linkers can comprise one or more amino acid residues, such as valine, phenylalanine, lysine, and homolysine.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

"Leaving group" refers to a functional group that can be substituted by another functional group. Certain leaving groups are well known in the art, and examples include, but are not limited to, a halide (e.g., chloride, bromide, iodide), methanesulfonyl (mesyl), p-toluenesulfonyl (tosyl), trifluoromethylsulfonyl (triflate), and trifluoromethylsulfonate.

The term "protecting group" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include, but are not limited to, acetyl, trifluoroacetyl, t-butoxycarbonyl (BOC), benzyloxycarbonyl (CBZ) and 9-fluorenylmethylenoxycarbonyl (Fmoc). For a general description of protecting groups and their use, see T. W. Greene, Protective Groups in Organic Synthesis, John Wiley & Sons, New York, 1991, or a later edition.

II. COMPOSITIONS AND METHODS

In one aspect, the invention is based, in part, on antibodies that bind to HER2 and immunoconjugates comprising such antibodies. Antibodies and immunoconjugates of the invention are useful, e.g., for the diagnosis or treatment of HER2-positive cancers.

A. Exemplary Anti-HER2 Antibodies

Provided herein are isolated antibodies that bind to domain I of HER2. In some embodiments, the antibodies do not interfere with trastuzumab and/or pertuzumab binding to HER2. In some embodiments, the antibodies do not interfere with trastuzumab binding to HER2 and do not interfere with pertuzumab binding to HER2. In any of the embodiments described herein, the antibodies may be monoclonal antibodies. In some embodiments, the antibodies may be human antibodies, humanized antibodies, or chimeric antibodies.

An exemplary naturally occurring human HER2 precursor protein sequence, with signal sequence (amino acids 1-22) is provided in SEQ ID NO: 1, and the corresponding mature HER2 protein sequence corresponds to amino acids 23-1255 of SEQ ID NO: 1. In some embodiments, domain I of HER2 has the amino acid sequence of SEQ ID NO: 35, domain II has the amino acid sequence of SEQ ID NO: 36, domain III has the amino acid sequence of SEQ ID NO: 37, and domain IV has the amino acid sequence of SEQ ID NO: 38 (see FIG. 16).

Antibody hu7C2 and Other Embodiments

In some embodiments, the invention provides an anti-HER2 antibody comprising at least one, two, three, four, five, or six HVRs selected from (a) HVR-H1 comprising the amino acid sequence of SEQ ID NO: 15; (b) HVR-H2 comprising the amino acid sequence of SEQ ID NO: 16; (c) HVR-H3 comprising the amino acid sequence of SEQ ID NO: 17; (d) HVR-L1 comprising the amino acid sequence of SEQ ID NO: 12; (e) HVR-L2 comprising the amino acid sequence of SEQ ID NO: 13; and (f) HVR-L3 comprising the amino acid sequence of SEQ ID NO: 14. In some embodiments, the invention provides an anti-HER2 antibody comprising an HVR-H2 comprising the amino acid sequence of SEQ ID NO: 16 and at least one, two, three, four, or five HVRs selected from (a) HVR-H1 comprising the amino acid sequence of SEQ ID NO: 15; (b) HVR-H3 comprising the amino acid sequence of SEQ ID NO: 17; (c) HVR-L1 comprising the amino acid sequence of SEQ ID NO: 12; (d) HVR-L2 comprising the amino acid sequence of SEQ ID NO: 13; and (e) HVR-L3 comprising the amino acid sequence of SEQ ID NO: 14.

In one aspect, the invention provides an antibody comprising at least one, at least two, or all three VH HVR sequences selected from (a) HVR-H1 comprising the amino acid sequence of SEQ ID NO: 15; (b) HVR-H2 comprising the amino acid sequence of SEQ ID NO: 16; and (c) HVR-H3 comprising the amino acid sequence of SEQ ID NO: 17. In one embodiment, the antibody comprises HVR-H3 comprising the amino acid sequence of SEQ ID NO: 17. In one embodiment, the antibody comprises HVR-H2 comprising the amino acid sequence of SEQ ID NO: 16. In another embodiment, the antibody comprises HVR-H3 comprising the amino acid sequence of SEQ ID NO: 17 and HVR-L3 comprising the amino acid sequence of SEQ ID NO: 14. In a further embodiment, the antibody comprises HVR-H3 comprising the amino acid sequence of SEQ ID NO: 17, HVR-L3 comprising the amino acid sequence of SEQ ID NO: 14, and HVR-H2 comprising the amino acid sequence of SEQ ID NO: 16. In a further embodiment, the antibody comprises (a) HVR-H1 comprising the amino acid sequence of SEQ ID NO: 15; (b) HVR-H2 comprising the amino acid sequence of SEQ ID NO: 16; and (c) HVR-H3 comprising the amino acid sequence of SEQ ID NO: 17.

In another aspect, the invention provides an antibody comprising at least one, at least two, or all three VL HVR sequences selected from (a) HVR-L1 comprising the amino acid sequence of SEQ ID NO: 12; (b) HVR-L2 comprising the amino acid sequence of SEQ ID NO: 13; and (c) HVR-L3 comprising the amino acid sequence of SEQ ID NO: 14. In one embodiment, the antibody comprises (a) HVR-L1 comprising the amino acid sequence of SEQ ID NO: 12; (b) HVR-L2 comprising the amino acid sequence of SEQ ID NO: 13; and (c) HVR-L3 comprising the amino acid sequence of SEQ ID NO: 14.

In another aspect, an antibody of the invention comprises (a) a VH domain comprising at least one, at least two, or all three VH HVR sequences selected from (i) HVR-H1 comprising the amino acid sequence of SEQ ID NO: 15, (ii) HVR-H2 comprising the amino acid sequence of SEQ ID NO: 16, and (iii) HVR-H3 comprising an amino acid sequence selected from SEQ ID NO: 17; and (b) a VL domain comprising at least one, at least two, or all three VL HVR sequences selected from (i) HVR-L1 comprising the amino acid sequence of SEQ ID NO: 12, (ii) HVR-L2 comprising the amino acid sequence of SEQ ID NO: 13, and (c) HVR-L3 comprising the amino acid sequence of SEQ ID NO: 14.

In another aspect, the invention provides an antibody comprising (a) HVR-H1 comprising the amino acid sequence of SEQ ID NO: 15; (b) HVR-H2 comprising the amino acid sequence of SEQ ID NO: 16; (c) HVR-H3 comprising the amino acid sequence of SEQ ID NO: 17; (d) HVR-L1 comprising the amino acid sequence of SEQ ID NO: 12; (e) HVR-L2 comprising the amino acid sequence of SEQ ID NO: 13; and (f) HVR-L3 comprising the amino acid sequence of SEQ ID NO: 14.

In any of the above embodiments, an anti-HER2 antibody is humanized. In one embodiment, an anti-HER2 antibody comprises HVRs as in any of the above embodiments, and further comprises a human acceptor framework, e.g. a human immunoglobulin framework or a human consensus framework. In certain embodiments, the human acceptor framework is the human VL kappa IV consensus ($VL_{KIV}$) framework and/or the VH framework $VH_1$. In certain embodiments, the human acceptor framework is the human VL kappa IV consensus ($VL_{KIV}$) framework and/or the VH framework $VH_1$ comprising any one of the mutations described herein.

In another aspect, an anti-HER2 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 11. In certain embodiments, a VH sequence having at least 90%, 91%, 92%, 93%, 94%, 95%, 96%, 97%, 98%, or 99% identity to the amino acid sequence of SEQ ID NO:11 contains substitutions (e.g., conservative substitutions), insertions, or deletions relative to the reference sequence, but an anti-HER2 antibody comprising that sequence retains the ability to bind to HER2. In certain embodiments, a total of 1 to 10 amino acids have been substituted, inserted and/or deleted in SEQ ID NO: 11. In certain embodiments, a total of 1 to 5 amino acids have been substituted, inserted and/or deleted in SEQ ID NO: 11. In certain embodiments, substitutions, insertions, or deletions occur in regions outside the HVRs (i.e., in the FRs). Optionally, the anti-HER2 antibody comprises the VH sequence of SEQ ID NO: 11, including post-translational modifications of that sequence. In a particular embodiment, the VH comprises one, two or three HVRs selected from: (a) HVR-H1 comprising the amino acid sequence of SEQ ID NO: 15, (b) HVR-H2 comprising the amino acid sequence of SEQ ID NO: 16, and (c) HVR-H3 comprising the amino acid sequence of SEQ ID NO: 17.

In another aspect, an anti-HER2 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 10. In certain embodiments, a VL sequence having at least 90%, 91%, 92%, 93%, 94%, 95%, 96%, 97%, 98%, or 99% identity to the amino acid sequence of SEQ ID NO:10 contains substitutions (e.g., conservative substitutions), insertions, or deletions relative to the reference sequence, but an anti-HER2 antibody comprising that sequence retains the ability to bind to HER2. In certain embodiments, a total of 1 to 10 amino acids have been substituted, inserted and/or deleted in SEQ ID NO: 10. In certain embodiments, a total of 1 to 5 amino acids have been substituted, inserted and/or deleted in SEQ ID NO: 10. In certain embodiments, the substitutions, insertions, or deletions occur in regions outside the HVRs (i.e., in the FRs). Optionally, the anti-HER2 antibody comprises the VL sequence of SEQ ID NO: 10, including post-translational modifications of that sequence. In a particular embodiment, the VL comprises one, two or three HVRs selected from (a) HVR-L1 comprising the amino acid sequence of SEQ ID NO: 12; (b) HVR-L2 comprising the amino acid sequence of SEQ ID NO: 13; and (c) HVR-L3 comprising the amino acid sequence of SEQ ID NO: 14.

In another aspect, an anti-HER2 antibody is provided, wherein the antibody comprises a VH as in any of the embodiments provided above, and a VL as in any of the embodiments provided above.

In one embodiment, the antibody comprises the VH and VL sequences in SEQ ID NO: 11 and SEQ ID NO: 10, respectively, including post-translational modifications of those sequences.

In a further aspect, provided are herein are antibodies that bind to the same epitope as an anti-HER2 antibody provided herein. For example, in certain embodiments, an antibody is provided that binds to the same epitope as an anti-HER2 antibody comprising a VH sequence of SEQ ID NO: 11 and a VL sequence of SEQ ID NO: 10, respectively.

In another aspect, an anti-HER2 antibody comprises a heavy chain sequence having at least 90%, 91%, 92%, 93%, 94%, 95%, 96%, 97%, 98%, 99%, or 100% sequence identity to the amino acid sequence of SEQ ID NO: 19. In certain embodiments, a heavy chain sequence having at least 90%, 91%, 92%, 93%, 94%, 95%, 96%, 97%, 98%, or 99% identity to the amino acid sequence of SEQ ID NO:19 contains substitutions (e.g., conservative substitutions), insertions, or deletions relative to the reference sequence, but an anti-HER2 antibody comprising that sequence retains the ability to bind to HER2. In certain embodiments, a total of 1 to 10 amino acids have been substituted, inserted and/or deleted in SEQ ID NO: 19. In certain embodiments, a total of 1 to 5 amino acids have been substituted, inserted and/or deleted in SEQ ID NO: 19. In certain embodiments, substitutions, insertions, or deletions occur in regions outside the HVRs (i.e., in the FRs). Optionally, the anti-HER2 antibody comprises the heavy chain sequence of SEQ ID NO: 19, including post-translational modifications of that sequence. In a particular embodiment, the heavy chain comprises one, two or three HVRs selected from: (a) HVR-H1 comprising the amino acid sequence of SEQ ID NO: 15, (b) HVR-H2 comprising the amino acid sequence of SEQ ID NO: 16, and (c) HVR-H3 comprising the amino acid sequence of SEQ ID NO: 17.

In another aspect, an anti-HER2 antibody is provided, wherein the antibody comprises a light chain having at least 90%, 91%, 92%, 93%, 94%, 95%, 96%, 97%, 98%, 99%, or 100% sequence identity to the amino acid sequence of SEQ ID NO: 18. In certain embodiments, a light chain sequence having at least 90%, 91%, 92%, 93%, 94%, 95%, 96%, 97%, 98%, or 99% identity to the amino acid sequence of SEQ ID NO:18 contains substitutions (e.g., conservative substitutions), insertions, or deletions relative to the reference sequence, but an anti-HER2 antibody comprising that sequence retains the ability to bind to HER2. In certain embodiments, a total of 1 to 10 amino acids have been substituted, inserted and/or deleted in SEQ ID NO: 18. In certain embodiments, a total of 1 to 5 amino acids have been substituted, inserted and/or deleted in SEQ ID NO: 18. In certain embodiments, the substitutions, insertions, or deletions occur in regions outside the HVRs (i.e., in the FRs). Optionally, the anti-HER2 antibody comprises the light chain sequence of SEQ ID NO: 18, including post-translational modifications of that sequence. In a particular embodiment, the light chain comprises one, two or three HVRs selected from (a) HVR-L1 comprising the amino acid sequence of SEQ ID NO: 12; (b) HVR-L2 comprising the amino acid sequence of SEQ ID NO: 13; and (c) HVR-L3 comprising the amino acid sequence of SEQ ID NO: 14.

In another aspect, an anti-HER2 antibody is provided, wherein the antibody comprises a heavy chain as in any of the embodiments provided above, and a light chain as in any of the embodiments provided above.

In one embodiment, the antibody comprises the heavy chain and light chain sequences in SEQ ID NO: 19 and SEQ ID NO: 18, respectively, including post-translational modifications of those sequences.

In a further aspect, provided are herein are antibodies that bind to the same epitope as an anti-HER2 antibody provided herein. For example, in certain embodiments, an antibody is provided that binds to the same epitope as an anti-HER2 antibody comprising a heavy chain sequence of SEQ ID NO: 19 and a light chain sequence of SEQ ID NO: 18, respectively.

Figure 2:
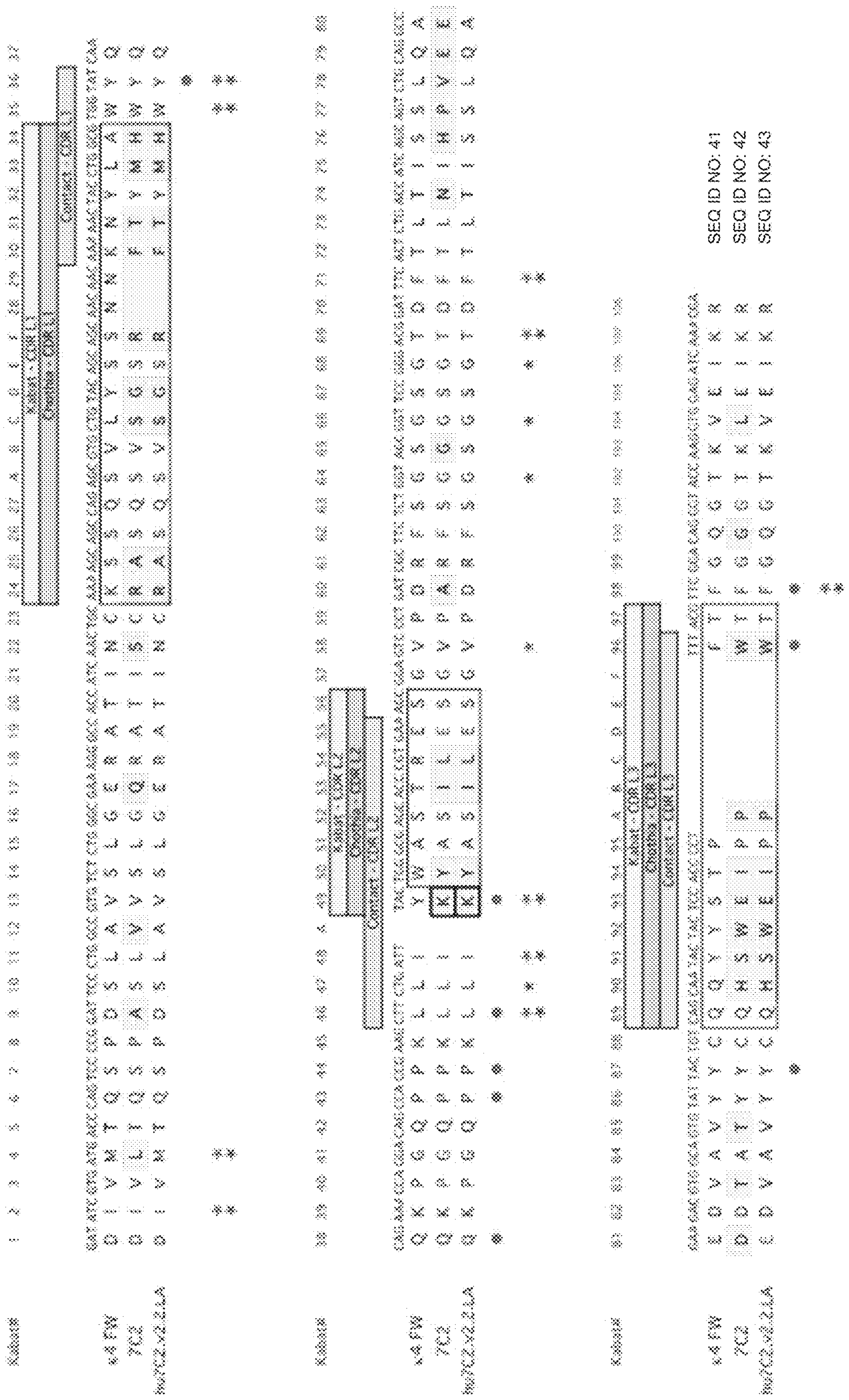
FIG. 2 shows an alignment of the human VL kappa IV ($VL_{KIV}$) consensus sequence and light chain variable region sequences of murine 7C2. B9 ("7C2") and humanized 7C2.v2.2. LA, as described in Example 1.

Provided herein are antibodies comprising a light chain variable domain comprising the HVR1-LC, HVR2-LC and HVR3-LC sequence according to Kabat numbering as depicted in FIG. 1 and a heavy chain variable domain comprising the HVR1-HC, HVR2-HC and HVR3-HC sequence according to Kabat numbering as depicted in FIG. 2. In some embodiments, the antibody comprises a light chain variable domain comprising the HVR1-LC, HVR2-LC and/or HVR3-LC sequence, and the FR1-LC, FR2-LC, FR3-LC and/or FR4-LC sequence as depicted in FIG. 1. In some embodiments, the antibody comprises a heavy chain variable domain comprising the HVR1-HC, HVR2-HC and/or HVR3-HC sequence, and the FR1-HC, FR2-HC, FR3-HC and/or FR4-HC sequence as depicted in FIG. 2.

In a further aspect of the invention, an anti-HER2 antibody according to any of the above embodiments is a monoclonal antibody, including a human antibody. In one embodiment, an anti-HER2 antibody is an antibody fragment, e.g., a Fv, Fab, Fab', scFv, diabody, or $F(ab')_2$ fragment. In another embodiment, the antibody is a substantially full length antibody, e.g., an IgG1 antibody, IgG2a antibody or other antibody class or isotype as defined herein.

In a further aspect, an anti-HER2 antibody according to any of the above embodiments may incorporate any of the features, singly or in combination, as described below.

1. Antibody Affinity

In certain embodiments, an antibody provided herein has a dissociation constant (Kd) of ≤1 μM, ≤100 nM, ≤50 nM, ≤10 nM, ≤5 nM, ≤1 nM, ≤0.1 nM, ≤0.01 nM, or ≤0.001 nM, and optionally is $\geq 10^{-13}$ M. (e.g. $10^{-8}$ M or less, e.g. from $10^{-8}$ M to $10^{-13}$ M, e.g., from $10^{-9}$ M to $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 μl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, NJ) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 μl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$ See, e.g., Chen et al., *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, $F(ab')_2$, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and $F(ab')_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005)(describing SDR (a-CDR) grafting); Padlan, *Mol. Immunol.* 28:489-498 (1991)(describing "resurfacing"); Dall'Acqua et al., *Methods* 36:43-60 (2005)(describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENOMOUSE™ technology; U.S. Pat. No. 5,770,429 describing HuMab® technology; U.S. Pat. No. 7,041,870 describing K-M MOUSE® technology, and U.S. Patent Application Publication No. US 2007/0061900, describing VelociMouse® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications*, pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006)(describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, NJ, 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, NJ, 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for HER2 and the other is for any other antigen. In certain embodiments, one of the binding specificities is for HER2 and the other is for CD3. See, e.g., U.S. Pat. No. 5,821,337. In certain embodiments, bispecific antibodies may bind to two different epitopes of HER2. Bispecific antibodies may also be used to localize cytotoxic agents to cells which express HER2. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). The term "knob-into-hole" or "KnH" technology as used herein refers to the technology directing the pairing of two polypeptides together in vitro or in vivo by introducing a protuberance (knob) into one polypeptide and a cavity (hole) into the other polypeptide at an interface in which they interact. For example, KnHs have been introduced in the Fc:Fc binding interfaces, CL:CH1 interfaces or VH/VL interfaces of antibodies (see, e.g., US 2011/0287009, US2007/0178552, WO 96/027011, WO 98/050431, Zhu et al., 1997, Protein Science 6:781-788, and WO2012/106587). In some embodiments, KnHs drive the pairing of two different heavy chains together during the manufacture of multispecific antibodies. For example, multispecific antibodies having KnH in their Fc regions can further comprise single variable domains linked to each Fc region, or further comprise different heavy chain variable domains that pair with similar or different light chain variable domains. KnH technology can be also be used to pair two different receptor extracellular domains together or any other polypeptide sequences that comprises different target recognition sequences (e.g., including affibodies, peptibodies and other Fc fusions).

The term "knob mutation" as used herein refers to a mutation that introduces a protuberance (knob) into a polypeptide at an interface in which the polypeptide interacts with another polypeptide. In some embodiments, the other polypeptide has a hole mutation.

The term "hole mutation" as used herein refers to a mutation that introduces a cavity (hole) into a polypeptide at an interface in which the polypeptide interacts with another polypeptide. In some embodiments, the other polypeptide has a knob mutation.

A brief nonlimiting discussion is provided below.

A "protuberance" refers to at least one amino acid side chain which projects from the interface of a first polypeptide and is therefore positionable in a compensatory cavity in the adjacent interface (i.e. the interface of a second polypeptide) so as to stabilize the heteromultimer, and thereby favor heteromultimer formation over homomultimer formation, for example. The protuberance may exist in the original interface or may be introduced synthetically (e.g., by altering nucleic acid encoding the interface). In some embodiments, nucleic acid encoding the interface of the first polypeptide is altered to encode the protuberance. To achieve this, the nucleic acid encoding at least one "original" amino acid residue in the interface of the first polypeptide is replaced with nucleic acid encoding at least one "import" amino acid residue which has a larger side chain volume than the original amino acid residue. It will be appreciated that there can be more than one original and corresponding import residue. The side chain volumes of the various amino residues are shown, for example, in Table 1 of US2011/0287009. A mutation to introduce a "protuberance" may be referred to as a "knob mutation."

In some embodiments, import residues for the formation of a protuberance are naturally occurring amino acid residues selected from arginine (R), phenylalanine (F), tyrosine (Y) and tryptophan (W). In some embodiments, an import residue is tryptophan or tyrosine. In some embodiment, the original residue for the formation of the protuberance has a small side chain volume, such as alanine, asparagine, aspartic acid, glycine, serine, threonine or valine.

A "cavity" refers to at least one amino acid side chain which is recessed from the interface of a second polypeptide and therefore accommodates a corresponding protuberance on the adjacent interface of a first polypeptide. The cavity may exist in the original interface or may be introduced synthetically (e.g. by altering nucleic acid encoding the interface). In some embodiments, nucleic acid encoding the interface of the second polypeptide is altered to encode the cavity. To achieve this, the nucleic acid encoding at least one "original" amino acid residue in the interface of the second polypeptide is replaced with DNA encoding at least one "import" amino acid residue which has a smaller side chain volume than the original amino acid residue. It will be appreciated that there can be more than one original and corresponding import residue. In some embodiments, import residues for the formation of a cavity are naturally occurring amino acid residues selected from alanine (A), serine (S), threonine (T) and valine (V). In some embodiments, an import residue is serine, alanine or threonine. In some embodiments, the original residue for the formation of the cavity has a large side chain volume, such as tyrosine, arginine, phenylalanine or tryptophan. A mutation to introduce a "cavity" may be referred to as a "hole mutation."

The protuberance is "positionable" in the cavity which means that the spatial location of the protuberance and cavity on the interface of a first polypeptide and second polypeptide respectively and the sizes of the protuberance and cavity are such that the protuberance can be located in the cavity without significantly perturbing the normal association of the first and second polypeptides at the interface. Since protuberances such as Tyr, Phe and Trp do not typically extend perpendicularly from the axis of the interface and have preferred conformations, the alignment of a protuberance with a corresponding cavity may, in some instances, rely on modeling the protuberance/cavity pair based upon a three-dimensional structure such as that obtained by X-ray crystallography or nuclear magnetic resonance (NMR). This can be achieved using widely accepted techniques in the art.

In some embodiments, a knob mutation in an IgG1 constant region is T366W (EU numbering). In some embodiments, a hole mutation in an IgG1 constant region comprises one or more mutations selected from T366S, L368A and Y407V (EU numbering). In some embodiments, a hole mutation in an IgG1 constant region comprises T366S, L368A and Y407V (EU numbering).

In some embodiments, a knob mutation in an IgG4 constant region is T366W (EU numbering). In some embodiments, a hole mutation in an IgG4 constant region comprises one or more mutations selected from T366S, L368A, and Y407V (EU numbering). In some embodiments, a hole mutation in an IgG4 constant region comprises T366S, L368A, and Y407V (EU numbering).

Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *J. Immunol.,* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to HER2 as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino Acids May be Grouped According to Common Side-Chain Properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex is used to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.,* 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and CytoTox 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103: 2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

In some embodiments, one or more amino acid modifications may be introduced into the Fc portion of the antibody provided herein in order to increase IgG binding to the neonatal Fc receptor. In certain embodiments, the antibody comprises the following three mutations according to EU numbering: M252Y, S254T, and T256E (the "YTE mutation")(U.S. Pat. No. 8,697,650; see also Dall'Acqua et al., Journal of Biological Chemistry 281(33):23514-23524 (2006). In certain embodiments, the YTE mutation does not affect the ability of the antibody to bind to its cognate antigen. In certain embodiments, the YTE mutation increases the antibody's serum half-life compared to the native (i.e., non-YTE mutant) antibody. In some embodiments, the YTE mutation increases the serum half-life of the antibody by 3-fold compared to the native (i.e., non-YTE mutant) antibody. In some embodiments, the YTE mutation increases the serum half-life of the antibody by 2-fold compared to the native (i.e., non-YTE mutant) antibody. In some embodiments, the YTE mutation increases the serum half-life of the antibody by 4-fold compared to the native (i.e., non-YTE mutant) antibody. In some embodiments, the YTE mutation increases the serum half-life of the antibody by at least 5-fold compared to the native (i.e., non-YTE mutant) antibody. In some embodiments, the YTE mutation increases the serum half-life of the antibody by at least 10-fold compared to the native (i.e., non-YTE mutant) antibody. See, e.g., U.S. Pat. No. 8,697,650; see also Dall'Acqua et al., Journal of Biological Chemistry 281(33): 23514-23524 (2006).

In certain embodiments, the YTE mutant provides a means to modulate antibody-dependent cell-mediated cytotoxicity (ADCC) activity of the antibody. In certain embodiments, the YTEO mutant provides a means to modulate ADCC activity of a humanized IgG antibody directed against a human antigen. See, e.g., U.S. Pat. No. 8,697,650; see also Dall'Acqua et al., Journal of Biological Chemistry 281(33):23514-23524 (2006).

In certain embodiments, the YTE mutant allows the simultaneous modulation of serum half-life, tissue distribution, and antibody activity (e.g., the ADCC activity of an IgG antibody). See, e.g., U.S. Pat. No. 8,697,650; see also Dall'Acqua et al., Journal of Biological Chemistry 281(33): 23514-23524 (2006).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

In certain embodiments, the proline at position329 (EU numbering)(P329) of a wild-type human Fc region is substituted with glycine or arginine or an amino acid residue large enough to destroy the proline sandwich within the Fc/Fc□ receptor interface, that is formed between the P329 of the Fc and tryptophane residues W87 and W110 of FcgRIII (Sondermann et al.: Nature 406, 267-273 (20 Jul. 2000)). In a further embodiment, at least one further amino acid substitution in the Fc variant is S228P, E233P, L234A, L235A, L235E, N297A, N297D, or P331S and still in another embodiment said at least one further amino acid substitution is L234A and L235A of the human IgG1 Fc region or S228P and L235E of the human IgG4 Fc region, all according to EU numbering (U.S. Pat. No. 8,969,526 which is incorporated by reference in its entirety).

In certain embodiments, a polypeptide comprises the Fc variant of a wild-type human IgG Fc region wherein the polypeptide has P329 of the human IgG Fc region substituted with glycine and wherein the Fc variant comprises at least two further amino acid substitutions at L234A and L235A of the human IgG1 Fc region or S228P and L235E of the human IgG4 Fc region, and wherein the residues are numbered according to the EU numbering (U.S. Pat. No. 8,969,526 which is incorporated by reference in its entirety). In certain embodiments, the polypeptide comprising the P329G, L234A and L235A (EU numbering) substitutions exhibit a reduced affinity to the human FcγRIIIA and FcγRIIA, for down-modulation of ADCC to at least 20% of the ADCC induced by the polypeptide comprising the wild-type human IgG Fc region, and/or for down-modulation of ADCP (U.S. Pat. No. 8,969,526 which is incorporated by reference in its entirety).

In a specific embodiment the polypeptide comprising an Fc variant of a wildtype human Fc polypeptide comprises a triple mutation: an amino acid substitution at position Pro329, a L234A and a L235A mutation according to EU numbering (P329/LALA)(U.S. Pat. No. 8,969,526 which is incorporated by reference in its entirety). In specific embodiments, the polypeptide comprises the following amino acid substitutions: P329G, L234A, and L235A according to EU numbering.

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

d) Cysteine Engineered Antibody Variants

In certain embodiments, it may be desirable to create cysteine engineered antibodies, e.g., a "THIOMAB™," in which one or more residues of an antibody are substituted with cysteine residues. In particular embodiments, the substituted residues occur at sites of the antibody that are available for conjugation. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: K149 (Kabat numbering) of the light chain; V205 (Kabat numbering) of the light chain; A118 (EU numbering) of the heavy chain; A140 (EU numbering) of the heavy chain; L174 (EU numbering) of the heavy chain; Y373 (EU numbering) of the heavy chain; and S400 (EU numbering) of the heavy chain Fc region. In specific embodiments, the antibodies described herein comprise the HC-A140C (EU numbering) cysteine substitution. In specific embodiments, the antibodies described herein comprise the LC-K149C (Kabat numbering) cysteine substitution. In specific embodiments, the antibodies described herein comprise the HC-A118C (EU numbering) cysteine substitution. Cysteine engineered antibodies may be generated as described, e.g., in U.S. Pat. No. 7,521,541.

In certain embodiments, the antibody comprises one of the following heavy chain cysteine substitutions:

| Chain (HC/LC) | Residue | EU Mutation Site # | Kabat Mutation Site # |
|---|---|---|---|
| HC | T | 114 | 110 |
| HC | A | 140 | 136 |
| HC | L | 174 | 170 |
| HC | L | 179 | 175 |
| HC | T | 187 | 183 |
| HC | T | 209 | 205 |
| HC | V | 262 | 258 |
| HC | G | 371 | 367 |
| HC | Y | 373 | 369 |
| HC | E | 382 | 378 |
| HC | S | 424 | 420 |
| HC | N | 434 | 430 |
| HC | Q | 438 | 434 |

-continued

In certain embodiments, the antibody comprises one of the following light chain cysteine substitutions:

| Chain (HC/LC) | Residue | EU Mutation Site # | Kabat Mutation Site # |
|---|---|---|---|
| LC | I | 106 | 106 |
| LC | R | 108 | 108 |
| LC | R | 142 | 142 |
| LC | K | 149 | 149 |
| LC | V | 205 | 205 |

A nonlimiting exemplary hu7C2.v2.2. LA light chain (LC) K149C THIOMAB™ has the heavy chain and light chain amino acid sequences of SEQ ID NOs: 19 and 23, respectively. A nonlimiting exemplary hu7C2.v2.2. LA heavy chain (HC) A118C THIOMAB™ has the heavy chain and light chain amino acid sequences of SEQ ID NOs: 24 and 18, respectively.

An exemplary S400C cysteine engineered heavy chain constant region is shown in SEQ ID NO: 28. The S400C cysteine engineered heavy chain constant region may be fused to the C-terminus of the hu7C2.v2.2. LA heavy chain variable region shown in SEQ ID NO: 11. The resulting hu7C2.v2.2. LA HC S400C heavy chain may be paired with a hu7C2.v2.2. LA kappa light chain, such as the light chain shown in SEQ ID NO: 18.

An exemplary V205C cysteine engineered light chain constant region is shown in SEQ ID NO: 25. The V205C cysteine engineered light chain constant region may be fused to the C-terminus of the hu7C2.v2.2. LA light chain variable region shown in SEQ ID NO: 10. The resulting hu7C2.v2.2. LA LC V205C light chain may be paired with a hu7C2.v2.2. LA IgG heavy chain, such as the heavy chain shown in SEQ ID NO: 19.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-HER2 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-HER2 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-HER2 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology, Vol.* 248 (B. K. C. Lo, ed., Humana Press, Totowa, NJ, 2003), pp. 245-254, describing expression of antibody fragments in *E. coli.*) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR$^-$ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology, Vol.* 248 (B. K. C. Lo, ed., Humana Press, Totowa, NJ), pp. 255-268 (2003).

C. Assays

Anti-HER2 antibodies provided herein may be identified, screened for, or characterized for their physical/chemical properties and/or biological activities by various assays known in the art.

In one aspect, an antibody of the invention is tested for its antigen binding activity, e.g., by known methods such as ELISA, BIACore®, FACS, or Western blot.

In another aspect, competition assays may be used to identify an antibody that competes with any of the antibodies described herein for binding to HER2. In certain embodiments, such a competing antibody binds to the same epitope (e.g., a linear or a conformational epitope) that is bound by an antibody described herein. Detailed exemplary methods for mapping an epitope to which an antibody binds are provided in Morris (1996) "Epitope Mapping Protocols," in *Methods in Molecular Biology* vol. 66 (Humana Press, Totowa, NJ).

In an exemplary competition assay, immobilized HER2 is incubated in a solution comprising a first labeled antibody that binds to HER2 (e.g., any of the antibodies described herein) and a second unlabeled antibody that is being tested for its ability to compete with the first antibody for binding to HER2. The second antibody may be present in a hybridoma supernatant. As a control, immobilized HER2 is incubated in a solution comprising the first labeled antibody but not the second unlabeled antibody. After incubation under conditions permissive for binding of the first antibody to HER2, excess unbound antibody is removed, and the amount of label associated with immobilized HER2 is measured. If the amount of label associated with immobilized HER2 is substantially reduced in the test sample relative to the control sample, then that indicates that the second antibody is competing with the first antibody for binding to HER2. See Harlow and Lane (1988) *Antibodies: A Laboratory Manual* ch. 14 (Cold Spring Harbor Laboratory, Cold Spring Harbor, NY).

D. Immunoconjugates

The invention also provides immunoconjugates comprising any anti-HER2 antibody provided herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes (i.e., a radioconjugate).

Immunoconjugates allow for the targeted delivery of a drug moiety to a tumor, and, in some embodiments intracellular accumulation therein, where systemic administration of unconjugated drugs may result in unacceptable levels of toxicity to normal cells (Polakis P. (2005) *Current Opinion in Pharmacology* 5:382-387).

Antibody-drug conjugates (ADC) are targeted chemotherapeutic molecules which combine properties of both antibodies and cytotoxic drugs by targeting potent cytotoxic drugs to antigen-expressing tumor cells (Teicher, B. A. (2009) *Current Cancer Drug Targets* 9:982-1004), thereby enhancing the therapeutic index by maximizing efficacy and minimizing off-target toxicity (Carter, P. J. and Senter P. D. (2008) *The Cancer Jour.* 14(3):154-169; Chari, R. V. (2008) *Acc. Chem. Res.* 41:98-107.

The ADC compounds of the invention include those with anticancer activity. In some embodiments, the ADC compounds include an antibody conjugated, i.e. covalently attached, to the drug moiety. In some embodiments, the antibody is covalently attached to the drug moiety through a linker. The antibody-drug conjugates (ADC) of the invention selectively deliver an effective dose of a drug to tumor tissue whereby greater selectivity, i.e. a lower efficacious dose, may be achieved while increasing the therapeutic index ("therapeutic window").

The drug moiety (D) of the antibody-drug conjugates (ADC) may include any compound, moiety or group that has a cytotoxic or cytostatic effect. Drug moieties may impart their cytotoxic and cytostatic effects by mechanisms including but not limited to tubulin binding, DNA binding or intercalation, and inhibition of RNA polymerase, protein synthesis, and/or topoisomerase. Exemplary drug moieties include, but are not limited to, a maytansinoid, dolastatin, auristatin, calicheamicin, pyrrolobenzodiazepine (PBD), nemorubicin and its derivatives, PNU-159682, anthracycline, duocarmycin, vinca alkaloid, taxane, trichothecene, CC1065, camptothecin, elinafide, and stereoisomers, isosteres, analogs, and derivatives thereof that have cytotoxic activity. Nonlimiting examples of such immunoconjugates are discussed in further detail below.

1. Exemplary Antibody-Drug Conjugates

An exemplary embodiment of an antibody-drug conjugate (ADC) compound comprises an antibody (Ab) which targets a tumor cell, a drug moiety (D), and a linker moiety (L) that attaches Ab to D. In some embodiments, the antibody is attached to the linker moiety (L) through one or more amino acid residues, such as lysine and/or cysteine.

An Exemplary ADC has Formula I:

$$Ab\text{-}(L\text{-}D)_p \qquad I$$

where p is 1 to about 20. In some embodiments, the number of drug moieties that can be conjugated to an antibody is limited by the number of free cysteine residues. In some embodiments, free cysteine residues are introduced into the antibody amino acid sequence by the methods described herein. Exemplary ADC of Formula I include, but are not limited to, antibodies that have 1, 2, 3, or 4 engineered cysteine amino acids (Lyon, R. et al (2012) *Methods in Enzym.* 502:123-138). In some embodiments, one or more free cysteine residues are already present in an antibody, without the use of engineering, in which case the existing free cysteine residues may be used to conjugate the antibody to a drug. In some embodiments, an antibody is exposed to reducing conditions prior to conjugation of the antibody in order to generate one or more free cysteine residues.

a) Exemplary Linkers

A "Linker" (L) is a bifunctional or multifunctional moiety that can be used to link one or more drug moieties (D) to an antibody (Ab) to form an antibody-drug conjugate (ADC) of Formula I. In some embodiments, antibody-drug conjugates (ADC) can be prepared using a Linker having reactive functionalities for covalently attaching to the drug and to the antibody. For example, in some embodiments, a cysteine thiol of an antibody (Ab) can form a bond with a reactive functional group of a linker or a drug-linker intermediate to make an ADC.

In one aspect, a linker has a functionality that is capable of reacting with a free cysteine present on an antibody to form a covalent bond. Nonlimiting exemplary such reactive functionalities include maleimide, haloacetamides, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates, and isothiocyanates. See, e.g., the conjugation method at page 766 of Klussman, et al (2004), *Bioconjugate Chemistry* 15(4):765-773, and the Examples herein.

In some embodiments, a linker has a functionality that is capable of reacting with an electrophilic group present on an antibody. Exemplary such electrophilic groups include, but are not limited to, aldehyde and ketone carbonyl groups. In some embodiments, a heteroatom of the reactive functionality of the linker can react with an electrophilic group on an antibody and form a covalent bond to an antibody unit. Nonlimiting exemplary such reactive functionalities include, but are not limited to, hydrazide, oxime, amino, hydrazine, thiosemicarbazone, hydrazine carboxylate, and arylhydrazide.

A linker may comprise one or more linker components. Exemplary linker components include 6-maleimidocaproyl ("MC"), maleimidopropanoyl ("MP"), valine-citrulline ("val-cit" or "vc"), alanine-phenylalanine ("ala-phe"), p-aminobenzyloxycarbonyl (a "PAB"), N-Succinimidyl 4-(2-pyridylthio) pentanoate ("SPP"), and 4-(N-maleimidomethyl)cyclohexane-1 carboxylate ("MCC"). Various linker components are known in the art, some of which are described below.

A linker may be a "cleavable linker," facilitating release of a drug. Nonlimiting exemplary cleavable linkers include acid-labile linkers (e.g., comprising hydrazone), protease-sensitive (e.g., peptidase-sensitive) linkers, photolabile linkers, or disulfide-containing linkers (Chari et al., Cancer Research 52:127-131 (1992); U.S. Pat. No. 5,208,020).

In Certain Embodiments, a Linker has the Following Formula II:

$$-A_a-W_w—Y_y— \qquad \text{II}$$

wherein A is a "stretcher unit", and a is an integer from 0 to 1; W is an "amino acid unit", and w is an integer from 0 to 12; Y is a "spacer unit", and y is 0, 1, or 2; and Ab, D, and p are defined as above for Formula I. Exemplary embodiments of such linkers are described in U.S. Pat. No. 7,498,298, which is expressly incorporated herein by reference.

In some embodiments, a linker component comprises a "stretcher unit" that links an antibody to another linker component or to a drug moiety. Nonlimiting exemplary stretcher units are shown below (wherein the wavy line indicates sites of covalent attachment to an antibody, drug, or additional linker components):

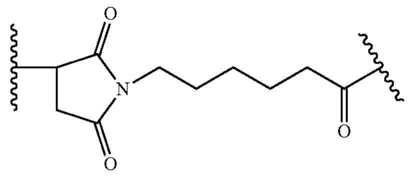

MC

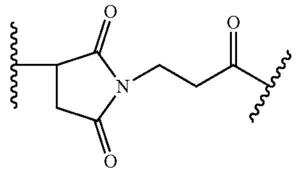

MP

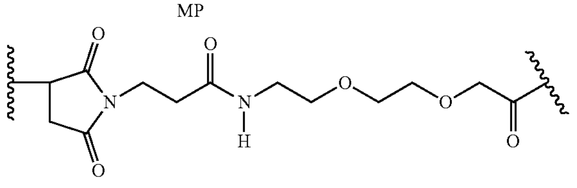

mPEG

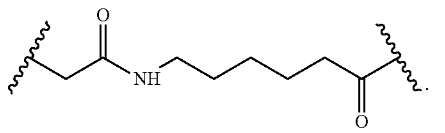

In some embodiments, a linker component comprises an "amino acid unit". In some such embodiments, the amino acid unit allows for cleavage of the linker by a protease, thereby facilitating release of the drug from the immunoconjugate upon exposure to intracellular proteases, such as lysosomal enzymes (Doronina et al. (2003) *Nat. Biotechnol.* 21:778-784). Exemplary amino acid units include, but are not limited to, dipeptides, tripeptides, tetrapeptides, and pentapeptides. Exemplary dipeptides include, but are not limited to, valine-citrulline (vc or val-cit), alanine-phenylalanine (af or ala-phe); phenylalanine-lysine (fk or phe-lys); phenylalanine-homolysine (phe-homolys); and N-methyl-valine-citrulline (Me-val-cit). Exemplary tripeptides include, but are not limited to, glycine-valine-citrulline (gly-val-cit) and glycine-glycine-glycine (gly-gly-gly). An amino acid unit may comprise amino acid residues that occur naturally and/or minor amino acids and/or non-naturally occurring amino acid analogs, such as citrulline. Amino acid units can be designed and optimized for enzymatic cleavage by a particular enzyme, for example, a tumor-associated protease, cathepsin B, C and D, or a plasmin protease.

In some embodiments, a linker component comprises a "spacer" unit that links the antibody to a drug moiety, either directly or through a stretcher unit and/or an amino acid unit. A spacer unit may be "self-immolative" or a "non-self-immolative." A "non-self-immolative" spacer unit is one in which part or all of the spacer unit remains bound to the drug moiety upon cleavage of the ADC. Examples of non-self-immolative spacer units include, but are not limited to, a glycine spacer unit and a glycine-glycine spacer unit. In some embodiments, enzymatic cleavage of an ADC containing a glycine-glycine spacer unit by a tumor-cell associated protease results in release of a glycine-glycine-drug moiety from the remainder of the ADC. In some such embodiments, the glycine-glycine-drug moiety is subjected to a hydrolysis step in the tumor cell, thus cleaving the glycine-glycine spacer unit from the drug moiety.

A "self-immolative" spacer unit allows for release of the drug moiety. In certain embodiments, a spacer unit of a linker comprises a p-aminobenzyl unit. In some such embodiments, a p-aminobenzyl alcohol is attached to an amino acid unit via an amide bond, and a carbamate, methylcarbamate, or carbonate is made between the benzyl alcohol and the drug (Hamann et al. (2005) *Expert Opin. Ther. Patents* (2005) 15:1087-1103). In some embodiments, the spacer unit is p-aminobenzyloxycarbonyl (PAB). In some embodiments, an ADC comprising a self-immolative linker has the structure:

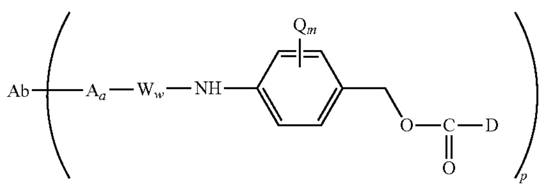

wherein Q is —$C_1$-$C_8$ alkyl, —O—($C_1$-$C_8$ alkyl), -halogen, -nitro, or -cyno; m is an integer ranging from 0 to 4; and p ranges from 1 to about 20. In some embodiments, p ranges from 1 to 10, 1 to 7, 1 to 5, or 1 to 4.

Other examples of self-immolative spacers include, but are not limited to, aromatic compounds that are electronically similar to the PAB group, such as 2-aminoimidazol-5-methanol derivatives (U.S. Pat. No. 7,375,078; Hay et al. (1999) *Bioorg. Med. Chem. Lett.* 9:2237) and ortho- or para-aminobenzylacetals. In some embodiments, spacers can be used that undergo cyclization upon amide bond hydrolysis, such as substituted and unsubstituted 4-aminobutyric acid amides (Rodrigues et al (1995) *Chemistry Biology* 2:223), appropriately substituted bicyclo[2.2.1] and bicyclo[2.2.2] ring systems (Storm et al (1972) *J Amer. Chem. Soc.* 94:5815) and 2-aminophenylpropionic acid amides (Amsberry, et al (1990) *J. Org. Chem.* 55:5867). Linkage of a drug to the α-carbon of a glycine residue is another example of a self-immolative spacer that may be useful in ADC (Kingsbury et al (1984) *J. Med. Chem.* 27:1447).

In some embodiments, linker L may be a dendritic type linker for covalent attachment of more than one drug moiety to an antibody through a branching, multifunctional linker moiety (Sun et al (2002) *Bioorganic & Medicinal Chemistry Letters* 12:2213-2215; Sun et al (2003) *Bioorganic & Medicinal Chemistry* 11:1761-1768). Dendritic linkers can increase the molar ratio of drug to antibody, i.e. loading, which is related to the potency of the ADC. Thus, where an antibody bears only one reactive cysteine thiol group, a multitude of drug moieties may be attached through a dendritic linker.

Nonlimiting exemplary linkers are shown below in the context of an ADC of Formula I:

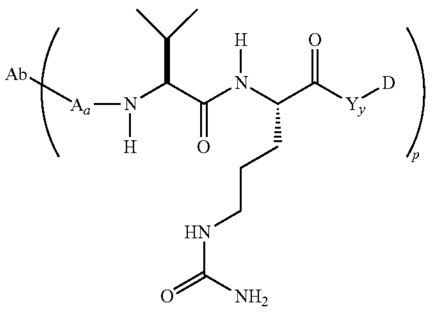

val-cit

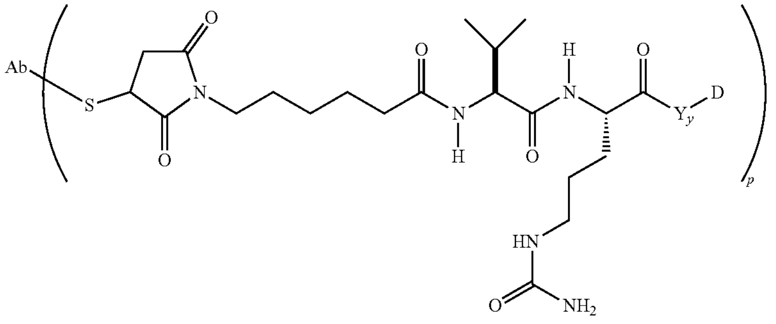

MC-val-cit

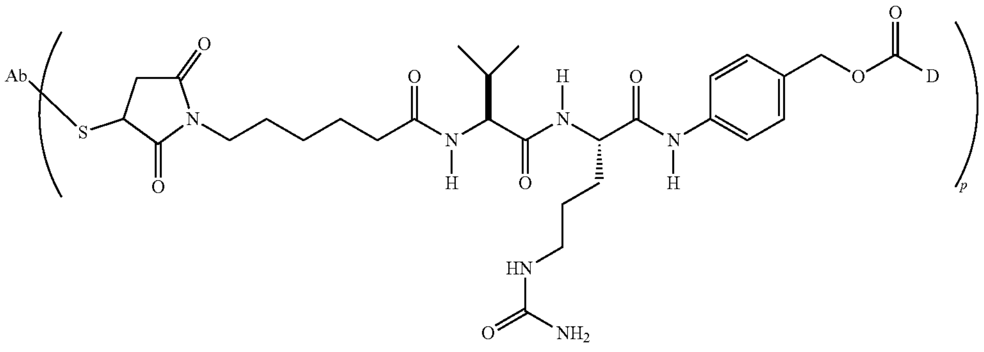

MC-val-cit-PAB

Further nonlimiting exemplary ADCs include the structures:

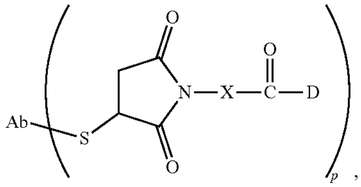

,

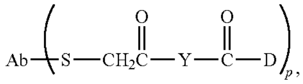

,

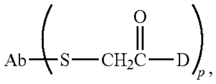

,

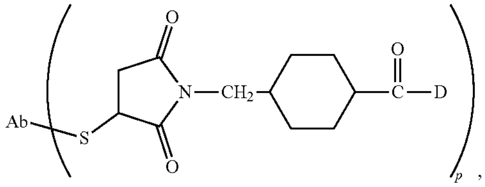

,

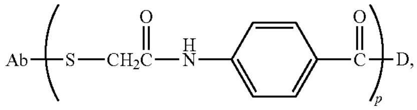

, where X is:

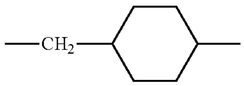

, $—(CH_2)_n—$, $—(CH_2CH_2O)_n—$,

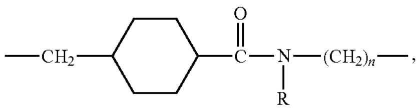

,

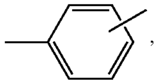

,

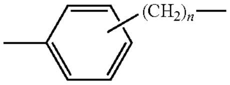

, or

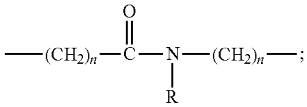

;

Y is:

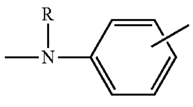

or

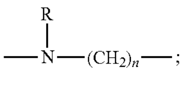

;

each R is independently H or $C_1$-$C_6$ alkyl; and n is 1 to 12.

Typically, peptide-type linkers can be prepared by forming a peptide bond between two or more amino acids and/or peptide fragments. Such peptide bonds can be prepared, for example, according to a liquid phase synthesis method (e.g., E. Schröder and K. Lübke (1965) "The Peptides", volume 1, pp 76-136, Academic Press).

In some embodiments, a linker is substituted with groups that modulate solubility and/or reactivity. As a nonlimiting example, a charged substituent such as sulfonate ($—SO_3^-$) or ammonium may increase water solubility of the linker reagent and facilitate the coupling reaction of the linker reagent with the antibody and/or the drug moiety, or facilitate the coupling reaction of Ab-L (antibody-linker intermediate) with D, or D-L (drug-linker intermediate) with Ab, depending on the synthetic route employed to prepare the ADC. In some embodiments, a portion of the linker is coupled to the antibody and a portion of the linker is coupled to the drug, and then the Ab-(linker portion)$^a$ is coupled to drug-(linker portion)$^b$ to form the ADC of Formula I. In some such embodiments, the antibody comprises more than one (linker portion)$^a$ substituents, such that more than one drug is coupled to the antibody in the ADC of Formula I.

The compounds of the invention expressly contemplate, but are not limited to, ADC prepared with the following linker reagents: bis-maleimido-trioxyethylene glycol (BMPEO), N-(β-maleimidopropyloxy)-N-hydroxy succinimide ester (BMPS), N-(ε-maleimidocaproyloxy) succinimide ester (EMCS), N-[γ-maleimidobutyryloxy]succinimide ester (GMBS), 1,6-hexane-bis-vinylsulfone (HBVS), succinimidyl 4-(N-maleimidomethyl)cyclohexane-1-carboxy-(6-amidocaproate) (LC-SMCC), m-maleimidobenzoyl-N-hydroxysuccinimide ester (MBS), 4-(4-N-Maleimidophenyl)butyric acid hydrazide (MPBH), succinimidyl 3-(bromoacetamido)propionate (SBAP), succinimidyl iodoacetate (SIA), succinimidyl (4-iodoacetyl) aminobenzoate (SIAB), N-succinimidyl-3-(2-pyridyldithio) propionate (SPDP), N-succinimidyl-4-(2-pyridylthio)pentanoate (SPP), succinimidyl 4-(N-maleimidomethyl)cyclohexane-1-carboxylate (SMCC), succinimidyl 4-(p-maleimidophenyl)butyrate (SMPB), succinimidyl 6-[(beta-maleimidopropionamido)hexanoate] (SMPH), iminothiolane (IT), sulfo-EMCS, sulfo-GMBS, sulfo-KMUS, sulfo-MBS, sulfo-SIAB, sulfo-SMCC, and sulfo-SMPB, and succinimidyl-(4-vinylsulfone)benzoate (SVSB), and including bis-maleimide reagents: dithiobismaleimidoethane (DTME), 1,4-Bismaleimidobutane (BMB), 1.4 Bismaleimidyl-2,3-dihydroxybutane (BMDB), bismaleimidohexane (BMEI), bismaleimidoethane (BMOE), BM(PEG)$_2$ (shown below), and BM(PEG)$_3$ (shown below); bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2, 4-dinitrobenzene). In some embodiments, bis-maleimide reagents allow the attachment of the thiol group of a cysteine in the antibody to a thiol-containing drug moiety, linker, or linker-drug intermediate. Other functional groups that are reactive with thiol groups include, but are not limited to, iodoacetamide, bromoacetamide, vinyl pyridine, disulfide, pyridyl disulfide, isocyanate, and isothiocyanate.

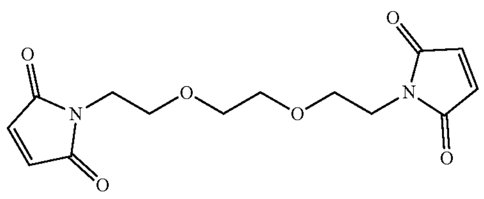

BM(PEG)$_2$

-continued

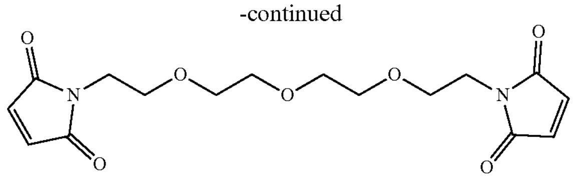

BM(PEG)3

Certain useful linker reagents can be obtained from various commercial sources, such as Pierce Biotechnology, Inc. (Rockford, IL), Molecular Biosciences Inc. (Boulder, CO), or synthesized in accordance with procedures described in the art; for example, in Toki et al (2002) *J. Org. Chem.* 67:1866-1872; Dubowchik, et al. (1997) *Tetrahedron Letters,* 38:5257-60; Walker, M. A. (1995) *J. Org. Chem.* 60:5352-5355; Frisch et al (1996) *Bioconjugate Chem.* 7:180-186; U.S. Pat. No. 6,214,345; WO 02/088172; US 2003130189; US2003096743; WO 03/026577; WO 03/043583; and WO 04/032828.

Carbon-14-labeled 1-isothiocyanatobenzyl-3-methyldiethylene triaminepentaacetic acid (MX-DTPA) is an exemplary chelating agent for conjugation of radionucleotide to the antibody. See, e.g., WO94/11026.

b) Exemplary Drug Moieties (1) Maytansine and Maytansinoids

In some embodiments, an immunoconjugate comprises an antibody conjugated to one or more maytansinoid molecules. Maytansinoids are derivatives of maytansine, and are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinoids are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody-drug conjugates because they are: (i) relatively accessible to prepare by fermentation or chemical modification or derivatization of fermentation products, (ii) amenable to derivatization with functional groups suitable for conjugation through non-disulfide linkers to antibodies, (iii) stable in plasma, and (iv) effective against a variety of tumor cell lines.

Certain maytansinoids suitable for use as maytansinoid drug moieties are known in the art and can be isolated from natural sources according to known methods or produced using genetic engineering techniques (see, e.g., Yu et al (2002) PNAS 99:7968-7973). Maytansinoids may also be prepared synthetically according to known methods.

Exemplary maytansinoid drug moieties include, but are not limited to, those having a modified aromatic ring, such as: C-19-dichloro (U.S. Pat. No. 4,256,746)(prepared, for example, by lithium aluminum hydride reduction of ansamitocin P2); C-20-hydroxy (or C-20-demethyl)+/−C-19-dichloro (U.S. Pat. Nos. 4,361,650 and 4,307,016)(prepared, for example, by demethylation using *Streptomyces* or *Actinomyces* or dechlorination using LAH); and C-20-demethoxy, C-20-acyloxy (—OCOR), +/−dichloro (U.S. Pat. No. 4,294,757)(prepared, for example, by acylation using acyl chlorides), and those having modifications at other positions of the aromatic ring.

Exemplary maytansinoid drug moieties also include those having modifications such as: C-9-SH (U.S. Pat. No. 4,424,219)(prepared, for example, by the reaction of maytansinol with $H_2S$ or $P_2S_5$); C-14-alkoxymethyl(demethoxy/$CH_2OR$) (U.S. Pat. No. 4,331,598); C-14-hydroxymethyl or acyloxymethyl ($CH_2OH$ or $CH_2OAc$)(U.S. Pat. No. 4,450,254) (prepared, for example, from Nocardia); C-15-hydroxy/acyloxy (U.S. Pat. No. 4,364,866)(prepared, for example, by the conversion of maytansinol by *Streptomyces*); C-15-methoxy (U.S. Pat. Nos. 4,313,946 and 4,315,929)(for example, isolated from *Trewia nudlflora*); C-18-N-demethyl (U.S. Pat. Nos. 4,362,663 and 4,322,348)(prepared, for example, by the demethylation of maytansinol by *Streptomyces*); and 4,5-deoxy (U.S. Pat. No. 4,371,533) (prepared, for example, by the titanium trichloride/LAH reduction of maytansinol).

Many positions on maytansinoid compounds are useful as the linkage position. For example, an ester linkage may be formed by reaction with a hydroxyl group using conventional coupling techniques. In some embodiments, the reaction may occur at the C-3 position having a hydroxyl group, the C-14 position modified with hydroxymethyl, the C-15 position modified with a hydroxyl group, and the C-20 position having a hydroxyl group. In some embodiments, the linkage is formed at the C-3 position of maytansinol or a maytansinol analogue.

Maytansinoid Drug Moieties Include Those Having the Structure:

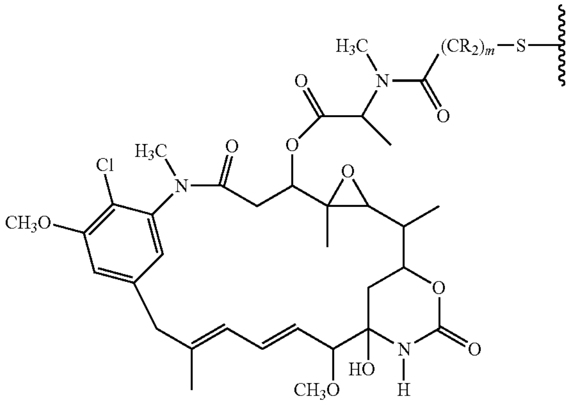

where the wavy line indicates the covalent attachment of the sulfur atom of the maytansinoid drug moiety to a linker of an ADC. Each R may independently be H or a $C_1$-$C_6$ alkyl. The alkylene chain attaching the amide group to the sulfur atom may be methanyl, ethanyl, or propyl, i.e., m is 1, 2, or 3 (U.S. Pat. Nos. 633,410; 5,208,020; Chari et al (1992) *Cancer Res.* 52:127-131; Liu et al (1996) *Proc. Natl. Acad. Sci USA* 93:8618-8623).

All stereoisomers of the maytansinoid drug moiety are contemplated for the ADC of the invention, i.e. any combination of R and S configurations at the chiral carbons (U.S. Pat. Nos. 7,276,497; 6,913,748; 6,441,163; 633,410 (RE39151); U.S. Pat. No. 5,208,020; Widdison et al (2006) J. Med. Chem. 49:4392-4408, which are incorporated by reference in their entirety). In some embodiments, the maytansinoid drug moiety has the following stereochemistry:

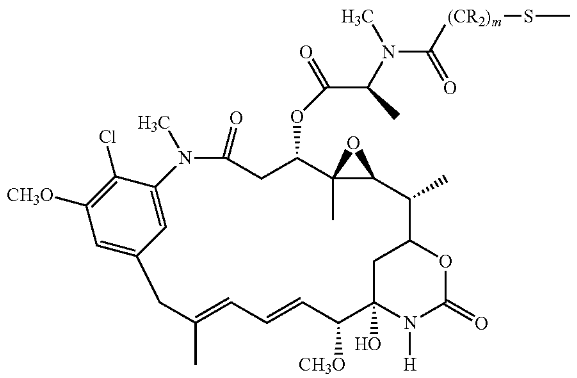

Exemplary embodiments of maytansinoid drug moieties include, but are not limited to, DM1; DM3; and DM4, having the structures:

DM1

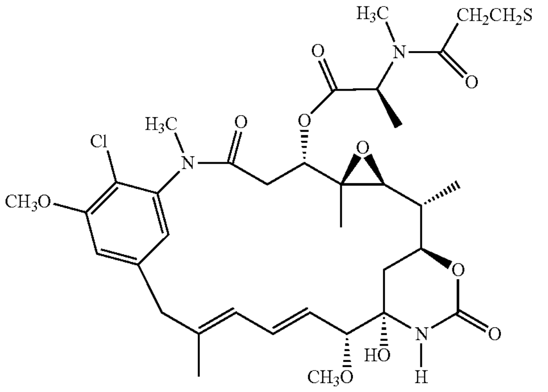

-continued

DM3

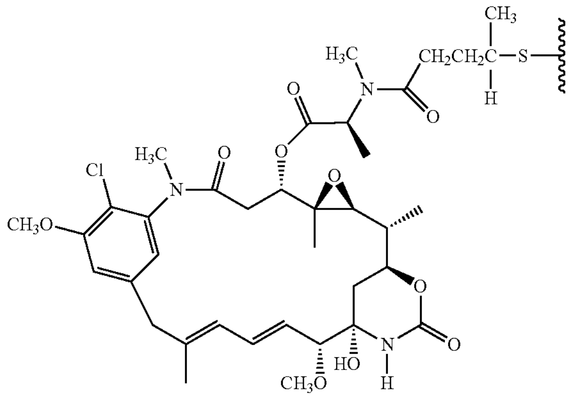

DM4

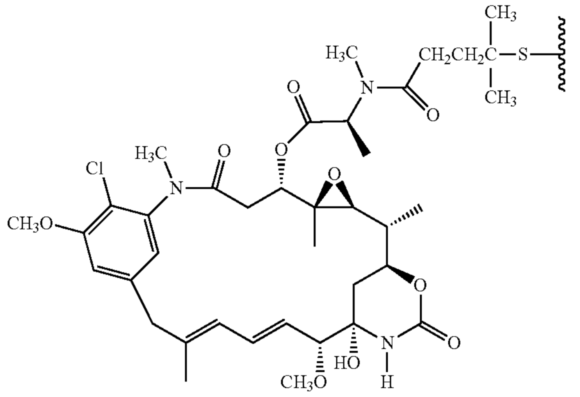

wherein the wavy line indicates the covalent attachment of the sulfur atom of the drug to a linker (L) of an antibody-drug conjugate.

Other exemplary maytansinoid antibody-drug conjugates have the following structures and abbreviations (wherein Ab is antibody and p is 1 to about 20. In some embodiments, p is 1 to 10, p is 1 to 7, p is 1 to 5, or p is 1 to 4):

Ab-SPP-DM1

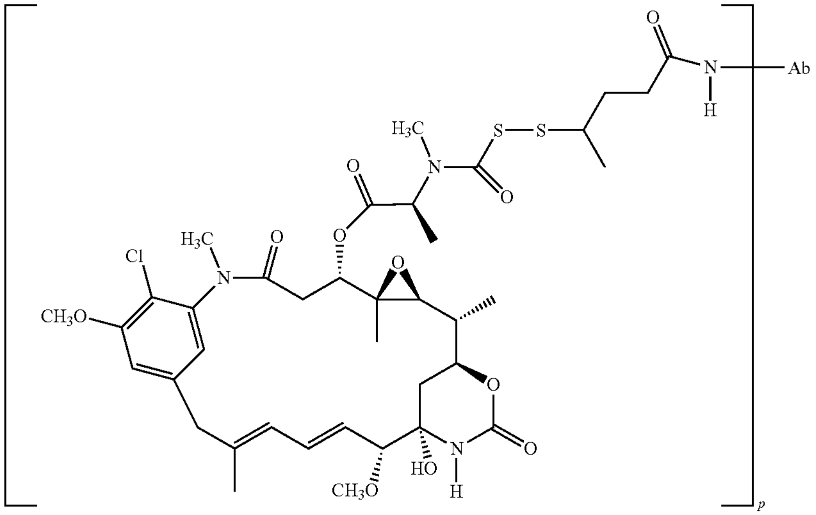

-continued

Ab-SMCC-DM1

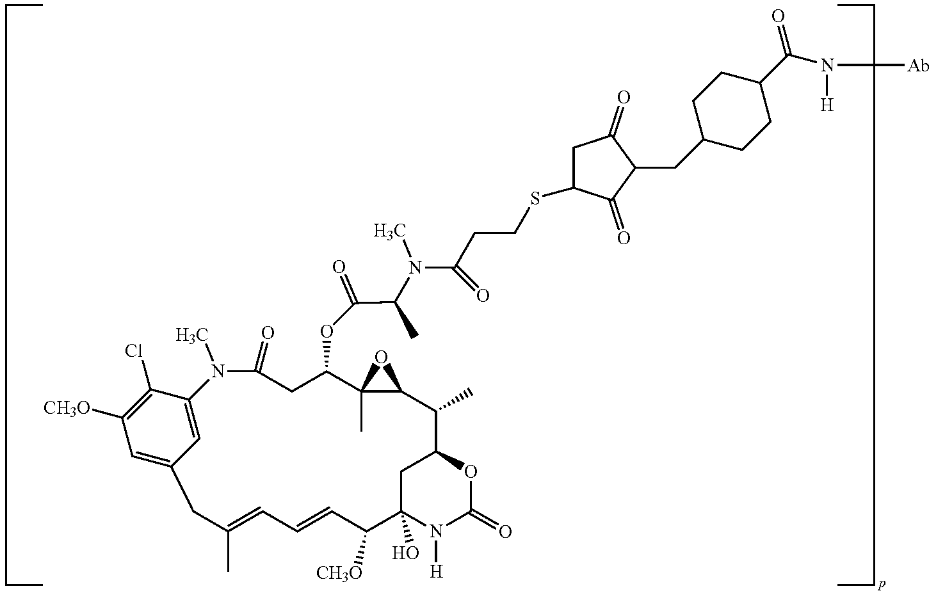

Exemplary antibody-drug conjugates where DM1 is linked through a BMPEO linker to a thiol group of the antibody have the structure and abbreviation:

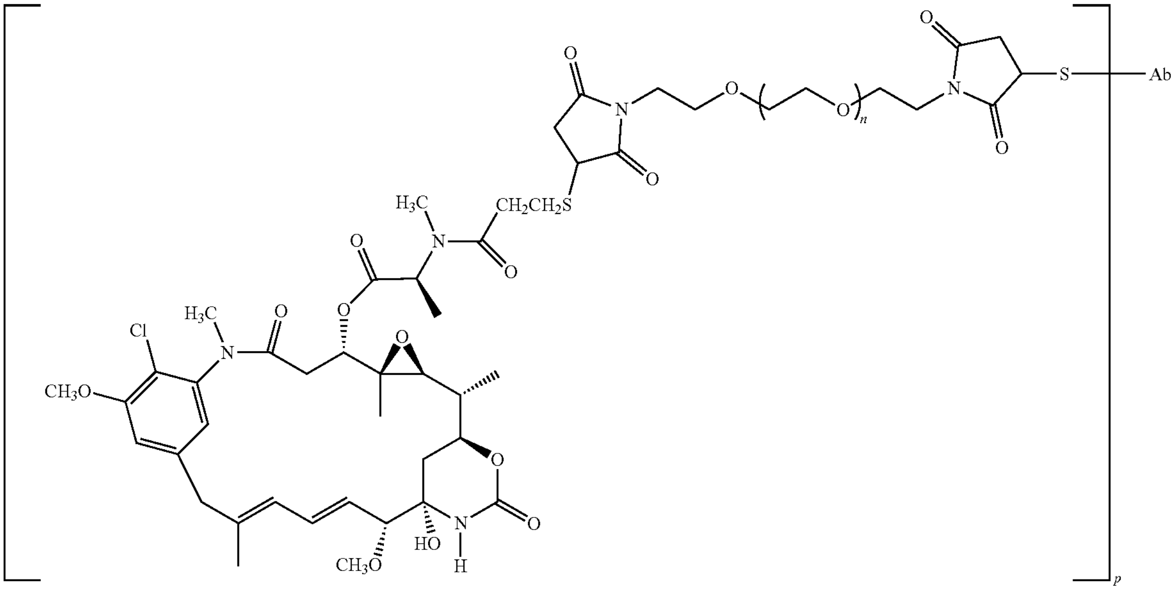

where Ab is antibody; n is 0, 1, or 2; and p is 1 to about 20. In some embodiments, p is 1 to 10, p is 1 to 7, p is 1 to 5, or p is 1 to 4.

Immunoconjugates containing maytansinoids, methods of making the same, and their therapeutic use are disclosed, for example, in U.S. Pat. Nos. 5,208,020 and 5,416,064; US 2005/0276812 A1; and European Patent EP 0 425 235 B1, the disclosures of which are hereby expressly incorporated by reference. See also Liu et al. *Proc. Natl. Acad. Sci. USA* 93:8618-8623 (1996); and Chari et al. *Cancer Research* 52:127-131 (1992).

In some embodiments, antibody-maytansinoid conjugates may be prepared by chemically linking an antibody to a maytansinoid molecule without significantly diminishing the biological activity of either the antibody or the maytansinoid molecule. See, e.g., U.S. Pat. No. 5,208,020 (the disclosure of which is hereby expressly incorporated by reference). In some embodiments, ADC with an average of 3-4 maytansinoid molecules conjugated per antibody molecule has shown efficacy in enhancing cytotoxicity of target cells without negatively affecting the function or solubility of the antibody. In some instances, even one molecule of toxin/antibody is expected to enhance cytotoxicity over the use of naked antibody.

Exemplary linking groups for making antibody-maytansinoid conjugates include, for example, those described herein and those disclosed in U.S. Pat. No. 5,208,020; EP Patent 0 425 235 B1; Chari et al. *Cancer Research* 52:127-131 (1992); US 2005/0276812 A1; and US 2005/016993 A1, the disclosures of which are hereby expressly incorporated by reference.

(2) Auristatins and Dolastatins

Drug moieties include dolastatins, auristatins, and analogs and derivatives thereof (U.S. Pat. Nos. 5,635,483; 5,780,588; 5,767,237; 6,124,431). Auristatins are derivatives of the marine mollusk compound dolastatin-10. While not intending to be bound by any particular theory, dolastatins and auristatins have been shown to interfere with microtubule dynamics, GTP hydrolysis, and nuclear and cellular division (Woyke et al (2001) *Antimicrob. Agents and Chemother.* 45(12):3580-3584) and have anticancer (U.S. Pat. No. 5,663,149) and antifungal activity (Pettit et al (1998) *Antimicrob. Agents Chemother.* 42:2961-2965). The dolastatin/auristatin drug moiety may be attached to the antibody through the N (amino) terminus or the C (carboxyl) terminus of the peptidic drug moiety (WO 02/088172; Doronina et al (2003) *Nature Biotechnology* 21(7):778-784; Francisco et al (2003) *Blood* 102(4):1458-1465).

Exemplary auristatin embodiments include the N-terminus linked monomethylauristatin drug moieties $D_E$ and $D_F$, disclosed in U.S. Pat. Nos. 7,498,298 and 7,659,241, the disclosures of which are expressly incorporated by reference in their entirety:

dently selected from H, $C_1$-$C_8$ alkyl and $C_3$-$C_8$ carbocycle and n is selected from 2, 3, 4, 5 and 6;

$R^6$ is selected from H and $C_1$-$C_8$ alkyl;

$R^7$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

each $R^8$ is independently selected from H, OH, $C_1$-$C_8$ alkyl, $C_3$-$C_8$ carbocycle and O—($C_1$-$C_8$ alkyl);

$R^9$ is selected from H and $C_1$-$C_8$ alkyl;

$R^{10}$ is selected from aryl or $C_3$-$C_8$ heterocycle;

Z is O, S, NH, or $NR^{12}$, wherein $R^{12}$ is $C_1$-$C_8$ alkyl;

$R^{11}$ is selected from H, $C_1$-$C_{20}$ alkyl, aryl, $C_3$-$C_8$ heterocycle, $-(R^{13}O)_m-R^{14}$, or $-(R^{13}O)_m-CH(R^{15})_2$;

m is an integer ranging from 1-1000;

$R^{13}$ is $C_2$-$C_8$ alkyl;

$R^{14}$ is H or $C_1$-$C_8$ alkyl;

each occurrence of $R^{15}$ is independently H, COOH, $-(CH_2)_n-N(R^{16})_2$, $-(CH_2)_n-SO_3H$, or $-(CH_2)_n-SO_3-C_1$-$C_8$ alkyl;

each occurrence of $R^{16}$ is independently H, $C_1$-$C_8$ alkyl, or $-(CH_2)_n-COOH$;

$R^{18}$ is selected from $-C(R^8)_2-C(R^8)_2$-aryl, $-C(R^8)_2-C(R^8)_2-(C_3$-$C_8$ heterocycle), and $-C(R^8)_2-C(R^8)_2-(C_3$-$C_8$ carbocycle); and n is an integer ranging from 0 to 6.

In one embodiment, $R^3$, $R^4$ and $R^7$ are independently isopropyl or sec-butyl and $R^5$ is —H or methyl. In an exemplary embodiment, $R^3$ and $R^4$ are each isopropyl, $R^5$ is —H, and $R^7$ is sec-butyl.

In yet another embodiment, $R^2$ and $R^6$ are each methyl, and $R^9$ is —H.

In still another embodiment, each occurrence of $R^8$ is $-OCH_3$.

$D_E$

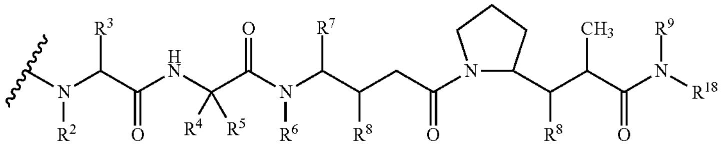

$D_F$

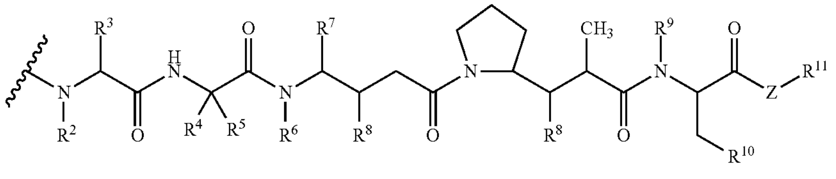

wherein the wavy line of $D_E$ and $D_F$ indicates the covalent attachment site to an antibody or antibody-linker component, and independently at each location:

$R^2$ is selected from H and $C_1$-$C_8$ alkyl;

$R^3$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^4$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^5$ is selected from H and methyl;

or $R^4$ and $R^5$ jointly form a carbocyclic ring and have the formula $-(CR^aR^b)_n-$ wherein $R^a$ and $R^b$ are indepen- In an exemplary embodiment, $R^3$ and $R^4$ are each isopropyl, $R^2$ and $R^6$ are each methyl, $R^5$ is —H, $R^7$ is sec-butyl, each occurrence of $R^8$ is $-OCH_3$, and $R^9$ is —H.

In one embodiment, Z is —O— or —NH—.

In one embodiment, $R^{10}$ is aryl.

In an exemplary embodiment, $R^{10}$ is -phenyl.

In an exemplary embodiment, when Z is —O—, $R^{11}$ is —H, methyl or t-butyl.

In one embodiment, when Z is —NH, $R^{11}$ is $-CH(R^{15})_2$, wherein $R^{15}$ is $-(CH_2)_n-N(R^{16})_2$, and $R^{16}$ is $-C_1$-$C_8$ alkyl or $-(CH_2)_n-COOH$.

In another embodiment, when Z is —NH, $R^{11}$ is $-CH(R^{15})_2$, wherein $R^{15}$ is $-(CH_2)_n-SO_3H$.

An exemplary auristatin embodiment of formula $D_E$ is MMAE, wherein the wavy line indicates the covalent attachment to a linker (L) of an antibody-drug conjugate:

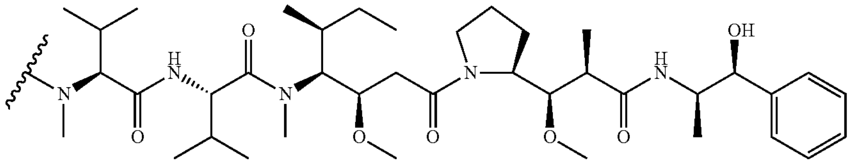

MMAE

An exemplary auristatin embodiment of formula $D_F$ is MMAF, wherein the wavy line indicates the covalent attachment to a linker (L) of an antibody-drug conjugate:

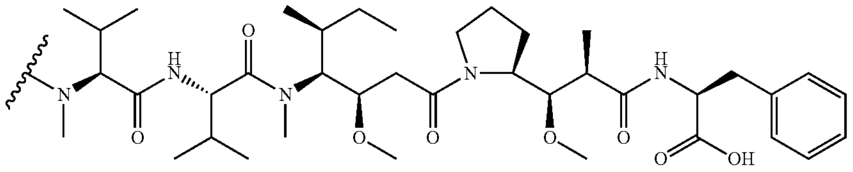

MMAF

Other exemplary embodiments include monomethylvaline compounds having phenylalanine carboxy modifications at the C-terminus of the pentapeptide auristatin drug moiety (WO 2007/008848) and monomethylvaline compounds having phenylalanine sidechain modifications at the C-terminus of the pentapeptide auristatin drug moiety (WO 2007/008603).

Nonlimiting exemplary embodiments of ADC of Formula I comprising MMAE or MMAF and various linker components have the following structures and abbreviations (wherein “Ab” is an antibody; p is 1 to about 8, “Val-Cit” is a valine-citrulline dipeptide; and “S” is a sulfur atom:

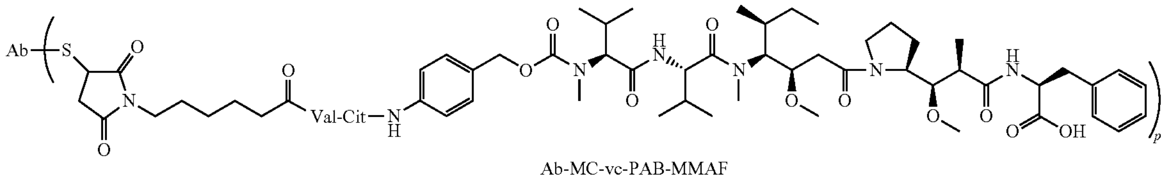

Ab-MC-vc-PAB-MMAF

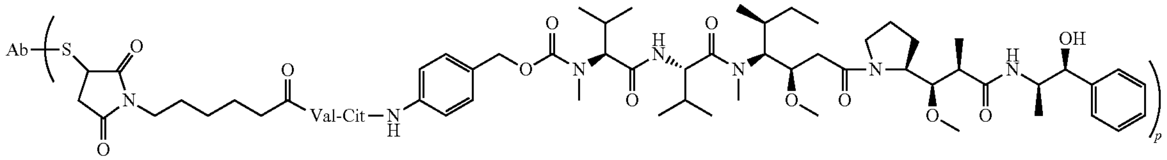

Ab-MC-vc-PAB-MMAE

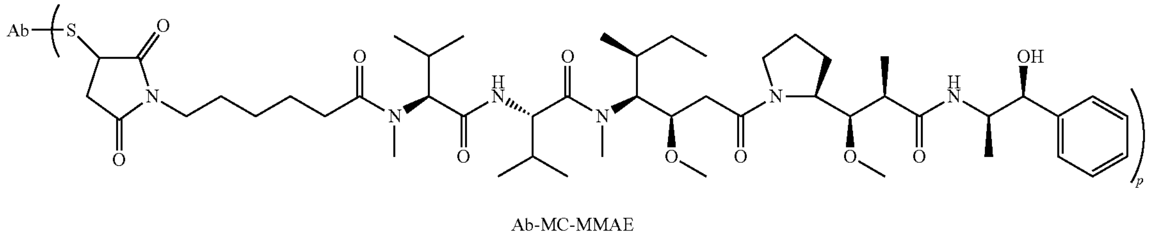

Ab-MC-MMAE

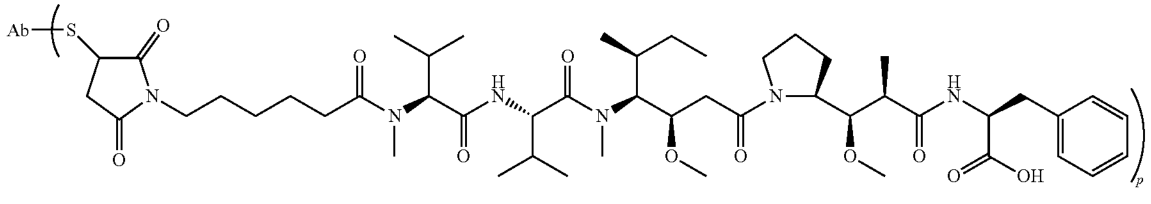

Ab-MC-MMAF

Nonlimiting exemplary embodiments of ADCs of Formula I comprising MMAF and various linker components further include Ab-MC-PAB-MMAF and Ab-PAB-MMAF. Immunoconjugates comprising MMAF attached to an antibody by a linker that is not proteolytically cleavable have been shown to possess activity comparable to immunoconjugates comprising MMAF attached to an antibody by a proteolytically cleavable linker (Doronina et al. (2006) *Bioconjugate Chem.* 17:114-124). In some such embodiments, drug release is believed to be effected by antibody degradation in the cell.

Typically, peptide-based drug moieties can be prepared by forming a peptide bond between two or more amino acids and/or peptide fragments. Such peptide bonds can be prepared, for example, according to a liquid phase synthesis method (see, e.g., E. Schröder and K. Lübke, "The Peptides", volume 1, pp 76-136, 1965, Academic Press). Auristatin/dolastatin drug moieties may, in some embodiments, be prepared according to the methods of: U.S. Pat. Nos. 7,498,298; 5,635,483; 5,780,588; Pettit et al (1989) *J. Am. Chem. Soc.* 111:5463-5465; Pettit et al (1998) *Anti-Cancer Drug Design* 13:243-277; Pettit, G. R., et al. *Synthesis,* 1996, 719-725; Pettit et al (1996) *J. Chem. Soc. Perkin Trans.* 1 5:859-863; and Doronina (2003) *Nat. Biotechnol.* 21(7):778-784.

In some embodiments, auristatin/dolastatin drug moieties of formulas $D_E$ such as MMAE, and $D_F$, such as MMAF, and drug-linker intermediates and derivatives thereof, such as MC-MMAF, MC-MMAE, MC-vc-PAB-MMAF, and MC-vc-PAB-MMAE, may be prepared using methods described in U.S. Pat. No. 7,498,298; Doronina et al. (2006) *Bioconjugate Chem.* 17:114-124; and Doronina et al. (2003) *Nat. Biotech.* 21:778-784 and then conjugated to an antibody of interest.

(3) Calicheamicin

In some embodiments, the immunoconjugate comprises an antibody conjugated to one or more calicheamicin molecules. The calicheamicin family of antibiotics, and analogues thereof, are capable of producing double-stranded DNA breaks at sub-picomolar concentrations (Hinman et al., (1993) *Cancer Research* 53:3336-3342; Lode et al., (1998) *Cancer Research* 58:2925-2928). Calicheamicin has intracellular sites of action but, in certain instances, does not readily cross the plasma membrane. Therefore, cellular uptake of these agents through antibody-mediated internalization may, in some embodiments, greatly enhances their cytotoxic effects. Nonlimiting exemplary methods of preparing antibody-drug conjugates with a calicheamicin drug moiety are described, for example, in U.S. Pat. Nos. 5,712,374; 5,714,586; 5,739,116; and 5,767,285.

In some embodiments, the calicheamicin drug moiety conjugated to the antibody is a compound having the formula:

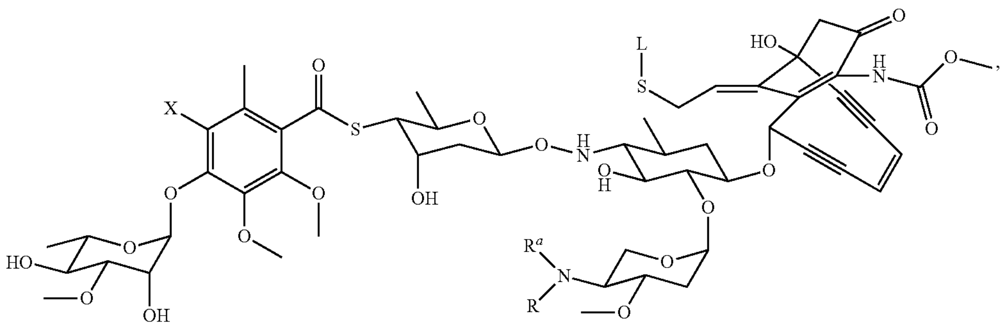

wherein X is Br or I;

L is a linker; R is hydrogen, $C_{1-6}$alkyl, or —C(=O) $C_{1-6}$alkyl; and $R^a$ is hydrogen or $C_{1-6}$alkyl.

In some embodiments, X is Br, $R^a$ is hydrogen and R is isopropyl.

In other embodiments, X is Br, $R^a$ is hydrogen and R is ethyl.

In other embodiments, X is I, $R^a$ is hydrogen and R is isopropyl.

In other embodiments, X is I, $R^a$ is hydrogen and R is ethyl.

In some embodiments, X is Br, $R^a$ is hydrogen and R—C(=O)$CH_3$.

In other embodiments, X is I, $R^a$ is hydrogen and R is —C(=O)$CH_3$.

In other embodiments, X is I, $R^a$ is ethyl and R is —C(=O)$CH_3$.

In other embodiments, X is Br, $R^a$ is ethyl and R is —C(=O)$CH_3$.

(4) Pyrrolobenzodiazepines

In some embodiments, an ADC comprises a pyrrolobenzodiazepine (PBD). In some embodiments, PBD dimers recognize and bind to specific DNA sequences. The natural product anthramycin, a PBD, was first reported in 1965 (Leimgruber, et al., (1965) *J. Am. Chem. Soc.,* 87:5793-5795; Leimgruber, et al., (1965) *J. Am. Chem. Soc.,* 87:5791-5793). Since then, a number of PBDs, both naturally-occurring and analogues, have been reported (Thurston, et al., (1994) Chem. Rev. 1994, 433-465 including dimers of the tricyclic PBD scaffold (U.S. Pat. Nos. 6,884,799; 7,049,311; 7,067,511; 7,265,105; 7,511,032; 7,528,126; 7,557,099). Without intending to be bound by any particular theory, it is believed that the dimer structure imparts the appropriate three-dimensional shape for isohelicity with the minor groove of B-form DNA, leading to a snug fit at the binding site (Kohn, In Antibiotics III. Springer-Verlag, New York, pp. 3-11 (1975); Hurley and Needham-VanDevanter, (1986) *Acc. Chem. Res.,* 19:230-237). Dimeric PBD compounds bearing C2 aryl substituents have been shown to be useful as cytotoxic agents (Hartley et al (2010) *Cancer Res.* 70(17):6849-6858; Antonow (2010) *J. Med. Chem.* 53(7):2927-2941; Howard et al (2009) *Bioorganic and Med. Chem. Letters* 19(22):6463-6466).

In some embodiments, PBD compounds can be employed as prodrugs by protecting them at the N10 position with a nitrogen protecting group which is removable in vivo (WO 00/12507; WO 2005/023814).

PBD dimers have been conjugated to antibodies and the resulting ADC shown to have anti-cancer properties (US 2010/0203007). Nonlimiting exemplary linkage sites on the PBD dimer include the five-membered pyrrolo ring, the tether between the PBD units, and the N10-C11 imine group (WO 2009/016516; US 2009/304710; US 2010/047257; US 2009/036431; US 2011/0256157; WO 2011/130598).

Nonlimiting exemplary PBD dimer components of ADCs are of Formula A:

A

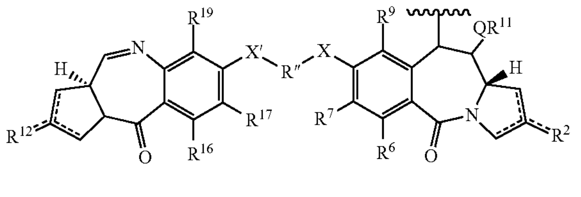

and salts and solvates thereof, wherein:

the wavy line indicates the covalent attachment site to the linker;

the dotted lines indicate the optional presence of a double bond between C1 and C2 or C2 and C3;

$R^2$ is independently selected from H, OH, =O, =$CH_2$, CN, R, OR, =CH—$R^D$, =$C(R^D)_2$, O—$SO_2$—R, $CO_2R$ and COR, and optionally further selected from halo or dihalo, wherein $R^D$ is independently selected from R, $CO_2R$, COR, CHO, $CO_2H$, and halo;

$R^6$ and $R^9$ are independently selected from H, R, OH, OR, SH, SR, $NH_2$, NHR, NRR', $NO_2$, $Me_3Sn$ and halo;

$R^7$ is independently selected from H, R, OH, OR, SH, SR, $NH_2$, NHR, NRR', $NO_2$, $Me_3Sn$ and halo;

Q is independently selected from O, S and NH;

$R^{11}$ is either H, or R or, where Q is O, $SO_3M$, where M is a metal cation;

R and R' are each independently selected from optionally substituted $C_{1-8}$ alkyl, $C_{1-12}$ alkyl, $C_{3-8}$ heterocyclyl, $C_{3-20}$ heterocycle, and $C_{5-20}$ aryl groups, and optionally in relation to the group NRR', R and R' together with the nitrogen atom to which they are attached form an optionally substituted 4-, 5-, 6- or 7-membered heterocyclic ring;

$R^{12}$, $R^{16}$, $R^{19}$ and $R^{17}$ are as defined for $R^2$, $R^6$, $R^9$ and $R^7$ respectively;

R" is a $C_{3-12}$ alkylene group, which chain may be interrupted by one or more heteroatoms, e.g. O, S, N(H), NMe and/or aromatic rings, e.g. benzene or pyridine, which rings are optionally substituted; and X and X' are independently selected from O, S and N(H).

In some embodiments, R and R' are each independently selected from optionally substituted $C_{1-12}$ alkyl, $C_{3-20}$ heterocycle, and $C_{5-20}$ aryl groups, and optionally in relation to the group NRR', R and R' together with the nitrogen atom to which they are attached form an optionally substituted 4-, 5-, 6- or 7-membered heterocyclic ring.

In some embodiments, $R^9$ and $R^{19}$ are H.

In some embodiments, $R^6$ and $R^{16}$ are H.

In some embodiments, $R^7$ are $R^{17}$ are both $OR^{7A}$, where $R^{7A}$ is optionally substituted $C_{1-4}$ alkyl. In some embodiments, $R^{7A}$ is Me. In some embodiments, $R^{7A}$ is $Ch_2Ph$, where Ph is a phenyl group.

In some embodiments, X is O.

In some embodiments, $R^{11}$ is H.

In some embodiments, there is a double bond between C2 and C3 in each monomer unit.

In some embodiments, $R^2$ and $R^{12}$ are independently selected from H and R. In some embodiments, $R^2$ and $R^{12}$ are independently R. In some embodiments, $R^2$ and $R^{12}$ are independently optionally substituted $C_{5-20}$ aryl or $C_{5-7}$ aryl or $C_{8-10}$ aryl. In some embodiments, $R^2$ and $R^{12}$ are independently optionally substituted phenyl, thienyl, napthyl, pyridyl, quinolinyl, or isoquinolinyl. In some embodiments, $R^2$ and $R^{12}$ are independently selected from =O, =$CH_2$, =CH—$R^D$, and =$C(R^D)_2$. In some embodiments, $R^2$ and $R^{12}$ are each =$CH_2$. In some embodiments, $R^2$ and $R^{12}$ are each H. In some embodiments, $R^2$ and $R^{12}$ are each =O. In some embodiments, $R^2$ and $R^{12}$ are each =$CF_2$. In some embodiments, $R^2$ and/or $R^{12}$ are independently =$C(R^D)_2$. In some embodiments, $R^2$ and/or $R^{12}$ are independently =CH—$R^D$.

In some embodiments, when $R^2$ and/or $R^{12}$ is =CH—$R^D$, each group may independently have either configuration shown below:

(I)

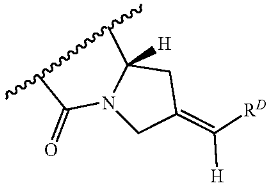

(II)

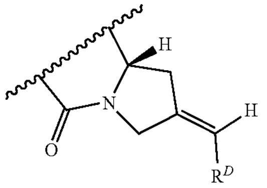

In some embodiments, a =CH—$R^D$ is in configuration (I).

In some embodiments, R" is a $C_3$ alkylene group or a $C_5$ alkylene group.

In some embodiments, an exemplary PBD dimer component of an ADC has the structure of Formula A(I):

A(I)

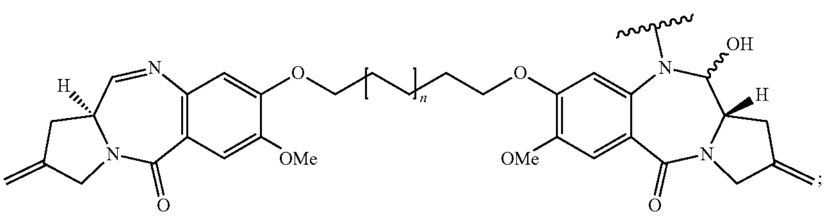

wherein n is 0 or 1.

In some embodiments, an exemplary PBD dimer component of an ADC has the structure of Formula A(II):

A(II)

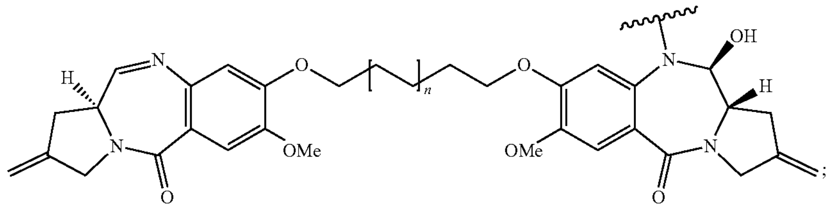

wherein n is 0 or 1.

In some embodiments, an exemplary PBD dimer component of an ADC has the structure of Formula A(III):

A(III)

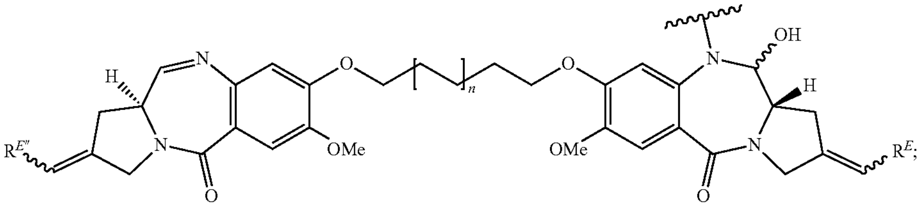

wherein $R^E$ and $R^{E''}$ are each independently selected from H or $R^D$, wherein $R^D$ is defined as above; and wherein n is 0 or 1.

In some embodiments, n is 0. In some embodiments, n is 1. In some embodiments, $R^E$ and/or $R^{E''}$ is H. In some embodiments, $R^E$ and $R^{E''}$ are H. In some embodiments, $R^E$ and/or $R^{E''}$ is $R^D$, wherein $R^D$ is optionally substituted $C_{1-12}$ alkyl. In some embodiments, $R^E$ and/or $R^{E''}$ is $R^D$, wherein $R^D$ is methyl.

In some embodiments, an exemplary PBD dimer component of an ADC has the structure of Formula A(IV):

A(IV)

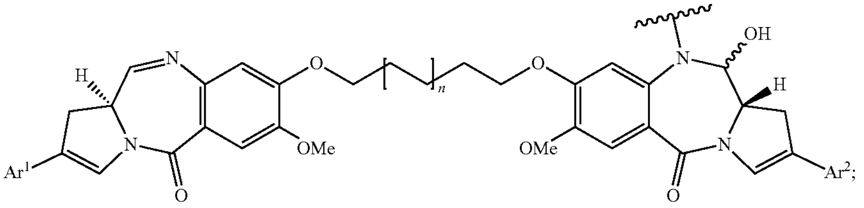

wherein $Ar^1$ and $Ar^2$ are each independently optionally substituted $C_{5-20}$ aryl; wherein $Ar^1$ and $Ar^2$ may be the same or different; and wherein n is 0 or 1.

In some embodiments, an exemplary PBD dimer component of an ADC has the structure of Formula A(V):

A(V)

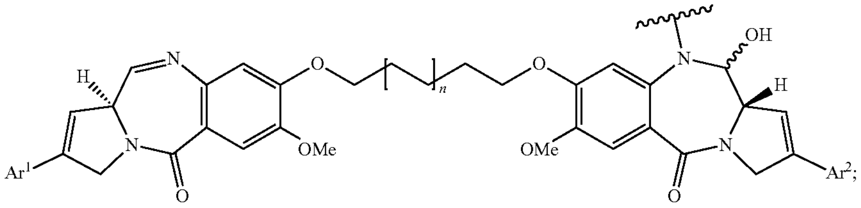

wherein $Ar^1$ and $Ar^2$ are each independently optionally substituted $C_{5-20}$ aryl; wherein $Ar^1$ and $Ar^2$ may be the same or different; and wherein n is 0 or 1.

In some embodiments, $Ar^1$ and $Ar^2$ are each independently selected from optionally substituted phenyl, furanyl, thiophenyl and pyridyl. In some embodiments, $Ar^1$ and $Ar^2$ are each independently optionally substituted phenyl. In some embodiments, $Ar^1$ and $Ar^2$ are each independently optionally substituted thien-2-yl or thien-3-yl. In some embodiments, $Ar^1$ and $Ar^2$ are each independently optionally substituted quinolinyl or isoquinolinyl. The quinolinyl or isoquinolinyl group may be bound to the PBD core through any available ring position. For example, the quinolinyl may be quinolin-2-yl, quinolin-3-yl, quinolin-4yl, quinolin-5-yl, quinolin-6-yl, quinolin-7-yl and quinolin-8-yl. In some embodiments, the quinolinyl is selected from quinolin-3-yl and quinolin-6-yl. The isoquinolinyl may be isoquinolin-1-yl, isoquinolin-3-yl, isoquinolin-4yl, isoquinolin-5-yl, isoquinolin-6-yl, isoquinolin-7-yl and isoquinolin-8-yl. In some embodiments, the isoquinolinyl is selected from isoquinolin-3-yl and isoquinolin-6-yl.

Further nonlimiting exemplary PBD dimer components of ADCs are of Formula B:

B

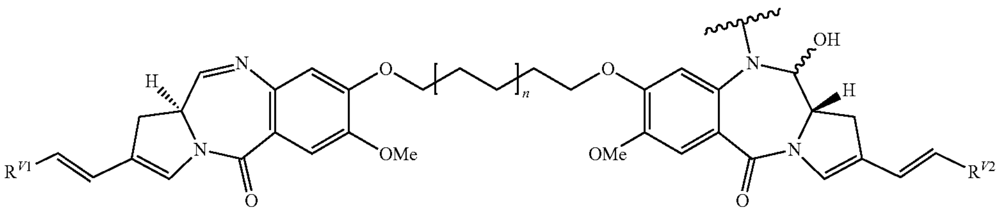

and salts and solvates thereof, wherein:

the wavy line indicates the covalent attachment site to the linker;

the wavy line connected to the OH indicates the S or R configuration;

$R^{V1}$ and $R^{V2}$ are independently selected from H, methyl, ethyl and phenyl (which phenyl may be optionally substituted with fluoro, particularly in the 4 position) and $C_{5-6}$ heterocyclyl; wherein $R^{V1}$ and $R^{V2}$ may be the same or different; and n is 0 or 1.

In some embodiments, $R^{V1}$ and $R^{V2}$ are independently selected from H, phenyl, and 4-fluorophenyl.

In some embodiments, a linker may be attached at one of various sites of the PBD dimer drug moiety, including the N10 imine of the B ring, the C-2 endo/exo position of the C ring, or the tether unit linking the A rings (see structures C(I) and C(II) below).

Nonlimiting exemplary PBD dimer components of ADCs include Formulas C(I) and C(II):

C(I)

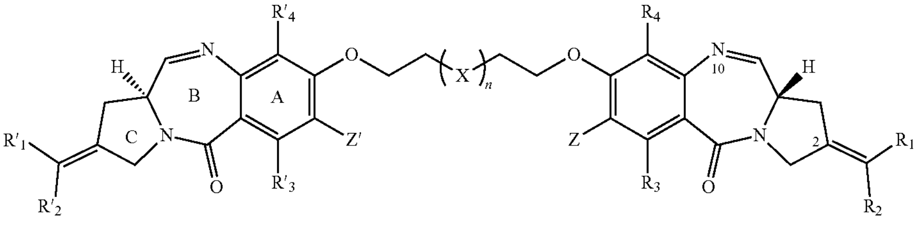

C(II)

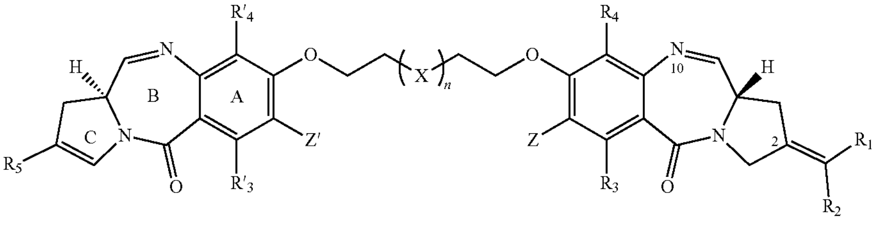

Formulas C(I) and C(II) are shown in their N10-C11 imine form. Exemplary PBD drug moieties also include the carbinolamine and protected carbinolamine forms as well, as shown in the table below:

| | | |
|---|---|---|
| 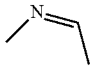 | 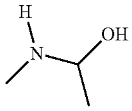 | 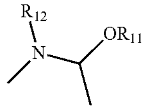 |
| Imine | Carbinolamine | Protected Carbinolamine |

wherein:

X is $CH_2$ (n=1 to 5), N, or O;

Z and Z' are independently selected from OR and $NR_2$, where R is a primary, secondary or tertiary alkyl chain containing 1 to 5 carbon atoms;

$R_1$, $R'_1$, $R_2$ and $R'_2$ are each independently selected from H, $C_1$-$C_8$ alkyl, $C_2$-$C_8$ alkenyl, $C_2$-$C_8$ alkynyl, $C_{5-20}$ aryl (including substituted aryls), $C_{5-20}$ heteroaryl groups, —$NH_2$, —NHMe, —OH, and —SH, where, in some embodiments, alkyl, alkenyl and alkynyl chains comprise up to 5 carbon atoms;

$R_3$ and $R'_3$ are independently selected from H, OR, NHR, and $NR_2$, where R is a primary, secondary or tertiary alkyl chain containing 1 to 5 carbon atoms;

$R_4$ and $R'_4$ are independently selected from H, Me, and OMe;

$R_5$ is selected from $C_1$-$C_8$ alkyl, $C_2$-$C_8$ alkenyl, $C_2$-$C_8$ alkynyl, $C_{5-20}$ aryl (including aryls substituted by halo, nitro, cyano, alkoxy, alkyl, heterocyclyl) and $C_{5-20}$ heteroaryl groups, where, in some embodiments, alkyl, alkenyl and alkynyl chains comprise up to 5 carbon atoms;

$R_{11}$ is H, $C_1$-$C_8$ alkyl, or a protecting group (such as acetyl, trifluoroacetyl, t-butoxycarbonyl (BOC), benzyloxycarbonyl (CBZ), 9-fluorenylmethylenoxycarbonyl (Fmoc), or a moiety comprising a self-immolating unit such as valine-citrulline-PAB);

$R_{12}$ is H, $C_1$-$C_8$ alkyl, or a protecting group;

wherein a hydrogen of one of $R_1$, $R'_1$, $R_2$, $R'_2$, $R_5$, or $R_{12}$ or a hydrogen of the —$OCH_2CH_2(X)_nCH_2CH_2O$— spacer between the A rings is replaced with a bond connected to the linker of the ADC.

Exemplary PBD dimer portions of ADC include, but are not limited to (the wavy line indicates the site of covalent attachment to the linker):

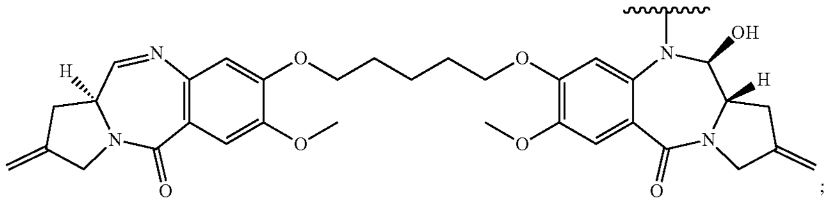
;

PBD dimer

Nonlimiting exemplary embodiments of ADCs comprising PBD dimers have the following structures:

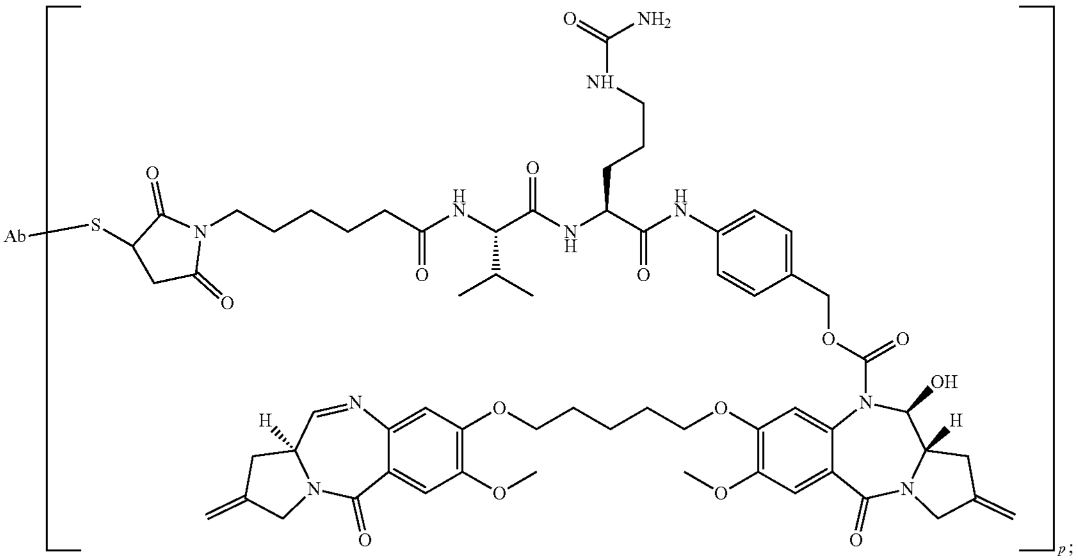

PBD dimer-val-cit-PAB-Ab

-continued

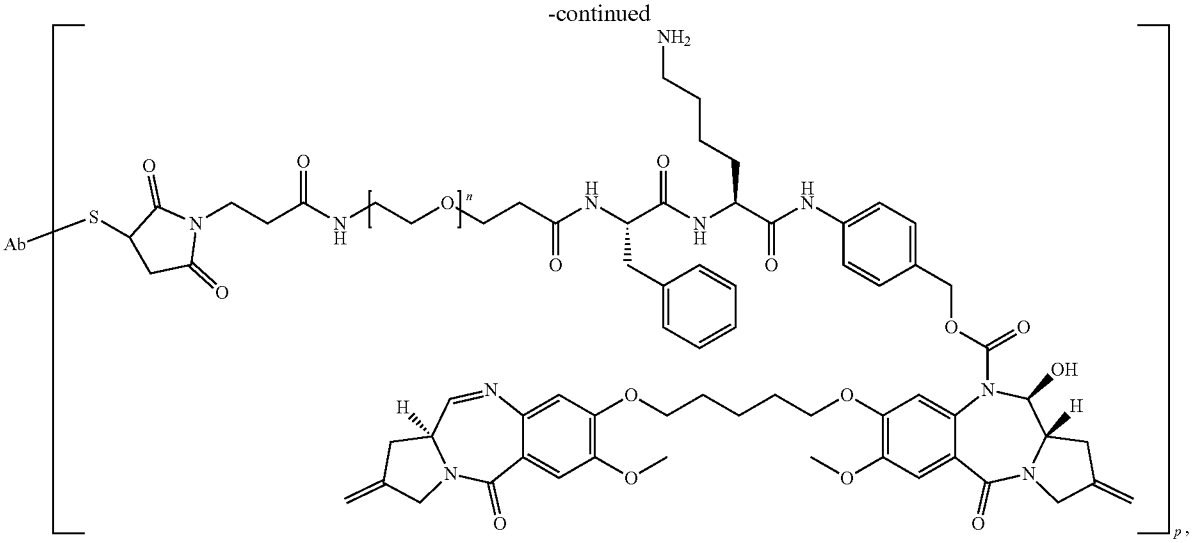

PBD dimer-Phe-Lys-PAB-Ab wherein:

n is 0 to 12. In some embodiments, n is 2 to 10. In some embodiments, n is 4 to 8. In some embodiments, n is selected from 4, 5, 6, 7, and 8.

A further non-limiting exemplary ADC comprising a PBD dimer may be made by conjugating a monomethyl disulfide N10-linked PBD (shown below) to an antibody:

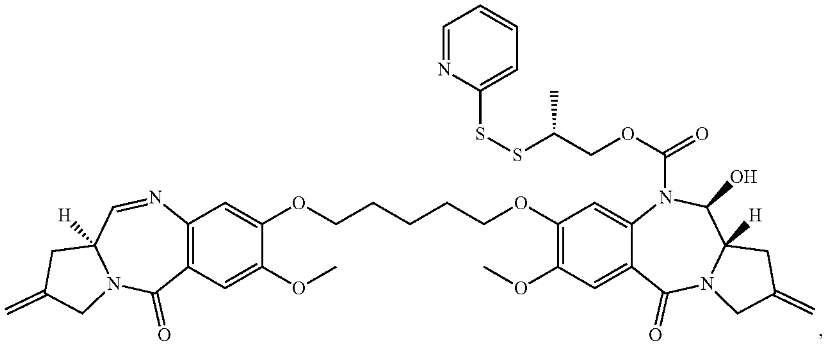

to produce a monomethyl disulfide N10-linked PBD antibody-drug conjugate:

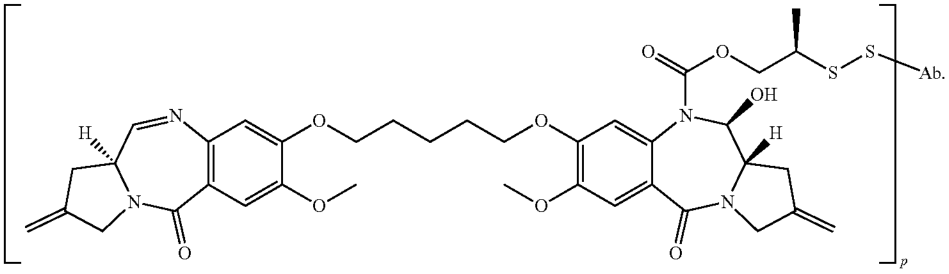

See, e.g., PCT Publication No. WO 2013/055987.

The linkers of PBD dimer-val-cit-PAB-Ab and the PBD dimer-Phe-Lys-PAB-Ab are protease cleavable, while the linker of PBD dimer-maleimide-acetal is acid-labile.

PBD dimers and ADC comprising PBD dimers may be prepared according to methods known in the art. See, e.g., WO 2009/016516; US 2009/304710; US 2010/047257; US 2009/036431; US 2011/0256157; WO 2011/130598; WO 2013/055987.

(5) Anthracyclines

In some embodiments, an ADC comprises an anthracycline. Anthracyclines are antibiotic compounds that exhibit cytotoxic activity. While not intending to be bound by any particular theory, studies have indicated that anthracyclines may operate to kill cells by a number of different mechanisms, including: 1) intercalation of the drug molecules into the DNA of the cell thereby inhibiting DNA-dependent nucleic acid synthesis; 2) production by the drug of free radicals which then react with cellular macromolecules to cause damage to the cells, and/or 3) interactions of the drug molecules with the cell membrane (see, e.g., C. Peterson et al., "Transport And Storage Of Anthracycline In Experimental Systems And Human Leukemia" in *Anthracycline Antibiotics In Cancer Therapy*; N. R. Bachur, "Free Radical Damage" id. at pp. 97-102). Because of their cytotoxic potential anthracyclines have been used in the treatment of numerous cancers such as leukemia, breast carcinoma, lung carcinoma, ovarian adenocarcinoma and sarcomas (see e.g., P. H. Wiernik, in *Anthracycline: Current Status And New Developments* p 11).

Nonlimiting exemplary anthracyclines include doxorubicin, epirubicin, idarubicin, daunomycin, nemorubicin, and derivatives thereof. Immunoconjugates and prodrugs of daunorubicin and doxorubicin have been prepared and studied (Kratz et al (2006) *Current Med. Chem.* 13:477-523; Jeffrey et al (2006) *Bioorganic & Med. Chem. Letters* 16:358-362; Torgov et al (2005) *Bioconj. Chem.* 16:717-721; Nagy et al (2000) *Proc. Natl. Acad. Sci. USA* 97:829-834; Dubowchik et al (2002) *Bioorg. & Med. Chem. Letters* 12:1529-1532; King et al (2002) *J. Med. Chem.* 45:4336-4343; EP 0328147; U.S. Pat. No. 6,630,579). The antibody-drug conjugate BR96-doxorubicin reacts specifically with the tumor-associated antigen Lewis-Y and has been evaluated in phase I and II studies (Saleh et al (2000) *J. Clin. Oncology* 18:2282-2292; Ajani et al (2000) *Cancer Jour.* 6:78-81; Tolcher et al (1999) *J. Clin. Oncology* 17:478-484).

PNU-159682 is a potent metabolite (or derivative) of nemorubicin (Quintieri, et al. (2005) *Clinical Cancer Research* 11(4):1608-1617). Nemorubicin is a semisynthetic analog of doxorubicin with a 2-methoxymorpholino group on the glycoside amino of doxorubicin and has been under clinical evaluation (Grandi et al (1990) *Cancer Treat. Rev.* 17:133; Ripamonti et al (1992) *Brit. J. Cancer* 65:703), including phase II/III trials for hepatocellular carcinoma (Sun et al (2003) *Proceedings of the American Society for Clinical Oncology* 22, Abs1448; Quintieri (2003) *Proceedings of the American Association of Cancer Research,* 44:1st Ed, Abs 4649; Pacciarini et al (2006) *Jour. Clin. Oncology* 24:14116).

A nonlimiting exemplary ADC comprising nemorubicin or nemorubicin derivatives is shown in Formula Ia:

(Ia)

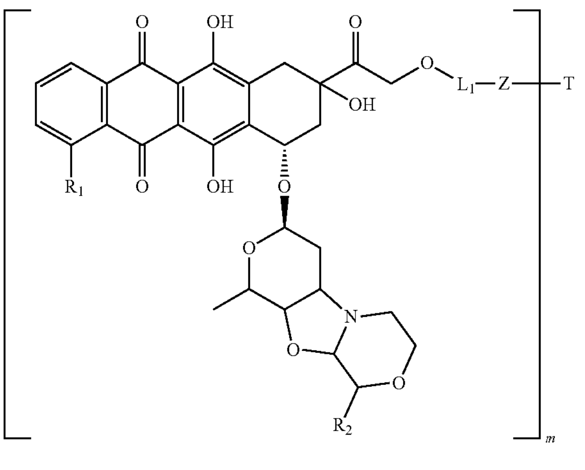

wherein $R_1$ is hydrogen atom, hydroxy or methoxy group and $R_2$ is a $C_1$-$C_5$ alkoxy group, or a pharmaceutically acceptable salt thereof;

$L_1$ and Z together are a linker (L) as described herein;

T is an antibody (Ab) as described herein; and m is 1 to about 20. In some embodiments, m is 1 to 10, 1 to 7, 1 to 5, or 1 to 4.

In some embodiments, $R_1$ and $R_2$ are both methoxy (—OMe).

A further nonlimiting exemplary ADC comprising nemorubicin or nemorubicin derivatives is shown in Formula Ib:

(Ib)

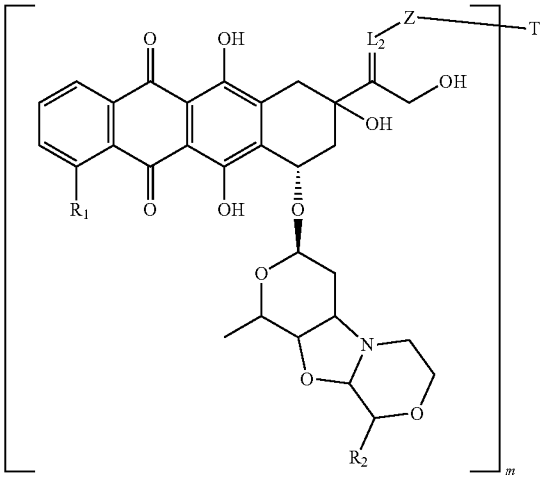

wherein $R_1$ is hydrogen atom, hydroxy or methoxy group and $R_2$ is a $C_1$-$C_5$ alkoxy group, or a pharmaceutically acceptable salt thereof;

$L_2$ and Z together are a linker (L) as described herein;

T is an antibody (Ab) as described herein; and m is 1 to about 20. In some embodiments, m is 1 to 10, 1 to 7, 1 to 5, or 1 to 4.

In some embodiments, $R_1$ and $R_2$ are both methoxy (—OMe).

In some embodiments, the nemorubicin component of a nemorubicin-containing ADC is PNU-159682. In some such embodiments, the drug portion of the ADC may have one of the following structures:

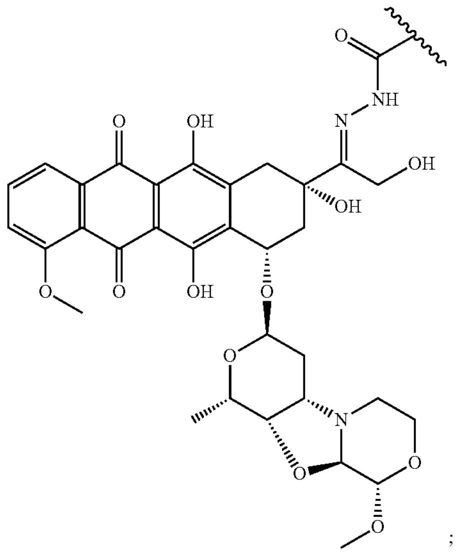
; or
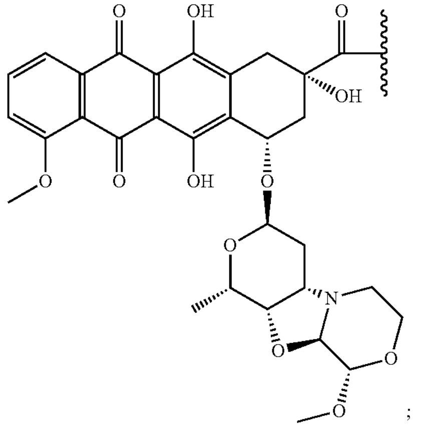
;
wherein the wavy line indicates the attachment to the linker (L).
Anthracyclines, including PNU-159682, may be conjugated to antibodies through several linkage sites and a variety of linkers (US 2011/0076287; WO2009/099741; US 2010/0034837; WO 2010/009124), including the linkers described herein.
Exemplary ADCs comprising a nemorubicin and linker include, but are not limited to:
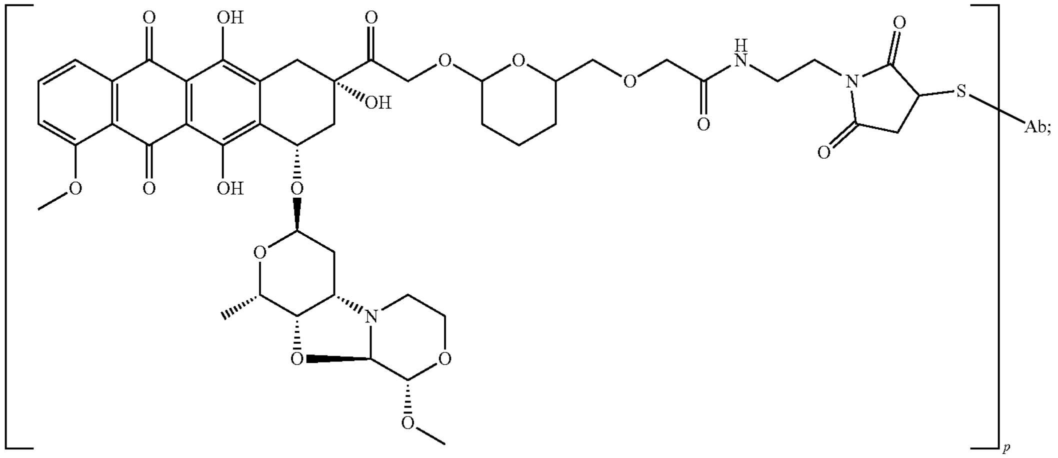
PNU-159682 maleimide acetal-Ab -continued
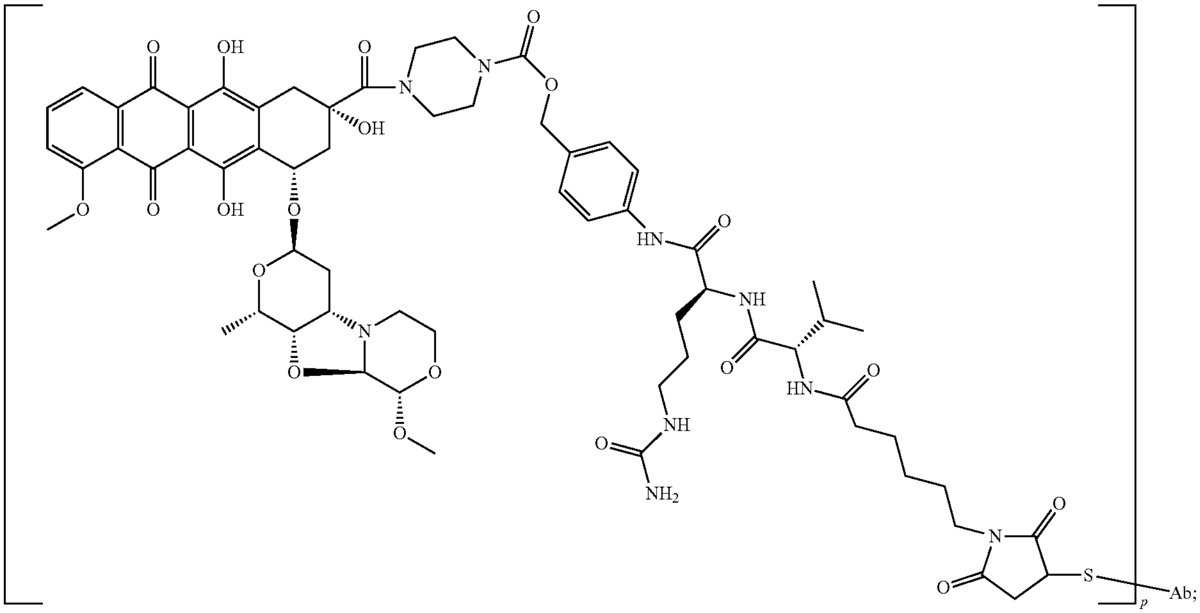
PNU-159682-val-cit-PAB-Ab
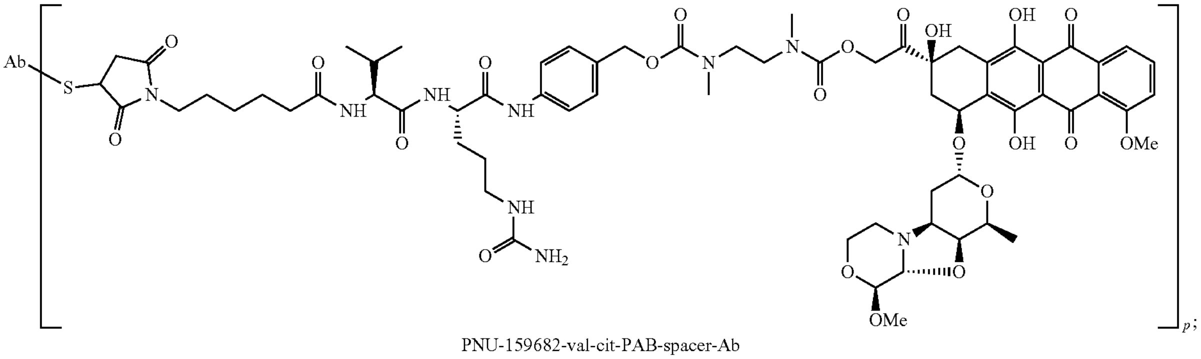
PNU-159682-val-cit-PAB-spacer-Ab -continued
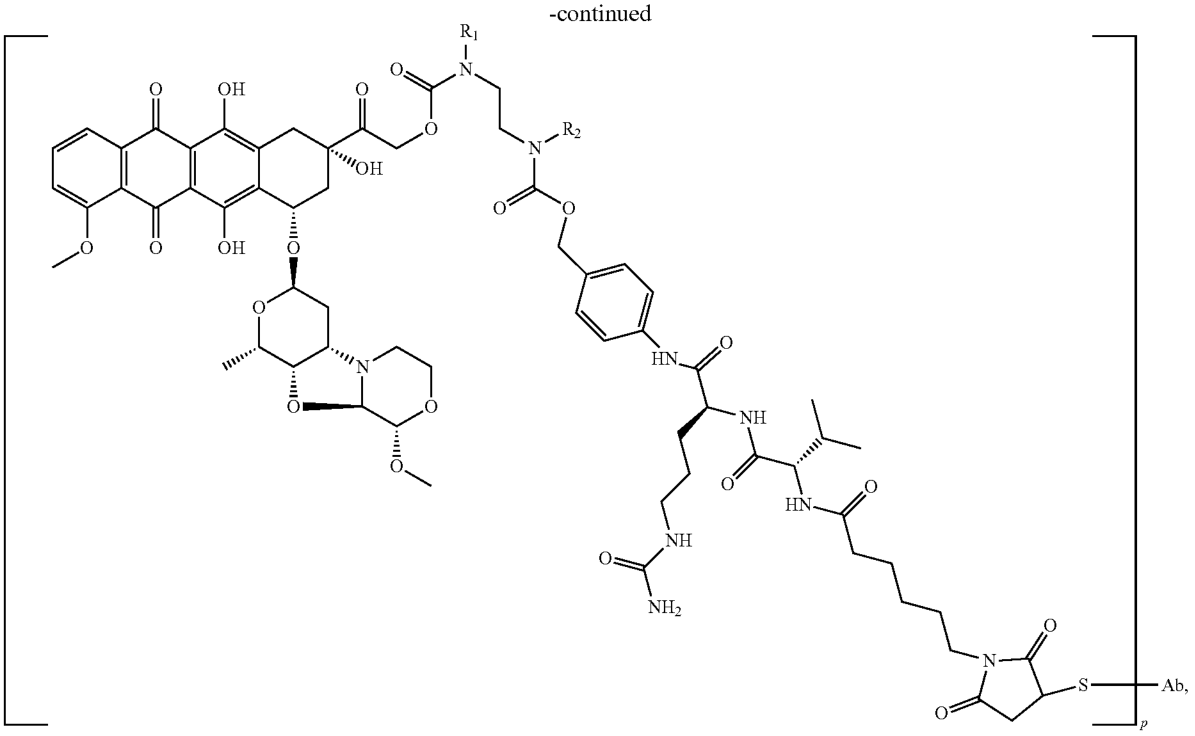
PNU-159682-val-cit-PAB-spacer($R^1R^2$)-Ab
wherein:
$R_1$ and $R_2$ are independently selected from H and $C_1$-$C_6$ alkyl; and
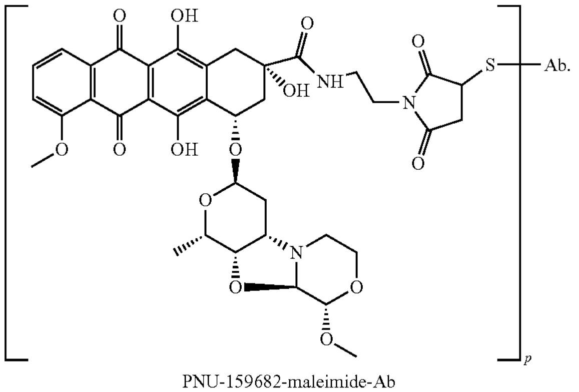
PNU-159682-maleimide-Ab
A further non-limiting exemplary ADC comprising a PBD dimer may be made by conjugating a pyridyl disulfide PNU amide (shown below) to an antibody:
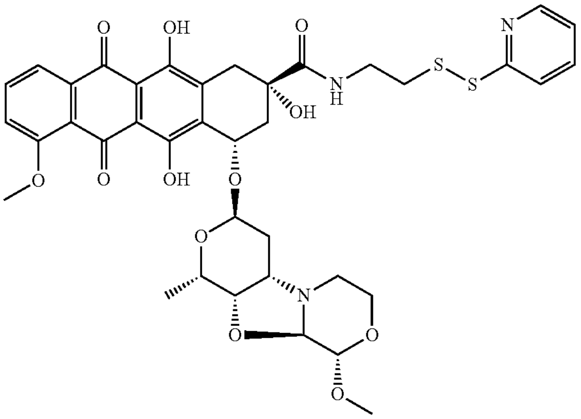 [SMILES: COc1cccc2c1C(=O)c1c(O)c3c(c(O)c1C2=O)C[C@@](O)(C(=O)NCCSSc1ccccn1)C[C@@H]3O[C@H]1C[C@H]2[C@H](O[C@@H]3[C@@H](OC)OCCN32)[C@H](C)O1]
to produce a disulfide-linked PNU-159682 antibody-drug conjugate:
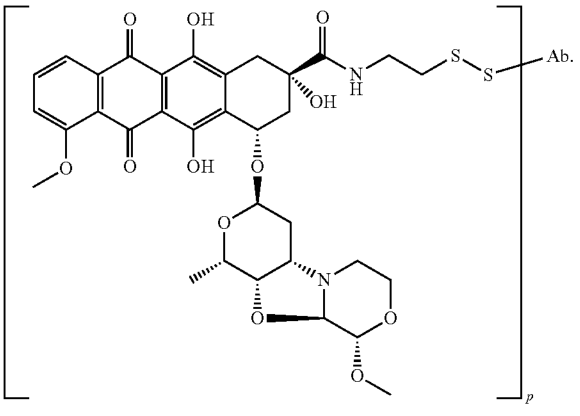

The linker of PNU-159682 maleimide acetal-Ab is acid-labile, while the linkers of PNU-159682-val-cit-PAB-Ab, PNU-159682-val-cit-PAB-spacer-Ab, and PNU-159682-val-cit-PAB-spacer($R^1R^2$)-Ab are protease cleavable.

(6) 1-(Chloromethyl)-2,3-dihydro-1H-benzo[e]indole (CBI) Dimer Drug Moieties In some embodiments, an ADC comprises 1-(chloromethyl)-2,3-dihydro-1H-benzo[e]indole (CBI). The 5-amino-1-(chloromethyl)-1,2-dihydro-3H-benz[e]indole (amino CBI) class of DNA minor groove alkylators are potent cytotoxins (Atwell, et al (1999) J. Med. Chem., 42:3400), and have been utilized as effector units in a number of classes of prodrugs designed for cancer therapy. These have included antibody conjugates, (Jeffrey, et al. (2005) J. Med. Chem., 48:1344), prodrugs for gene therapy based on nitrobenzyl carbamates (Hay, et al (2003) J. Med. Chem. 46:2456) and the corresponding nitro-CBI derivatives as hypoxia-activated prodrugs (Tercel, et al (2011) Angew. Chem., Int. Ed., 50:2606-2609). The CBI and pyrrolo[2,1-c][1,4]benzodiazepine (PBD) pharmacophores have been linked together by an alkyl chain (Tercel et al (2003) J. Med. Chem 46:2132-2151).

In some embodiments, an ADC comprises a 1-(chloromethyl)-2,3-dihydro-1H-benzo[e]indole (CBI) dimer. In some such embodiments, the dimer is a heterodimer wherein one half of the dimer is a CBI moiety and the other half of the dimer is a PBD moiety.

In some embodiments, a CBI dimer comprises the formula:

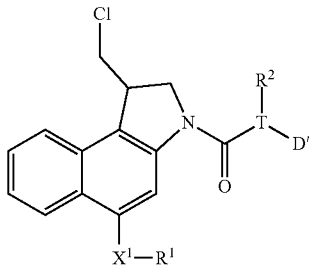

where $R^1$ is selected from H, $P(O)_3H_2$, $C(O)NR^aR^b$, or a bond to a linker (L);

$R^2$ is selected from H, $P(O)_3H_2$, $C(O)NR^aR^b$, or a bond to a linker (L);

$R^a$ and $R^b$ are independently selected from H and $C_1$-$C_6$ alkyl optionally substituted with one or more F, or $R^a$ and $R^b$ form a five or six membered heterocyclyl group;

T is a tether group selected from $C_3$-$C_{12}$ alkylene, Y, ($C_1$-$C_6$ alkylene)-Y—($C_1$-$C_6$ alkylene), ($C_1$-$C_6$ alkylene)-Y—($C_1$-$C_6$ alkylene)-Y—($C_1$-$C_6$ alkylene), ($C_2$-$C_6$ alkenylene)-Y—($C_2$-$C_6$ alkenylene), and ($C_2$-$C_6$ alkynylene)-Y—($C_2$-$C_6$ alkynylene);

where Y is independently selected from O, S, $NR^1$, aryl, and heteroaryl;

where alkylene, alkenylene, aryl, and heteroaryl are independently and optionally substituted with F, OH, O($C_1$-$C_6$ alkyl), $NH_2$, $NHCH_3$, $N(CH_3)_2$, $OP(O)_3H_2$, and $C_1$-$C_6$ alkyl, where alkyl is optionally substituted with one or more F;

or alkylene, alkenylene, aryl, and heteroaryl are independently and optionally substituted with a bond to L;

D' is a drug moiety selected from:

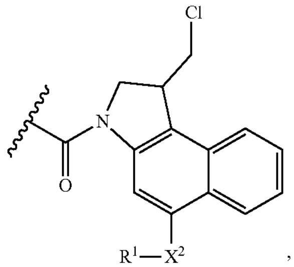

,

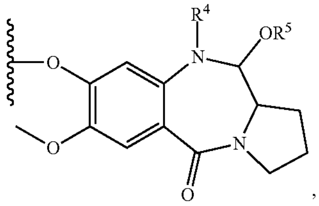

, and

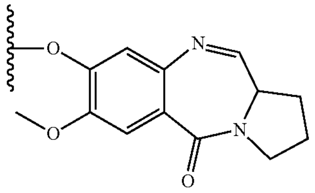

where the wavy line indicates the site of attachment to T;

$X^1$ and $X^2$ are independently selected from O and $NR^3$, where $R^3$ is selected from H and $C_1$-$C_6$ alkyl optionally substituted with one or more F;

$R^4$ is H, $CO_2R$, or a bond to a linker (L), where R is $C_1$-$C_6$ alkyl or benzyl; and $R^5$ is H or $C_1$-$C_6$ alkyl.

Linker-drug intermediates 51-86 of Table A were prepared by coupling a CBI dimer or a CBI/PBD heterodimer drug moiety with a linker reagent, according to the procedures of WO 2015/023355, incorporated by reference herein in its entirety.

TABLE A
| Linker-CBI dimer and CBI/PBD heterodimer drug intermediates 51-86 | | |
|---|---|---|
| No | Structure | Name |
| 51 | 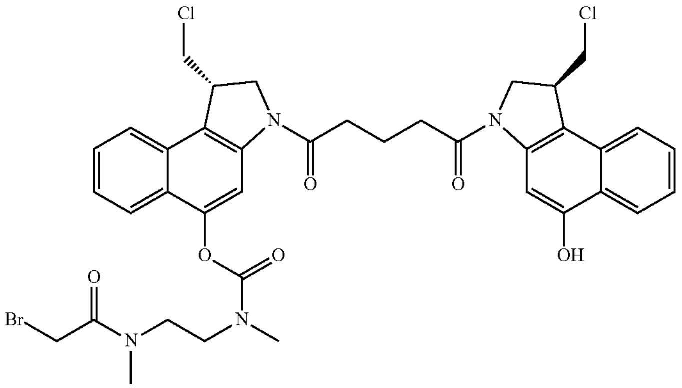 [SMILES: CN(CCN(C)C(=O)Oc1cc2c(c3ccccc13)[C@H](CCl)CN2C(=O)CCCC(=O)N1C[C@@H](CCl)c2c1cc(O)c1ccccc21)C(=O)CBr] | (S)-1-(chloromethyl)-3-(5-((S)-1-(chloromethyl)-5-hydroxy-1H-benzo[e]indol-3(2H)-yl)-5-oxopentanoyl)-2,3-dihydro-1H-benzo[e]indol-5-yl 2-(2-bromo-N-methylacetamido)ethyl(methyl) carbamate |

TABLE A-continued
| Linker-CBI dimer and CBI/PBD heterodimer drug intermediates 51-86 | | |
|---|---|---|
| No | Structure | Name |
| 52 | 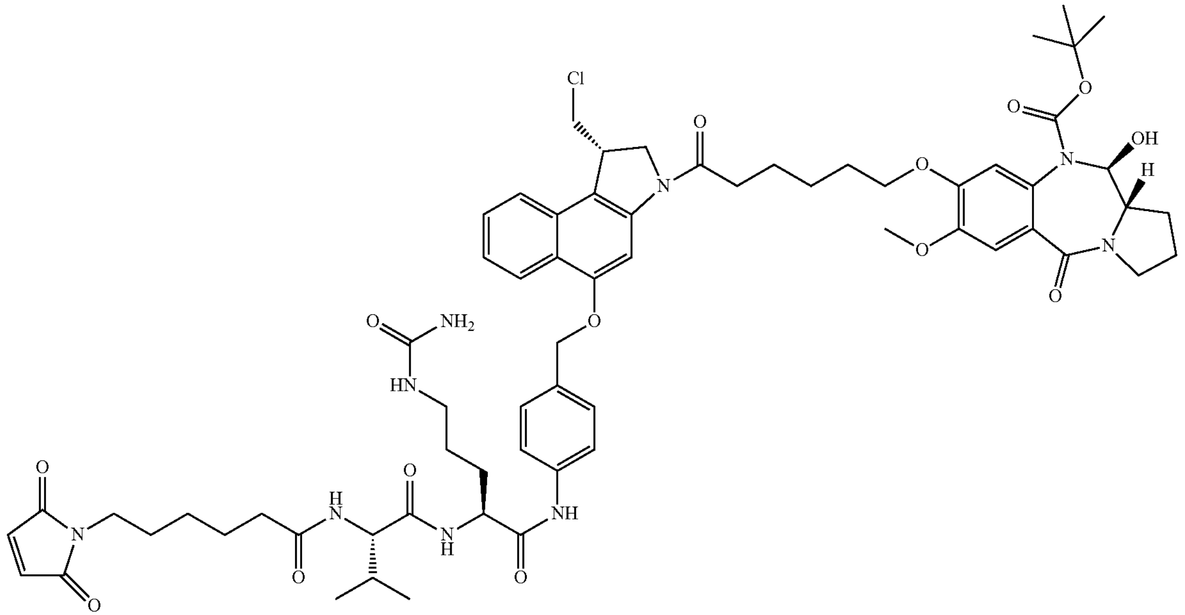 [SMILES: COc1cc2c(cc1OCCCCCC(=O)N1C[C@@H](CCl)c3c1cc(OCc1ccc(NC(=O)[C@H](CCCNC(N)=O)NC(=O)[C@@H](NC(=O)CCCCCN4C(=O)C=CC4=O)C(C)C)cc1)c1ccccc31)N(C(=O)OC(C)(C)C)[C@@H](O)[C@@H]1CCCN1C2=O] | (11S,11aS)-tert-butyl 8-(6-((S)-1-(chloromethyl)-5-(4-((S)-2-((S)-2-(6-(2,5-dioxo-2,5-dihydro-1H-pyrrol-1-yl)hexanamido)-3-methylbutanamido)-5-ureidopentanamido)benzyloxy)-1H-benzo[e]indol-3(2H)-yl)-6-oxohexyloxy)-11-hydroxy-7-methoxy-5-oxo-2,3,11,11a-tetrahydro-1H-benzo[e]pyrrolo[1,2-a][1,4]diazepine-10(5H)-carboxylate |

TABLE A-continued
| Linker-CBI dimer and CBI/PBD heterodimer drug intermediates 51-86 | | |
|---|---|---|
| No | Structure | Name |
| 53 | 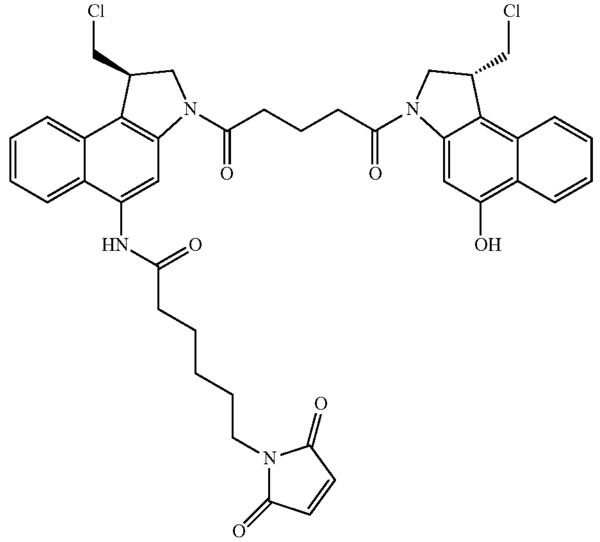 [SMILES: O=C(CCCCCN1C(=O)C=CC1=O)Nc1cc2c(c3ccccc13)[C@@H](CCl)CN2C(=O)CCCC(=O)N1C[C@H](CCl)c2c1cc(O)c1ccccc21] | N-(€-1-(chloromethyl)-3-(5-(€-1-(chloromethyl)-5-hydroxy-1H-benzo[e]indol-3(2H)-yl)-5-oxopentanoyl)-2,3-dihydro-1H-benzo[e]indol-5-yl)-6-(2,5-dioxo-2,5-dihydro-1H-pyrrol-1-yl)hexanamide |

TABLE A-continued
| Linker-CBI dimer and CBI/PBD heterodimer drug intermediates 51-86 | | |
|---|---|---|
| No | Structure | Name |
| 54 | 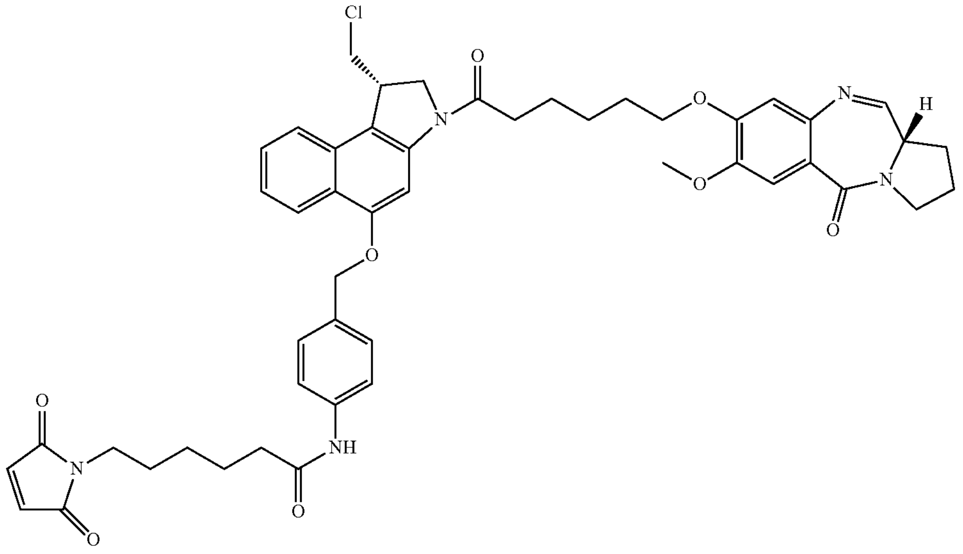 [SMILES: COc1cc2c(cc1OCCCCCC(=O)N1C[C@@H](CCl)c3c1cc(OCc1ccc(NC(=O)CCCCCN4C(=O)C=CC4=O)cc1)c1ccccc31)N=C[C@@H]1CCCN1C2=O] | N-(4-(((S)-1-(chloromethyl)-3-(6-((S)-7-methoxy-5-oxo-2,3,5,11a-tetrahydro-1H-benzo[e]pyrrolo[1,2-a][1,4]diazepin-8-yloxy)hexanoyl)-2,3-dihydro-1H-benzo[e]indol-5-yloxy)methyl)phenyl)-6-(2,5-dioxo-2,5-dihydro-1H-pyrrol-1-yl)hexanamide |

TABLE A-continued
| Linker-CBI dimer and CBI/PBD heterodimer drug intermediates 51-86 | | |
|---|---|---|
| No | Structure | Name |
| 55 | 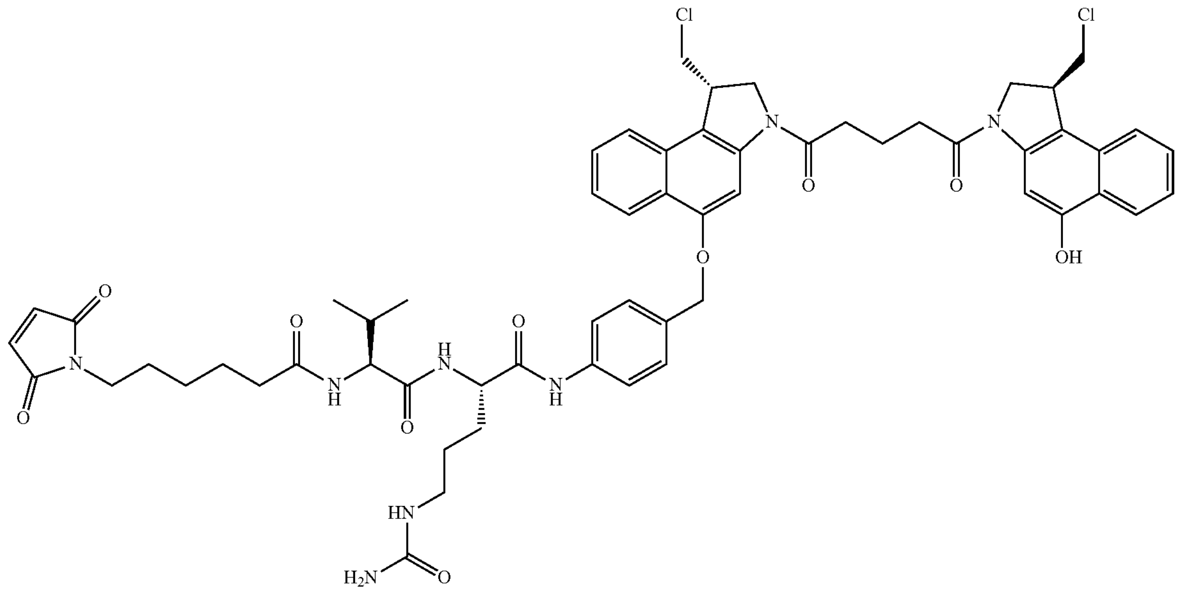 [SMILES: CC(C)[C@H](NC(=O)CCCCCN1C(=O)C=CC1=O)C(=O)N[C@@H](CCCNC(N)=O)C(=O)Nc1ccc(COc2cc3c(c4ccccc24)[C@H](CCl)CN3C(=O)CCCC(=O)N2C[C@@H](CCl)c3c2cc(O)c2ccccc32)cc1] | N-((S)-1-((S)-1-(4-(((S)-1-(chloromethyl)-3-(5-((S)-1-(chloromethyl)-5-hydroxy-1H-benzo[e]indol-3(2H)-yl)-5-oxopentanoyl)-2,3-dihydro-1H-benzo[e]indol-5-yloxy)methyl)phenylamino)-1-oxo-5-ureidopentan-2-ylamino)-3-methyl-1-oxobutan-2-yl)-6-(2,5-dioxo-2,5-dihydro-1H-pyrrol-1-yl)hexanamide |

TABLE A-continued
| Linker-CBI dimer and CBI/PBD heterodimer drug intermediates 51-86 | | |
|---|---|---|
| No | Structure | Name |
| 56 | 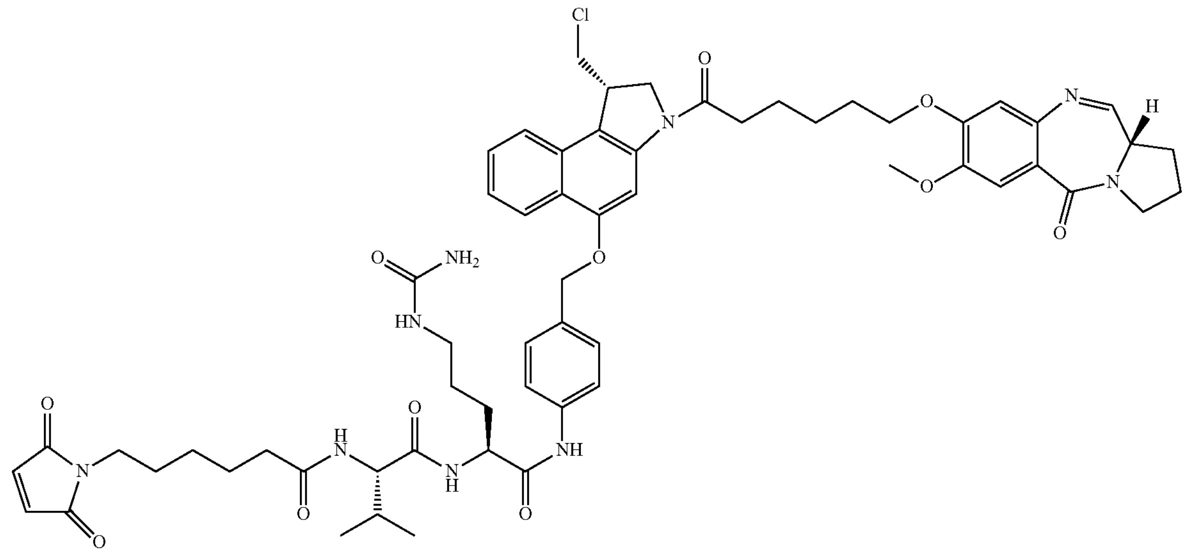 [SMILES: COc1cc2c(cc1OCCCCCC(=O)N1C[C@@H](CCl)c3c1cc(OCc1ccc(NC(=O)[C@H](CCCNC(N)=O)NC(=O)[C@@H](NC(=O)CCCCCN4C(=O)C=CC4=O)C(C)C)cc1)c1ccccc31)N=C[C@@H]1CCCN1C2=O] | N-((S)-1-((S)-1-(4-(((S)-1-(chloromethyl)-3-(6-((S)-7-methoxy-5-oxo-2,3,5,11a-tetrahydro-1H-benzo[e]pyrrolo[1,2-a][1,4]diazepin-8-yloxy)hexanoyl)-2,3-dihydro-1H-benzo[e]indol-5-yloxy)methyl)phenylamino)-1-oxo-5-ureidopentan-2-ylamino)-3-methyl-1-oxobutan-2-yl)-6-(2,5-dioxo-2,5-dihydro-1H-pyrrol-1-yl)hexanamide |

TABLE A-continued

| Linker-CBI dimer and CBI/PBD heterodimer drug intermediates 51-86 | | |
|---|---|---|
| No | Structure | Name |
| 57 | 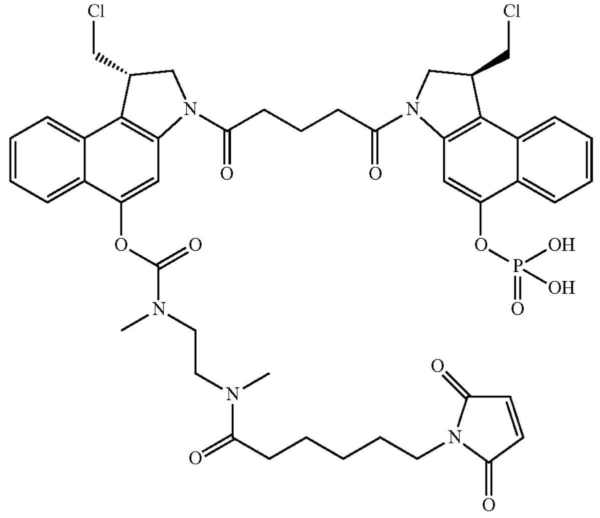 [SMILES: CN(CCN(C)C(=O)Oc1cc2c(c3ccccc13)[C@H](CCl)CN2C(=O)CCCC(=O)N1C[C@@H](CCl)c2c1cc(OP(=O)(O)O)c1ccccc21)C(=O)CCCCCN1C(=O)C=CC1=O] | (S)-1-(chloromethyl)-3-(5-((S)-1-(chloromethyl)-5-(phosphonooxy)-1H-benzo[e]indol-3(2H)-yl)-5-oxopentanoyl)-2,3-dihydro-1H-benzo[e]indol-5-yl 2-(6-(2,5-dioxo-2,5-dihydro-1H-pyrrol-1-yl)-N-methylhexanamido)ethyl(methyl) carbamate |
| 58 | 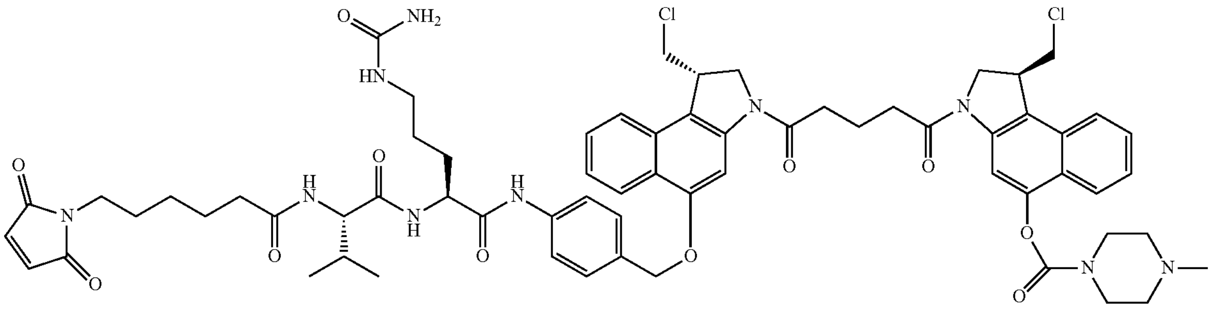 [SMILES: CC(C)[C@H](NC(=O)CCCCCN1C(=O)C=CC1=O)C(=O)N[C@@H](CCCNC(N)=O)C(=O)Nc1ccc(COc2cc3c(c4ccccc24)[C@H](CCl)CN3C(=O)CCCC(=O)N2C[C@@H](CCl)c3c2cc(OC(=O)N2CCN(C)CC2)c2ccccc32)cc1] | (S)-1-(chloromethyl)-3-(5-((S)-1-(chloromethyl)-5-(4-((S)-2-((S)-2-(6-(2,5-dioxo-2,5-dihydro-1H-pyrrol-1-yl)hexanamido)-3-methylbutanamido)-5-ureidopentanamido)benzyloxy)-1H-benzo[e]indol-3(2H)-yl)-5-oxopentanoyl)-2,3-dihydro-1H-benzo[e]indol-5-yl 4-methylpiperazine-1-carboxylate |

TABLE A-continued

| Linker-CBI dimer and CBI/PBD heterodimer drug intermediates 51-86 | | |
|---|---|---|
| No | Structure | Name |
| 59 | 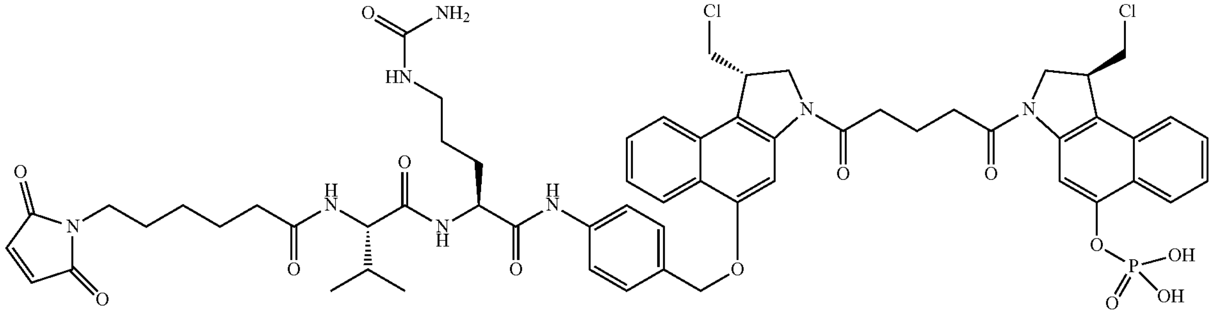 [SMILES: CC(C)[C@H](NC(=O)CCCCCN1C(=O)C=CC1=O)C(=O)N[C@@H](CCCNC(N)=O)C(=O)Nc1ccc(COc2cc3c(c4ccccc24)[C@H](CCl)CN3C(=O)CCCC(=O)N2C[C@@H](CCl)c3c2cc(OP(=O)(O)O)c2ccccc32)cc1] | (S)-1-(chloromethyl)-3-(5-((S)-1-(chloromethyl)-5-(4-((S)-2-((S)-2-(6-(2,5-dioxo-2,5-dihydro-1H-pyrrol-1-yl)hexanamido)-3-methylbutanamido)-5-ureidopentanamido)benzyloxy)-1H-benzo[e]indol-3(2H)-yl)-5-oxopentanoyl)-2,3-dihydro-1H-benzo[e]indol-5-yl dihydrogen phosphate |
| 60 | 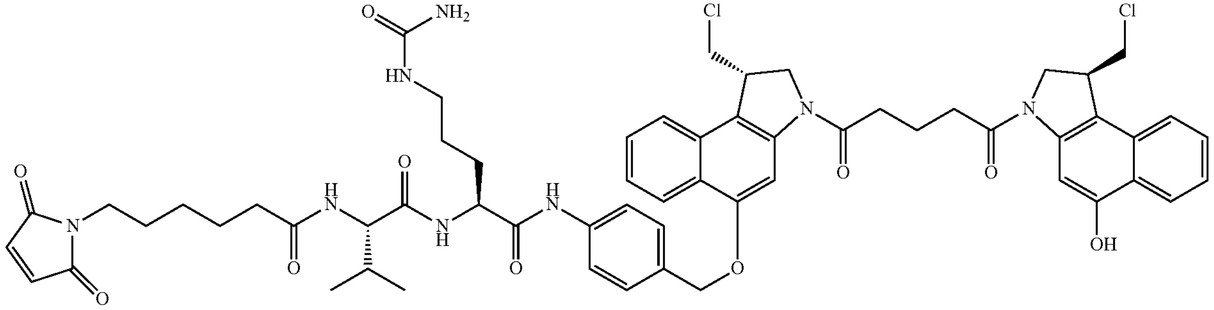 [SMILES: CC(C)[C@H](NC(=O)CCCCCN1C(=O)C=CC1=O)C(=O)N[C@@H](CCCNC(N)=O)C(=O)Nc1ccc(COc2cc3c(c4ccccc24)[C@H](CCl)CN3C(=O)CCCC(=O)N2C[C@@H](CCl)c3c2cc(O)c2ccccc32)cc1] | N-((S)-1-((S)-1-(4-(((S)-1-(chloromethyl)-3-(5-((S)-1-(chloromethyl)-5-hydroxy-1H-benzo[e]indol-3(2H)-yl)-5-oxopentanoyl)-2,3-dihydro-1H-benzo[e]indol-5-yloxy)methyl)phenylamino)-1-oxo-5-ureidopentan-2-ylamino)-3-methyl-1-oxobutan-2-yl)-6-(2,5-dioxo-2,5-dihydro-1H-pyrrol-1-yl)hexanamide |
| 61 | 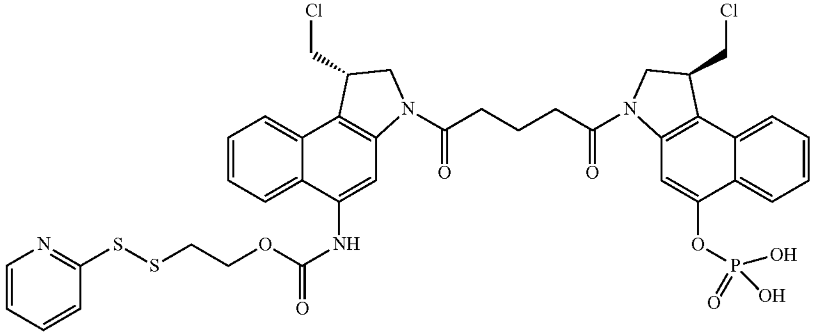 [SMILES: O=C(Nc1cc2c(c3ccccc13)[C@H](CCl)CN2C(=O)CCCC(=O)N1C[C@@H](CCl)c2c1cc(OP(=O)(O)O)c1ccccc21)OCCSSc1ccccn1] | 2-(94midazol-2-yldisulfanyl)ethyl (S)-1-(chloromethyl)-3-(5-((S)-1-(chloromethyl)-5-(phosphonooxy)-1H-benzo[e]indol-3(2H)-yl)-5-oxopentanoyl)-2,3-dihydro-1H-benzo[e]indol-5-ylcarbamate |

TABLE A-continued

| Linker-CBI dimer and CBI/PBD heterodimer drug intermediates 51-86 | | |
|---|---|---|
| No | Structure | Name |
| 62 | 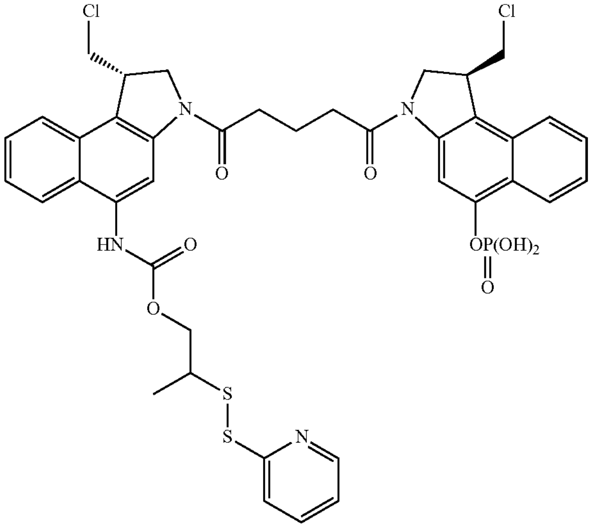 | 2-(94midazol-2-yldisulfanyl)propyl (S)-1-(chloromethyl)-3-(5-((S)-1-(chloromethyl)-5-(phosphonooxy)-1H-benzo[e]indol-3(2H)-yl)-5-oxopentanoyl)-2,3-dihydro-1H-benzo[e]indol-5-ylcarbamate |
| 63 | 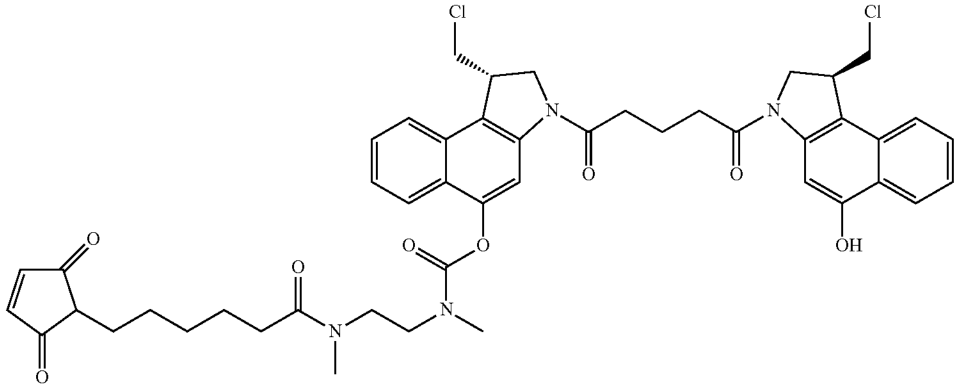 [SMILES: CN(CCN(C)C(=O)Oc1cc2c(c3ccccc13)[C@H](CCl)CN2C(=O)CCCC(=O)N1C[C@@H](CCl)c2c1cc(O)c1ccccc21)C(=O)CCCCCC1C(=O)C=CC1=O] | (S)-1-(chloromethyl)-3-(5-((S)-1-(chloromethyl)-5-hydroxy-1H-benzo[e]indol-3(2H)-yl)-5-oxopentanoyl)-2,3-dihydro-1H-benzo[e]indol-5-yl 2-(6-(2,5-dioxo-2,5-dihydro-1H-pyrrol-1-yl)-N-methylhexanamido)ethyl(methyl) carbamate |

TABLE A-continued

| Linker-CBI dimer and CBI/PBD heterodimer drug intermediates 51-86 | | |
|---|---|---|
| No | Structure | Name |
| 64 | 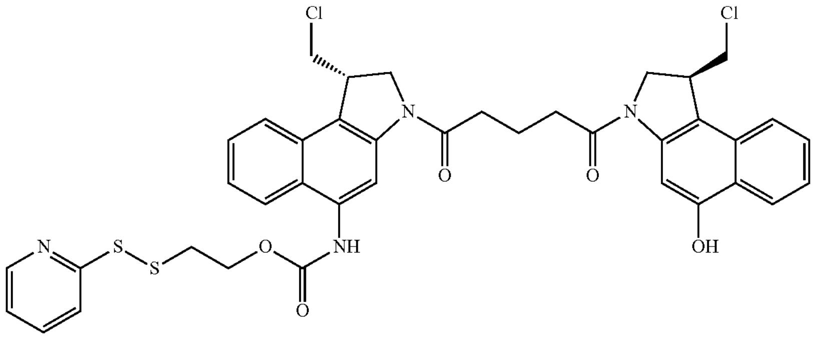 [SMILES: O=C(Nc1cc2c(c3ccccc13)[C@H](CCl)CN2C(=O)CCCC(=O)N1C[C@@H](CCl)c2c1cc(O)c1ccccc21)OCCSSc1ccccn1] | 2-(94midazol-2-yldisulfanyl)ethyl (S)-1-(chloromethyl)-3-(5-((S)-1-(chloromethyl)-5-hydroxy-1H-benzo[e]indol-3(2H)-yl)-5-oxopentanoyl)-2,3-dihydro-1H-benzo[e]indol-5-ylcarbamate |
| 65 | 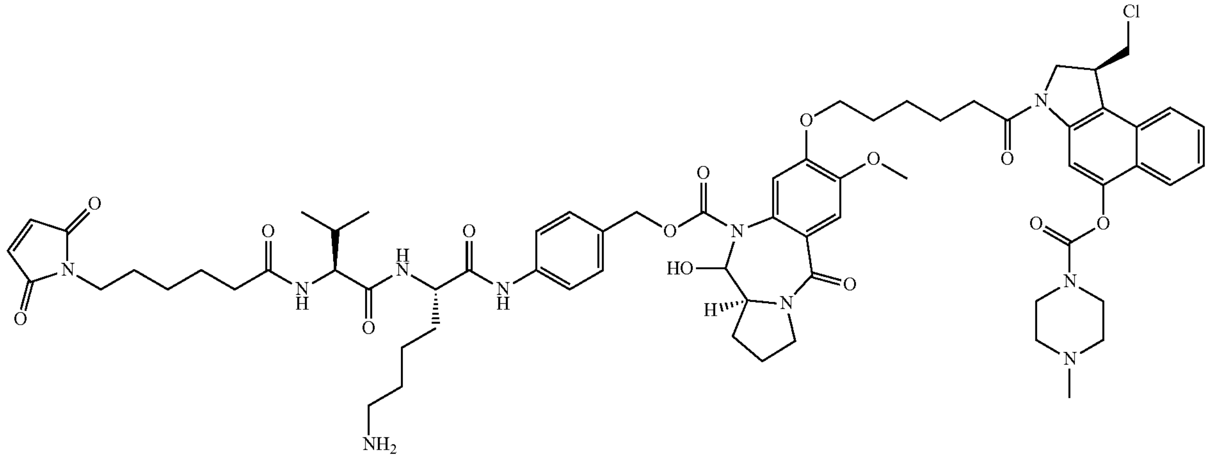 [SMILES: COc1cc2c(cc1OCCCCCC(=O)N1C[C@@H](CCl)c3c1cc(OC(=O)N1CCN(C)CC1)c1ccccc31)N(C(=O)OCc1ccc(NC(=O)[C@H](CCCCN)NC(=O)[C@@H](NC(=O)CCCCCN3C(=O)C=CC3=O)C(C)C)cc1)C(O)[C@@H]1CCCN1C2=O] | (11aS)-4-((S)-6-amino-2-((S)-2-(6-(2,5-dioxo-2,5-dihydro-1H-pyrrol-1-yl)hexanamido)-3-methylbutanamido)hexanamido) benzyl 8-(6-((S)-1-(chloromethyl)-5-(4-methylpiperazine-1-carbonyloxy)-1H-benzo[e]indol-3(2H)-yl)-6-oxohexyloxy)-11-hydroxy-7-methoxy-5-oxo-2,3,11,11a-tetrahydro-1H-benzo[e]pyrrolo[1,2-a][1,4]diazepine-10(5H)-carboxylate |

TABLE A-continued
| Linker-CBI dimer and CBI/PBD heterodimer drug intermediates 51-86 | | |
|---|---|---|
| No | Structure | Name |
| 66 | 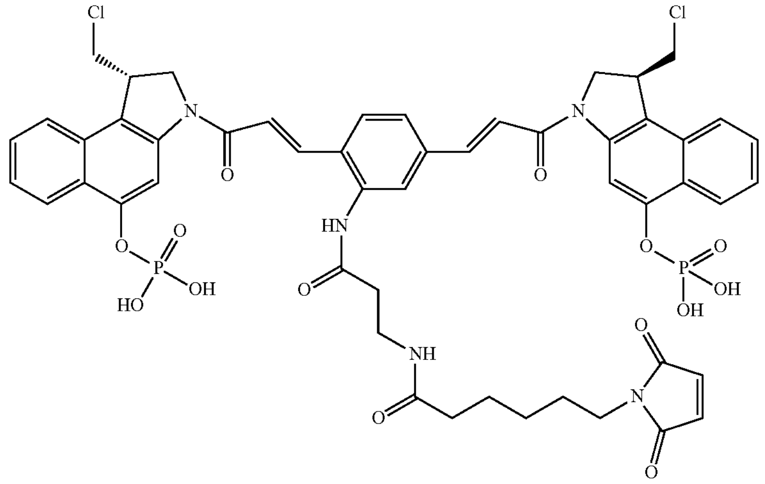 [SMILES: O=C(CCCCCN1C(=O)C=CC1=O)NCCC(=O)Nc1cc(/C=C/C(=O)N2C[C@@H](CCl)c3c2cc(OP(=O)(O)O)c2ccccc32)ccc1/C=C/C(=O)N1C[C@@H](CCl)c2c1cc(OP(=O)(O)O)c1ccccc21] | N-(3-(2,5-bis(€-3-((S)-1-(chloromethyl)-5-phosphonoxy-1H-benzo[e]indol-3(2H)-yl)-3-oxoprop-1-enyl)phenylamino)-3-oxopropyl)-6-(2,5-dioxo-2,5-dihydro-1H-pyrrol-1-yl)hexanamide |
| 67 | 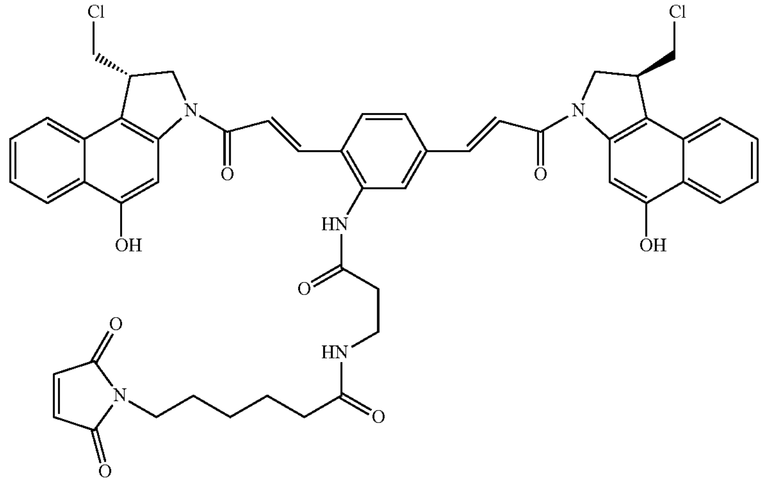 [SMILES: O=C(CCCCCN1C(=O)C=CC1=O)NCCC(=O)Nc1cc(/C=C/C(=O)N2C[C@@H](CCl)c3c2cc(O)c2ccccc32)ccc1/C=C/C(=O)N1C[C@@H](CCl)c2c1cc(O)c1ccccc21] | N-(3-(2,5-bis(€-3-((S)-1-(chloromethyl)-5-hydroxy-1H-benzo[e]indol-3(2H)-yl)-3-oxoprop-1-enyl)phenylamino)-3-oxopropyl)-6-(2,5-dioxo-2,5-dihydro-1H-pyrrol-1-yl)hexanamide |

TABLE A-continued
| Linker-CBI dimer and CBI/PBD heterodimer drug intermediates 51-86 | | |
|---|---|---|
| No | Structure | Name |
| 68 | 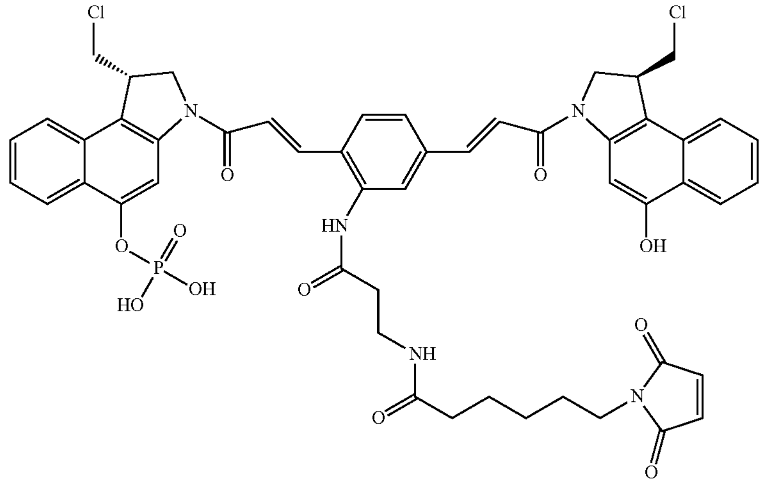 [SMILES: O=C(CCCCCN1C(=O)C=CC1=O)NCCC(=O)Nc1cc(/C=C/C(=O)N2C[C@@H](CCl)c3c2cc(O)c2ccccc32)ccc1/C=C/C(=O)N1C[C@@H](CCl)c2c1cc(OP(=O)(O)O)c1ccccc21] | (S)-1-(chloromethyl)-3-(€-3-(4-(€-3-((S)-1-(chloromethyl)-5-hydroxy-1H-benzo[e]indol-3(2H)-yl)-3-oxoprop-1-enyl)-2-(3-(6-(2,5-dioxo-2,5-dihydro-1H-pyrrol-1-yl)hexanamido)propanamido)phenyl) acryloyl)-2,3-dihydro-1H-benzo[e]indol-5-yl dihydrogen phosphate |

TABLE A-continued
| Linker-CBI dimer and CBI/PBD heterodimer drug intermediates 51-86 | | |
|---|---|---|
| No | Structure | Name |
| 69 | 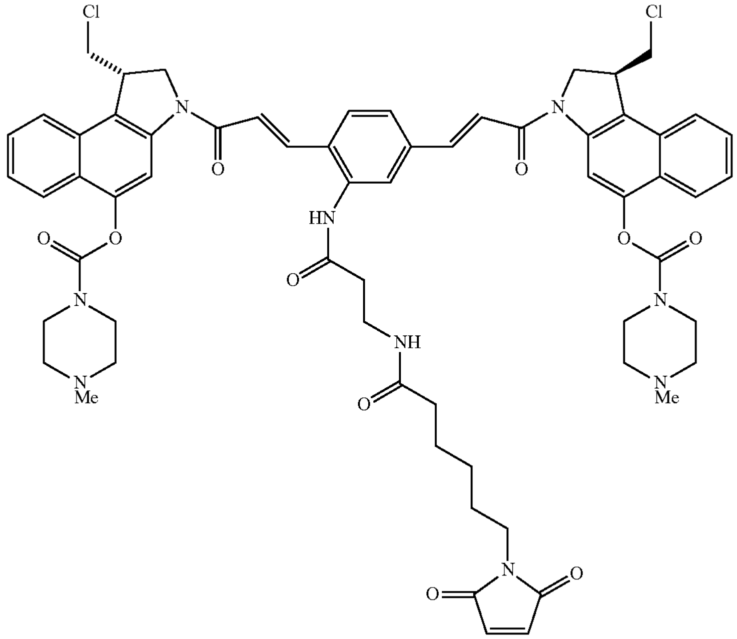 [SMILES: CN1CCN(C(=O)Oc2cc3c(c4ccccc24)[C@H](CCl)CN3C(=O)/C=C/c2ccc(/C=C/C(=O)N3C[C@@H](CCl)c4c3cc(OC(=O)N3CCN(C)CC3)c3ccccc43)c(NC(=O)CCNC(=O)CCCCCN3C(=O)C=CC3=O)c2)CC1] | N-(3-(2,5-bis(€-3-((S)-1-(chloromethyl)-5-(4-methylpiperazine-1-carbonyloxy)-1H-benzo[e]indol-3(2H)-yl)-3-oxoprop-1-enyl)phenylamino)-3-oxopropyl)-6-(2,5-dioxo-2,5-dihydro-1H-pyrrol-1-yl)hexanamide |

TABLE A-continued
| Linker-CBI dimer and CBI/PBD heterodimer drug intermediates 51-86 | | |
|---|---|---|
| No | Structure | Name |
| 70 | 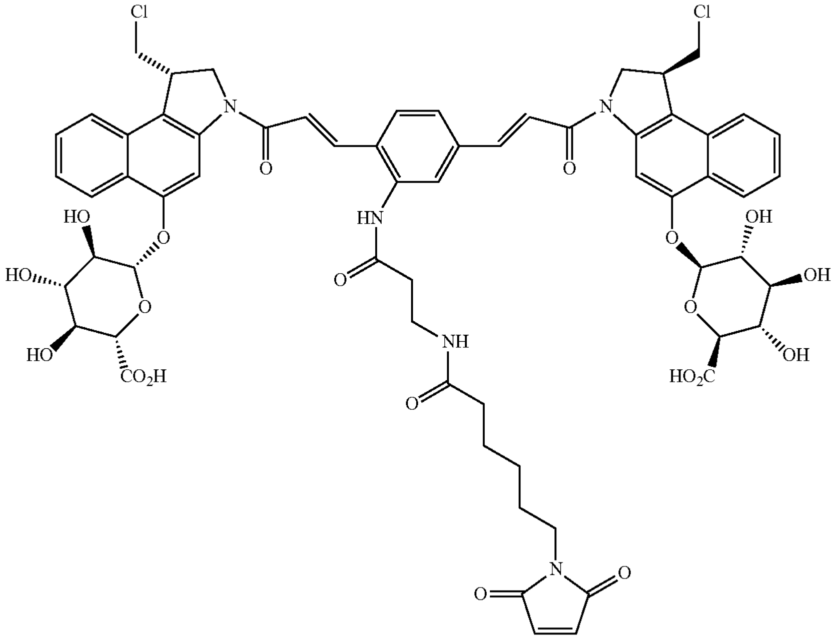 [SMILES: O=C(CCCCCN1C(=O)C=CC1=O)NCCC(=O)Nc1cc(/C=C/C(=O)N2C[C@@H](CCl)c3c2cc(O[C@@H]2O[C@H](C(=O)O)[C@@H](O)[C@H](O)[C@H]2O)c2ccccc32)ccc1/C=C/C(=O)N1C[C@@H](CCl)c2c1cc(O[C@@H]1O[C@H](C(=O)O)[C@@H](O)[C@H](O)[C@H]1O)c1ccccc21] | N-(3-(2,5-bis(€-3-((S)-1-(chloromethyl)-5-((2S,3S,4S,5R,6S)-3,4,5-trihydroxy-tetrahydro-2H-pyran-2-carboxyl-6-oxy)-1H-benzo[e]indol-3(2H)-yl)-3-oxoprop-1-enyl)phenylamino)-3-oxopropyl)-6-(2,5-dioxo-2,5-dihydro-1H-pyrrol-1-yl)hexanamide |

TABLE A-continued

| Linker-CBI dimer and CBI/PBD heterodimer drug intermediates 51-86 | | |
|---|---|---|
| No | Structure | Name |
| 71 | 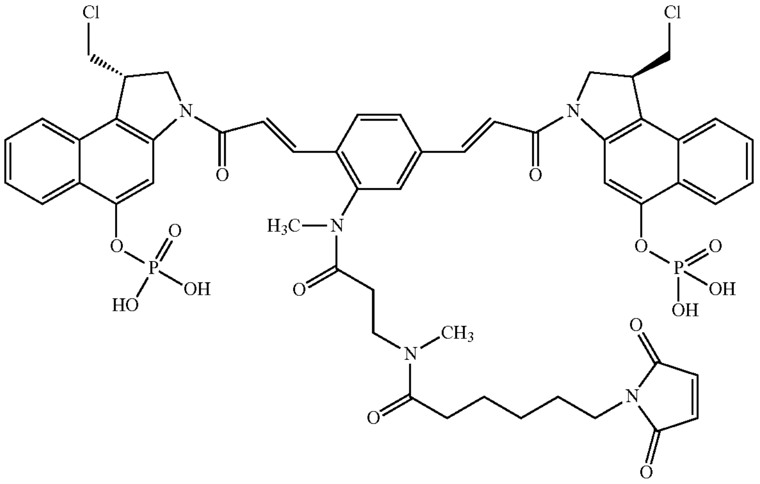 [SMILES: CN(CCC(=O)N(C)c1cc(/C=C/C(=O)N2C[C@@H](CCl)c3c2cc(OP(=O)(O)O)c2ccccc32)ccc1/C=C/C(=O)N1C[C@@H](CCl)c2c1cc(OP(=O)(O)O)c1ccccc21)C(=O)CCCCCN1C(=O)C=CC1=O] | N-(3-(2,5-bis(€-3-((S)-1-(chloromethyl)-5-phosphonoxy-1H-benzo[e]indol-3(2H)-yl)-3-oxoprop-1-enyl)phenylamino)-6-(2,5-dioxo-2,5-dihydro-1H-pyrrol-1-yl)-N-methyl-N-(3-(methylamino)-3-oxopropyl)hexanamide |
| 72 | 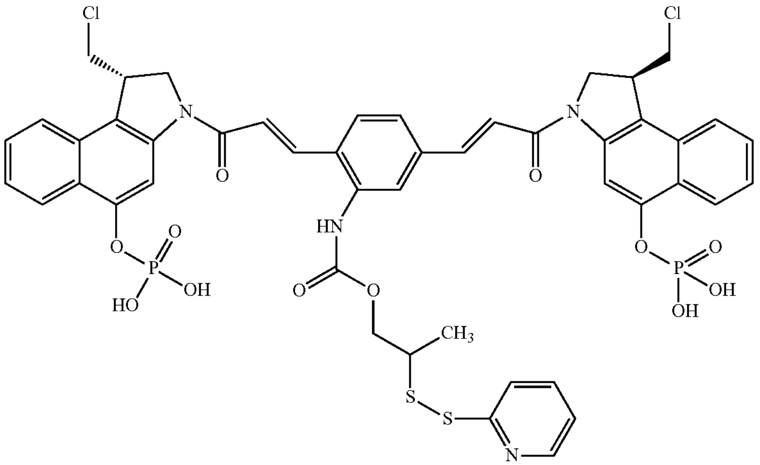 [SMILES: CC(COC(=O)Nc1cc(/C=C/C(=O)N2C[C@@H](CCl)c3c2cc(OP(=O)(O)O)c2ccccc32)ccc1/C=C/C(=O)N1C[C@@H](CCl)c2c1cc(OP(=O)(O)O)c1ccccc21)SSc1ccccn1] | 2-(96midazol-2-yldisulfanyl)propyl 2,5-bis(€-3-((S)-1-(chloromethyl)-5-(phosphonooxy)-1H-benzo[e]indol-3(2H)-yl)-3-oxoprop-1-enyl)phenylcarbamate |

TABLE A-continued
| Linker-CBI dimer and CBI/PBD heterodimer drug intermediates 51-86 | | |
|---|---|---|
| No | Structure | Name |
| 73 | 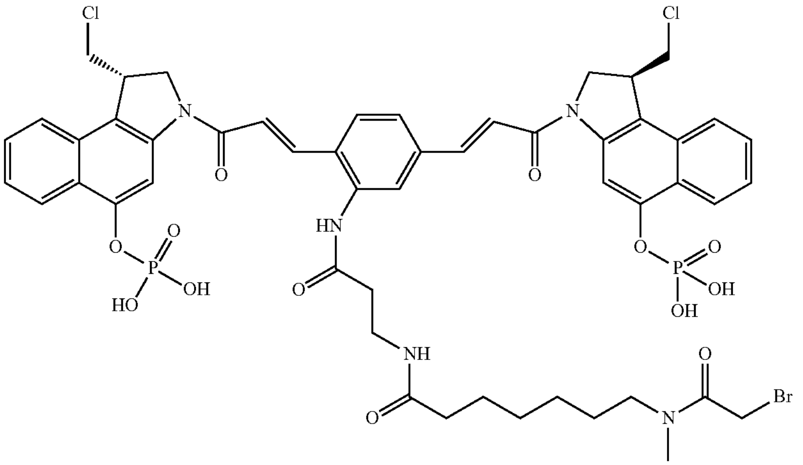 [SMILES: CN(CCCCCCC(=O)NCCC(=O)Nc1cc(/C=C/C(=O)N2C[C@@H](CCl)c3c2cc(OP(=O)(O)O)c2ccccc32)ccc1/C=C/C(=O)N1C[C@@H](CCl)c2c1cc(OP(=O)(O)O)c1ccccc21)C(=O)CBr] | N-(3-(2,5-bis(€-3-((S)-1-(chloromethyl)-5-phosphonoxy-1H-benzo[e]indol-3(2H)-yl)-3-oxoprop-1-enyl)phenylamino)-7-(2-bromo-N-methylacetamido)-N-(3-oxopropyl)heptanamide |
| 74 | 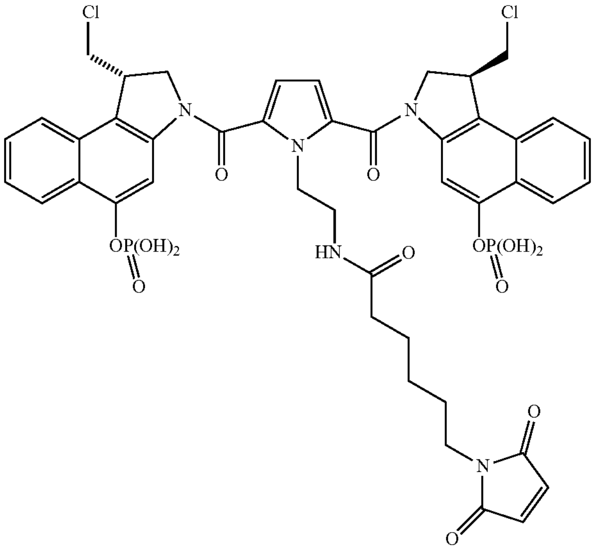 | N-(2-(2,5-bis((S)-1-(chloromethyl)-5-phosphonoxy-2,3-dihydro-1H-benzo[e]indole-3-carbonyl)-1H-pyrrol-1-yl)ethyl)-6-(2,5-dioxo-2,5-dihydro-1H-pyrrol-1-yl)hexanamide |

TABLE A-continued
| Linker-CBI dimer and CBI/PBD heterodimer drug intermediates 51-86 | | |
|---|---|---|
| No | Structure | Name |
| 75 | 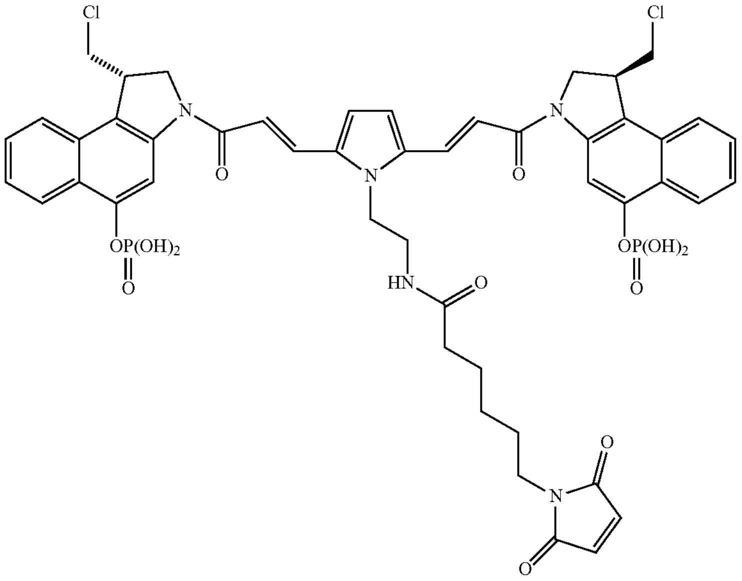 | N-(2-(2,5-bis(€-3-((S)-1-(chloromethyl)-5-phosphonoxy-1H-benzo[e]indol-3(2H)-yl)-3-oxoprop-1-enyl)-1H-pyrrol-1-yl)ethyl)-6-(2,5-dioxo-2,5-dihydro-1H-pyrrol-1-yl)hexanamide |

TABLE A-continued
| Linker-CBI dimer and CBI/PBD heterodimer drug intermediates 51-86 | | |
|---|---|---|
| No | Structure | Name |
| 76 | 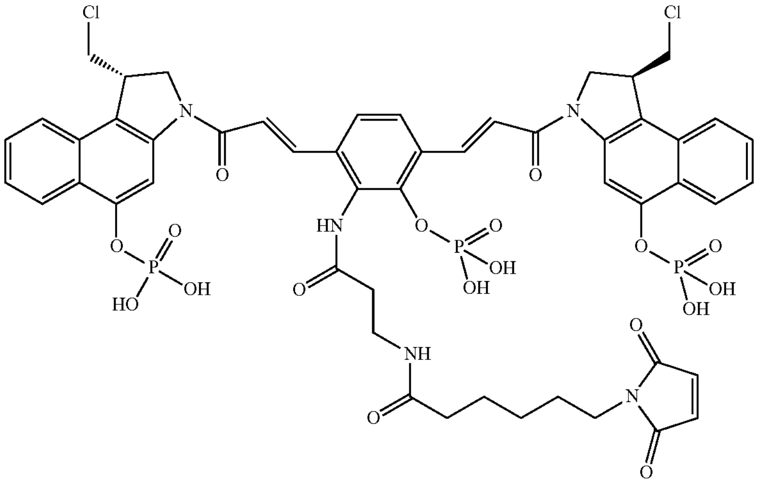 [SMILES: O=C(CCCCCN1C(=O)C=CC1=O)NCCC(=O)Nc1c(/C=C/C(=O)N2C[C@@H](CCl)c3c2cc(OP(=O)(O)O)c2ccccc32)ccc(/C=C/C(=O)N2C[C@@H](CCl)c3c2cc(OP(=O)(O)O)c2ccccc32)c1OP(=O)(O)O] | N-(3-(2,5-bis(€-3-((S)-1-(chloromethyl)-5-phosphonoxy-1H-benzo[e]indol-3(2H)-yl)-3-oxoprop-1-enyl)phenylamino,2-phosphonoxy)-3-oxopropyl)-6-(2,5-dioxo-2,5-dihydro-1H-pyrrol-1-yl)hexanamide |

TABLE A-continued
| Linker-CBI dimer and CBI/PBD heterodimer drug intermediates 51-86 | | |
|---|---|---|
| No | Structure | Name |
| 77 | 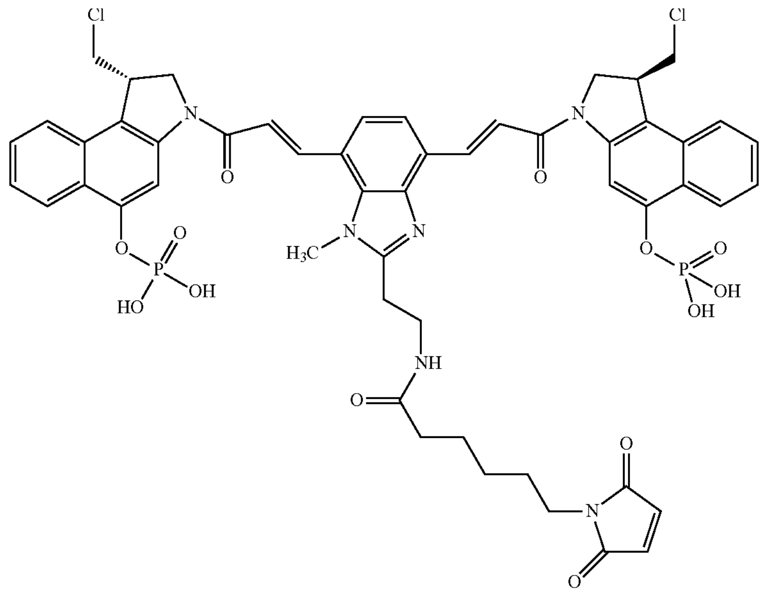 [SMILES: Cn1c(CCNC(=O)CCCCCN2C(=O)C=CC2=O)nc2c(/C=C/C(=O)N3C[C@@H](CCl)c4c3cc(OP(=O)(O)O)c3ccccc43)ccc(/C=C/C(=O)N3C[C@@H](CCl)c4c3cc(OP(=O)(O)O)c3ccccc43)c21] | N-(3-(2,5-bis(€-3-((S)-1-(chloromethyl)-5-phosphonoxy-1H-benzo[e]indol-3(2H)-yl)-3-oxoprop-1-enyl)-1-methyl-1H-benzo[d]97midazole-2-yl)ethyl)-6-(2,5-dioxo-2,5-dihydro-1H-pyrrol-1-yl)hexanamide |

TABLE A-continued

| Linker-CBI dimer and CBI/PBD heterodimer drug intermediates 51-86 | | |
|---|---|---|
| No | Structure | Name |
| 78 | 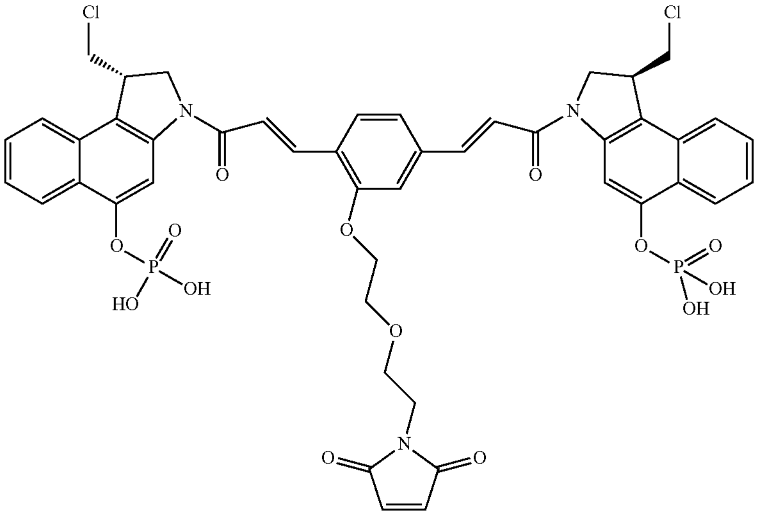 [SMILES: O=C1C=CC(=O)N1CCOCCOc1cc(/C=C/C(=O)N2C[C@@H](CCl)c3c2cc(OP(=O)(O)O)c2ccccc32)ccc1/C=C/C(=O)N1C[C@@H](CCl)c2c1cc(OP(=O)(O)O)c1ccccc21] | [(1S)-1-(chloromethyl)-3-[€-3-[4-[€-3-[(1S)-1-(chloromethyl)-5-phosphonooxy-1,2-dihydrobenzo[e]indol-3-yl]-3-oxo-prop-1-enyl]-2-[2-[2-(2,5-dioxopyrrol-1-yl)ethoxy]ethoxy]phenyl]prop-2-enoyl]-1,2-dihydrobenzo[e]indol-5-yl] dihydrogen phosphate |
| 79 | 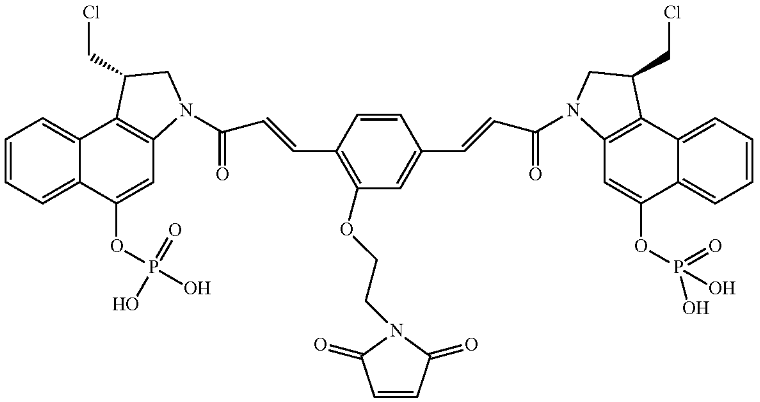 [SMILES: O=C1C=CC(=O)N1CCOc1cc(/C=C/C(=O)N2C[C@@H](CCl)c3c2cc(OP(=O)(O)O)c2ccccc32)ccc1/C=C/C(=O)N1C[C@@H](CCl)c2c1cc(OP(=O)(O)O)c1ccccc21] | [(1S)-1-(chloromethyl)-3-[€-3-[4-[€-3-[(1S)-1-(chloromethyl)-5-phosphonooxy-1,2-dihydrobenzo[e]indol-3-yl]-3-oxo-prop-1-enyl]-2-[2-(2,5-dioxopyrrol-1-yl)ethoxy]phenyl]prop-2-enoyl]-1,2-dihydrobenzo[e]indol-5-yl] dihydrogen phosphate |

TABLE A-continued

| Linker-CBI dimer and CBI/PBD heterodimer drug intermediates 51-86 | | |
| --- | --- | --- |
| No | Structure | Name |
| 80 | 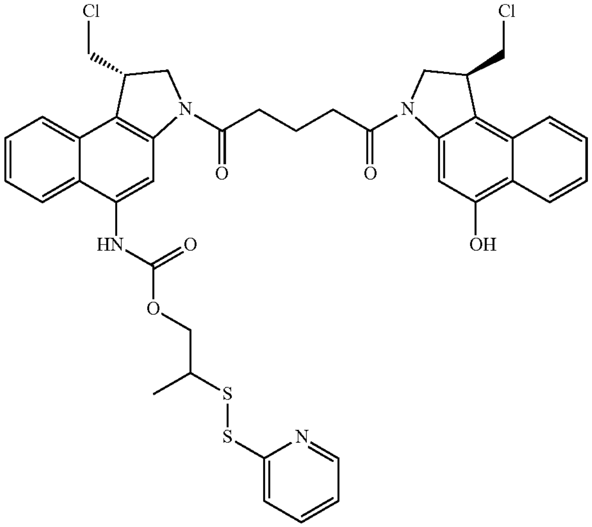 [SMILES: CC(COC(=O)Nc1cc2c(c3ccccc13)[C@H](CCl)CN2C(=O)CCCC(=O)N1C[C@@H](CCl)c2c1cc(O)c1ccccc21)SSc1ccccn1] | 2-(2-pyridyldisulfanyl)propyl N-[1-(chloromethyl)-3-[5-[1-(chloromethyl)-5-hydroxy-1,2-dihydrobenzo[e]indol-3-yl]-5-oxo-pentanoyl]-1,2-dihydrobenzo[e]indol-5-yl]carbamate |
| 81 | 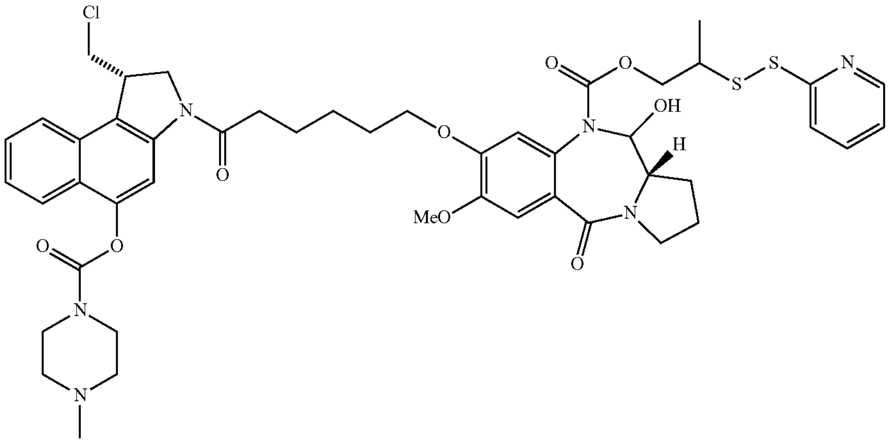 [SMILES: COc1cc2c(cc1OCCCCCC(=O)N1C[C@@H](CCl)c3c1cc(OC(=O)N1CCN(C)CC1)c1ccccc31)N(C(=O)OCC(C)SSc1ccccn1)C(O)[C@@H]1CCCN1C2=O] | 2-(2-pyridyldisulfanyl)propyl 3-[6-[1-(chloromethyl)-5-(4-methylpiperazine-1-carbonyl)oxy-1,2-dihydrobenzo[e]indol-3-yl]-6-oxo-hexoxy]-6-hydroxy-2-methoxy-11-oxo-6a,7,8,9-tetrahydro-6H-pyrrolo[2,1-c][1,4]benzodiazepine-5-carboxylate |

TABLE A-continued

| Linker-CBI dimer and CBI/PBD heterodimer drug intermediates 51-86 | | |
|---|---|---|
| No | Structure | Name |
| 82 | 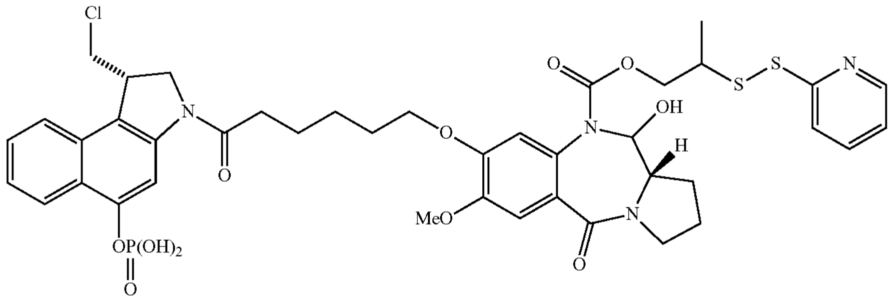 | 2-(2-pyridyldisulfanyl)propyl 3-[6-[1-(chloromethyl)-5-phosphonooxy-1,2-dihydrobenzo[e]indol-3-yl]-6-oxo-hexoxy]-6-hydroxy-2-methoxy-11-oxo-6a,7,8,9-tetrahydro-6H-pyrrolo[2,1-c][1,4]benzodiazepine-5-carboxylate |
| 83 | 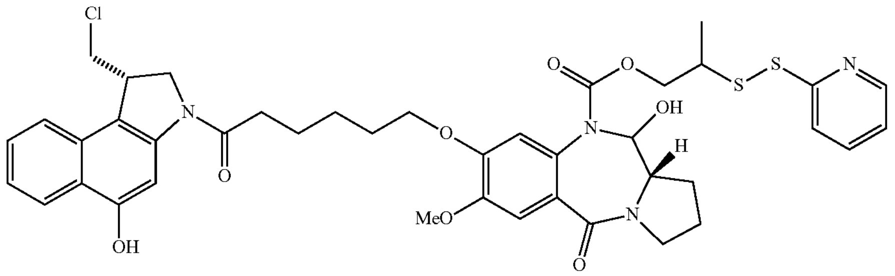 [SMILES: COc1cc2c(cc1OCCCCCC(=O)N1C[C@@H](CCl)c3c1cc(O)c1ccccc31)N(C(=O)OCC(C)SSc1ccccn1)C(O)[C@@H]1CCCN1C2=O] | 2-(2-pyridyldisulfanyl)propyl 3-[6-[1-(chloromethyl)-5-hydroxy-1,2-dihydrobenzo[e]indol-3-yl]-6-oxo-hexoxy]-6-hydroxy-2-methoxy-11-oxo-6a,7,8,9-tetrahydro-6H-pyrrolo[2,1-c][1,4]benzodiazepine-5-carboxylate |

TABLE A-continued
| Linker-CBI dimer and CBI/PBD heterodimer drug intermediates 51-86 | | |
|---|---|---|
| No | Structure | Name |
| 84 | 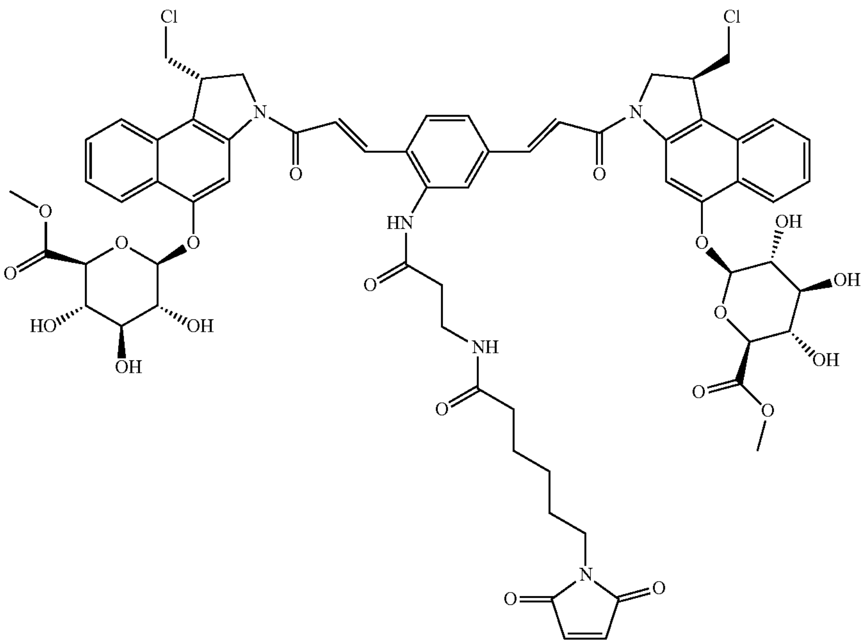 [SMILES: COC(=O)[C@H]1O[C@@H](Oc2cc3c(c4ccccc24)[C@H](CCl)CN3C(=O)/C=C/c2ccc(/C=C/C(=O)N3C[C@@H](CCl)c4c3cc(O[C@@H]3O[C@H](C(=O)OC)[C@@H](O)[C@H](O)[C@H]3O)c3ccccc43)c(NC(=O)CCNC(=O)CCCCCN3C(=O)C=CC3=O)c2)[C@H](O)[C@@H](O)[C@@H]1O] | (1S)-1-(chloromethyl)-3-((2E)-3-{4-((1E)-3-{(1S)-1-(chloromethyl)-5-[(6-methyl-β-D-glucopyranuronosyl)oxy]-1,2-dihydro-3H-benzo[e]indol-3-yl}-3-oxo-1-propenyl)-2-[(3-{[6-(2,5-dioxo-2,5-dihydro-1H-pyrrol-1-yl) hexanoyl]amino} propanoyl)amino]phenyl}-2-propenoyl)-1,2-dihydro-3H-benzo[e]indol-5-yl methyl β-D-glucopyranosiduronate |

TABLE A-continued
| Linker-CBI dimer and CBI/PBD heterodimer drug intermediates 51-86 | | |
|---|---|---|
| No | Structure | Name |
| 85 | 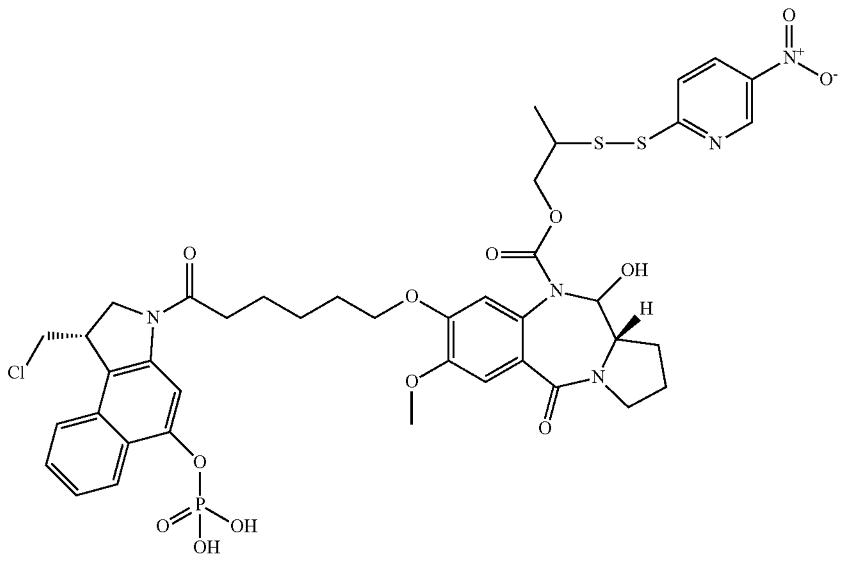 [SMILES: COc1cc2c(cc1OCCCCCC(=O)N1C[C@@H](CCl)c3c1cc(OP(=O)(O)O)c1ccccc31)N(C(=O)OCC(C)SSc1ccc([N+](=O)[O-])cn1)C(O)[C@@H]1CCCN1C2=O] | 2-((5-nitropyridin-2-yl)disulfanyl)propyl (11aS)-8-((6-((S)-1-(chloromethyl)-5-(phosphonooxy)-1,2-dihydro-3H-benzo[e]indol-3-yl)-6-oxohexyl)oxy)-11-hydroxy-7-methoxy-5-oxo-2,3,11,11a-tetrahydro-1H-benzo[e]pyrrolo[1,2-a][1,4]diazepine-10(5H)-carboxylate |

TABLE A-continued
| Linker-CBI dimer and CBI/PBD heterodimer drug intermediates 51-86 | | |
|---|---|---|
| No | Structure | Name |
| 86 | 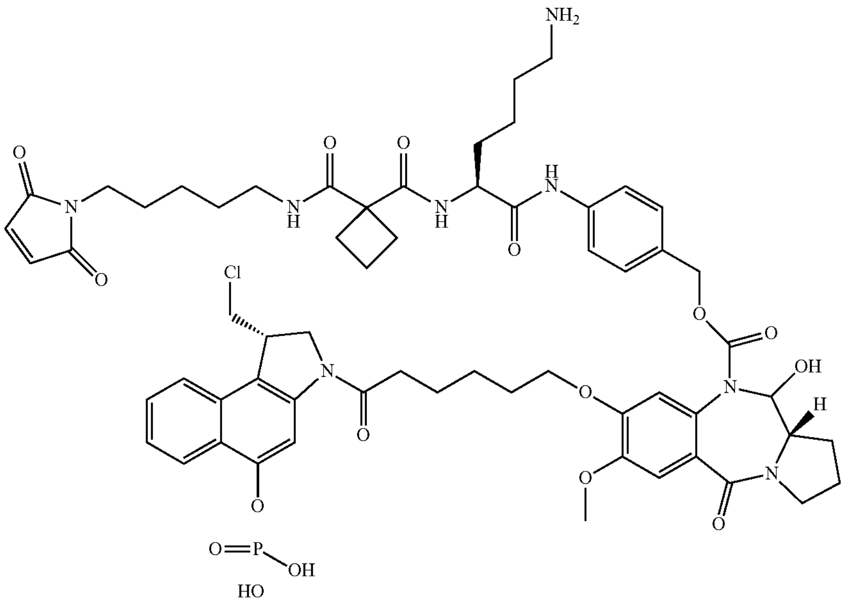 | 4-((S)-6-amino-2-(1-((5-(2,5-dioxo-2,5-dihydro-1H-pyrrol-1-yl)pentyl)carbamoyl)cyclobutane-1-carboxamido)hexanamido)benzyl (11aS)-8-((6-((S)-1-(chloromethyl)-5-(phosphonooxy)-1,2-dihydro-3H-benzo[e]indol-3-yl)-6-oxohexyl)oxy)-11-hydroxy-7-methoxy-5-oxo-2,3,11,11a-tetrahydro-1H-benzo[e]pyrrolo[1,2-a][1,4]diazepine-10(5H)-carboxylate |

Linker-drug intermediates 87 and 88 of Table B were prepared by coupling a PBD dimer drug moiety with a linker reagent according to the procedures of WO 2013/055987, incorporated by reference herein in its entirety.

TABLE B

| PBD dimer drug intermediates 87-88 | | |
|---|---|---|
| No. | Structure | Name |
| 87 | 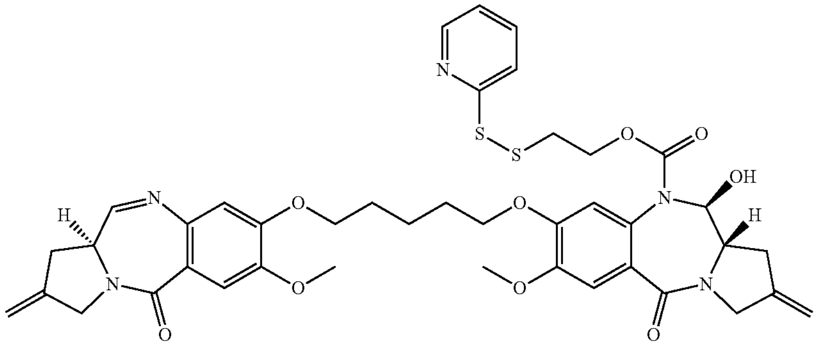 | 2-(pyridin-2-yldisulfanyl)ethyl (11,11aS)-11-hydroxy-7-methoxy-8-((5-(((S)-7-methoxy-2-methylene-5-oxo-2,3,5,11a-tetrahydro-1H-benzo[e]pyrrolo[1,2-a][1,4]diazepin-8-yl)oxy)pentyl)oxy)-2-methylene-5-oxo-2,3,11,11a-tetrahydro-1H-benzo[e]pyrrolo[1,2-a][1,4]diazepine-10(5H)-carboxylate |
| 88 | 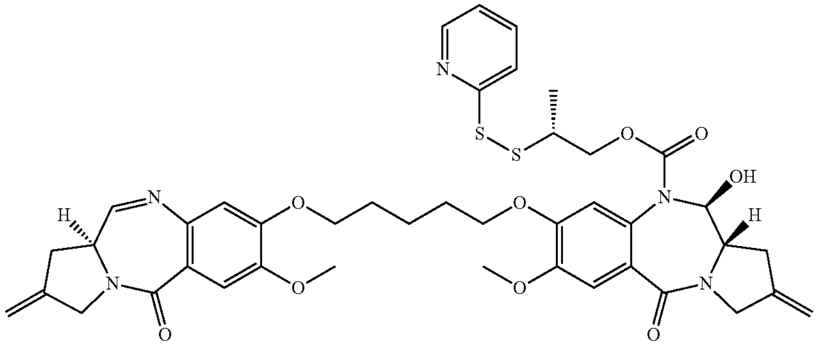 | (R)-2-(pyridin-2-yldisulfanyl)propyl (11S,11aS)-11-hydroxy-7-methoxy-8-((5-(((S)-7-methoxy-2-methylene-5-oxo-2,3,5,11a-tetrahydro-1H-benzo[e]pyrrolo[1,2-a][1,4]diazepin-8-yl)oxy)pentyl)oxy)-2-methylene-5-oxo-2,3,11,11a-tetrahydro-1H-benzo[e]pyrrolo[1,2-a][1,4]diazepine-10(5H)-carboxylate |

Linker-drug intermediates 89 and 90 of Table C were prepared by coupling a CBI dimer drug moiety with a peptidomimetic linker reagent according to the procedures of WO 2015/095227, incorporated by reference herein in its entirety.

TABLE C

| CBI dimer peptidomimetic linker drug intermediates 89-90 | | |
|---|---|---|
| No. | Structure | Name |
| 89 | 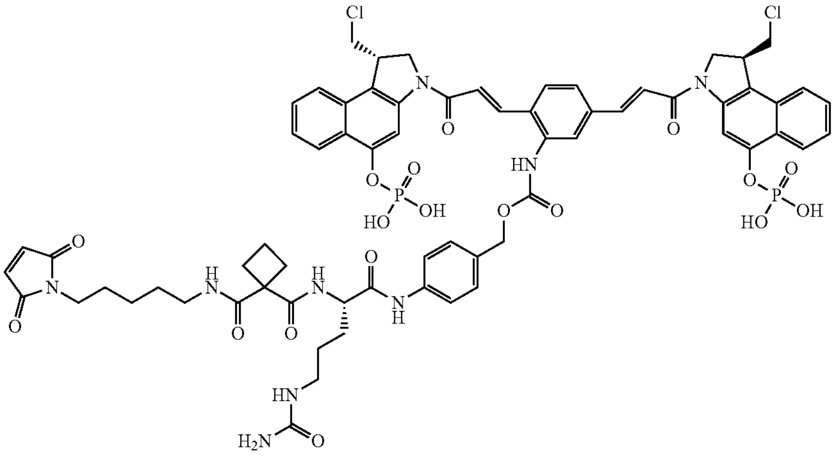 [SMILES: NC(=O)NCCC[C@H](NC(=O)C1(C(=O)NCCCCCN2C(=O)C=CC2=O)CCC1)C(=O)Nc1ccc(COC(=O)Nc2cc(/C=C/C(=O)N3C[C@@H](CCl)c4c3cc(OP(=O)(O)O)c3ccccc43)ccc2/C=C/C(=O)N2C[C@@H](CCl)c3c2cc(OP(=O)(O)O)c2ccccc32)cc1] | 4-((S)-2-(1-((5-(2,5-dioxo-2,5-dihydro-1H-pyrrol-1-yl)pentyl)carbamoyl)cyclobutane-1-carboxamido)-5-ureidopentanamido)benzyl (2,5-bis((E)-3-((S)-1-(chloromethyl)-5-(phosphonooxy)-1,2-dihydro-3H-benzo[e]indol-3-yl)-3-oxoprop-1-en-1-yl)phenyl)carbamate |

TABLE C-continued

CBI dimer peptidomimetic linker drug intermediates 89-90

| No. | Structure | Name |
| --- | --- | --- |
| 90 | 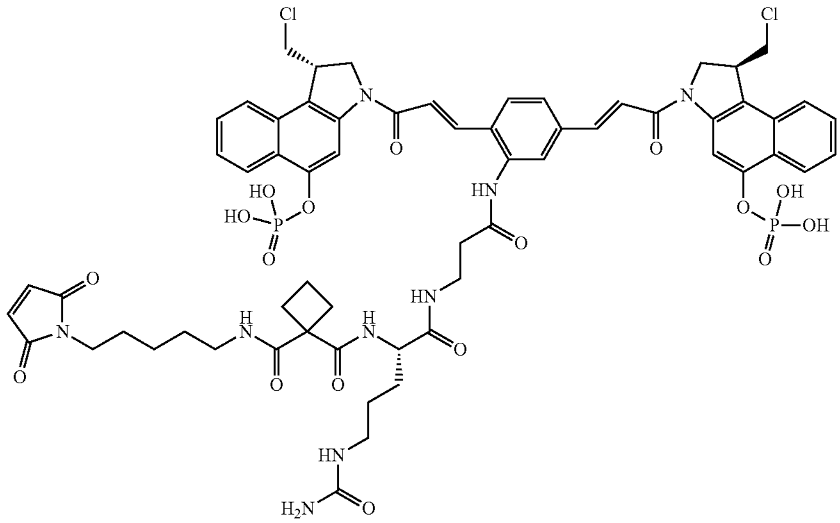 [SMILES: NC(=O)NCCC[C@H](NC(=O)C1(C(=O)NCCCCCN2C(=O)C=CC2=O)CCC1)C(=O)NCCC(=O)Nc1cc(/C=C/C(=O)N2C[C@@H](CCl)c3c2cc(OP(=O)(O)O)c2ccccc32)ccc1/C=C/C(=O)N1C[C@@H](CCl)c2c1cc(OP(=O)(O)O)c1ccccc21] | (S)-1-(chloromethyl)-3-((E)-3-(4-((E)-3-((S)-1-(chloromethyl)-5-(phosphonooxy)-1,2-dihydro-3H-benzo[e]indol-3-yl)-3-oxoprop-1-en-1-yl)-2-(3-((S)-2-(1-((5-(2,5-dioxo-2,5-dihydro-1H-pyrrol-1-yl)pentyl)carbamoyl)cyclobutane-1-carboxamido)-5-ureidopentanamido)propanamido)phenyl)acryloyl)-2,3-dihydro-1H-benzo[e]indol-5-yl dihydrogen phosphate |

Exemplary CBI dimer portions of ADCs include, but are not limited to, the following CBI-PBD dimers (the wavy line indicates the site of covalent attachment to the linker):

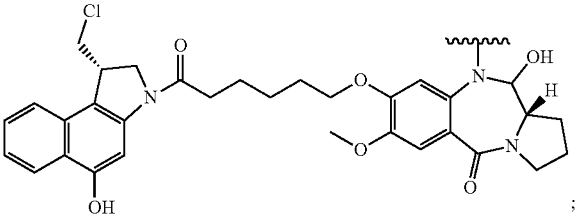

;

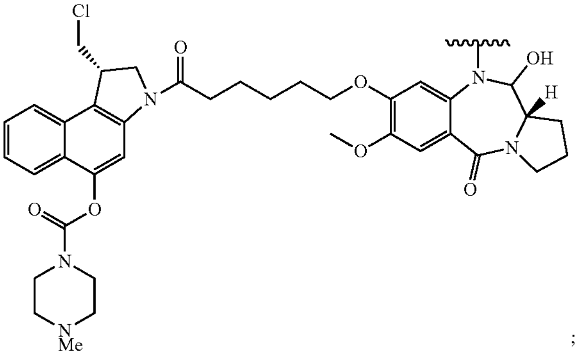

;

-continued

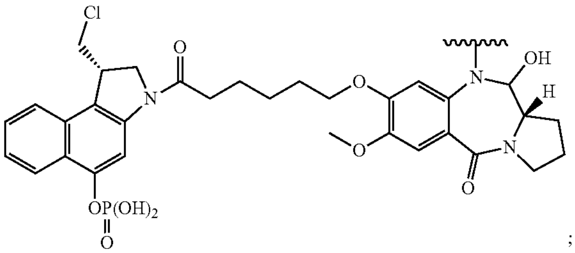

;

and the following CBI-CBI dimer:

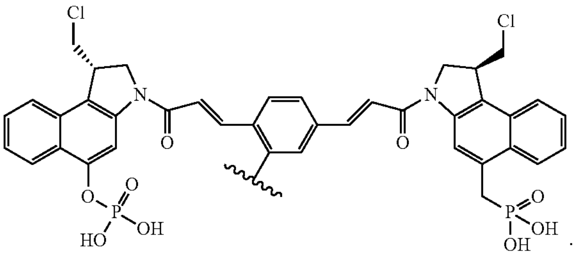 [SMILES: *c1cc(/C=C/C(=O)N2C[C@@H](CCl)c3c2cc(CP(=O)(O)O)c2ccccc32)ccc1/C=C/C(=O)N1C[C@@H](CCl)c2c1cc(OP(=O)(O)O)c1ccccc21]

.

Nonlimiting exemplary embodiments of ADCs comprising CBI dimers have the following structures:

14
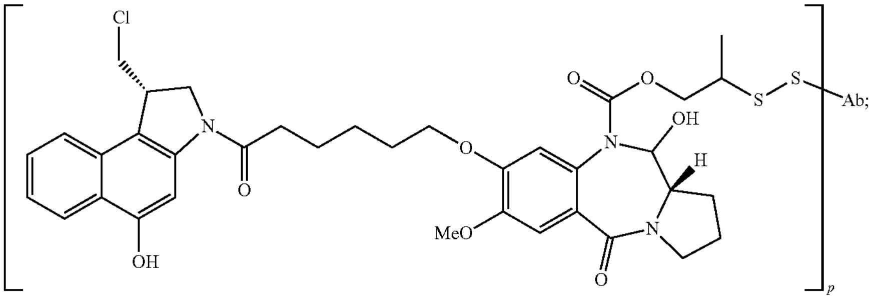
or
CBI-PBD-disulfide-Ab
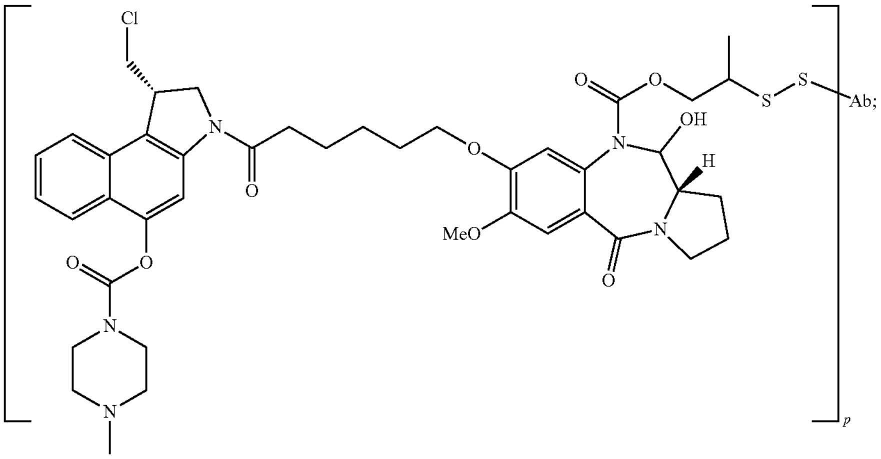
CBI-PBD (piperazine-carbamate prodrug)-disulfide-Ab
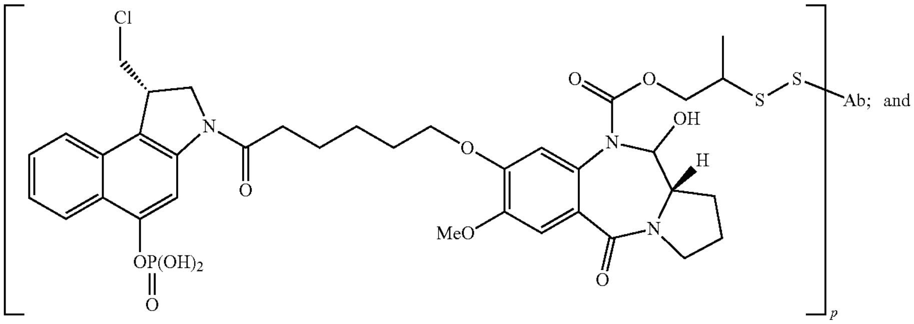
and
CBI-PBD (phosphate)-disulfide-Ab
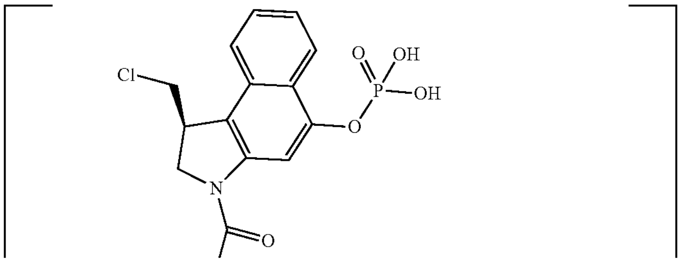

-continued
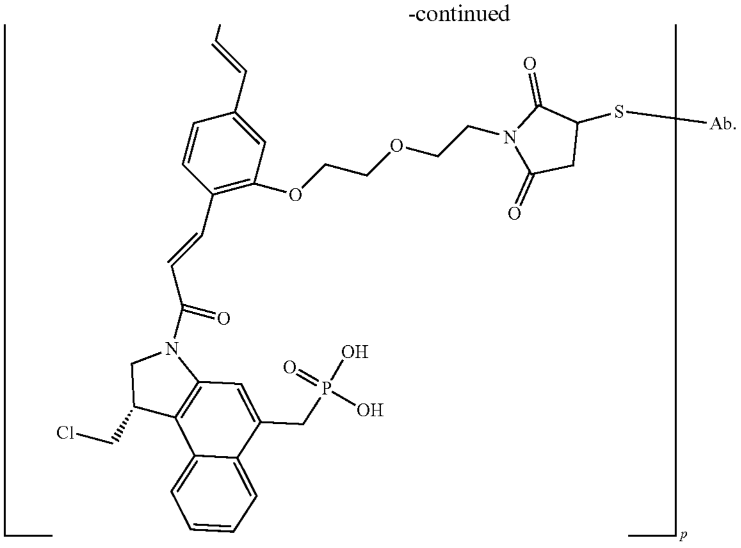
CBI-CBI (phosphate)-acetal-maleimide-Ab
Nonlimiting exemplary CBI-PBD heterodimer linker-drug intermediates that can be conjugated to antibodies to form ADCs include, but are not limited to:
83
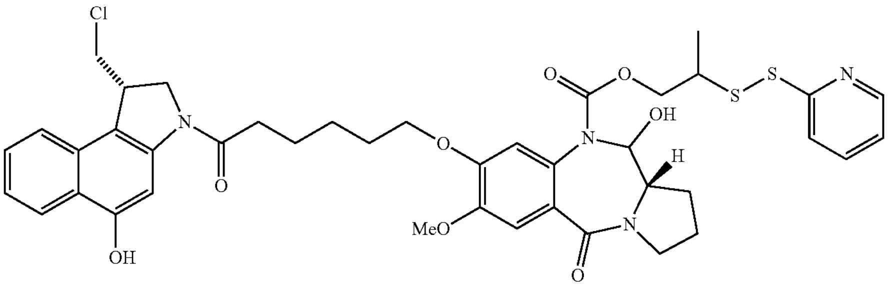
;
CBI-PBD-2-propyl pyridyl disulfide
81
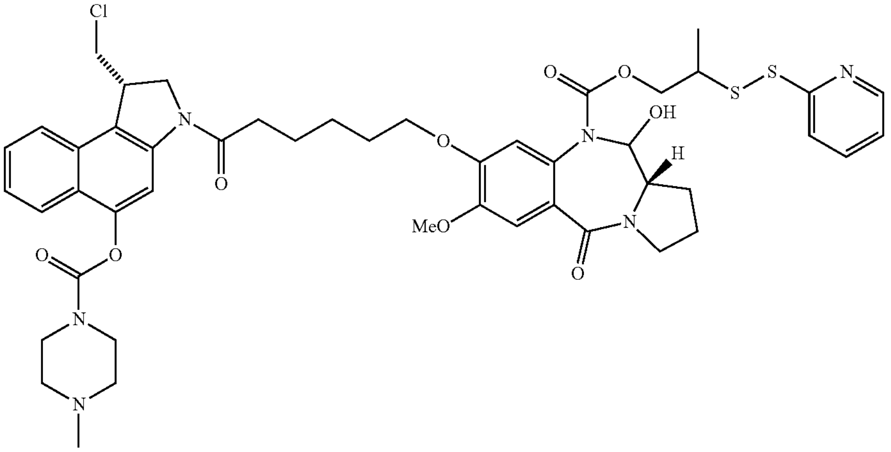
;
CBI-PBD-2-propyl pyridyl disulfide -continued
82
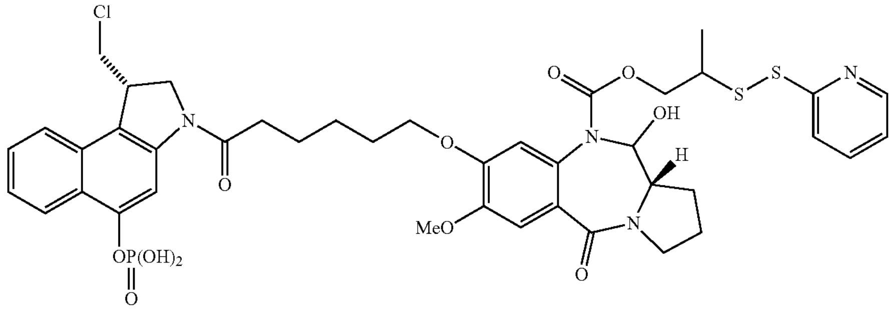
;
CBI-PBD-2-propyl pyridyl disulfide
85
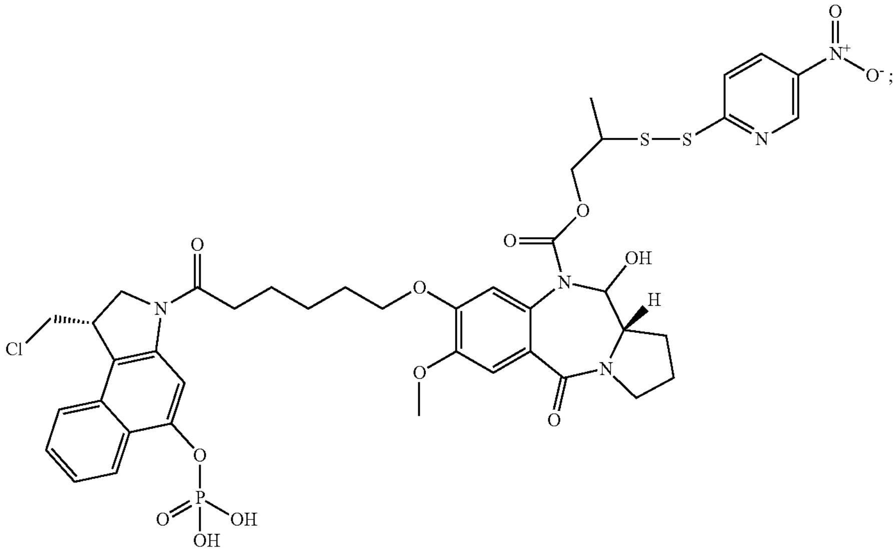
; and
CBI-PBD-(phosphate)-2-propyl, nitropyridyl disulfide
86
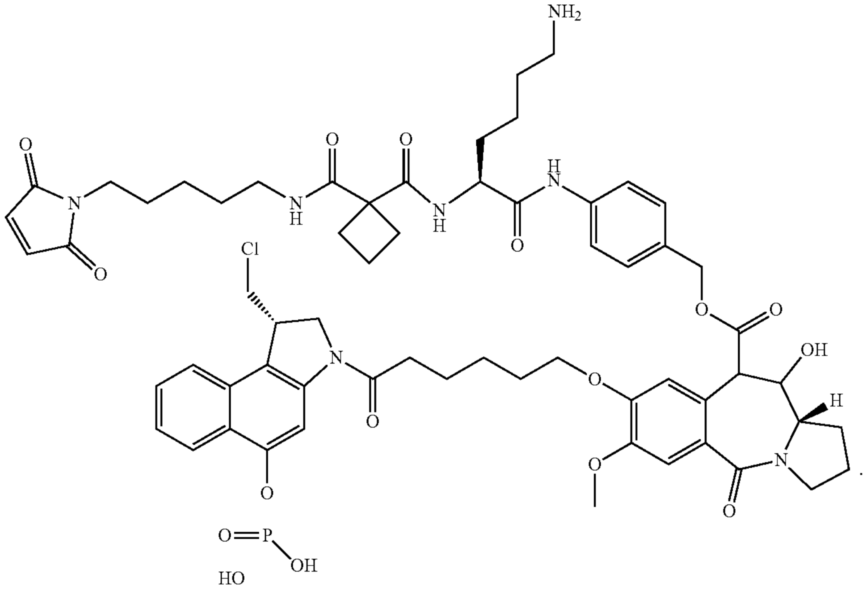
.
CBI-PBD-(phosphate)-peptidomimetic linker Nonlimiting exemplary CBI-CBI homodimer linker-drug intermediates that can be conjugated to antibodies to form ADCs include, but are not limited to:
78
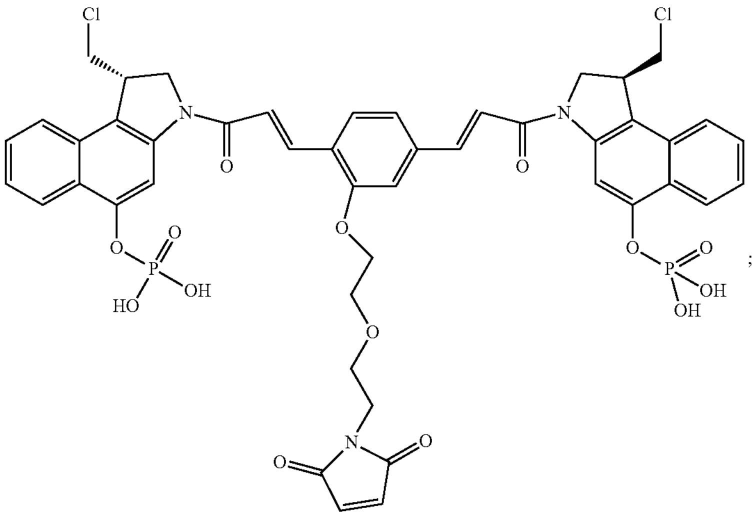
;
CBI-CBI (phosphate)-acetal-maleimide
89
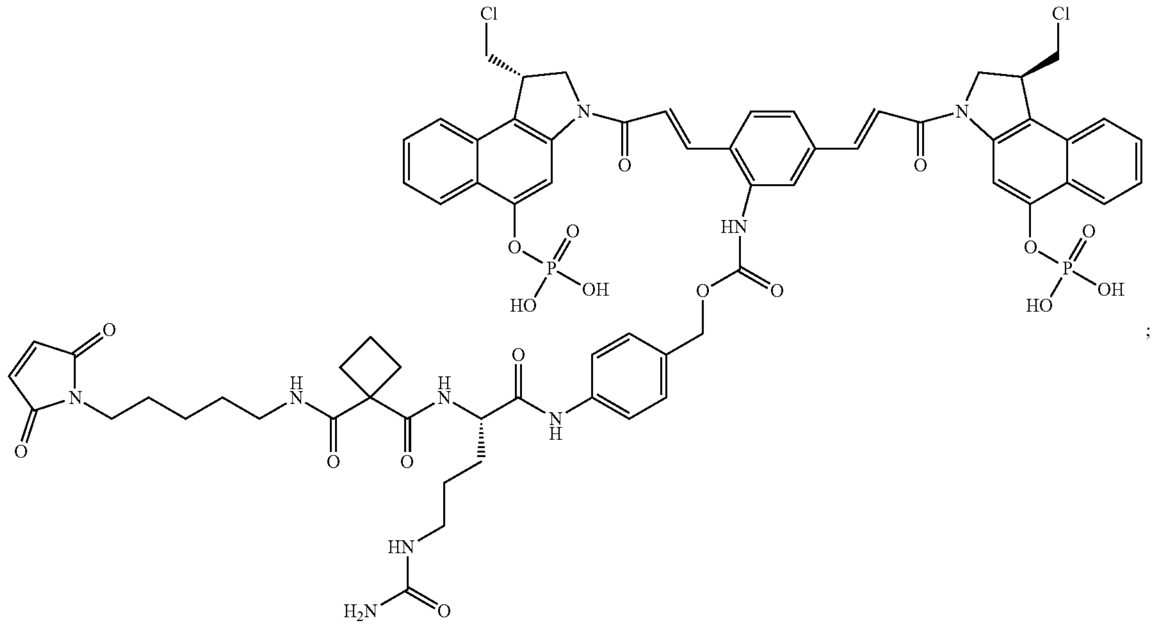
; and
CBI-CBI (phosphate)-peptidomimetic PAB linker -continued

90

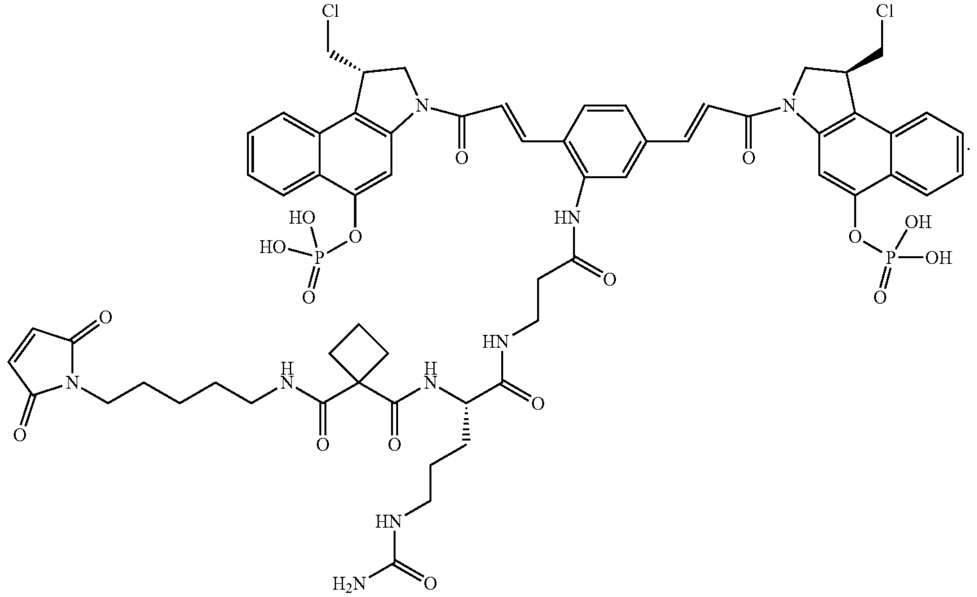

CBI-CBI (phosphate)-peptidomimetic EDA linker (7) Amatoxin

In some embodiments, the immunoconjugate comprises an antibody conjugated to one or more amatoxin molecules. Amatoxins are cyclic peptides composed of 8 amino acids. They can be isolated from *Amanita phalloides* mushrooms or prepared synthetically. Amatoxins specifically inhibit the DNA-dependent RNA polymerase II of mammalian cells, and thereby also the transcription and protein biosynthesis of the affected cells. Inhibition of transcription in a cell causes stop of growth and proliferation. See e.g., Moldenhauer et al. JNCI 104:1-13 (2012), WO2010115629, WO2012041504, WO2012119787, WO2014043403, WO2014135282, and WO2012119787, which are hereby incorporated by reference in its entirety. In some embodiments, the one or more amatoxin molecules are one or more α-amanitin molecules.

(8) Other Drug Moieties

Drug moieties also include geldanamycin (Mandler et al (2000) *J. Nat. Cancer Inst.* 92(19):1573-1581; Mandler et al (2000) *Bioorganic & Med. Chem. Letters* 10:1025-1028; Mandler et al (2002) *Bioconjugate Chem.* 13:786-791); and enzymatically active toxins and fragments thereof, including, but not limited to, diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. See, e.g., WO 93/21232.

Drug moieties also include compounds with nucleolytic activity (e.g., a ribonuclease or a DNA endonuclease).

In certain embodiments, an immunoconjugate may comprise a radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. In some embodiments, when an immunoconjugate is used for detection, it may comprise a radioactive atom for scintigraphic studies, for example $Tc^{99}$ or $I^{123}$, or a spin label for nuclear magnetic resonance (NMR) imaging (also known as magnetic resonance imaging, MRI), such as zirconium-89, iodine-123, iodine-131, indium-111, fluorine-19, carbon-13, nitrogen-15, oxygen-17, gadolinium, manganese or iron. Zirconium-89 may be complexed to various metal chelating agents and conjugated to antibodies, e.g., for PET imaging (WO 2011/056983).

The radio- or other labels may be incorporated in the immunoconjugate in known ways. For example, a peptide may be biosynthesized or chemically synthesized using suitable amino acid precursors comprising, for example, one or more fluorine-19 atoms in place of one or more hydrogens. In some embodiments, labels such as $Tc^{99}$, $I^{123}$, $Re^{186}$, $Re^{188}$ and $In^{111}$ can be attached via a cysteine residue in the antibody. In some embodiments, yttrium-90 can be attached via a lysine residue of the antibody. In some embodiments, the IODOGEN method (Fraker et al (1978) *Biochem. Biophys. Res. Commun.* 80: 49-57 can be used to incorporate iodine-123. "Monoclonal Antibodies in Immunoscintiography" (Chatal, CRC Press 1989) describes certain other methods.

In certain embodiments, an immunoconjugate may comprise an antibody conjugated to a prodrug-activating enzyme. In some such embodiments, a prodrug-activating enzyme converts a prodrug (e.g., a peptidyl chemotherapeutic agent, see WO 81/01145) to an active drug, such as an anti-cancer drug. Such immunoconjugates are useful, in some embodiments, in antibody-dependent enzyme-mediated prodrug therapy ("ADEPT"). Enzymes that may be conjugated to an antibody include, but are not limited to, alkaline phosphatases, which are useful for converting phosphate-containing prodrugs into free drugs; arylsulfatases, which are useful for converting sulfate-containing prodrugs into free drugs; cytosine deaminase, which is useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), which are useful for converting peptide-containing prodrugs into free drugs; D-alanylcarboxypeptidases, which are useful for converting prodrugs that contain D-amino acid substituents; carbohydrate-cleaving enzymes such as β-galactosidase and neuraminidase, which are useful for converting glycosylated prodrugs into free drugs; β-lactamase, which is useful for converting drugs derivatized with β-lactams into free drugs; and penicillin amidases, such as penicillin V amidase and penicillin G amidase, which are useful for converting drugs derivatized at their amine nitrogens with phenoxyacetyl or phenylacetyl groups, respectively, into free drugs. In some embodiments, enzymes may be covalently bound to antibodies by recombinant DNA techniques well known in the art. See, e.g., Neuberger et al., *Nature* 312:604-608 (1984).

c) Drug Loading

Drug loading is represented by p, the average number of drug moieties per antibody in a molecule of Formula I. Drug loading may range from 1 to 20 drug moieties (D) per antibody. ADCs of Formula I include collections of antibodies conjugated with a range of drug moieties, from 1 to 20. The average number of drug moieties per antibody in preparations of ADC from conjugation reactions may be characterized by conventional means such as mass spectroscopy, ELISA assay, and HPLC. The quantitative distribution of ADC in terms of p may also be determined. In some instances, separation, purification, and characterization of homogeneous ADC where p is a certain value from ADC with other drug loadings may be achieved by means such as reverse phase HPLC or electrophoresis.

For some antibody-drug conjugates, p may be limited by the number of attachment sites on the antibody. For example, where the attachment is a cysteine thiol, as in certain exemplary embodiments above, an antibody may have only one or several cysteine thiol groups, or may have only one or several sufficiently reactive thiol groups through which a linker may be attached. In certain embodiments, higher drug loading, e.g. p>5, may cause aggregation, insolubility, toxicity, or loss of cellular permeability of certain antibody-drug conjugates. In certain embodiments, the average drug loading for an ADC ranges from 1 to about 8; from about 2 to about 6; or from about 3 to about 5. Indeed, it has been shown that for certain ADCs, the optimal ratio of drug moieties per antibody may be less than 8, and may be about 2 to about 5 (U.S. Pat. No. 7,498,298).

In certain embodiments, fewer than the theoretical maximum of drug moieties are conjugated to an antibody during a conjugation reaction. An antibody may contain, for example, lysine residues that do not react with the drug-linker intermediate or linker reagent, as discussed below. Generally, antibodies do not contain many free and reactive cysteine thiol groups which may be linked to a drug moiety; indeed most cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, an antibody is subjected to denaturing conditions to reveal reactive nucleophilic groups such as lysine or cysteine.

The loading (drug/antibody ratio) of an ADC may be controlled in different ways, and for example, by: (i) limiting the molar excess of drug-linker intermediate or linker reagent relative to antibody, (ii) limiting the conjugation reaction time or temperature, and (iii) partial or limiting reductive conditions for cysteine thiol modification.

It is to be understood that where more than one nucleophilic group reacts with a drug-linker intermediate or linker reagent, then the resulting product is a mixture of ADC compounds with a distribution of one or more drug moieties attached to an antibody. The average number of drugs per antibody may be calculated from the mixture by a dual ELISA antibody assay, which is specific for antibody and specific for the drug. Individual ADC molecules may be identified in the mixture by mass spectroscopy and separated by HPLC, e.g. hydrophobic interaction chromatography (see, e.g., McDonagh et al (2006) Prot. Engr. Design & Selection 19(7):299-307; Hamblett et al (2004) Clin. Cancer Res. 10:7063-7070; Hamblett, K. J., et al. "Effect of drug loading on the pharmacology, pharmacokinetics, and toxicity of an anti-CD30 antibody-drug conjugate," Abstract No. 624, American Association for Cancer Research, 2004 Annual Meeting, Mar. 27-31, 2004, Proceedings of the AACR, Volume 45, March 2004; Alley, S. C., et al. "Controlling the location of drug attachment in antibody-drug conjugates," Abstract No. 627, American Association for Cancer Research, 2004 Annual Meeting, Mar. 27-31, 2004, Proceedings of the AACR, Volume 45, March 2004). In certain embodiments, a homogeneous ADC with a single loading value may be isolated from the conjugation mixture by electrophoresis or chromatography.

d) Certain Methods of Preparing Immunoconjugates

An ADC of Formula I may be prepared by several routes employing organic chemistry reactions, conditions, and reagents known to those skilled in the art, including: (1) reaction of a nucleophilic group of an antibody with a bivalent linker reagent to form Ab-L via a covalent bond, followed by reaction with a drug moiety D; and (2) reaction of a nucleophilic group of a drug moiety with a bivalent linker reagent, to form D-L, via a covalent bond, followed by reaction with a nucleophilic group of an antibody. Exemplary methods for preparing an ADC of Formula I via the latter route are described in U.S. Pat. No. 7,498,298, which is expressly incorporated herein by reference.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; and (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol) or tricarbonylethylphosphine (TCEP), such that the antibody is fully or partially reduced. Each cysteine bridge will thus form, theoretically, two reactive thiol nucleophiles. Additional nucleophilic groups can be introduced into antibodies through modification of lysine residues, e.g., by reacting lysine residues with 2-iminothiolane (Traut's reagent), resulting in conversion of an amine into a thiol. Reactive thiol groups may also be introduced into an antibody by introducing one, two, three, four, or more cysteine residues (e.g., by preparing variant antibodies comprising one or more non-native cysteine amino acid residues).

Antibody-drug conjugates of the invention may also be produced by reaction between an electrophilic group on an antibody, such as an aldehyde or ketone carbonyl group, with a nucleophilic group on a linker reagent or drug. Useful nucleophilic groups on a linker reagent include, but are not limited to, hydrazide, oxime, amino, hydrazine, thiosemicarbazone, hydrazine carboxylate, and arylhydrazide. In one embodiment, an antibody is modified to introduce electrophilic moieties that are capable of reacting with nucleophilic substituents on the linker reagent or drug. In another embodiment, the sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the antibody that can react with appropriate groups on the drug (Hermanson, Bioconjugate Techniques). In another embodiment, antibodies containing N-terminal serine or threonine residues can react with sodium meta-periodate, resulting in production of an aldehyde in place of the first amino acid (Geoghegan & Stroh, (1992) *Bioconjugate Chem.* 3:138-146; U.S. Pat. No. 5,362,852). Such an aldehyde can be reacted with a drug moiety or linker nucleophile.

Exemplary nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Nonlimiting exemplary cross-linker reagents that may be used to prepare ADC are described herein in the section titled "Exemplary Linkers." Methods of using such cross-linker reagents to link two moieties, including a proteinaceous moiety and a chemical moiety, are known in the art.

In some embodiments, a fusion protein comprising an antibody and a cytotoxic agent may be made, e.g., by recombinant techniques or peptide synthesis. A recombinant DNA molecule may comprise regions encoding the antibody and cytotoxic portions of the conjugate either adjacent to one another or separated by a region encoding a linker peptide which does not destroy the desired properties of the conjugate.

In yet another embodiment, an antibody may be conjugated to a "receptor" (such as streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a drug or radionucleotide).

E. Trastuzumab-MCC-DM1 and Pertuzumab

Trastuzumab-MCC-DM1 (T-DM1)

The present invention includes therapeutic treatments with trastuzumab-MCC-DM1 (T-DM1, also referred to as trastuzumab emtansine), an antibody-drug conjugate (CAS Reg. No. 139504-50-0), which has the structure:

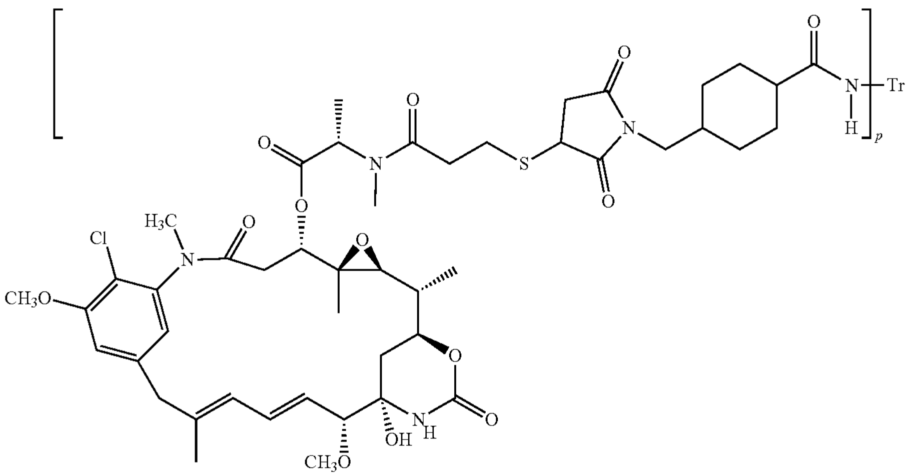

where Tr is trastuzumab linked through linker moiety MCC to the maytansinoid drug moiety DM1 (U.S. Pat. Nos. 5,208,020; 6,441,163). The drug to antibody ratio or drug loading is represented by p in the above structure of trastuzumab-MCC-DM1, and ranges in integer values from 1 to about 8. Trastuzumab-MCC-DM1 includes all mixtures of variously loaded and attached antibody-drug conjugates where 1, 2, 3, 4, 5, 6, 7, and 8 drug moieties are covalently attached to the antibody trastuzumab (U.S. Pat. Nos. 7,097,840; 8,337,856; US 2005/0276812; US 2005/0166993).

Trastuzumab can be produced by a mammalian cell (Chinese Hamster Ovary, CHO) suspension culture. The HER2 (or c-erbB2) proto-oncogene encodes a transmembrane receptor protein of 185 kDa, which is structurally related to the epidermal growth factor receptor. Trastuzumab is an antibody that has antigen binding residues of, or derived from, the murine 4D5 antibody (ATCC CRL 10463, deposited with American Type Culture Collection, 12301 Parklawn Drive, Rockville, Md. 20852 under the Budapest Treaty on May 24, 1990). Exemplary humanized 4D5 antibodies include huMAb4D5-1, huMAb4D5-2, huMAb4D5-

3, huMAb4D5-4, huMAb4D5-5, huMAb4D5-6, huMAb4D5-7 and huMAb4D5-8 (trastuzumab, HERCEPTIN®) as in U.S. Pat. No. 5,821,337. In some embodiments, the antibody portion of T-DM1 comprises the light and heavy chain amino acid sequences shown in SEQ ID NO: 30 and SEQ ID NO. 29, respectively.

Trastuzumab-MCC-DM1 may be prepared according to Example 1 of U.S. Application Publication No. 20110165155, for example.

As a general proposition, the initial pharmaceutically effective amount of trastuzumab-MCC-DM1 administered per dose will be in the range of about 0.3 to 15 mg/kg/day of patient body weight.

A commercial T-DM1 formulation (KADCYLA®, ado-trastuzumab emtansine) is a sterile, white to off-white preservative free lyophilized powder in single-use vials. Each vial contains 100 mg or 160 mg ado-trastuzumab emtansine. Following reconstitution, each single-use vial contains ado-trastuzumab emtansine (20 mg/mL), polysorbate 20 [0.02% (w/v)], sodium succinate (10 mM), and sucrose [6% (w/v)] with a pH of 5.0 and density of 1.026 g/mL. The resulting solution containing 20 mg/mL ado-trastuzumab emtansine is administered by intravenous infusion following dilution. In some embodiments, ado-trastuzumab emtansine is administered at a dose of 3.6 mg/kg every three weeks. In some embodiments, ado-trastuzumab emtansine is administered at a dose of 2.4 mg/kg every week.

Pertuzumab Compositions

The pertuzumab composition comprises a mixture of a main species pertuzumab antibody, as hereinabove defined, and one or more variants thereof. The preferred embodiment herein of a pertuzumab main species antibody is one comprising a light chain amino acid sequence of SEQ ID NO: 32, and a heavy chain amino acid sequence of SEQ ID NO: 31 (including deamidated and/or oxidized variants of those sequences). In some embodiments, the composition comprises a mixture of the main species pertuzumab antibody and an amino acid sequence variant thereof comprising an amino-terminal leader extension, e.g., comprising a light chain amino acid sequence of SEQ ID NO: 34, and a heavy chain amino acid sequence of SEQ ID NO: 33. Preferably, the amino-terminal leader extension is on a light chain of the antibody variant (e.g. on one or two light chains of the antibody variant). The main species HER2 antibody or the antibody variant may be an full length antibody or antibody fragment (e.g. Fab of F(ab')2 fragments), but preferably both are full length antibodies. The antibody variant herein may comprise an amino-terminal leader extension on any one or more of the heavy or light chains thereof. Preferably, the amino-terminal leader extension is on one or two light chains of the antibody. The amino-terminal leader extension preferably comprises or consists of VHS—. Presence of the amino-terminal leader extension in the composition can be detected by various analytical techniques including, but not limited to, N-terminal sequence analysis, assay for charge heterogeneity (for instance, cation exchange chromatography or capillary zone electrophoresis), mass spectrometry, etc. The amount of the antibody variant in the composition generally ranges from an amount that constitutes the detection limit of any assay (preferably N-terminal sequence analysis) used to detect the variant to an amount less than the amount of the main species antibody. Generally, about 20% or less (e.g. from about 1% to about 15%, for instance from 5% to about 15%) of the antibody molecules in the composition comprise an amino-terminal leader extension. Such percentage amounts are preferably determined using quantitative N-terminal sequence analysis or cation exchange analysis (preferably using a high-resolution, weak cation-exchange column, such as a PROPAC WCX-10™ cation exchange column). Aside from the amino-terminal leader extension variant, further amino acid sequence alterations of the main species antibody and/or variant are contemplated, including but not limited to an antibody comprising a C-terminal lysine residue on one or both heavy chains thereof, a deamidated antibody variant, etc.

Moreover, the main species antibody or variant may further comprise glycosylation variations, non-limiting examples of which include antibody comprising a G1 or G2 oligosaccharide structure attached to the Fc region thereof, antibody comprising a carbohydrate moiety attached to a light chain thereof (e.g. one or two carbohydrate moieties, such as glucose or galactose, attached to one or two light chains of the antibody, for instance attached to one or more lysine residues), antibody comprising one or two non-glycosylated heavy chains, or antibody comprising a sialylated oligosaccharide attached to one or two heavy chains thereof etc.

The composition may be recovered from a genetically engineered cell line, e.g. a Chinese Hamster Ovary (CHO) cell line expressing the HER2 antibody, or may be prepared by peptide synthesis.

For more information regarding exemplary pertuzumab compositions, see U.S. Pat. Nos. 7,560,111 and 7,879,325 as well as US 2009/0202546A1.

A commercial formulation of pertuzumab (PERJETA®) contains pertuzumab 420 mg/14 mL (30 mg/mL) in the form of a preservative-free solution for IV infusion. In some embodiments, pertuzumab therapy comprises administration of an initial loading dose of 840 mg, following by administration of a flat maintenance dose of 420 mg every three weeks.

F. Methods and Compositions for Diagnostics and Detection

In certain embodiments, any of the anti-HER2 antibodies provided herein is useful for detecting the presence of HER2 in a biological sample. The term "detecting" as used herein encompasses quantitative or qualitative detection. A "biological sample" comprises, e.g., a cell or tissue (e.g., biopsy material, including cancerous or potentially cancerous breast tissue).

In one embodiment, an anti-HER2 antibody for use in a method of diagnosis or detection is provided. In a further aspect, a method of detecting the presence of HER2 in a biological sample is provided. In certain embodiments, the method comprises contacting the biological sample with an anti-HER2 antibody as described herein under conditions permissive for binding of the anti-HER2 antibody to HER2, and detecting whether a complex is formed between the anti-HER2 antibody and HER2 in the biological sample. Such method may be an in vitro or in vivo method. In one embodiment, an anti-HER2 antibody is used to select subjects eligible for therapy with an anti-HER2 antibody, e.g. where HER2 is a biomarker for selection of patients. In a further embodiment, the biological sample is a cell or tissue.

In a further embodiment, an anti-HER2 antibody is used in vivo to detect, e.g., by in vivo imaging, a HER2-positive cancer in a subject, e.g., for the purposes of diagnosing, prognosing, or staging cancer, determining the appropriate course of therapy, or monitoring response of a cancer to therapy. One method known in the art for in vivo detection is immuno-positron emission tomography (immuno-PET), as described, e.g., in van Dongen et al., *The Oncologist*

12:1379-1389 (2007) and Verel et al., *J. Nucl. Med.* 44:1271-1281 (2003). In such embodiments, a method is provided for detecting a HER2-positive cancer in a subject, the method comprising administering a labeled anti-HER2 antibody to a subject having or suspected of having a HER2-positive cancer, and detecting the labeled anti-HER2 antibody in the subject, wherein detection of the labeled anti-HER2 antibody indicates a HER2-positive cancer in the subject. In certain of such embodiments, the labeled anti-HER2 antibody comprises an anti-HER2 antibody conjugated to a positron emitter, such as $^{68}$Ga, $^{18}$F, $^{64}$Cu, $^{86}$Y, $^{76}$Br, $^{89}$Zr, and $^{124}$I. In a particular embodiment, the positron emitter is $^{89}$Zr.

In further embodiments, a method of diagnosis or detection comprises contacting a first anti-HER2 antibody immobilized to a substrate with a biological sample to be tested for the presence of HER2, exposing the substrate to a second anti-HER2 antibody, and detecting whether the second anti-HER2 is bound to a complex between the first anti-HER2 antibody and HER2 in the biological sample. A substrate may be any supportive medium, e.g., glass, metal, ceramic, polymeric beads, slides, chips, and other substrates. In certain embodiments, a biological sample comprises a cell or tissue. In certain embodiments, the first or second anti-HER2 antibody is any of the antibodies described herein.

Exemplary disorders that may be diagnosed or detected according to any of the above embodiments include HER2-positive cancers, such as HER2-positive breast cancer and HER2-positive gastric cancer. In some embodiments, HER2-positive cancer has an immunohistochemistry (IHC) score of 2+ or 3+ and/or an in situ hybridization (ISH) amplification ratio ≥2.0.

In certain embodiments, labeled anti-HER2 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luciferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like. In another embodiment, a label is a positron emitter. Positron emitters include but are not limited to $^{68}$Ga, $^{18}$F, $^{64}$Cu, $^{86}$Y, $^{76}$Br, $^{89}$Zr, and $^{124}$I. In a particular embodiment, a positron emitter is $^{89}$Zr.

G. Pharmaceutical Formulations

Pharmaceutical formulations of an anti-HER2 antibody or immunoconjugate as described herein are prepared by mixing such antibody or immunoconjugate having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody or immunoconjugate formulations are described in U.S. Pat. No. 6,267,958. Aqueous antibody or immunoconjugate formulations include those described in U.S. Pat. No. 6,171,586 and WO2006/044908, the latter formulations including a histidine-acetate buffer.

The formulation herein may also contain more than one active ingredient as necessary for the particular indication being treated, preferably those with complementary activities that do not adversely affect each other.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody or immunoconjugate, which matrices are in the form of shaped articles, e.g. films, or microcapsules.

The formulations to be used for in vivo administration are generally sterile. Sterility may be readily accomplished, e.g., by filtration through sterile filtration membranes.

H. Therapeutic Methods and Compositions

Any of the anti-HER2 antibodies or immunoconjugates provided herein may be used in methods, e.g., therapeutic methods.

In one aspect, an anti-HER2 antibody or immunoconjugate provided herein is used in a method of inhibiting proliferation of a HER2-positive cell, the method comprising exposing the cell to the anti-HER2 antibody or immunoconjugate under conditions permissive for binding of the anti-HER2 antibody or immunoconjugate to HER2 on the surface of the cell, thereby inhibiting the proliferation of the cell. In certain embodiments, the method is an in vitro or an in vivo method. In further embodiments, the cell is a breast cancer cell or a gastric cancer cell.

Inhibition of cell proliferation in vitro may be assayed using the CellTiter-Glo™ Luminescent Cell Viability Assay, which is commercially available from Promega (Madison, WI). That assay determines the number of viable cells in culture based on quantitation of ATP present, which is an indication of metabolically active cells. See Crouch et al. (1993) *J. Immunol. Meth.* 160:81-88, U.S. Pat. No. 6,602,677. The assay may be conducted in 96- or 384-well format, making it amenable to automated high-throughput screening (HTS). See Cree et al. (1995) *AntiCancer Drugs* 6:398-404. The assay procedure involves adding a single reagent (Cell-Titer-Glo® Reagent) directly to cultured cells. This results in cell lysis and generation of a luminescent signal produced by a luciferase reaction. The luminescent signal is proportional to the amount of ATP present, which is directly proportional to the number of viable cells present in culture. Data can be recorded by luminometer or CCD camera imaging device. The luminescence output is expressed as relative light units (RLU).

In another aspect, an anti-HER2 antibody or immunoconjugate for use as a medicament is provided. In further aspects, an anti-HER2 antibody or immunoconjugate for use in a method of treatment is provided. In certain embodiments, an anti-HER2 antibody or immunoconjugate for use in treating HER2-positive cancer is provided. In certain embodiments, the invention provides an anti-HER2 antibody or immunoconjugate for use in a method of treating an individual having a HER2-positive cancer, the method comprising administering to the individual an effective amount of the anti-HER2 antibody or immunoconjugate. In one such embodiment, the method further comprises administering to the individual an effective amount of at least one additional therapeutic agent, e.g., as described below.

In a further aspect, the invention provides for the use of an anti-HER2 antibody or immunoconjugate in the manufacture or preparation of a medicament. In one embodiment, the medicament is for treatment of HER2-positive cancer. In a further embodiment, the medicament is for use in a method of treating HER2-positive cancer, the method comprising administering to an individual having HER2-positive cancer an effective amount of the medicament. In one such embodiment, the method further comprises administering to the individual an effective amount of at least one additional therapeutic agent, e.g., as described below.

In a further aspect, the invention provides a method for treating HER2-positive cancer. In one embodiment, the method comprises administering to an individual having such HER2-positive cancer an effective amount of an anti-HER2 antibody or immunoconjugate. In one such embodiment, the method further comprises administering to the individual an effective amount of at least one additional therapeutic agent, as described below.

A HER2-positive cancer according to any of the above embodiments may be, e.g., HER2-positive breast cancer or HER2-positive gastric cancer. In some embodiments, HER2-positive cancer has an immunohistochemistry (IHC) score of 2+ or 3+ and/or an in situ hybridization (ISH) amplification ratio ≥2.0.

An "individual," "patient," or "subject" according to any of the above embodiments may be a human.

In a further aspect, the invention provides pharmaceutical formulations comprising any of the anti-HER2 antibodies or immunoconjugate provided herein, e.g., for use in any of the above therapeutic methods. In one embodiment, a pharmaceutical formulation comprises any of the anti-HER2 antibodies or immunoconjugates provided herein and a pharmaceutically acceptable carrier. In another embodiment, a pharmaceutical formulation comprises any of the anti-HER2 antibodies or immunoconjugates provided herein and at least one additional therapeutic agent, e.g., as described below.

Antibodies or immunoconjugates of the invention can be used either alone or in combination with other agents in a therapy. For instance, an antibody or immunoconjugate of the invention (e.g., a hu7C2.v.2.2. LA antibody-drug conjugate (hu7C2 ADC)) may be co-administered with at least one additional therapeutic agent. In some embodiments, the additional therapeutic agent is also an antibody or immunoconjugate that binds to HER2. In some embodiments, the additional therapeutic agent is (i) an antibody or immunoconjugate that binds to domain II of HER2, and/or (ii) an antibody or immunoconjugate that binds to domain IV or HER2. In some embodiments, the additional therapeutic agent is (i) an antibody or immunoconjugate that binds to epitope 2C4, and/or (ii) an antibody or immunoconjugate that binds to epitope 4D5.

In some embodiments, a hu7C2.v.2.2. LA antibody-drug conjugate (hu7C2 ADC) is co-administered with one or more additional therapeutic agents selected from trastuzumab (Herceptin®), T-DM1 (Kadcyla®) and pertuzumab (Perjeta®). In some embodiments, an hu7C2 ADC is co-administered with trastuzumab. In some embodiments, a hu7C2 ADC is co-administered with T-DM1. In some embodiments, a hu7C2 ADC is co-administered with pertuzumab. In some embodiments, a hu7C2 ADC is co-administered with trastuzumab and pertuzumab. In some embodiments, a hu7C2 ADC is co-administered with T-DM1 and pertuzumab.

Such combination therapies noted above encompass combined administration (where two or more therapeutic agents are included in the same or separate formulations), and separate administration, in which case, administration of the antibody or immunoconjugate of the invention can occur prior to, simultaneously, and/or following, administration of the additional therapeutic agent and/or adjuvant. Antibodies or immunoconjugates of the invention can also be used in combination with radiation therapy.

An antibody or immunoconjugate of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies or immunoconjugates of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody or immunoconjugate need not be, but is optionally formulated with one or more agents currently used to prevent or treat the disorder in question. The effective amount of such other agents depends on the amount of antibody or immunoconjugate present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody or immunoconjugate of the invention (when used alone or in combination with one or more other additional therapeutic agents) will depend on the type of disease to be treated, the type of antibody or immunoconjugate, the severity and course of the disease, whether the antibody or immunoconjugate is administered for preventive or therapeutic purposes, previous therapy, the patient's clinical history and response to the antibody or immunoconjugate, and the discretion of the attending physician. The antibody or immunoconjugate is suitably administered to the patient at one time or over a series of treatments. Depending on the type and severity of the disease, about 1 mg/kg to 15 mg/kg (e.g. 0.1 mg/kg-10 mg/kg) of antibody or immunoconjugate can be an initial candidate dosage for administration to the patient, whether, for example, by one or more separate administrations, or by continuous infusion. One typical daily dosage might range from about 1 mg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody or immunoconjugate would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using both an immunoconjugate of the invention and an anti-HER2 antibody.

I. Articles of Manufacture

Articles of manufacture, or "kits", containing a hu7C2.v.2.2. LA antibody-drug conjugate (hu7C2 ADC) and trastuzumab-MCC-DM1 and/or pertuzumab useful for the treatment methods herein are provided. In some embodiments, the kit comprises a container comprising a hu7C2 ADC. In some embodiments, the kit further comprises a container comprising trastuzumab-MCC-DM1. In some embodiments, the kit further comprises container comprising pertuzumab. In some embodiments, a kit further comprises a container comprising trastuzumab-MCC-DM1 and a container comprising pertuzumab. In some embodiments, the kit comprises two or more of hu7C2 ADC, trastuzumab-MCC-DM1, and pertuzumab in the same container. The kit may further comprise a label or package insert, on or associated with the container. The term"package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold hu7C2 ADC and, optionally, trastuzumab-MCC-DM1 and/or pertuzumab or a formulation thereof which is effective for use in a treatment method herein, and may have a sterile access port (for example, the container may be an intravenous solution bag or a vial having a stopper pierceable by a hypodermic injection needle). The label or package insert indicates that the composition is used in a treatment method as described and claimed herein. The article of manufacture may also contain a further container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of hu7C2 ADC and, optionally, trastuzumab-MCC-DM1 and/or pertuzumab. For example, if the kit comprises a first composition comprising hu7C2 ADC and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of hu7C2 ADC and, optionally, trastuzumab-MCC-DM1 and/or pertuzumab, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with hu7C2 ADC, and optionally, (b) a second container with trastuzumab-MCC-DM1 contained therein and/or with pertuzumab contained therein. In some embodiments, a kit may comprise (a) a first container with hu7C2 ADC, (b) a second container with trastuzumab-MCC-DM1 contained therein, and (c) a third container with pertuzumab contained therein. In some embodiments, the kit may further comprise a container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Where the kit comprises a composition of hu7C2 ADC and trastuzumab-MCC-DM1 and/or pertuzumab, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

One embodiment of an article of manufacture herein comprises an intravenous (IV) bag containing a stable mixture of a hu7C2 ADC and pertuzumab and/or T-DM1 suitable for administration to a cancer patient. Optionally, the mixture is in saline solution; for example comprising about 0.9% NaCl or about 0.45% NaCl. An exemplary IV bag is a polyolefin or polyvinyl chloride infusion bag, e.g. a 250 mL IV bag. According to some embodiments of the invention, the mixture includes about 420 mg or about 840 mg of pertuzumab and from about 100 mg to about 160 mg T-DM1.

Optionally, the mixture in the IV bag is stable for up to 24 hours at 5° C. or 30° C. Stability of the mixture can be evaluated by one or more assays selected from the group consisting of: color, appearance and clarity (CAC), concentration and turbidity analysis, particulate analysis, size exclusion chromatography (SEC), ion-exchange chromatography (IEC), capillary zone electrophoresis (CZE), image capillary isoelectric focusing (iCIEF), and potency assay.

III. EXAMPLES

The following are examples of methods and compositions of the invention. It is understood that various other embodiments may be practiced, given the general description provided above.

Example 1

Humanization of Murine Antibody 7C2

Figure 3:
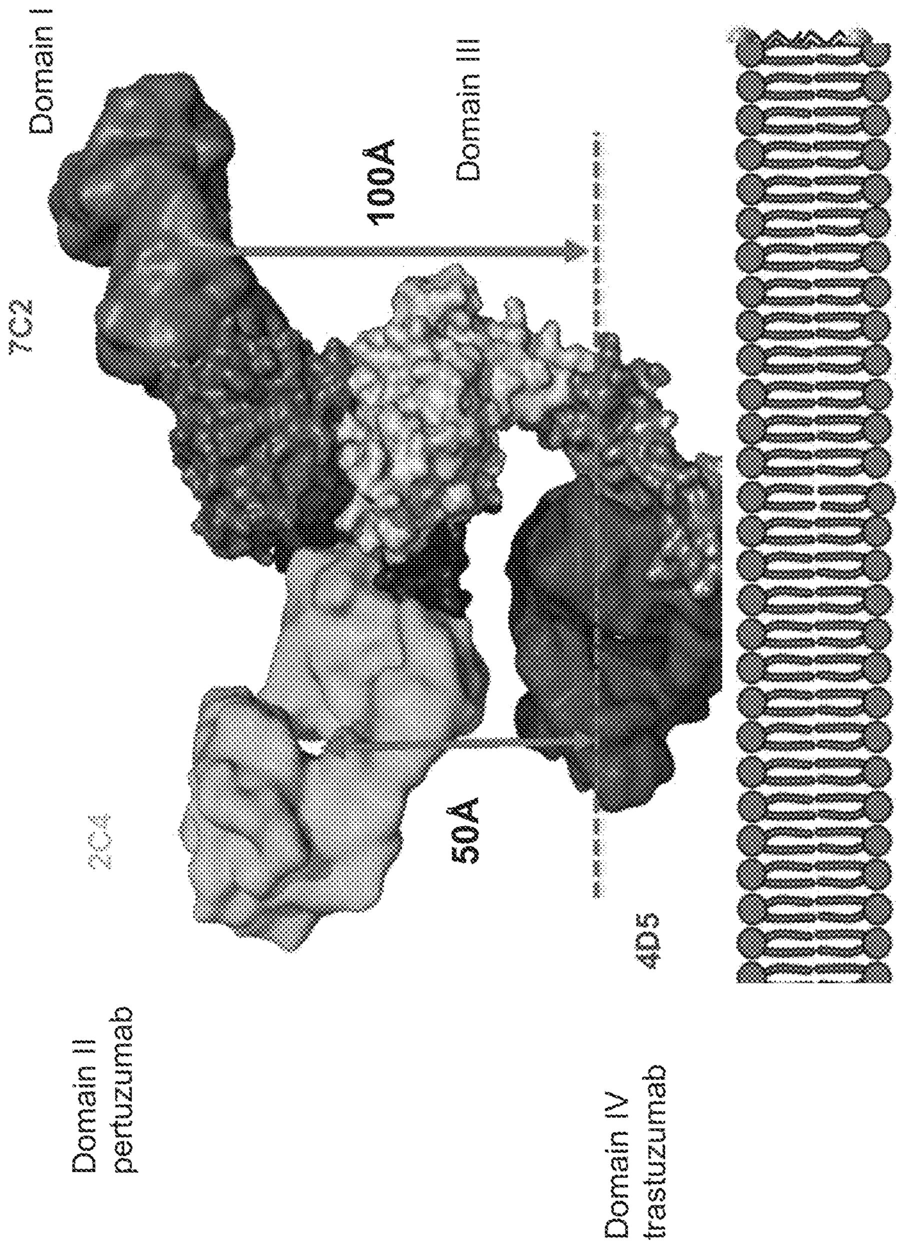
FIG. 3 shows the Her2 extracellular domain structure, with domains I to IV indicated, and the domains to which anti-Her2 antibodies trastuzumab, pertuzumab, and 7C2 bind.

Anti-HER2 murine antibody 7C2 binds to an epitope in domain I of HER2. See, e.g., PCT Publication No. WO 98/17797. This epitope is distinct from the epitope bound by trastuzumab, which binds to domain IV of HER2, and the epitope bound by pertuzumab, which binds to domain II of HER2. See FIGS. 3, 16, and 18. By binding domain IV, trastuzumab disrupts ligand-independent HER2-HER3 complexes, thereby inhibiting downstream signaling (e.g. PI3K/AKT). In contrast, pertuzumab binding to domain II prevents ligand-driven HER2 interaction with other HER family members (e.g. HER3, HER1 or HER4), thus also preventing downstream signal transduction. Binding of MAb 7C2 to domain I does not result in interference of trastuzumab or pertuzumab binding to domains IV and II, respectively, thereby offering the potential of combining a MAb 7C2 ADC with trastuzumab, trastuzumab emtansine (T-DM-1), and/or pertuzumab.

Murine antibody 7C2 (7C2. B9, see PCT Publication No. WO 98/17797) was humanized as follows.

A. Materials and Methods

Residue numbers are according to Kabat (Kabat et al., Sequences of proteins of immunological interest, 5th Ed., Public Health Service, National Institutes of Health, Bethesda, MD (1991)).

Direct hypervariable region grafts onto the acceptor human consensus framework. Variants constructed during the humanization of 7C2 were assessed in the form of an IgG. The VL and VH domains from murine 7C2 were aligned with the human VL kappa IV ($VL_{KIV}$) and human VH subgroup I ($VH_I$) consensus sequences. Hypervariable regions (HVR) from the murine 7C2 (7C2. B9) antibody were engineered into $VL_{KIV}$ and $VH_I$ acceptor frameworks to generate CDR-graft variants. From the mu7C2 VL domain, positions 24-34 (L1), 50-56 (L2) and 89-97 (L3) were grafted into $VL_{KI}$. From the mu7C2 VH domain, positions 26-35 (H1), 50-65 (H2) and 95-102 (H3) were grafted into $VH_I$ (FIGS. 1 and 2). The HVR definitions are defined by their sequence hypervariability (Wu, T. T. & Kabat, E. A. (1970)), their structural location (Chothia, C. & Lesk, A. M. (1987)) and their involvement in antigen-antibody contacts (MacCallum et al. J. Mol. Biol. 262: 732-745 (1996)). To evaluate framework vernier positions that might be important, selected vernier positions were mutated back to the murine sequence. The vernier positions include positions 4 and 49 in VL and positions 37, 67, 69, 71 and 73 in VH. Three different versions of VL sequences and VH sequences were synthesized (Blue Heron, Bothell, WA) and subsequently subcloned into mammalian expression vectors. By combining the different versions of LC with HC, a total of nine different hu7C2 graft variants (v1.1, v1.2, v1.3, v2.1, v2.2, v2.3, v3.1, v3.2 and v3.3) were generated.

Affinity maturation library. A monovalent Fab-g3 display phagemid vector with 2 open reading frames under control of a single phoA promoter was used. The first open reading frame consists of the stII signal sequence fused to the VL and CH1 domains of the acceptor light chain and the second consists of the stII signal sequence fused to the VH and CH1 domains of the acceptor heavy chain followed by the minor phage coat protein P3. The HVR graft variant (7C2.v2.1) was generated by Kunkel mutagenesis using separate oligonucleotides for each hypervariable region, and displayed on phage as a Fab.

To improve affinity, phage libraries containing changes in each hypervariable region were generated. Sequence diversity was introduced separately at each position in the hypervariable regions of 7C2.v2.1 using Kunkel mutagenesis. Positions in the hypervariable region of 7C2.v2.1 were each fully randomized one at a time to all possible 20 amino acids using oligonucleotides encoding NNS. A total of 68 libraries, each consisting of 20 members, were made having a single position located within one of the hypervariable regions of 7C2 fully randomized. Libraries with positions in the same hypervariable region were pooled to generate a total of six libraries.

Generation of phage libraries. Oligonucleotides designed to introduce diversity into each hypervariable region as outlined above were phosphorylated separately in 20 μl reactions containing 660 ng of oligonucleotide, 50 mM Tris pH 7.5, 10 mM $MgCl_2$, 1 mM ATP, 20 mM DTT, and 5 U polynucleotide kinase for 1 h at 37° C.

To generate the affinity maturation library, 68 individual Kunkel mutagenesis reactions were performed in a 96-well PCR plate. From the phosphorylated oligonucleotides reactions (above), 2 μl was added to 500 ng Kunkel template in 50 mM Tris pH 7.5, 10 mM $MgCl_2$ in a final volume of 25 μl. The mixture was annealed at 90° C. for 1 min, 50° C. for 3 min and then cooled on ice. The annealed template was then filled in by adding 0.5 μl 10 mM ATP, 0.5 μl 10 mM dNTPs (10 mM each of dATP, dCTP, dGTP and dTTP), 1 μl 100 mM DTT, 1 μl 10× TM buffer (0.5 M Tris pH 7.5, 0.1 M $MgCl_2$), 80 U T4 ligase, and 4 U T7 polymerase in a total volume of 30 μl for 2 h at room temperature. These filled-in and ligated products were then each transformed into XL1-blue cells. The libraries containing positions in the same CDR region were pooled and recovered in 10 ml SOC media for 1 hour at 37° C. Carbenicillin (50 μg/ml) and M13/KO7 helper phage (MOI 10) were added. The cultures were incubated for another 30 mins at 37° C. and transferred to 500 ml 2YT containing 50 μg/ml carbenicillin and 50 μg/ml kanamycin and grown 20 h at 37° C.

Phage Selections. Her2 extracellular domain (Her2 ECD) was biotinylated through free amines using NHS-PEG4-Biotin (Pierce). For biotinylation reactions, a 4-fold molar excess of biotin reagent was used in PBS. Reactions were followed by dialysis in PBS.

Phage were harvested from the cell culture supernatant and suspended in PBS containing 1% BSA. The phage libraries were incubated with biotinylated Her2 ECD at room temperature and the phage bound to biotin-Her2 was then captured for 5 min on neutrAvidin (10 μg/ml) that had been immobilized in PBS on MaxiSorp microtiter plates (Nunc) overnight at 4° C. Microtiter wells were washed extensively with PBS containing 0.05% Tween 20 (PBST) and bound phage were eluted by incubating the wells with 20 mM HCl, 500 mM KCl for 30 min. Eluted phage were neutralized with 1 M Tris, pH 7.5 and amplified using XL1-Blue cells and M13/KO7 helper phage and grown overnight at 37° C. in 2YT, 50 μg/ml carbenicillin and 50 μg/ml Kanamycin. The titers of phage eluted from a target containing well were compared to titers of phage recovered from a non-target containing well to assess enrichment. Selection stringency was increased by both decreasing concentration of biotinylated Her2 ECD (from 5 nM to 0.2 nM) during binding and increasing the competition time (from 0 to 60 min at room temperature) with 1 μM of unlabeled Her2 ECD in solution.

Surface plasmon resonance assessment of variants. 7C2 variants were expressed as IgG by 293 transient transfection. IgG was purified with protein G affinity chromatography. The affinity of each 7C2 IgG variant for Her2 was determined by surface plasmon resonance using a BIAcoreT100. Biacore Series S CM5 sensor chips were immobilized with monoclonal mouse anti-human IgG (Fc) antibody (Human antibody capture kit, GE Healthcare). Serial 3-fold dilutions of each 7C2 variant were injected at a flow rate of 30 μl/min. Each sample was analyzed with 3-minute association and 10-minute dissociation. After each injection the chip was regenerated using 3 M $MgCl_2$. Binding response was corrected by subtracting the RU from a flow cell capturing an irrelevant IgG at similar density. A 1:1 Languir model of simultaneous fitting of $k_{on}$ and $k_{off}$ was used for kinetics analysis.

B. Results and Discussion

Humanization of 7C2. The human acceptor frameworks used for humanization of 7C2 are based on the human VL kappa IV consensus ($VL_{KIV}$) and the human $VH_I$ consensus. The VL and VH domains of murine 7C2 were aligned with the human $VL_{KIV}$ and $VH_I$ domains; hypervariable regions were identified and grafted into the human acceptor framework to generate 7C2.v1.1. The monovalent affinity of 7C2.v1.1 is decreased 2.5-fold relative to mu7C2. B9 as assessed by SPR (see Table 2).

TABLE 2

Affinity of 7C2 CDR grafted antibodies

| | | VL | | |
|---|---|---|---|---|
| | $K_D$ (nM) | K4 | K4.K49 | K4.L4.K49 |
| VH | VH1 | v1.1 (20 nM) | v2.1 (16 nM) | v3.1 (15 nM) |
| | VH1.V71 | v1.2 (13 nM) | v2.2 (11 nM) | v3.2 (10 nM) |

TABLE 2-continued

Affinity of 7C2 CDR grafted antibodies

| | VL | | |
|---|---|---|---|
| $K_D$ (nM) | K4 | K4.K49 | K4.L4.K49 |
| VH1.L37.A67.L69. V71.K73 | v1.3 (11 nM) | v2.3 (10 nM) | v3.3 (9 nM) |

To improve the binding affinity of 7C2.v1.1, positions 4 and 49 in the light chain and positions 37, 67, 69, 71 and 73 in the heavy chain were changed to residues found at these positions in mu7C2. B9. Combinations of these altered light and heavy chains with chains from 7C2.v1.1 were transfected into 293 cells, expressed as IgG and purified, and assessed for binding to Her2 ECD by SPR (see Table 2). Variant 7C2.v3.3, which contains 2 altered positions in light chain and 5 altered positions in heavy chain, had a monovalent affinity comparable to chimeric mu7C2. B9 (see Table 2).

Affinity maturation libraries were explored in an effort to recruit further improvements using the framework of 7C2.v2.1, which contains minimal altered vernier position (Y49K) in light chain. For each hypervariable region, all 20 amino acids were introduced separately at individual position using Kunkle mutagenesis (a total of 68 libraries, each containing 20 members, pooled into six affinity maturation libraries). The six affinity maturation libraries were panned for 4 rounds in solution with biotinylated Her2 ECD. Selection stringency was gradually increased by decreasing the concentration of biotin-Her2 ECD (from 5 to 0.2 nM) and increasing the competition time (from 0 to 1 hour at room temperature) with saturated amount of unlabeled Her2 ECD. A two thousand fold of phage enrichment was observed for the H2 library.

A total of 588 clones from the last round were picked for DNA sequence analysis. Individual sequence changes were identified in each HVR (see Table 3). The most abundant clones had changes in VH at position S53 to Met or Leu. The S53M and S53L variants were expressed as IgG and SPR analysis indicate that S53M and S53L have comparable affinity to Her2. The S53L variant was selected since methionine is prone to oxidation during the manufacturing process. A potential iso-aspartic acid forming site in HVR-H2 was eliminated with a S55A mutation (see Table 4).

TABLE 3

Kinetics of affinity-improved variants

| Variant | HVR-H1 | HVR-H2 | HVR-H3 | $k_a$ (1/Ms) | $k_d$ (1/s) | $K_D$ (nM) |
|---|---|---|---|---|---|---|
| v2.1 | GYWMN (SEQ ID NO: 15) | MIHPSDSEIRANQKFRD (SEQ ID NO: 8) | GTYDGGFEY (SEQ ID NO: 17) | 2.6E+05 | 4.1E-03 | 15.5 |
| v2.1. S53M | | MIHPMDSEIRANQKFRD (SEQ | | 2.7E+05 | 6.7E-04 | 2.4 |

TABLE 3-continued

Kinetics of affinity-improved variants

| Variant | HVR-H1 | HVR-H2 | HVR-H3 | $k_a$ (1/Ms) | $k_d$ (1/s) | $K_D$ (nM) |
|---|---|---|---|---|---|---|
| | | ID NO: 20) | | | | |
| v2.1. S53L | | MIHP LDSE IRAN QKFR D (SEQ ID NO: 21) | | 2.5E+05 | 8.5E-04 | 3.4 |
| v2.1. E101K | | | GTYDG YGFK (SEQ ID NO: 22) | 2.2E+05 | 1.5E-03 | 6.8 |

TABLE 4

Summary of hu7C2 variant affinities

| hu7C2 variant | $K_D$ (nM) |
|---|---|
| mu7C2.B9 | 8 |
| hu7C2.v2.2 | 11 |
| hu7C2.v2.2.LA (S53L, S55A); HVR-H2 of SEQ ID NO: 16 | 3 |

An alignment of the human $VL_{KIV}$ and $VH_I$ domains and the heavy chain and light chain variable regions of mu7C2. B9 ("7C2") and hu7C2.v2.2. LA (referred to in the following examples as "hu7C2") is shown in FIGS. 1 and 2.

Example 2

Production of hu7C2 Antibody Drug Conjugates

For larger scale antibody production, antibodies were produced in CHO cells. Vectors coding for heavy chain and light chain were transfected into CHO cells and IgG was purified from cell culture media by protein A affinity chromatography.

A. Synthesis of Pyridyl Disulfide PNU Amide Linker Drug Intermediate

The pyridyl disulfide PNU amide linker drug intermediate ((2S,4S)-4-[[(1S,3R,4aS,9S,9aR,10aS)-9-methoxy-1-methyl-3,4,4a,6,7,9,9a,10α-octahydro-1H-pyrano[1,2]oxazolo[3,4-13][1,4]oxazin-3-yl]oxy]-2,5,12-trihydroxy-7-methoxy-6,11-dioxo-N-[2-(2-pyridyldisulfanyl)ethyl]-3,4-dihydro-1H-tetracene-2-carboxamide; "LD-51") having the following formula:

LD-51

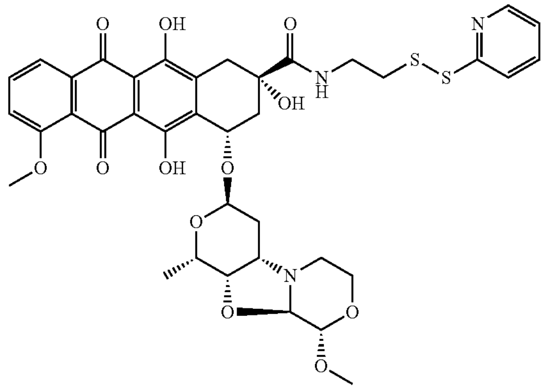

was synthesized as follows. Following Example 3 of U.S. Pat. No. 8,389,697, to a solution of PNU-159682 (15.3 mg, 0.02038 mmol), prepared as reported in WO 1998/02446 and Example 1 of U.S. Pat. No. 8,470,984, in 3 ml of methanol and 2 ml of $H_2O$, a solution of $NaIO_4$ (5.1 mg, 0.0238 mmol) in 1 ml of $H_2O$ was added. The reaction mixture was stirred at room temperature for 3 hours, until no starting material was detectable (TLC and HPLC analysis). The solvents were removed under reduced pressure and the crude red solid (2S,4S)-2,5,12-trihydroxy-7-methoxy-4-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-6,11-dioxo-1,2,3,4,6,11-hexahydrotetracene-2-carboxylic acid 51a was used without further purifications in the next step. MS (ESI): 628 $[M+H]^+$.

51a

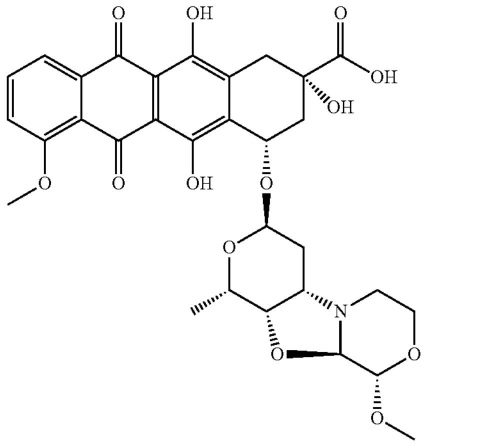

To a solution of the crude intermediate 51a in anhydrous dichloromethane under argon atmosphere, was added anhydrous triethylamine, TBTU (O-(Benzotriazol-1-yl)-N,N,N',N'-tetramethyluronium tetrafluoroborate, also called: N,N,N',N'-Tetramethyl-O-(benzotriazol-1-yl)uronium tetrafluoroborate, CAS No. 125700-67-6, Sigma-Aldrich B-2903), and N-hydroxysuccinimide to form the intermediate NHS ester of 51a. Alternatively, other coupling reagents such as DCC or EDC can be used. After one hour, 2-(pyridin-2-yldisulfanyl)ethanamine hydrochloride (CAS No. 106139-15-5) was added. The reaction mixture was stirred at room temperature for 30 min, until disappearance of the starting material (HPLC-MS analysis). The solvent was evaporated under vacuum and the residue was then purified by flash column chromatography on silica gel, affording LD-51. MS (ESI): 796.88 $[M+H]^+$.

B. Synthesis of CBI-PBD Linker Drug Intermediates

The CBI-PBD dimer (piperazine-carbamate prodrug)-2-propyl pyridyl disulfide linker-drug intermediate (2-(2-pyridyldisulfanyl)propyl 3-[6-[1-(chloromethyl)-5-(4-methylpiperazine-1-carbonyl)oxy-1,2-dihydrobenzo[e]indol-3-yl]-6-oxo-hexoxy]-6-hydroxy-2-methoxy-11-oxo-6a,7,8,9-tetrahydro-6H-pyrrolo[2,1-c][1,4]benzodiazepine-5-carboxylate; compound 81 from Table A) having the formula:

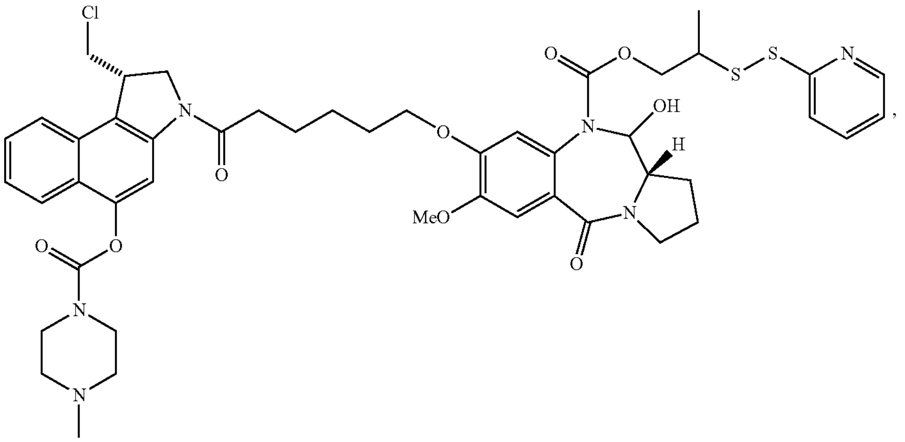 [SMILES: COc1cc2c(cc1OCCCCCC(=O)N1C[C@@H](CCl)c3c1cc(OC(=O)N1CCN(C)CC1)c1ccccc31)N(C(=O)OCC(C)SSc1ccccn1)C(O)[C@@H]1CCCN1C2=O]

Figure 9:
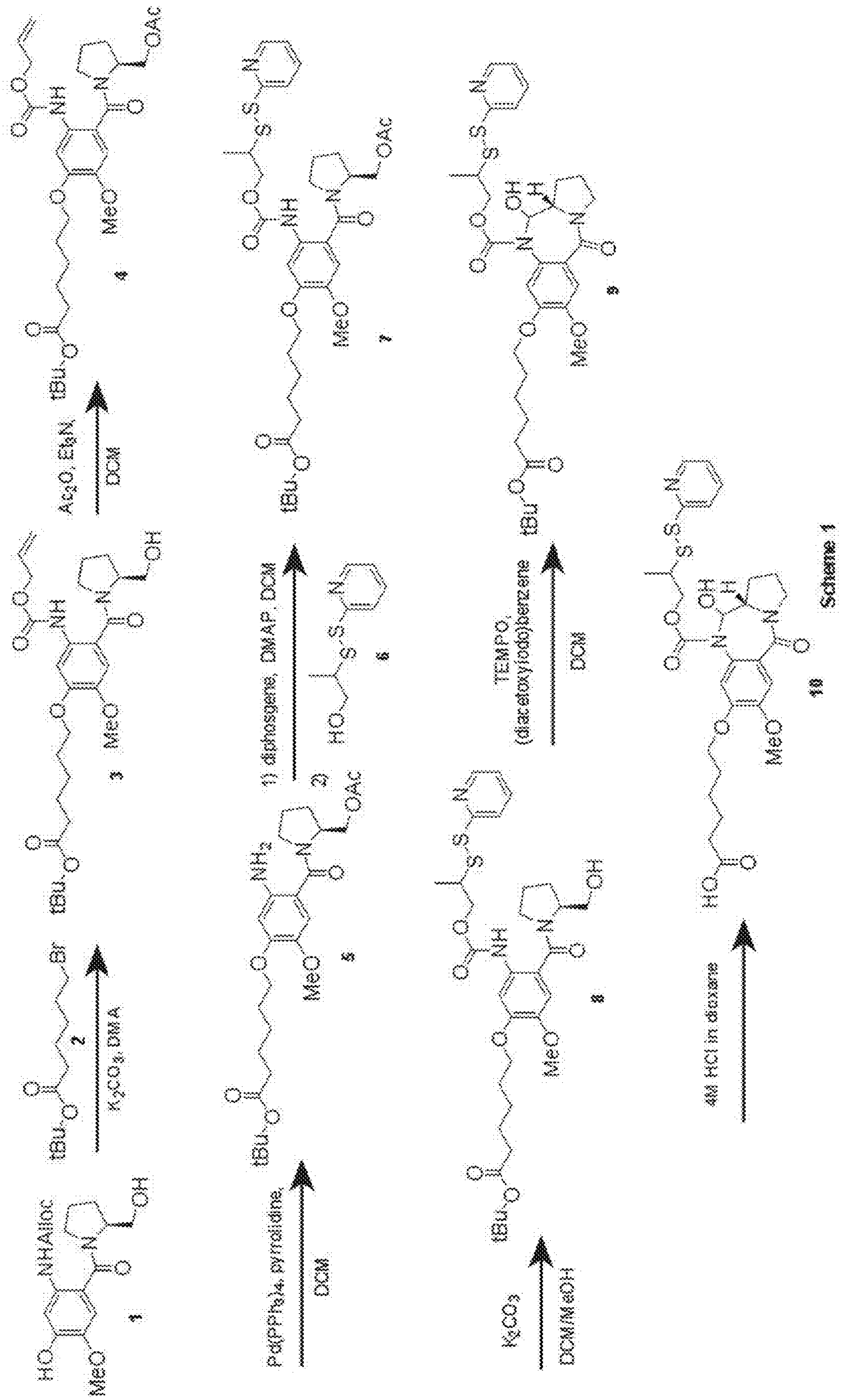
FIGS. 9 and 10 show an exemplary synthesis method for making certain CB-PBD linker drug intermediates, as described in Example 3.
Figure 10:
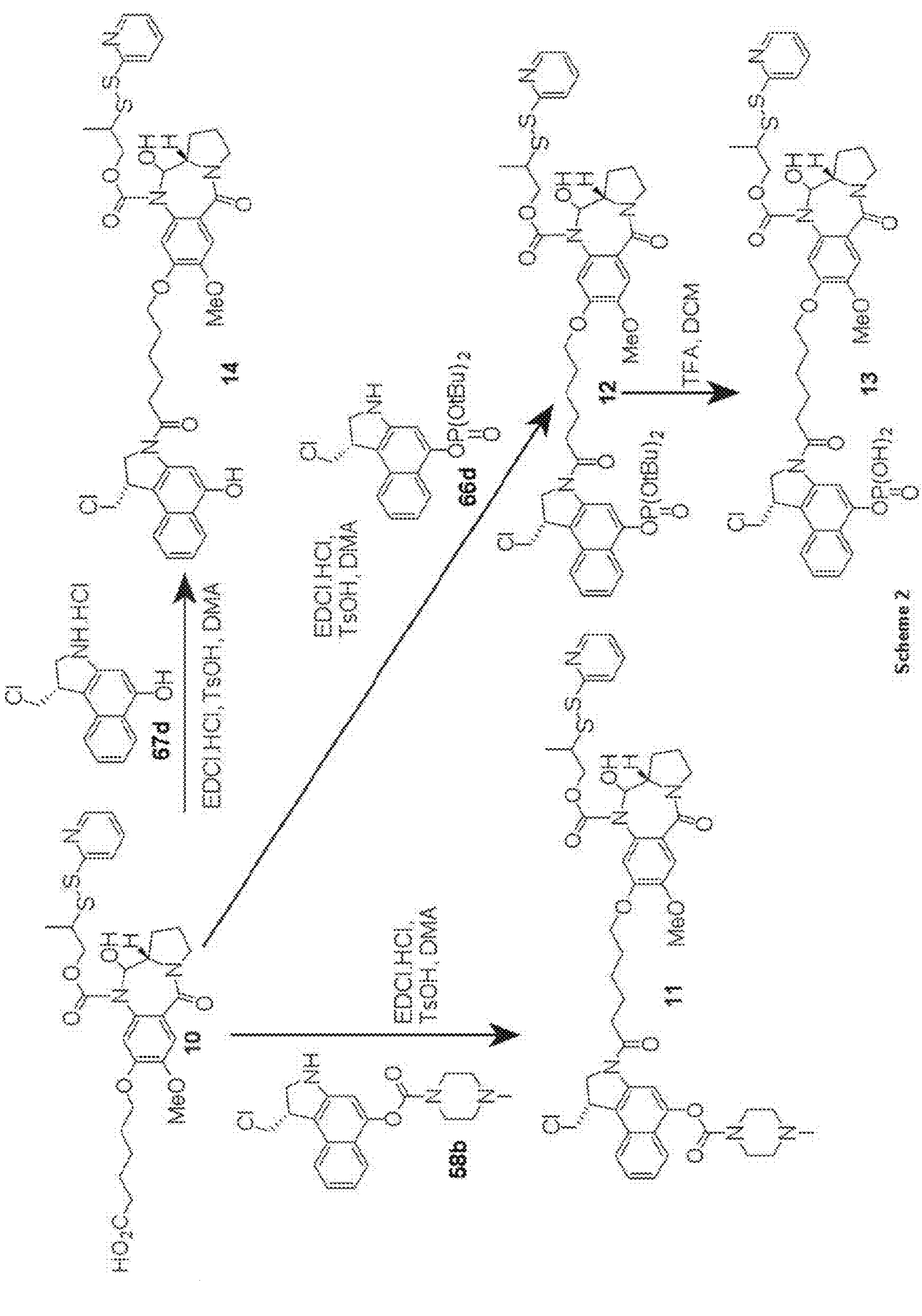

- and the CBI-PBD dimer (phosphate)-2-propyl pyridyl disulfide linker-drug intermediate (2-(2-pyridyldisulfanyl)propyl 3-[6-[1-(chloromethyl)-5-phosphonooxy-1,2-dihydrobenzo[e]indol-3-yl]-6-oxo-hexoxy]-6-hydroxy-2-methoxy-11-oxo-6a,7,8,9-tetrahydro-6H-pyrrolo[2,1-c][1,4]benzodiazepine-5-carboxylate; compound 82 from Table A) having the formula:

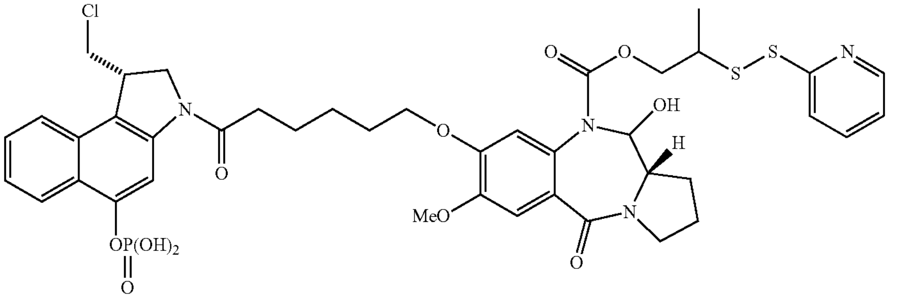

were synthesized as follows. For the reaction scheme, including reagent and intermediate formulae, see FIGS. 9 and 10. This synthesis is also suitable for producing 2-(2-pyridyldisulfanyl)propyl 3-[6-[1-(chloromethyl)-5-hydroxy-1,2-dihydrobenzo[e]indol-3-yl]-6-oxo-hexoxy]-6-hydroxy-2-methoxy-11-oxo-6a,7,8,9-tetrahydro-6H-pyrrolo[2,1-c][1,4]benzodiazepine-5-carboxylate ("CBI-PBD-2-propyl pyridyl disulfide").

A mixture of 1 (1.40 g, 4.00 mmol, prepared following literature procedure: *J. Med. Chem.* 2003, 46, 2132-2151), 2 (1.31 g, 5.22 mmol, prepared following literature procedure: WO2004065491 A1) and $K_2CO_3$ (829 mg, 6.00 mmol) in dry DMA (15 mL) was stirred at r.t. for 43 h. The mixture was then diluted with EtOAc and $H_2O$, well mixed and the layers separated. The organic layer was washed with $H_2O$ (3×), brine (1×) and dried ($Na_2SO_4$) and the solvent removed under vacuum. The crude product was purified by column chromatography on silica gel using EtOAc:Hex 50:50 to 67:33 to 100:0 to give compound 3 (1.74 g, 84%) as a yellow oil. $^{1}H$ NMR δ (400 MHz, $CDCl_3$) 8.77 (br s, 1H), 7.79 (s, 1H), 6.82 (s, 1H), 6.02-5.92 (m, 1H), 5.36 (dq, J=17.2, 1.5 Hz, 1H), 5.26 (dq, J=10.4, 1.2 Hz, 1H), 4.69-4.60 (m, 2H), 4.47-4.39 (m, 1H), 4.28 (br s, 1H), 4.09-4.05 (m, 2H), 3.83 (s, 3H), 3.90-3.80 (m, 1H), 3.74-3.70 (m, 1H), 3.65-3.59 (m, 1H), 3.54-3.47 (m, 1H), 2.25 (t, J=7.4 Hz, 2H), 2.20-2.15 (m, 1H), 1.93-1.84 (m, 3H), 1.81-1.72 (m, 1H), 1.70-1.63 (m, 3H), 1.53-1.47 (m, 2H), 1.44 (s, 9H). HRMS m/z 543.2666 $[(M+Na)^+$ calcd for $C_{27}H_{40}N_2NaO_8$ 543.2677].

4

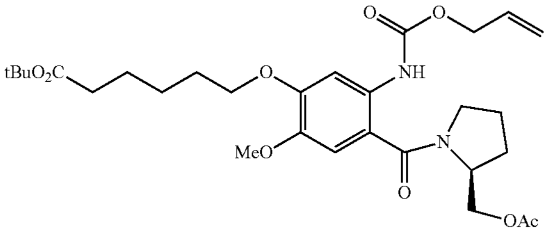

$Et_3N$ (1.32 mL, 9.47 mmol) was added to a solution of 3 (821 mg, 1.58 mmol) in dry DCM (6 mL) at r.t. Acetic anhydride (0.75 mL, 7.93 mmol) was then added and the mixture stirred at r.t. for 4.5 h. The reaction mixture was cooled to 0° C. and dry MeOH (1 mL) added and the mixture stirred at 0° C. for 15 mins. EtOAc (120 mL) was then added and the mixture washed with $H_2O$ (2×), brine (1×), dried ($Na_2SO_4$) and solvent removed under vacuum to give compound 4 (891 mg, quantitative) which was used in the next step without purification. $^{1}H$ NMR δ (400 MHz, $CDCl_3$) 8.88 (br s, 1H), 7.82 (s, 1H), 6.81 (s, 1H), 6.01-5.91 (m, 1H), 5.36 (dq, J=17.2, 1.5 Hz, 1H), 5.25 (dq, J=10.4, 1.3 Hz, 1H), 4.65-4.62 (m, 2H), 4.61-4.54 (m, 1H), 4.32-4.22 (m, 2H), 4.09-4.06 (m, 2H), 3.83 (s, 3H), 3.55-3.47 (m, 2H), 2.26-2.23 (m, 2H), 2.18-2.12 (m, 1H), 2.07 (s, 3H), 1.97-1.77 (m, 5H), 1.70-1.63 (m, 2H), 1.54-1.47 (m, 2H), 1.44 (s, 9H). HRMS m/z 585.2774 $[(M+Na)^+$ calcd for $C_{29}H_{42}N_2NaO_9$ 585.2783].

5

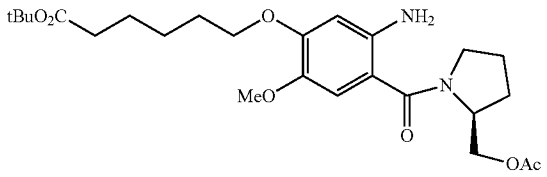

Pyrrolidine (1.6 mL, 19.2 mmol) was added to a solution of 4 (1.06 g, 1.88 mmol) in dry DCM (20 mL) at r.t. $Pd(PPh_3)_4$ (109 mg, 0.0943 mmol) was then added and the reaction mixture stirred at r.t. for 40 mins. The reaction mixture was washed with 0.25 M HCl solution (2×75 mL), dried ($Na_2SO_4$) and solvent removed under vacuum. The crude product was purified by column chromatography on silica gel using EtOAc:Hex 50:50 to 100:0 to give compound 5 (726 mg, 81%) as a yellow oil. $^{1}H$ NMR δ (400 MHz, DMSO-$d_6$) 6.67 (s, 1H), 6.35 (s, 1H), 5.08 (s, 2H), 4.35-4.30 (m, 1H), 4.13-4.06 (m, 2H), 3.87 (t, J=6.4 Hz, 2H), 3.63 (s, 3H), 3.50-3.44 (m, 1H), 3.42-3.35 (m, 1H), 2.21 (t, J=7.2 Hz, 2H), 2.07-2.00 (m, 1H), 2.01 (s, 3H), 1.89-1.82 (m, 1H), 1.77-1.67 (m, 4H), 1.59-1.51 (m, 2H), 1.44-1.36 (m, 2H), 1.39 (s, 9H). HRMS m/z 501.2573 $[(M+Na)^+$ calcd for $C_{25}H_{38}N_2NaO_7$ 501.2571].

7

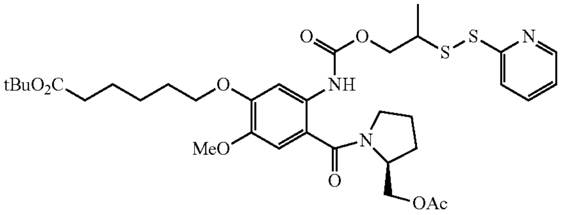

Diphosgene (0.22 mL, 1.82 mmol) was added to a mixture of 5 (726 mg, 1.52 mmol) and DMAP (557 mg, 4.56 mmol) in dry DCM (25 mL) at r.t. under nitrogen. After 30 mins a solution of 6 (2.60 g, 12.9 mmol; freshly made by the procedure mentioned above—no number previously assigned to alcohol) in dry DCM (25 mL) was added and the mixture stirred at r.t. overnight. After 18 h the reaction mixture was washed with $H_2O$ (1×), dried ($Na_2SO_4$) and solvent removed under vacuum. The crude product was purified by column chromatography on silica gel using DCM:EtOAc 100:0 to 95:5 to 94:6 until excess 6 eluted and then EtOAc:Hex 70:30 to give compound 7 (920 mg, 86%) as a pale yellow oil. $^{1}H$ NMR δ (400 MHz, DMSO-$d_6$) 9.16 (br s, 1H), 8.45-8.43 (m, 1H), 7.83-7.78 (m, 2H), 7.25-7.21 (m, 1H), 7.15 (d, J=2.8 Hz, 1H), 6.87 (s, 1H), 4.29 (br s, 1H), 4.17-3.99 (m, 4H), 3.92 (t, J=6.4 Hz, 2H), 3.75 (s, 3H), 3.42-3.30 (m, 3H), 2.20 (t, J=7.2 Hz, 2H), 2.06-1.95 (m, 4H), 1.83 (br s, 1H), 1.77-1.68 (m, 4H), 1.58-1.49 (m, 2H), 1.43-1.36 (m, 2H), 1.39 (s, 9H), 1.29 (d, J=6.8 Hz, 3H). HRMS m/z 706.2832 $[(M+H)^+$ calcd for $C_{34}H_{48}N_3O_9S_2$ 706.2826].

8

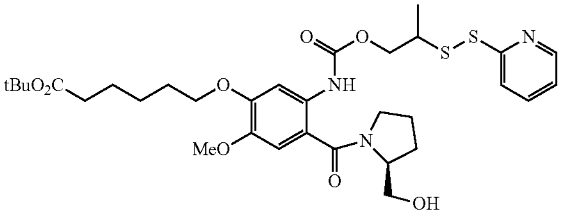

A mixture of 7 (949 mg, 1.34 mmol) and $K_2CO_3$ (1.85 g, 13.4 mmol) in DCM-MeOH (34 mL/17 mL) was stirred at r.t. for 45 mins. The mixture was diluted with DCM, poured into ice $H_2O$ (200 mL), well mixed and the layers separated. The aqueous layer was extracted with DCM (1×), the combined organic layers were dried ($Na_2SO_4$) and solvent removed under vacuum. The crude product was purified by column chromatography on silica gel using DCM:EtOAc 100:0 to 50:50 to give compound 8 (808 mg, 91%) as a pale yellow oil. $^{1}H$ NMR δ (400 MHz, DMSO-$d_6$) 9.20 (br s, 1H), 8.44 (d, J=4.7 Hz, 1H), 7.81-7.80 (m, 2H), 7.25-7.20 (m, 2H), 6.94 (s, 1H), 4.75 (t, J=5.6 Hz, 1H), 4.17-3.99 (m, 3H), 3.92 (t, J=6.4 Hz, 2H), 3.74 (s, 3H), 3.60-3.46 (m, 2H), 3.37-3.20 (m, 3H), 2.20 (t, J=7.2 Hz, 2H), 1.93-1.76 (m, 3H), 1.75-1.68 (m, 3H), 1.58-1.51 (m, 2H), 1.44-1.36 (m, 2H), 1.39 (s, 9H), 1.29 (d, J=6.9 Hz, 3H). HRMS m/z 664.2721 $[(M+H)^+$ calcd for $C_{32}H_{46}N_3O_8S_2$ 664.2724].

9

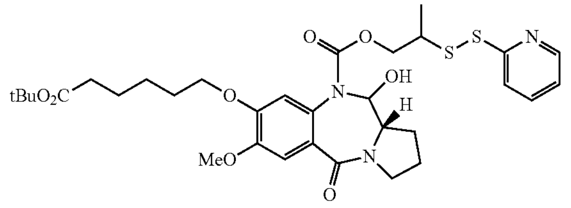

(Diacetoxyiodo)benzene (259 mg, 0.804 mmol) was added to a mixture of 8 (349 mg, 0.526 mmol) and TEMPO (82.2 mg, 0.526 mmol) in dry DCM (10 mL) at r.t. and the reaction mixture stirred overnight. After 24 h the mixture was diluted with DCM and saturated aqueous $Na_2S_2O_3$ and well mixed. The layers were separated and the organic layer was washed with saturated aqueous $Na_2S_2O_3$ (1×), saturated aqueous $NaHCO_3$ (1×), dried ($Na_2SO_4$) and solvent removed under vacuum. The crude product was purified by column chromatography on silica gel using EtOAc:Hex 70:30 to 100:0 to give compound 9 (248 mg, 71%) as a white foam. $^1$H NMR δ (400 MHz, DMSO-$d_6$) 8.45-8.43 (m, 1H), 7.79-7.69 (m, 1H), 7.51-7.48 (m, 1H), 7.24-7.20 (m, 1H), 7.10 (s, 1H), 6.96 and 6.91 (2s, 1H), 6.55 (t, J=5.9 Hz, 1H), 5.46 (dd, J=8.9, 6.1 Hz, 1H), 4.31-4.21 (m, 1H), 4.02-3.84 (m, 3H), 3.80 and 3.79 (2s, 3H), 3.52-3.46 (m, 1H), 3.40-3.18 (m, 3H), 2.19-2.13 (m, 2H), 2.09-2.00 (m, 1H), 1.96-1.85 (m, 3H), 1.70-1.67 (m, 2H), 1.56-1.45 (m, 2H), 1.40-1.34 (m, 2H), 1.38 and 1.37 (2s, 9H), 1.15-1.10 (m, 3H). HRMS m/z 662.2592 [(M+H)$^+$ calcd for $C_{32}H_{44}N_3O_8S_2$ 662.2564].

10

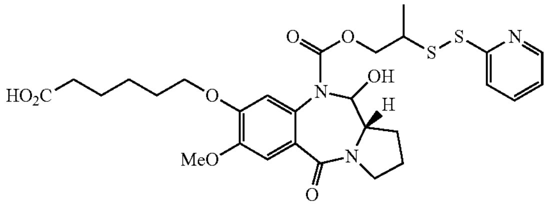

A mixture of 9 (254 mg, 0.384 mmol) and 4 M HCl in dioxane (11 mL) was stirred at r.t. for 1 h 15 mins. The solvent was removed under vacuum at 25-30° C. to give compound 10 (162 mg, 70%) which was used in the next step without purification.

11

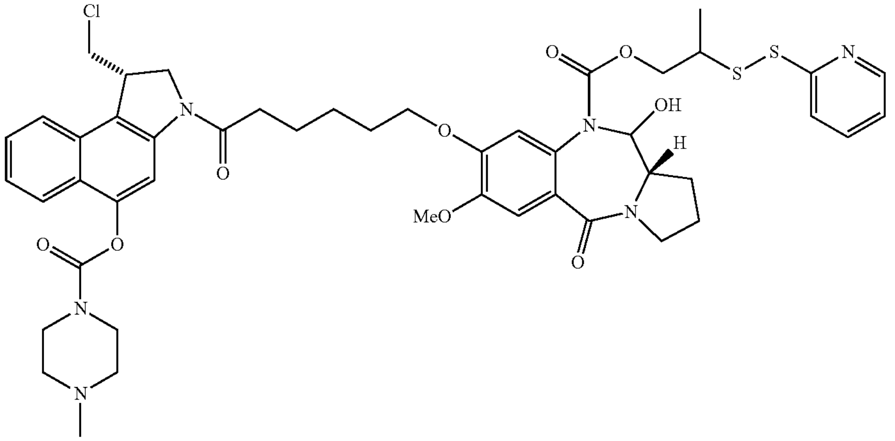

A mixture of 10 (161 mg, 0.266 mmol), 58b (195 mg, 0.542 mmol, freshly made by the procedure mentioned above), EDCI·HCl (253 mg, 1.32 mmol) and TsOH (19.5 mg, 0.113 mmol) in dry DMA (5 mL) was stirred at r.t. overnight, under nitrogen. After 23 h the reaction mixture was diluted with EtOAc and saturated aqueous $NaHCO_3$ and well mixed. The layers were separated and the aqueous layer extracted with EtOAc (1×). The combined organic layers were washed with $H_2O$ (1×), brine (1×), dried ($Na_2SO_4$) and solvent removed under vacuum. The crude product was purified by column chromatography on silica gel using DCM:MeOH 100:0 to 93:7 and the material recolumned using DCM:MeOH 99:1 to 94:6 to give 11 (Compound No. 81, 118 mg, 47%, HPLC purity: 98.0%) as a pale yellow foam. $^1$H NMR δ (400 MHz, DMSO-$d_6$) 8.43-8.41 (m, 1H), 8.22 (s, 1H), 7.96 (d, J=8.4 Hz, 1H), 7.83 (d, J=8.4 Hz, 1H), 7.73-7.66 (m, 1H), 7.61-7.56 (m, 1H), 7.51-7.45 (m, 2H), 7.22-7.17 (m, 1H), 7.10 (s, 1H), 6.97 and 6.92 (2s, 1H), 6.56 (t, J=6.0 Hz, 1H), 5.46 (dd, J=9.1, 6.2 Hz, 1H), 4.42-4.20 (m, 4H), 4.05-3.76 (m, 7H), 3.80 and 3.79 (2s, 3H), 3.52-3.47 (m, 1H), 3.38-3.11 (m, 4H), 2.09-1.99 (m, 1H), 1.94-1.88 (m, 3H), 1.77-1.74 (m, 2H), 1.65-1.62 (m, 2H), 1.48-1.42 (m, 2H), 1.35-1.23 (m, 1H), 1.15-1.10 (m, 3H), 9H partially obscured by DMSO. HRMS m/z 969.3070 [(M+Na)$^+$ calcd for $C_{47}H_{55}ClN_6NaO_9S_2$ 969.3053].

Compound 82 was Prepared as Follows:

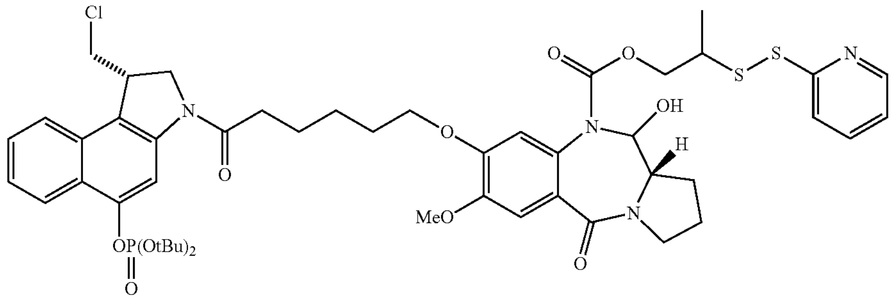

12

A mixture of 10 (162 mg, 0.267 mmol), 66d (178 mg, 0.418 mmol, freshly made by the procedure mentioned above), EDCI·HCl (184 mg, 0.960 mmol) and TsOH (11 mg, 0.0639 mmol) in dry DMA (5 mL) was stirred at r.t. overnight, under nitrogen. After 18.5 h the reaction mixture was diluted with EtOAc and $H_2O$ and well mixed. The layers were separated and the organic layer washed with saturated aqueous $NaHCO_3$ (1×), $H_2O$ (1×), brine (1×), dried ($Na_2SO_4$) and solvent removed under vacuum. The crude product was purified by column chromatography on silica gel using EtOAc:MeOH 100:0 to 95:5 to give a yellow residue. This was further purified by preparative HPLC (column: Synergi-MAX RP 4μ, 21.20×250 mm; flow rate: 12 mL/min; mobile phase: solvent A: $H_2O$/ammonium formate buffer pH 3.45, solvent B: MeCN/$H_2O$ 90:10; method: gradient, solvent A:solvent B 90:10 to 10:90 to 0:100 over 30 min) to give compound 12 (89.3 mg, 33%, HPLC purity: 99.5%) as a white foam. $^1$H NMR δ (400 MHz, DMSO-$d_6$) 8.56 (s, 1H), 8.43-8.41 (m, 1H), 8.04 (d, J=8.2 Hz, 1H), 7.92 (d, J=8.4 Hz, 1H), 7.73-7.67 (m, 1H), 7.60-7.56 (m, 1H), 7.51-7.45 (m, 2H), 7.22-7.17 (m, 1H), 7.10 (s, 1H), 6.98 and 6.92 (2s, 1H), 6.55 (t, J=5.6 Hz, 1H), 5.47-5.44 (m, 1H), 4.40-4.36 (m, 1H), 4.30-4.19 (m, 3H), 4.04-3.86 (m, 4H), 3.86-3.75 (m, 1H), 3.80 and 3.79 (2s, 3H), 3.52-3.46 (m, 1H), 3.38-3.22 (m, 3H), 3.21-3.15 (m, 1H), 2.09-1.99 (m, 1H), 1.94-1.85 (m, 3H), 1.78-1.74 (m, 2H), 1.69-1.60 (m, 2H), 1.55-1.40 (m, 2H), 1.47 and 1.47 (2s, 18H), 1.28-1.23 (m, 1H), 1.15-1.10 (m, 3H). HRMS m/z 1035.3162 [(M+Na)$^+$ calcd for $C_{49}H_{62}ClN_4NaO_{11}PS_2$ 1035.3175].

A mixture of 12 (84.0 mg, 0.0829 mmol) and TFA (1 mL) in dry DCM (2 mL) was stirred at r.t. for 40 mins. The solvent was then removed under vacuum at 25° C. to give a green residue. The residue was dissolved in DCM, the solution diluted with EtOAc and the DCM removed under vacuum to give a white solid and the remaining solvent decanted. This process was repeated and the resulting solid was triturated with EtOAc and dried to give 13 (Compound 82 of Table A, 43.8 mg, 59%, HPLC purity: 93.8%) as a white solid. $^1$H NMR δ (400 MHz, DMSO-$d_6$) 8.47 (s, 1H), 8.44-8.42 (m, 1H), 8.08 (d, J=8.3 Hz, 1H), 7.90 (d, J=8.3 Hz, 1H), 7.74-7.68 (m, 1H), 7.58-7.54 (m, 1H), 7.51-7.48 (m, 1H), 7.47-7.43 (m, 1H), 7.22-7.18 (m, 1H), 7.10 (s, 1H), 6.98 and 6.93 (2s, 1H), 5.46 (d, J=9.5 Hz, 1H), 4.39-4.18 (m, 4H), 4.04-3.95 (m, 3H), 3.90-3.85 (m, 1H), 3.84-3.76 (m, 1H), 3.80 and 3.80 (2s, 3H), 3.52-3.47 (m, 1H), 3.40-3.27 (m, 3H), 3.21-3.15 (m, 1H), 2.10-2.02 (m, 1H), 1.94-1.88 (m, 3H), 1.78-1.74 (m, 2H), 1.69-1.60 (m, 2H), 1.48-1.42 (m, 2H), 1.35-1.23 (m, 1H), 1.16-1.10 (m, 3H), 3H not observed. HRMS m/z 923.1938 [(M+Na)$^+$ calcd for $C_{41}H_{46}ClN_4NaO_{11}PS_2$ 923.1923].

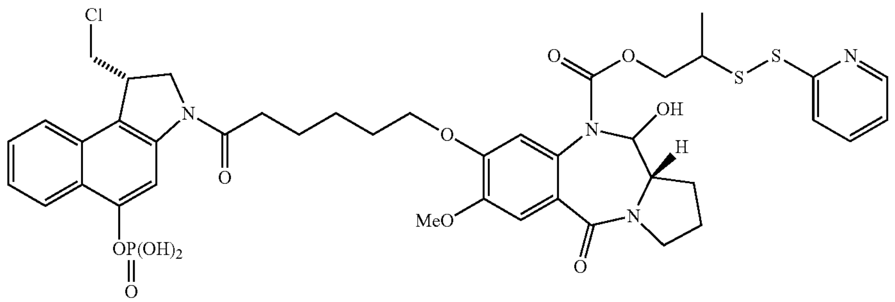

13

Compound 83 was prepared as follows:

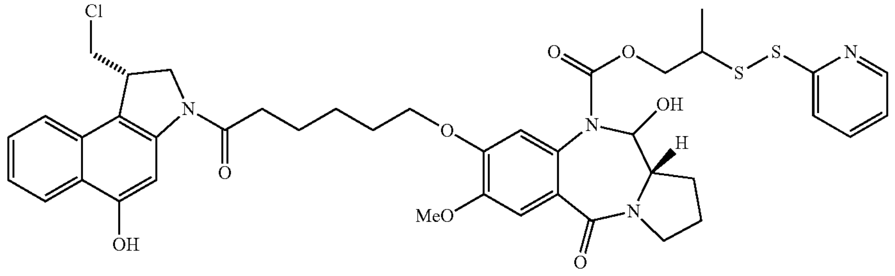 [SMILES: COc1cc2c(cc1OCCCCCC(=O)N1C[C@@H](CCl)c3c1cc(O)c1ccccc31)N(C(=O)OCC(C)SSc1ccccn1)C(O)[C@@H]1CCCN1C2=O]

A mixture of 10 (45.0 mg, 0.0743 mmol), 67d (24.3 mg, 0.0899 mmol, freshly made by the procedure mentioned above), EDCI·HCl (42.7 mg, 0.223 mmol) and TsOH (3 mg, 0.0174 mmol) in dry DMA (3 mL) was stirred at r.t. under nitrogen for 5 h. Additional portions of 67d (24.3 mg, 0.0899 mmol) and EDCI·HCl (16.0 mg, 0.0835 mmol) were added to the mixture and the reaction stirred at r.t. overnight. After 22 h the reaction mixture was diluted with EtOAc and washed with $H_2O$ (2×), brine (1×), dried ($Na_2SO_4$) and solvent removed under vacuum. The crude product was purified by column chromatography on silica gel using EtOAc to give a green powder. This was further purified carrying out column chromatography on silica gel using EtOAc a second time to give 14 (Compound 83 of Table A, 8.3 mg, 13.5%, HPLC purity: 81.2%) as a beige solid. $^1H$ NMR δ (400 MHz, DMSO-$d_6$) 10.33 (s, 1H), 8.43-8.42 (m, 1H), 8.07 (d, J=8.1 Hz, 1H), 7.98 (s, 1H), 7.77 (d, J=8.4 Hz, 1H), 7.74-7.67 (m, 1H), 7.50-7.46 (m, 2H), 7.33-7.29 (m, 1H), 7.24-7.18 (m, 1H), 7.10 (s, 1H), 6.98 and 6.92 (2s, 1H), 6.56 (t, J=6.0 Hz, 1H), 5.47-5.44 (m, 1H), 4.33-4.21 (m, 2H), 4.15-4.13 (m, 2H), 4.05-3.93 (m, 3H), 3.90-3.75 (m, 2H), 3.80 and 3.79 (2s, 3H), 3.52-3.47 (m, 1H), 3.38-3.13 (m, 4H), 2.10-1.99 (m, 1H), 1.94-1.89 (m, 3H), 1.77-1.74 (m, 2H), 1.66-1.62 (m, 2H), 1.52-1.41 (m, 2H), 1.32-1.24 (m, 1H), 1.15-1.10 (m, 3H). HRMS m/z 843.2258 $[(M+Na)^+$ calcd for $C_{41}H_{45}ClN_4NaO_8S_2$ 843.2260].

Compound 85 was Prepared as Follows:

To a solution of 82 (15 mg, 16.64 umol) in DMF (1.0 mL) was added a solution of 5-nitropyridine-2-thiol (25.99 mg, 166.41 umol) at 20° C. The reaction mixture was stirred at 20° C. for 1 h. The reaction mixture was filtered and purified by prep-HPLC (FA) to give 2-((5-nitropyridin-2-yl)disulfanyl)propyl (11aS)-8-((6-((S)-1-(chloromethyl)-5-(phosphonooxy)-1,2-dihydro-3H-benzo[e]indol-3-yl)-6-oxohexyl)oxy)-11-hydroxy-7-methoxy-5-oxo-2,3,11,11α-tetrahydro-1H-benzo[e]pyrrolo[1,2-a][1,4]diazepine-10(5H)-carboxylate 85 (7.5 mg, 47.62%) as a gray solid. LCMS: (10-80, CD_NEG, 3.0 min), 1.161 min, MS=944.2 $[M-1]^-$; $^1H$ NMR (400 MHz, $CDCl_3$) δ 9.18 (s, 1H), 8.41 (br, 1H, J=7.6 Hz), 8.11 (br, 1H), 7.80 (d, 1H, J=8.0 Hz), 7.67 (d, 1H, J=8.4 Hz), 7.46 (d, 1H, J=7.6 Hz), 7.30 (s, 1H), 7.07 (s, 1H), 6.99-6.93 (m, 1H), 5.52 (d, 1H, J=8.4 Hz), 4.26-4.14 (m, 4H), 3.98-3.80 (m, 4H), 3.76 (s, 3H), 3.40-3.26 (m, 5H), 2.40-2.28 (m, 2H), 2.10-1.80 (m, 5H), 1.79-1.55 (m, 5H), 1.40 (br, 1H), 1.19 (s, 1H), 1.12 (d, 3H, J=8.8 Hz).

Compound 86 was Prepared as Follows:

Step A: Synthesis of (S)-di-tert-butyl (1-(chloromethyl)-3-(2,2,2-trifluoroacetyl)-2,3-dihydro-1H-benzo[e]indol-5-yl)phosphate 1u

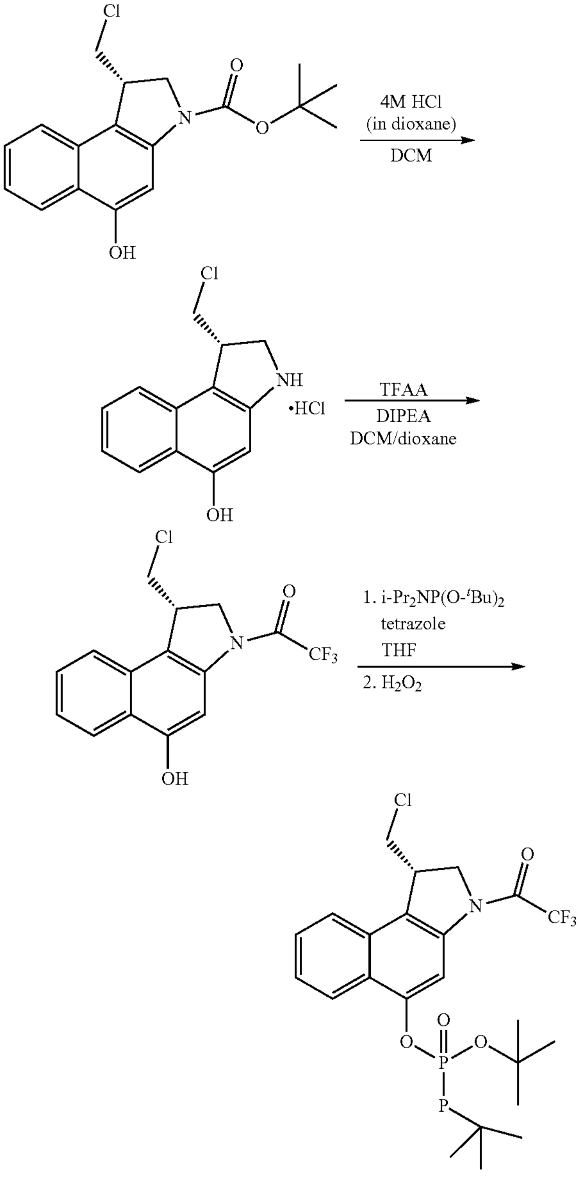

1u

To a stirred homogeneous solution of tert-butyl (S)-1-(chloromethyl)-5-hydroxy-1,2-dihydro-3H-benzo[e]indole-3-carboxylate (3.34 g, 10.0 mmol) in dry DCM (25 mL) at 20° C. under a nitrogen atmosphere was added 4M HCl in dioxane (12.5 mL, 50.0 mmol). After addition the reaction mixture was stirred at 20° C. under nitrogen for a further 20 h. The mixture was diluted with petroleum ether (250 mL) and stirred at 20° C. under nitrogen for 20 min. Solvents were decanted and the procedure was repeated once more with petroleum ether (250 mL). The resulting solid was dried under vacuum at 25° C. for 1 h to give (S)-1-(chloromethyl)-2,3-dihydro-1H-benzo[e]indol-5-ol hydrochloride (2.7 g, 100%); $^1$H NMR [$(CD_3)_2SO$] δ 10.80 (s, 1H), 8.15 (d, J=8.3 Hz, 1H), 7.87 (d, J=8.2 Hz, 1H), 7.58 (br t, J=7.5 Hz, 1H), 7.43 (br t, J=7.4 Hz, 1H), 6.81 (s, 1H), 4.27-4.17 (m, 1H), 4.01 (dd, J=11.0, 3.2 Hz, 1H), 3.93-3.74 (m, 3H), 2 protons not observed. The crude product was used for the next step without further purification.

To a stirred heterogeneous mixture of (S)-1-(chloromethyl)-2,3-dihydro-1H-benzo[e]indol-5-ol hydrochloride (2.7 g, 10.0 mmol) in dry DCM (10 mL) and dioxane (30 mL) at 0° C. under a nitrogen atmosphere was added trifluoroacetic anhydride (TFAA)(3.4 mL, 24.0 mmol), followed by diisopropylethylamine (DIPEA)(8.71 mL, 50.0 mmol). After addition the reaction mixture was stirred at 0° C. under nitrogen for a further 50 min. Ethyl acetate (400 mL) was added and 1N HCl (200 mL) were added at 0° C. and the mixture stirred for 20 min under nitrogen. The ethyl acetate layer was separated, washed successively with 1N HCl (200 mL) and water (2×200 mL), and then dried ($MgSO_4$) and evaporated under reduced pressure at a bath temperature of 25° C. to give (5)-1-(1-(chloromethyl)-5-hydroxy-1,2-dihydro-3H-benzo[e]indol-3-yl)-2,2,2-trifluoroethan-1-one (3.3 g, 100%) as a green-grey solid. This material was used for the next step without further purification.

To a stirred homogeneous solution of (5)-1-(1-(chloromethyl)-5-hydroxy-1,2-dihydro-3H-benzo[e]indol-3-yl)-2,2,2-trifluoroethan-1-one (3.3 g, 10.0 mmol) in dry THF (40 mL) at 20° C. under a nitrogen atmosphere was added di-tert-butyl-N,N-diisopropylphosphoramidite (4.31 mL, 13.0 mmol). After addition the reaction mixture was stirred at 20° C. under nitrogen for 5-10 min and then tetrazole (3% solution in $CH_3CN$, 38.0 mL, 13.0 mmol) was added dropwise over 17 min. The final reaction mixture was stirred further at 20° C. under nitrogen for 19 h. The mixture was cooled in an ice-bath and 30% $H_2O_2$ (11.3 mL, 100.0 mmol) was added. After addition the reaction mixture was stirred at 20° C. for a further 1 h 30 min. The mixture was diluted with ethyl acetate (300 mL) and 10% aqueous $Na_2S_2O_3$ (500 mL) at stirred at 0° C. for 20 min. The ethyl acetate layer was separated and washed successively with water (200 mL), saturated $NaHCO_3$ (200 mL), and water (200 mL) and then dried ($MgSO_4$) and evaporated under reduced pressure at a bath temperature of 25° C. to give an amber oil. Purification by chromatography on a silica gel (eluting with ethyl acetate:petroleum ether 1:3) gave 1u (4.7 g, 90%) as a colorless foamy solid, mp 39-42° C.; $[\alpha]_D$–61.8° (c 1.02, $CHCl_3$). Anal. ($C_{23}H_{28}ClF_3NO_5P$) Calc: C, 52.93; H, 5.41; N, 2.68. Found: C, 53.05; H, 5.43; N, 2.80.

Step B: Synthesis of ((S)-1-(2-((((4-((S)-2-(((allyloxy)carbonyl)amino)-6-((tert-butoxycarbonyl)amino)hexanamido)benzyl)oxy)carbonyl)amino)-4-((6-((S)-1-(chloromethyl)-5-((di-tert-butoxyphosphoryl)oxy)-1,2-dihydro-3H-benzo[e]indol-3-yl)-6-oxohexyl)oxy)-5-methoxybenzoyl)pyrrolidin-2-yl)methyl acetate 3g

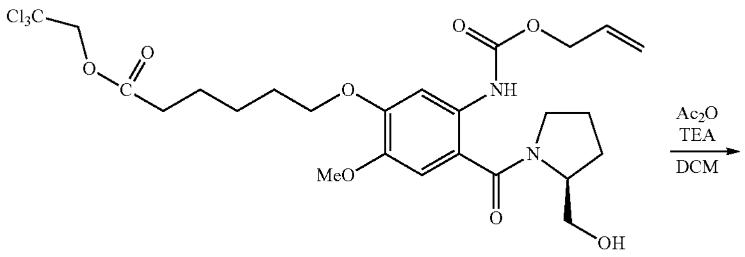

3a

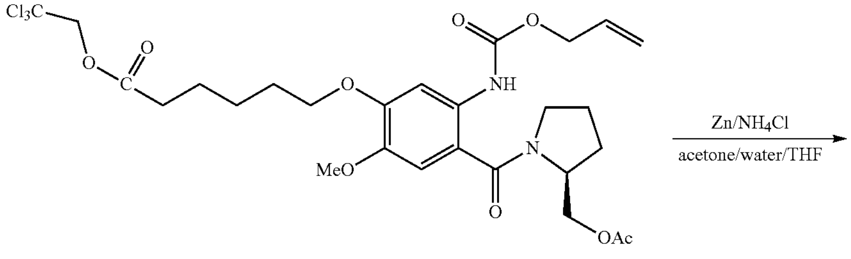

3b

-continued

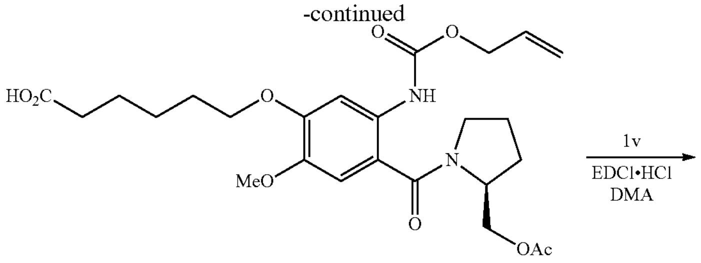

3c

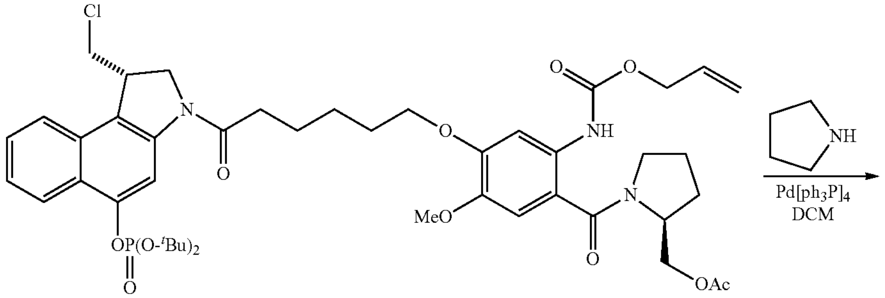

3d

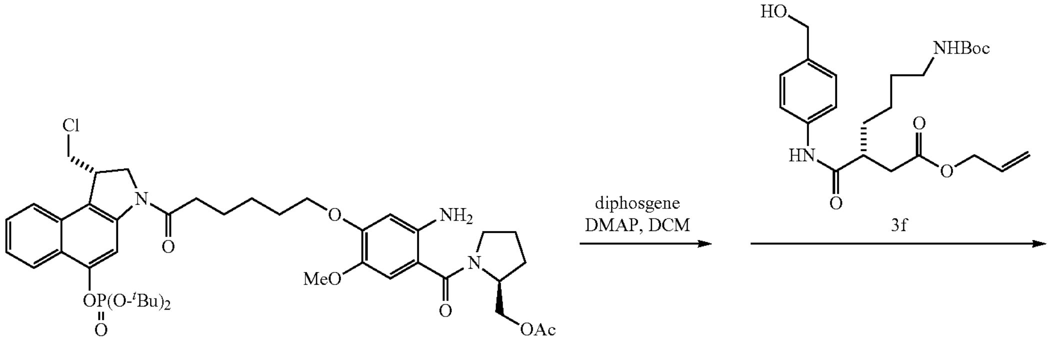

3e

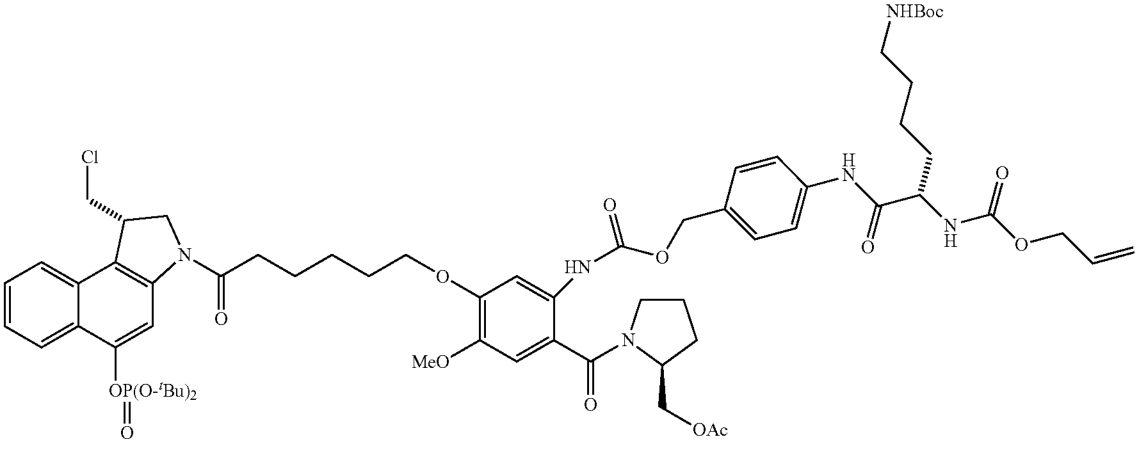

3g

To a stirred solution of 2,2,2-trichloroethyl (S)-6-(5-(((allyloxy)carbonyl)amino)-4-(2-(hydroxymethyl)pyrrolidine-1-carbonyl)-2-methoxyphenoxy)hexanoate 3a (4.14 g, 6.95 mmol) (J. Med. Chem. 2003, 46, 2132-2151) in dry DCM (25 mL) was added acetic anhydride (3.30 mL, 34.8 mmol) and triethylamine (5.81 mL, 41.7 mmol). The mixture was stirred at 20° C. for 3 h 30 min. Dry MeOH (4.0 mL) was added and the mixture was stirred for 30 min. The mixture was partitioned between EtOAc (400 mL) and water (400 mL). The EtOAc layer was separated, washed with water (2×200 mL), and then dried ($MgSO_4$) and evaporated to give 2,2,2-trichloroethyl (S)-6-(4-(2-(acetoxymethyl)pyrrolidine-1-carbonyl)-5-(((allyloxy)carbonyl)amino)-2-methoxyphenoxy)hexanoate 3b (4.28 g, 96%) as an oil; $[\alpha]_D$–57.4° (c 0.21, $CHCl_3$); $^1H$ NMR [$(CD_3)_2SO$] δ 9.10 (s, 1H), 7.17 (s, 1H), 6.87 (s, 1H), 6.01-5.87 (m, 1H), 5.32 (dd, J=17.2, 1.5 Hz, 1H), 5.21 (dd, J=10.4, 1.4 Hz, 1H), 4.89 (s, 2H), 4.54 (d, J=5.4 Hz, 2H), 4.39-4.20 (m, 3H), 3.93 (t, J=6.4 Hz, 2H), 3.75 (s, 3H), 3.46-3.27 (m, 2H), 2.13-1.90 (m, 4H), 1.89-1.60 (m, 7H), 1.54-1.40 (m, 2H), 2 protons obscured by DMSO peak. HRMS (ESI) m/z calc. for $C_{27}H_{36}Cl_3N_2O_9$: 637.1481, found: 637.1475 [$MH^+$]; calc. for $C_{27}H_{35}Cl_3N_2NaO_9$: 659.1300, found: 659.1303 [$MNa^+$]; calc. for $C_{27}H_{35}Cl_3KN_2O_9$: 675.1040, found: 675.1035 [$MK^+$].

To a stirred solution of 3b (4.27 g, 6.69 mmol) in acetone (75 mL), water (50 mL), and THF (30 mL) was added zinc powder (17.5 g, 268 mmol) and $NH_4Cl$ (28.6 g, 535 mmol). The mixture was stirred at 20° C. under a nitrogen atmosphere for 42 h. Acetone (100 mL) was added, the mixture was stirred for 10 min, and the supernatant was decanted. The procedure was repeated twice and the combined supernatants were evaporated under reduced pressure to remove acetone and THF. The residue was diluted with water (50 mL) and acidified with aqueous 1N HCl to pH ca. 1. The acidic mixture was washed with petroleum ether (2×200 mL) and extracted with EtOAc (400 mL). The EtOAc extract was washed with water (200 mL) and dried ($MgSO_4$) and the solvent was evaporated to give (S)-6-(4-(2-(acetoxymethyl)pyrrolidine-1-carbonyl)-5-(((allyloxy)carbonyl)amino)-2-methoxyphenoxy)hexanoic acid 3c (2.72 g, 80%) as an oil; $[\alpha]_D$−73.5° (c 1.12, $CHCl_3$); $^1H$ NMR [$(CD_3)_2SO$] δ 11.99 (s, exchangeable with $D_2O$, 1H), 9.10 (s, exchangeable with $D_2O$, 1H), 7.17 (s, 1H), 6.87 (s, 1H), 6.00-5.86 (m, 1H), 5.32 (dd, J=17.2, 1.5 Hz, 1H), 5.20 (dd, J=10.4, 1.5 Hz, 1H), 4.57-4.52 (m, 2H), 4.37-4.03 (m, 3H), 3.93 (t, J=6.5 Hz, 2H), 3.75 (s, 3H), 3.40-3.10 (m, 2H), 2.23 (t, J=7.3 Hz, 2H), 2.07-1.93 (m, 4H), 1.89-1.66 (m, 5H), 1.62-1.49 (m, 2H), 1.47-1.34 (m, 2H). HRMS (ESI) m/z calc. for $C_{25}H_{35}N_2O_9$: 507.2337, found: 507.2340 [$MH^+$]; calc. for $C_{25}H_{34}KN_2O_9$: 545.1896, found: 545.1906 [$MK^+$]; calc. for $C_{25}H_{34}N_2NaO_9$: 529.2157, found: 529.2169 [$MNa^+$].

To a stirred solution of (S)-di-tert-butyl (1-(chloromethyl)-3-(2,2,2-trifluoroacetyl)-2,3-dihydro-1H-benzo[e]indol-5-yl)phosphate 1u (1.38 g, 2.64 mmol) in MeOH (10 mL) at 0° C. under a nitrogen atmosphere was added $Cs_2CO_3$ (1.03 g, 3.17 mmol). The mixture was stirred at 0° C. for 2 h 30 min and then partitioned between EtOAc (200 mL) and water (150 mL). The EtOAc layer was separated and washed again with water (100 mL), and then dried ($MgSO_4$) and evaporated under reduced pressure at a bathe temperature of 25° C. to give the (S)-di-tert-butyl (1-(chloromethyl)-2,3-dihydro-1H-benzo[e]indol-5-yl)phosphate 1v (1.17 g) as a pale yellow foamy solid which was treated with 3c (1.24 g, 2.45 mmol), EDCI·HCl (1.41 g, 7.35 mmol) and p-toluenesulfonic acid (84 mg, 0.49 mmol) in dry DMA (14 mL) at 0-20° C. for 22 h. The mixture was partitioned between EtOAc (400 mL) and water (300 mL). The EtOAc layer was separated and washed again with water (100 mL), and then dried ($MgSO_4$) and evaporated. Purification by chromatography on silica gel (eluting with EtOAc:petroleum ether 2:1) gave ((S)-1-(2-(((allyloxy)carbonyl)amino)-4-((6-((S)-1-(chloromethyl)-5-((di-tert-butoxyphosphoryl)oxy)-1,2-dihydro-3H-benzo[e]indol-3-yl)-6-oxohexyl)oxy)-5-methoxybenzoyl)pyrrolidin-2-yl)methyl acetate 3d (1.49 g, 66%) as a pale yellow foamy solid, mp 55-59° C.; $[\alpha]_D$−68.0° (c 1.00, $CHCl_3$); $^1H$ NMR [$(CD_3)_2SO$] δ 9.10 (s, exchangeable with $D_2O$, 1H), 8.56 (s, 1H), 8.03 (d, J=8.1 Hz, 1H), 7.92 (d, J=8.4 Hz, 1H), 7.57 (t, J=8.1 Hz, 1H), 7.47 (t, J=7.6 Hz, 1H), 7.19 (s, 1H), 6.86 (s, 1H), 5.99-5.86 (m, 1H), 5.32 (dd, J=17.2, 1.6 Hz, 1H), 5.20 (dd, J=10.4, 1.5 Hz, 1H), 4.53 (d, J=5.4 Hz, 2H), 4.45-3.84 (m, 10H), 3.74 (s, 3H), 3.44-3.26 (m, 2H), 2.68-2.47 (m, 2H), 2.02 (br s, 3H), 1.93-1.43 (m, 10H), 1.474 and 1.469 (2 s, 18H). HRMS (ESI) m/z calc. for $C_{46}H_{62}ClN_3O_{12}P$: 914.3754, found: 914.3749 [$MH^+$]; calc. for: $C_{46}H_{61}ClKN_3O_{12}P$: 952.3313, found: 952.3381 [$MK^+$]; calc. for $C_{46}H_{61}ClN_3NaO_{12}P$: 936.3574, found: 936.3589 [$MNa^+$].

To a stirred solution of 3d (548 mg, 0.60 mmol) in DCM (8 mL) at 20° C. under a nitrogen atmosphere was added $Pd(Ph_3P)_4$ (17.1 mg; 9.8% Pd) and pyrrolidine (0.49 mL, 6.00 mmol). The mixture was stirred at 20° C. for 30 min and then partitioned between EtOAc (200 mL) and water (150 mL). The EtOAc layer was separated and washed again with water (50 mL), and then dried ($MgSO_4$) and evaporated under reduced pressure at a bath temperature of 25° C. The crude product was purified by chromatography on silica gel (eluting with EtOAc:MeOH 50:1) to give ((S)-1-(2-amino-4-((6-((S)-1-(chloromethyl)-5-((di-tert-butoxyphosphoryl)oxy)-1,2-dihydro-3H-benzo[e]indol-3-yl)-6-oxohexyl)oxy)-5-methoxybenzoyl)pyrrolidin-2-yl)methyl acetate 3e (323 mg, 65%) as a pale yellow foamy solid, mp 46-49° C.; $[\alpha]_D$−85.2° (c 0.36, $CHCl_3$); $^1H$ NMR [$(CD_3)_2SO$] δ 8.56 (s, 1H), 8.04 (d, J=8.3 Hz, 1H), 7.93 (d, J=8.4 Hz, 1H), 7.58 (t, J=8.2 Hz, 1H), 7.47 (t, J=8.1 Hz, 1H), 6.67 (s, 1H), 6.37 (s, 1H), 5.09 (s, exchangeable with $D_2O$, 2H), 4.46-3.85 (m, 10H), 3.63 (s, 3H), 3.52-3.34 (m, 2H), 2.69-2.50 (m, 2H), 2.08-1.94 (m, 1H), 2.01 (s, 3H), 1.91-1.61 (m, 7H), 1.58-1.44 (m, 2H), 1.476 and 1.470 (2 s, 18H). HRMS (ESI) m/z calc. for $C_{42}H_{58}ClN_3O_{10}P$: 830.3522, found: 830.3543 [$MH^+$].

To a stirred solution of 3e (293 mg, 0.35 mmol) and DMAP (202 mg, 1.65 mmol) in dry DCM (7 mL) at 20° C. under a nitrogen atmosphere was added a solution of diphosgene in dry DCM (0.05 M, 6.7 mL, 0.33 mmol). The mixture was stirred for 25 min and then a solution of allyl tert-butyl (6-((4-(hydroxymethyl)phenyl)amino)-6-oxohexane-1,5-diyl)(S)-dicarbamate 3f (1.54 g, 3.54 mmol) in dry DCM (20 mL) was added. The mixture was stirred at 20° C. under a nitrogen atmosphere for 68 h and then partitioned between EtOAc (300 mL) and water (200 mL). The EtOAc layer was separated, washed again with water (100 mL) and then dried ($MgSO_4$) and evaporated at a bath temperature of 30° C. The resulting orange oil was purified by chromatography on silica gel (eluting with EtOAc:MeOH:petroleum ether 30:0.5:10) to afford ((S)-1-(2-((((4-((S)-2-(((allyloxy)carbonyl)amino)-6-((tert-butoxycarbonyl)amino)hexanamido)benzypoxy)carbonyl)amino)-4-((6-((S)-1-(chloromethyl)-5-((di-tert-butoxyphosphoryl)oxy)-1,2-dihydro-3H-benzo[e]indol-3-yl)-6-oxohexyl)oxy)-5-methoxybenzoyl)pyrrolidin-2-yl)methyl acetate 3g (385 mg, 84%) as a foamy solid, mp 72-75° C.; $[\alpha]_D$−55.2° (c 0.53, $CHCl_3$); $^1H$ NMR [$(CD_3)_2SO$] δ 10.04 (s, exchangeable with $D_2O$, 1H), 9.12 (br s, exchangeable with $D_2O$, 1H), 8.56 (s, 1H), 8.03 (d, J=8.3 Hz, 1H), 7.92 (d, J=8.4 Hz, 1H), 7.65-7.52 (m, 3H, reduced to 2H after $D_2O$), 7.46 (t, J=7.8 Hz, 2H), 7.31 (d, J=8.5 Hz, 2H), 7.20 (br s, 1H), 6.86 (s, 1H), 6.75 (poorly resolved t, exchangeable with $D_2O$, 1H), 5.97-5.83 (m, 1H), 5.30 (br d, J=17.3 Hz, 1H), 5.17 (br d, J=10.6 Hz, 1H), 5.18-4.97 (m, 2H), 4.51-3.85 (m, 13H), 3.74 (s, 3H), 3.43-3.23 (m, 2H, partially obscured by water peak), 2.94-2.83 (m, 2H), 2.65-2.50 (m, 2H, partially obscured by DMSO peak), 2.07-1.91 (m, 1H), 2.01 (br s, 3H), 1.88-1.43 (m, 11H), 1.473-1.468 (2 s, 18H), 1.43-1.20 (m, 4H), 1.35 (s, 9H). HRMS (ESI) m/z calc. for $C_{65}H_{89}ClN_6O_{17}P$: 1291.5665, found: 1291.5705 [$MH^+$]; calc. for $C_{65}H_{88}ClKN_6O_{17}P$: 1329.5262, found: 1329.5264 [$MK^+$]; calc. for $C_{65}H_{88}ClN_6NaO_{17}P$: 1313.5554, found: 1313.5524 [$MNa^+$].

Step C: Synthesis of 86
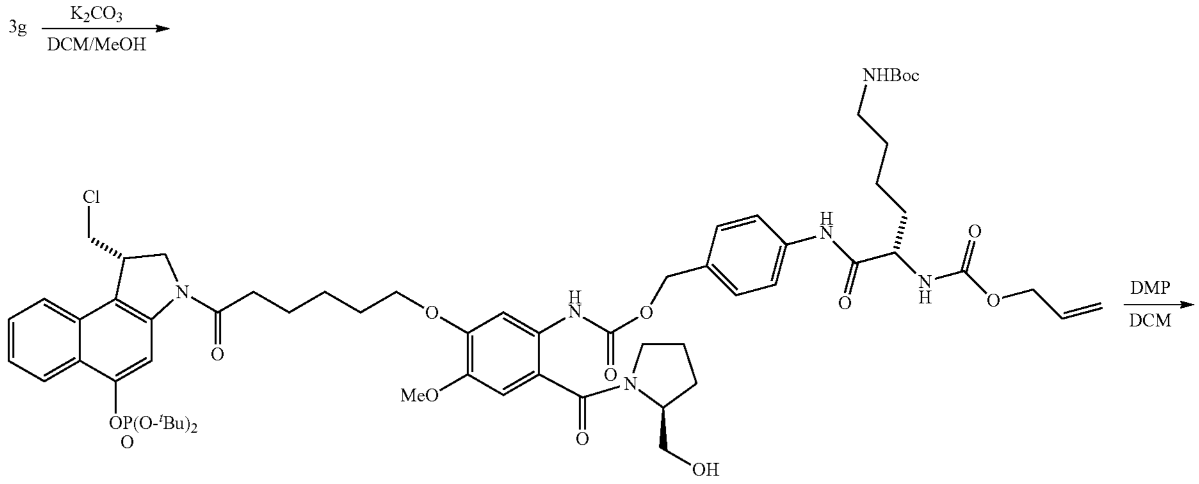
3h
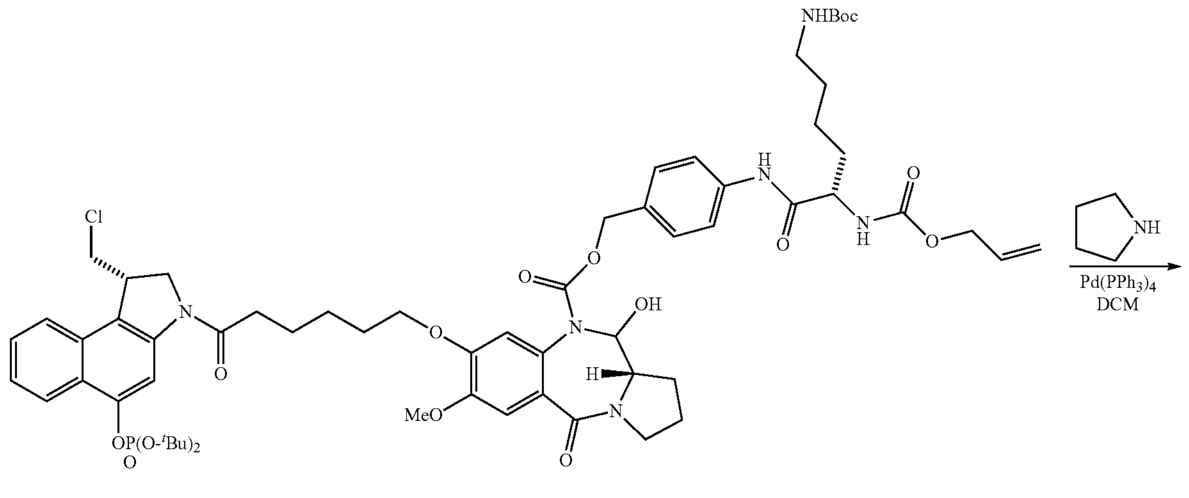
3i
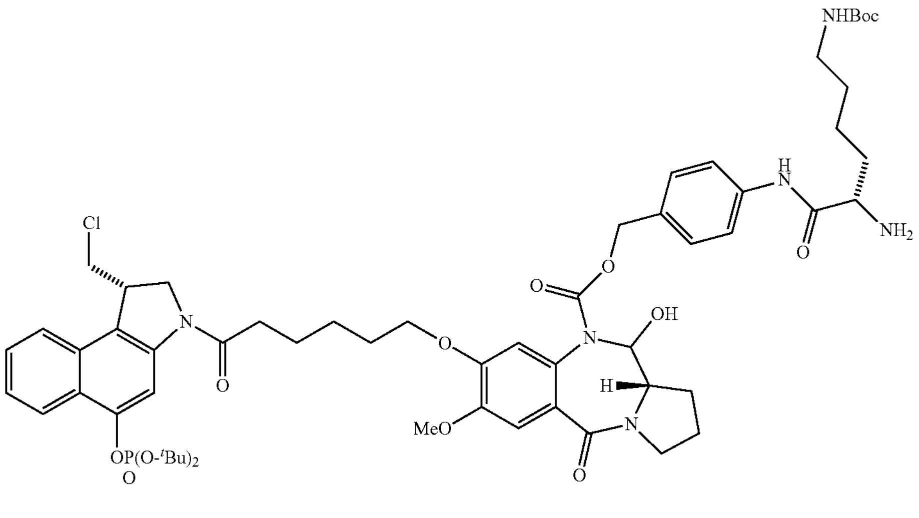
3j

A mixture of 3g (366 mg, 0.28 mmol) and $K_2CO_3$ (1.14 g, 8.24 mmol) in DCM (9 mL) and MeOH (9 mL) was stirred at 0° C. for 3 h 30 min. The mixture was stirred with cold EtOAc (200 mL) and ice-water (150 mL) for 10 min. The EtOAc layer was separated, washed again with water (100 mL), and then dried ($MgSO_4$) and evaporated at a bath temperature of 25° C. to give allyl tert-butyl ((S)-6-((4-((((5-((6-((S)-1-(chloromethyl)-5-((di-tert-butoxyphosphoryl)oxy)-1,2-dihydro-3H-benzo[e]indol-3-yl)-6-oxohexyl)oxy)-2-((S)-2-(hydroxymethyl)pyrrolidine-1-carbonyl)-4-methoxyphenyl)carbamoyl)oxy)methyl)phenyl)amino)-6-oxohexane-1,5-diyl)dicarbamate 3h (343 mg, 97%) as a colorless foamy solid, mp 71-75° C.; $[\alpha]_D$−58.2° (c 0.57, $CHCl_3$); $^1H$ NMR $[(CD_3)_2SO]$ δ 10.04 (s, exchangeable with $D_2O$, 1H), 9.11 (br s, exchangeable with $D_2O$, 1H), 8.56 (s, 1H), 8.03 (d, J=8.3 Hz, 1H), 7.92 (d, J=8.4 Hz, 1H), 7.65-7.53 (m, 3H, reduced to 2H after $D_2O$), 7.46 (t, J=7.6 Hz, 2H), 7.32 (d, J=8.6 Hz, 2H), 7.27 (br s, 1H), 6.93 (s, 1H), 6.75 (poorly resolved t, exchangeable with $D_2O$, 1H), 5.97-5.82 (m, 1H), 5.29 (br d, J=17.2 Hz, 1H), 5.17 (br d, J=10.5 Hz, 1H), 5.03 (br s, 2H), 4.73 (t, J=5.8 Hz, exchangeable with $D_2O$, 1H), 4.50-3.82 (m, 11H), 3.74 (s, 3H), 3.62-3.44 (m, 2H), 3.40-3.21 (m, 2H, partially obscured by water peak), 2.95-2.80 (m, 2H), 2.65-2.50 (m, 2H, partially obscured by DMSO peak), 1.93-1.21 (m, 16H), 1.473-1.468 (2 s, 18H), 1.35 (s, 9H). HRMS (ESI) m/z calc. for $C_{63}H_{86}ClKN_6O_{16}P$: 1287.5158, found: 1287.5113 $[MK^+]$; calc. for $C_{63}H_{86}ClN_6NaO_{16}P$: 1271.5419, found: 1271.5381 $[MNa^+]$.

To a stirred solution of 3h (322 mg, 0.26 mmol) in dry DCM (14 mL) at 0° C. was added Dess-Martin periodinane (DMP)(131 mg, 0.31 mmol) portionwise over 3 min. The reaction mixture was stirred at 0° C. for a further 2 h, then at 20° C. for 50 h. The mixture was diluted with DCM (40 mL) and 10% $Na_2S_2O_3$ (40 mL), stirred at 20° C. for 10 min, and then partitioned between DCM (200 mL) and saturated $NaHCO_3$ solution (150 mL). The DCM layer was separated and the aqueous layer was further extracted with DCM (2×50 mL). The combined DCM extracts were washed with saturated $NaHCO_3$ solution (2×100 mL) and water (2×100 mL), and then dried ($MgSO_4$) and evaporated at a bath temperature of 25° C. The resulting orange oil was purified by chromatography on silica gel (eluting with $CHCl_3$:MeOH 40:1) to give 4-((S)-2-(((allyloxy)carbonyl)amino)-6-((tert-butoxycarbonyl)amino)hexanamido)benzyl (11aS)-8-((6-((S)-1-(chloromethyl)-5-((di-tert-butoxyphosphoryl)oxy)-1,2-dihydro-3H-benzo[e]indol-3-yl)-6-oxohexyl)oxy)-11-hydroxy-7-methoxy-5-oxo-2,3,11,11α-tetrahydro-1H-benzo[e]pyrrolo[1,2-a][1,4]diazepine-10(5H)-carboxylate 3i (228 mg, 71%) as a pale brown foamy solid, mp 98° C. (decomp); $[\alpha]_D$+74.5° (c 0.26, $CHCl_3$); $^1H$ NMR $[(CD_3)_2SO]$ δ 10.02 (s, exchangeable with $D_2O$, 1H), 8.56 (s, 1H), 8.04 (d, J=8.3 Hz, 1H), 7.92 (d, J=8.4 Hz, 1H), 7.65-7.47 (m, 5H, reduced to 4H after $D_2O$), 7.25-7.12 (m, 2H, br s and 1H on $D_2O$ exchange), 7.03 (s, 1H), 6.83-6.64 (m, 2H), 6.48 (br s, exchangeable with $D_2O$, 1H), 5.96-5.80 (m, 1H), 5.52-5.39 (m, d on $D_2O$ exchange, J=9.6 Hz, 1H), 5.27 (br d, J=16.8 Hz, 1H), 5.21-5.10 (m, 2H), 4.81 (br d, J=12.3 Hz, 1H), 4.54-3.85 (m, 8H), 3.83-3.70 (m, 5H), 3.53-3.21 (m, 3H, partially obscured by water peak), 2.93-2.82 (m, 2H), 2.64-2.47 (m, 2H, partially obscured by DMSO peak), 2.10-1.20 (m, 16H), 1.470 and 1.464 (2 s, 18H), 1.34 (s, 9H). HRMS (ESI) m/z calc. for $C_{63}H_{84}ClKN_6O_{16}P$: 1285.5002, found: 1285.4938 $[MK^+]$; calc. for $C_{63}H_{84}ClN_6NaO_{16}P$: 1269.5262, found: 1269.5220 $[MNa^+]$.

To a stirred solution of 3i (125 mg, 0.10 mmol) in DCM (2 mL) at 20° C. under a nitrogen atmosphere was added $Pd(Ph_3P)_4$ (2.9 mg; 9.8% Pd) and pyrrolidine (0.08 mL, 1.00 mmol). The mixture was stirred at 20° C. and monitored by TLC (EtOAc:MeOH 20:1). After 40 min more $Pd(Ph_3P)_4$ (5.8 mg; 9.8% Pd) and pyrrolidine (0.16 mL, 2.00 mmol) were added and the mixture was stirred for another 3 h. The mixture was partitioned between EtOAc (100 mL) and water (100 mL). The EtOAc layer was separated and washed again with water (50 mL), and then dried ($MgSO_4$) and evaporated at a bath temperature of 25° C. The crude 4-((S)-2-amino-6-((tert-butoxycarbonyl)amino)hexanamido)benzyl (11aS)-8-((6-((S)-1-(chloromethyl)-5-((di-tert-butoxyphosphoryl)oxy)-1,2-dihydro-3H-benzo[e]indol-3-yl)-6-oxohexyl)oxy)-11-hydroxy-7-methoxy-5-oxo-2,3,11,11α-tetrahydro-1H-benzo[e]pyrrolo[1,2-a][1,4]diazepine-10(5H)-carboxylate 3j (94 mg, 81%) was used for the next step without further purification. HRMS (ESI) m/z calc. for $C_{59}H_{81}ClN_6O_{14}P$: 1163.5231, found: 1163.5188 $[MH^+]$.

A solution of 3j (91 mg, 0.078 mmol) in dry DMA (1.0 mL) was treated with a pre-formed (at 20° C. for 10 min) mixture of 1-((5-(2,5-dioxo-2,5-dihydro-1H-pyrrol-1-yl)pentyl)carbamoyl)cyclobutanecarboxylic acid 1p (36 mg, 0.12 mmol), EDCI·HCl (34 mg, 0.18 mmol), and TsOH (4.0 mg, 0.023 mmol) in dry DMA (0.5 mL) at 20° C. under a nitrogen atmosphere. After 10 min DIPEA (0.016 mL, 0.078 mmol) was added and the reaction mixture was stirred for 23 h. The mixture was partitioned between EtOAc (100 mL) and water (100 mL). The EtOAc layer was separated and washed further with saturated $NaHCO_3$ (50 mL), water (50 mL), and then dried ($MgSO_4$). Evaporation of solvent at a bath temperature of 25° C. gave a crude product which was purified by chromatography on silica gel (eluting with $CHCl_3$:EtOAc:MeOH 30:10:2) to give 4-((S)-6-((tert-butoxycarbonyl)amino)-2-(1-((5-(2,5-dioxo-2,5-dihydro-1H-pyrrol-1-yl)pentyl)carbamoyl)cyclobutane-1-carboxamido)hexanamido)benzyl (11aS)-8-((6-((S)-1-(chloromethyl)-5-(phosphonooxy)-1,2-dihydro-3H-benzo[e]indol-3-yl)-6-oxohexyl)oxy)-11-hydroxy-7-methoxy-5-oxo-2,3,11,11α-tetrahydro-1H-benzo[e]pyrrolo[1,2-a][1,4]diazepine-10(5H)-carboxylate 3k (63 mg, 56%) as a pale brown foamy solid; mp 67-70° C.; $[\alpha]_D$+23.9° (c 2.09, $CHCl_3$); $^1H$ NMR $[(CD_3)_2SO]$ δ 10.05 (s, exchangeable with $D_2O$, 1H), 8.56 (s, 1H), 8.03 (d, J=8.3 Hz, 1H), 7.92 (d, J=8.4 Hz, 1H), 7.84-7.71 (m, 2H, exchangeable with $D_2O$), 7.62-7.52 (m, 3H), 7.46 (t, J=7.7 Hz, 1H), 7.22-7.13 (m, 2H), 7.03 (br s, 1H), 6.96 (s, 2H), 6.71 (br s, 2H, reduced to 1H after $D_2O$), 6.49 (br s, exchangeable with $D_2O$, 1H), 5.51-5.41 (m, but d on $D_2O$ exchange with J=9.5 Hz, 1H), 5.15 (d, J=12.2 Hz, 1H), 4.82 (br d, J=12.4 Hz, 1H), 4.47-3.85 (m, 8H), 3.77 (br s, 3H), 3.52-3.20 (m, 3H, partially obscured by water peak), 3.12-3.20 (m, but t on $D_2O$ exchange with J=6.7 Hz, 2H), 2.92-2.80 (m, 2H), 2.65-2.50 (m, 2H, partially obscured by DMSO peak), 2.39 (t, J=7.9 Hz, 2H), 2.07-1.24 (m, 28H), 1.469 and 1.463 (2 s, 18H), 1.33 (s, 9H). HRMS (ESI) m/z calc. for $C_{74}H_{98}ClN_8NaO_{18}P$: 1475.6317, found: 1475.6267 $[MNa^+]$.

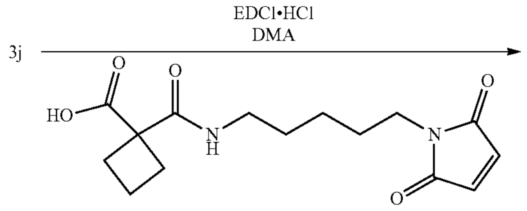

1p

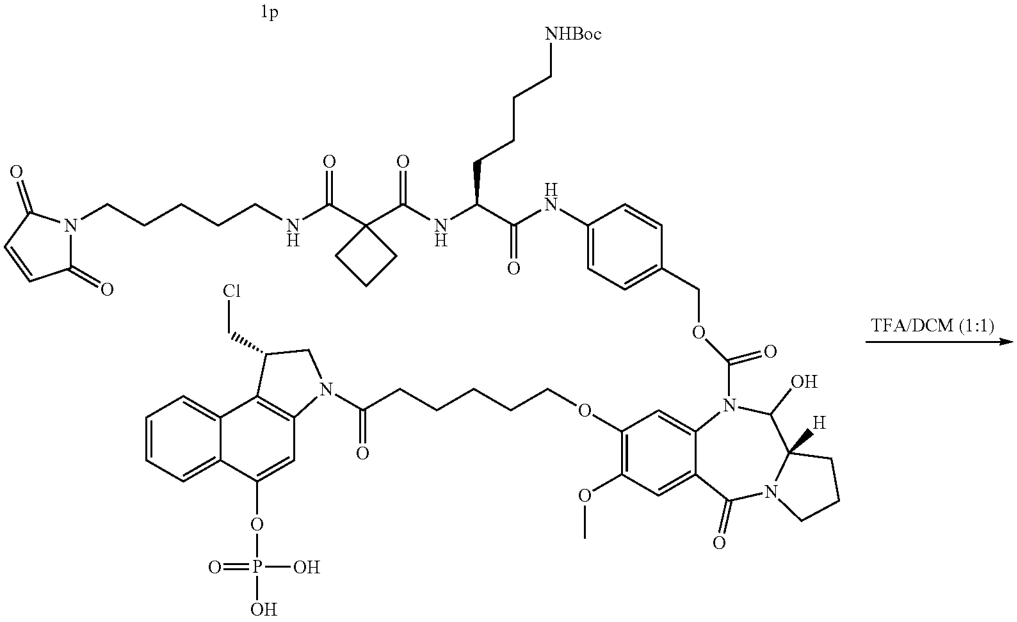

3k

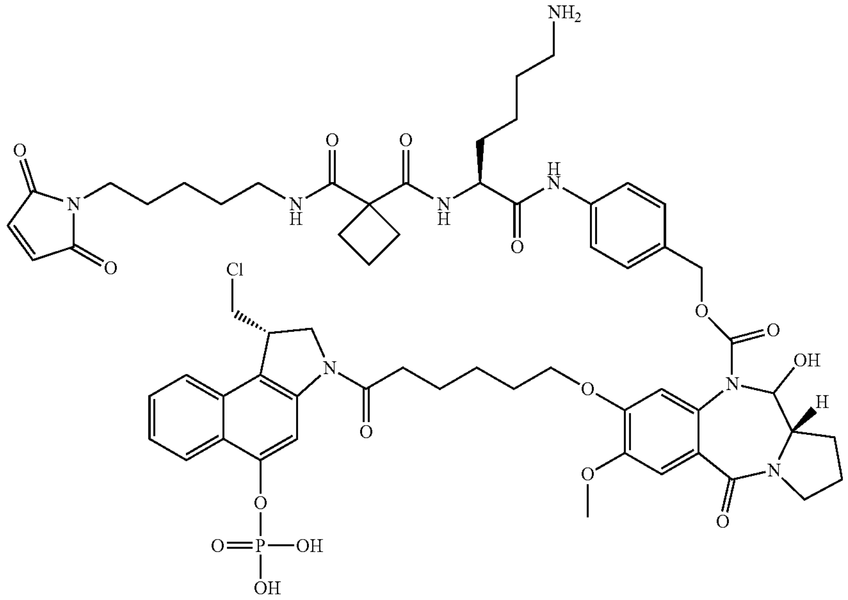

86

To a stirred solution of 3k (45 mg, 0.031 mmol) in DCM (1.0 mL) at 20° C. under nitrogen was added TFA (1.0 mL) and the mixture was stirred for 15 min. Petroleum ether (20 mL) was added and the mixture was stirred for 30 min. The supernatant was decanted and the procedure was repeated using EtOAc:petroleum ether (1:5)(2×20 mL). The resulting solid was collected and purified by preparative HPLC [Synergi PolarRP column; aqueous TFA (pH=2.56; 90% to 2%)/10% water in $CH_3CN$ (10% to 98%); gradient elution over 23 min with a flow rate of 12 mL/min] to give pure 86 (17.5 mg, 38%) as a beige solid, purity (HPLC): 99.1%; $[\alpha]_D$+54.9° (c 0.18, MeOH); $^1H$ NMR $[(CD_3)_2SO]$ δ 10.20 (s, exchangeable with $D_2O$, 1H), 8.50 (s, 1H), 8.20-7.78 (m, 7H, reduced to 1H after $D_2O$), 8.12 (d, J=9.1 Hz, 1H), 7.72-7.47 (m, 4H, reduced to 3H after $D_2O$), 7.40 (t, J=7.5 Hz, 1H), 7.17 (br d, J=7.3 Hz, 2H), 7.03 (br s, 1H), 6.97 (s, 2H), 6.66 (br s, exchangeable with $D_2O$, 1H), 5.51 (br s, 1H), 5.48 (br d, J=9.7 Hz, 1H), 5.32-5.18 (m, but d after $D_2O$, J=12.6 Hz, 1H), 4.75 (br d, J=12.4 Hz, 1H), 4.44-3.81 (m, 8H), 3.77 (s, 3H), 3.52-3.21 (m, 5H, partially obscured by water peak), 3.04 (q, but t after $D_2O$ with J=6.8 Hz, 2H), 2.80-2.68 (m, 2H), 2.39 (t, J=7.7 Hz, 2H), 2.12-1.08 (m, 28H). HRMS (ESI) m/z calc. for $C_{61}H_{75}ClN_8O_{16}P$: 1241.4722, found: 1241.4700 [$MH^+$]; calc. for $C_{61}H_{74}ClN_8NaO_{16}P$: 1263.4541, found: 1263.4531 [$MNa^+$].

C. Synthesis of CBI Dimer Linker Drug Intermediates

Figure 11:
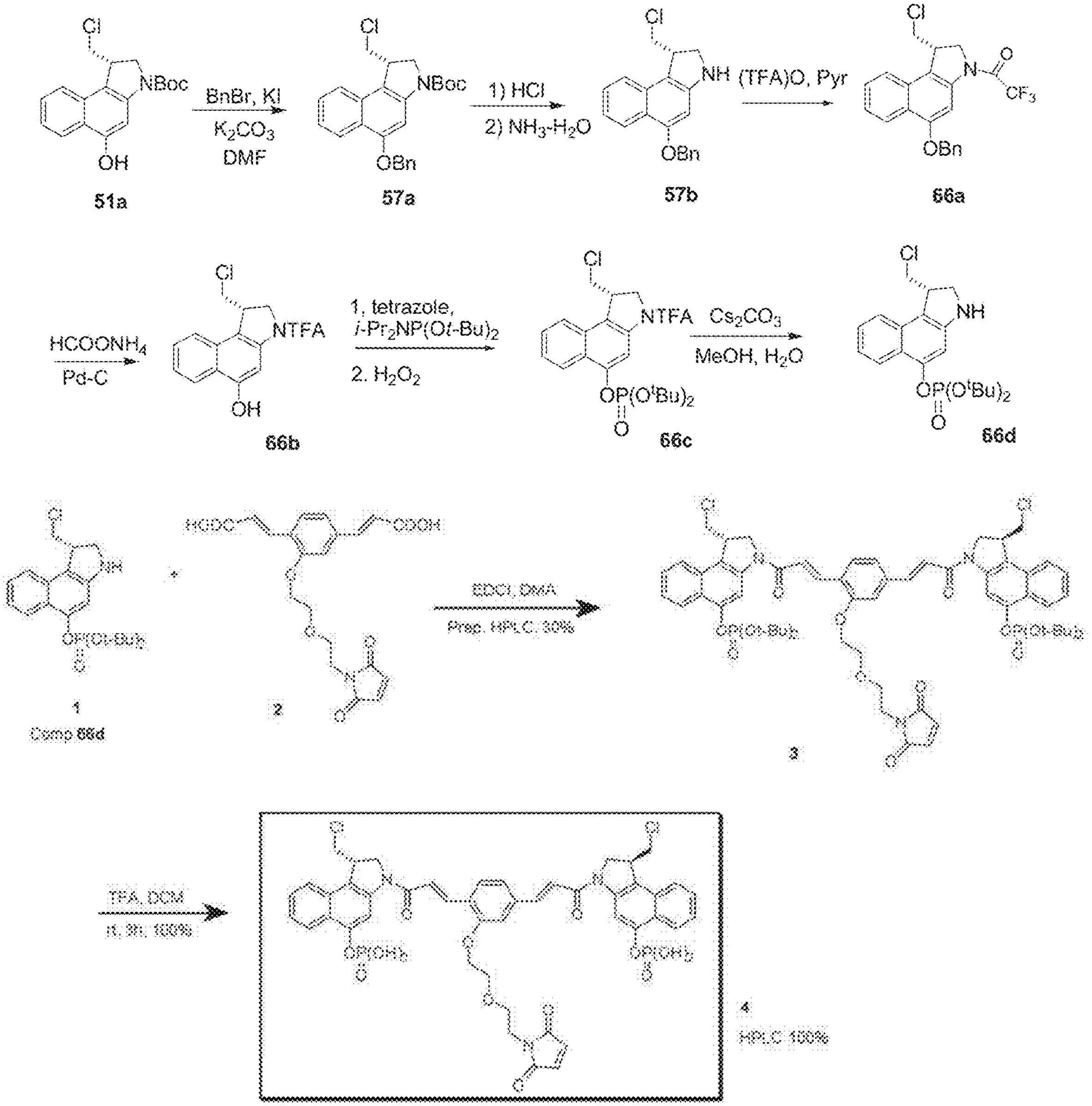
FIG. 11 shows an exemplary synthesis method for making certain CBI-CBI linker drug intermediates, as described in Example 3.

The CBI-CBI dimer ([(1S)-1-(chloromethyl)-3-[(E)-3-[4-[(E)-3-[(1S)-1-(chloromethyl)-5-phosphonooxy-1,2-dihydrobenzo[e]indol-3-yl]-3-oxo-prop-1-enyl]-2-[2-[2-(2,5-dioxopyrrol-1-yl)ethoxy]ethoxy]phenyl]prop-2-enoyl]-1,2-dihydrobenzo[e]indol-5-yl]dihydrogen phosphate; compound 78 of Table A) having the formula:

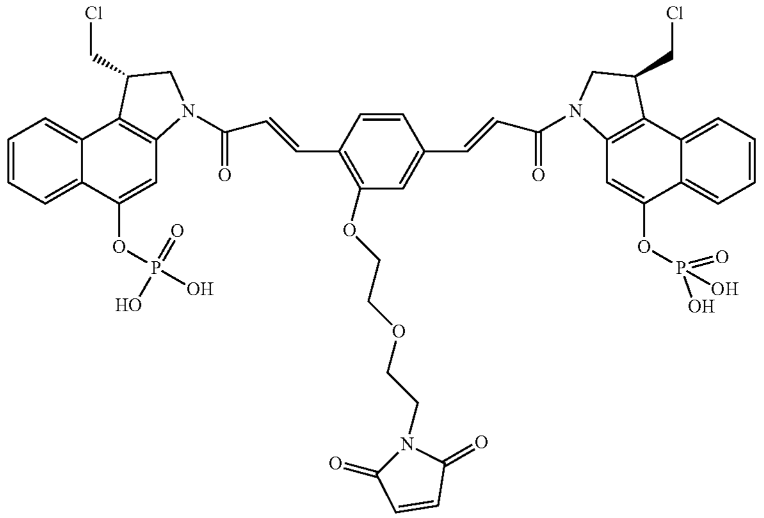 [SMILES: O=C1C=CC(=O)N1CCOCCOc1cc(/C=C/C(=O)N2C[C@@H](CCl)c3c2cc(OP(=O)(O)O)c2ccccc32)ccc1/C=C/C(=O)N1C[C@@H](CCl)c2c1cc(OP(=O)(O)O)c1ccccc21]

was synthesized as follows. For the reaction scheme, including reagent and intermediate formulae, see FIG. 11.

At room temperature to a solution of (S)-tert-Butyl 1-(chloromethyl)-5-hydroxy-1H-benzo[e]indole-3(2H)-carboxylate 51a (2.00 g, 5.99 mmol) in DMF (5 mL) was added benzyl bromide (7.13 mL, 59.90 mmol), potassium iodide KI (50 mg, 0.30 mmol) and potassium carbonate $K_2CO_3$ (4.14 g, 30.00 mmol). The mixture was stirred for 2 h and then diluted with ethyl acetate. The precipitate was filtered off. The filtrate was redistributed between ethyl acetate and water. The aqueous phase was extracted with ethyl acetate three times. The combined organic extracts were washed with water and brine, dried over anhydrous $Na_2SO_4$, and filtered through celite. The solvent was removed by rotary evaporator and the excess benzyl bromide was pumped off. The resultant residue was purified by column chromatography using a mixture of ethyl acetate and petroleum ether (v/v 1:10) as eluent to give (S)-tert-butyl 5-(benzyloxy)-1-(chloromethyl)-1H-benzo[e]indole-3(2H)-carboxylate 57a as a white solid (1.97 g, 78%); mp 186-188° C. $^1H$ NMR ($CDCl_3$) δ 8.29 (d, J=8.3 Hz, 1H), 7.86 (br s, 1H), 7.65 (d, J=8.29 Hz, 1H), 7.55-7.49 (m, 3H), 7.45-7.41 (m, 2H), 7.38-7.31 (m, 2H), 5.26 (s, 2H), 4.26 (br s, 1H), 4.13 (t, J=10.8 Hz, 1H), 4.00-3.92 (m, 2H), 3.44 (t, J=10.5 Hz, 1H), 1.61 (s, 9H) ppm. LRMS (APCI) found m/z 424.8 (M+H). $C_{25}H_{27}ClNO_3$ requires 424.2. (Boger D., Ishizakilb T., Kitos P. and Suntornwat O., (1990) *J. Org. Chem.,* 55, 5823-5832.)

To a solution of (S)-tert-butyl 5-(benzyloxy)-1-(chloromethyl)-1H-benzo[e]indole-3(2H)-carboxylate 57a, prepared from (S)-tert-Butyl 1-(chloromethyl)-5-hydroxy-1H-benzo[e]indole-3(2H)-carboxylate 51a (1.595 g, 3.76 mmol) in DCM (15 mL) cooled in an ice bath was added 4N HCl in dioxane (40 mL). The mixture was allowed to warm up to room temperature and stirred for 2 h. All volatile components were pumped off. The resultant residue was redistributed between ethyl acetate and cold aqueous 5% ammonia. The aqueous phase was extracted with ethyl acetate three times. The combined organic extracts were washed with water followed by brine, dried over anhydrous $Na_2SO_4$, and filtered through celite. The solvent was removed to give (S)-5-(benzyloxy)-1-(chloromethyl)-2,3-dihydro-1H-benzo[e]indole 57b as a brown gum, which was used directly; $^1H$ NMR (DMSO) δ 8.04 (d, J=8.2 Hz, 1H), 7.61 (d, J=8.3 Hz, 1H), 7.53 (d, J=7.2 Hz, 2H), 7.45-7.34 (m, 4H), 7.14 (t, J=7.3 Hz, 1H), 6.60 (s, 1H), 5.24 (s, 2H), 3.96-3.92 (m, 1H), 3.84 (dd, J=3.4, 10.7 Hz, 1H), 3.70 (t, J=9.3 Hz, 1H), 3.60 (dd, J=2.4, 10.0 Hz, 1H), 3.55 (t, J=10.3 Hz, 1H) ppm. HRMS (ESI) found m/z 324.1150 (M+H). $C_{20}H_{19}ClNO$ requires 324.1150.

Intermediate 57b was cooled in an ice bath and pyridine (15 mL) was added, followed by trifluoroacetic anhydride (3.14 mL, 22.57 mmol). The resultant mixture was stirred for 10 min and ice was added. The mixture was redistributed between ethyl acetate and water. The aqueous phase was extracted with ethyl acetate three times. The combined organic extracts were washed with water followed by brine, dried over anhydrous $Na_2SO_4$, and filtered through celite. The solvent was removed and the resultant residue was purified by column chromatography using a mixture of ethyl acetate and petroleum ether (v/v 1:10) as eluent to give (S)-1-(5-(benzyloxy)-1-(chloromethyl)-1H-benzo[e]indol-3(2H)-yl)-2,2,2-trifluoroethanone 66a as a white solid (1.11 g, 70%); mp 167-170° C. $^1H$ NMR ($CDCl_3$) δ 8.37 (d, J=8.3

Hz, 1H), 8.05 (s, 1H), 7.72 (d, J=8.2 Hz, 1H), 7.61-7.54 (m, 3H), 7.49-7.42 (m, 3H), 7.39-7.35 (m, 1H), 5.30 (AB q, J=11.7, 15.7 Hz, 2H), 4.63-4.59 (m, 1H), 4.43-4.38 (m, 1H), 4.15-4.09 (m, 1H), 3.97-3.93 (m, 1H), 3.49 (dd, J=9.9, 11.3 Hz, 1H) ppm. HRMS (ESI) found m/z 442.0799 (M+Na). $C_{22}H_{17}ClF_3NNaO_2$ requires 442.0795.

At −10° C., to a solution of 66a (1.10 g, 2.62 mmol) in THF (20 mL) was added 25% aqueous ammonium formate (20 mL) followed by Pd—C catalyst (10%, wet, 550 mg) and the mixture was stirred for 2 h before more Pd—C catalyst (550 mg) was added. The resultant mixture was stirred at −10° C. overnight and the catalyst was filtered off through celite. THF was removed from the filtrate and the residue was redistributed between ethyl acetate and water. The aqueous phase was extracted with ethyl acetate three times. The combined organic extracts were washed with water followed by brine, dried over anhydrous $Na_2SO_4$, and filtered through celite. The solvent was removed and the resultant residue was purified by column chromatography using a mixture of ethyl acetate and petroleum ether (v/v 1:5) as eluent to give (S)-1-(1-(chloromethyl)-5-hydroxy-1H-benzo[e]indol-3(2H)-yl)-2,2,2-trifluoroethanone 66b as an off-white solid (758 mg, 88%); mp 209-212° C. $^1$H NMR ($CDCl_3$) δ 8.33 (d, J=8.2 Hz, 1H), 8.10 (s, 1H), 7.85 (s, 1H), 7.64 (d, J=8.2 Hz, 1H), 7.60-7.56 (m, 1H), 7.51-7.47 (m, 1H), 4.60-4.56 (m, 1H), 4.41-4.36 (m, 1H), 4.00-3.95 (m, 1H), 3.93-3.90 (m, 1H), 3.44 (dd, J=9.8, 11.3 Hz, 1H) ppm. HRMS (ESI) found m/z 352.0331 (M+Na). $C_{15}H_{11}ClF_3NNaO_2$ requires 352.0323.

To a solution of 66b (250 mg, 0.76 mmol) in THF (15 mL) was added tetrazole (3% in acetonitrile, 13.5 mL, 4.55 mmol) followed by di-tert-butyl-N,N-di-isopropyl phosphoramidite (1.51 mL, 4.55 mmol). The mixture was stirred at room temperature overnight then cooled in an ice bath and $H_2O_2$ (30% aqueous solution, 0.78 mL, 7.58 mmol) was added dropwise. The resultant mixture was allowed to warm up to room temperature and stirred for 5 h. The reaction was quenched by the addition of 10% aqueous sodium sulphite with cooling in an ice bath. Organic volatiles were removed by rotary evaporator. The resultant mixture was redistributed between ethyl acetate and water. The aqueous phase was extracted with ethyl acetate three times. The combined organic extracts were washed with water followed by brine, dried over anhydrous $Na_2SO_4$, and filtered through celite. The solvent was removed and the resultant residue was purified by Florisil® (US Silica) column chromatography using gradient mixtures of ethyl acetate and petroleum ether (v/v 1:6 to 1:3) as eluent to give (S)-di-tert-butyl 1-(chloromethyl)-3-(2,2,2-trifluoroacetyl)-2,3-dihydro-1H-benzo[e]indol-5-yl phosphate 66c as colorless oil (367 mg, 93%); $^1$H NMR (DMSO) δ 8.44 (d, J=1.0 Hz, 1H), 8.11 (d, J=8.1 Hz, 1H), 8.06 (d, J=8.2 Hz, 1H), 7.69-7.65 (m, 1H), 7.63-7.59 (m, 1H), 4.61-4.56 (m, 1H), 4.46-4.41 (m, 1H), 4.15-4.12 (m, 1H), 4.06-4.00 (m, 1H), 1.50 (s, 9H), 1.48 (s, 9H) ppm. $^{31}$P NMR (DMSO) δ−15.54 ppm. HRMS (ESI) found m/z 544.1236 (M+Na). $C_{23}H_{28}ClF_3NNaO_5P$ requires 544.1238.

To a solution of 66c (239 mg, 0.46 mmol) in MeOH (2 mL) cooled in an ice bath was added $CsCO_3$ (298 mg, 0.92 mmol) and several drops of water. The mixture was stirred in the ice bath for 1 h and then redistributed between ethyl acetate and water. The aqueous phase was extracted with ethyl acetate three times. The combined organic extracts were washed with water and brine, dried over anhydrous $Na_2SO_4$, filtered through celite, and the solvent was removed. The resultant residue was dissolved in ethyl acetate and filtered through a pad of Florisil® (US Silica) column chromatography to give (S)-di-tert-butyl 1-(chloromethyl)-2,3-dihydro-1H-benzo[e]indol-5-yl phosphate 66d as an off-white gum (183 mg, 94%) which was used directly without further purification; $^1$H NMR (DMSO) δ 8.08 (d, J=8.4 Hz, 1H), 7.58 (d, J=8.3 Hz, 1H), 7.46-7.42 (m, 1H), 7.25-7.21 (m, 1H), 7.13 (d, J=0.8 Hz, 1H), 4.00-3.93 (m, 1H), 3.87-3.78 (m, 2H), 3.54-3.42 (m, 2H), 1.50 (s, 9H), 1.49 (s, 9H) ppm. $^{31}$P NMR (DMSO) δ−15.58 ppm. HRMS (ESI) found m/z 426.1587 (M+H). $C_{21}H_{30}ClNO_4P$ requires 426.1595.

To 76 mg (0.18 mmol) of 1 (66d, freshly made by the procedure mention above) was added 2 (18 mg, 0.045 mmol), EDCI hydrochloride (69 mg, 0.36 mmol), toluenesulfonic acid (0.8 mg, 0.005 mmol) and DMA (0.25 mL). After the mixture was stirred overnight, most of DMA was removed under vacuum and the residue was redistributed between ethyl acetate and water. The aqueous phase was extracted with ethyl acetate three times. The combined organic extracts were washed with water followed by brine, dried over anhydrous $Na_2SO_4$, and filtered through a pad of Celite. The solvent was removed and the resultant residue was dissolved in the minimum DCM and precipitated by adding heptane to give crude product (54 mg), which was further purified by preparative HPLC (Column: Synergi-Max RP 4μ, 250×21.20 mm; Mobile phase: AB=from 20% to 1% (A: ammonium formate pH 3.45, B: 90% acetonitrile in water); flow rate 12 mL/min, gradient method; wavelength: 254 nm, 325 nm) to give 3 (17 mg, 30%) as a yellow solid. $^1$H NMR ($CDCl_3$) δ 8.72 (br s, 2H), 8.23 (d, J=8.4 Hz, 2H), 7.96 (d, J=15.2 Hz, 1H), 7.83 (d, J=15.3 Hz, 1H), 7.71 (d, J=8.2 Hz, 2H), 7.54-7.50 (m, 3H), 7.42-7.39 (m, 2H), 7.26-7.12 (m, 3H), 6.95-6.88 (m, 1H), 6.67 (s, 2H), 4.57-4.52 (m, 2H), 4.47-4.38 (m, 2H), 4.28-4.24 (m, 2H), 4.16-4.09 (m, 2H), 4.00-3.94 (m, 4H), 3.78 (apparent s, 4H), 3.55-3.48 (m, 2H), 1.57 (s, 36H) ppm. $^{31}$P NMR ($CDCl_3$) δ−15.64 (s) ppm. HRMS (ESI) found m/z 1238.3862 (M+Na). $C_{62}H_{73}Cl_2N_3NaO_{14}P_2$ requires 1238.3837.

To a solution of 3 (16 mg, 0.013 mmol) in DCM (1 mL) cooled in an ice bath was added TFA (0.5 mL, 3.24 mmol). The mixture was allowed to warm up to room temperature and stirred for 3 h. All the volatile components were pumped off and the resultant residue was triturated with ethyl acetate to give Compound 78 as a yellow solid (13 mg, 100%, HPLC purity 100%). $^1$H NMR (DMSO) δ 8.60 (s, 2H), 8.12 (d, J=8.4 Hz, 2H), 7.95-7.87 (m, 4H), 7.72 (d, J=15.1 Hz, 1H), 7.61-7.57 (m, 2H), 7.53-7.45 (m, 4H), 7.38-7.32 (m, 2H), 6.97 (s, 2H), 4.60-4.48 (m, 4H), 4.30-4.28 (m, 4H), 4.08-3.88 (m, 6H), 3.68-3.58 (m, 4H). $^{31}$P NMR (DMSO) δ−5.94 (s) ppm. HRMS (ESI) found m/z 1014.1301 (M+Na). $C_{46}H_{41}Cl_2N_3NaO_{14}P_2$ requires 1014.1333.

D. Conjugation of Linker-Drug Moieties to Antibodies

Hu7C2 antibody-drug conjugates (ADCs) are produced by conjugating hu7C2.v.2.2. LA with a heavy chain A118C mutation (thio-hu7C2-HC A118C) or a light chain K149C mutation (thio-hu7C2-LC-K149C) to the selected drug-linker moiety. As initially isolated, the engineered cysteine residues in antibodies exist as mixed disulfides with cellular thiols (e.g., glutathione) and are thus unavailable for conjugation. Partial reduction of these antibodies (e.g., with DTT), purification, and reoxidation with dehydroascorbic acid (DHAA) gives antibodies with free cysteine sulfhydryl groups available for conjugation, as previously described, e.g., in Junutula et al. (2008) *Nat. Biotechnol.* 26:925-932 and US 2011/0301334. Briefly, the antibodies are combined with the drug-linker moiety to allow conjugation of the drug-linker moiety to the free cysteine residues of the antibody. After several hours, the ADCs are purified. The drug load (average number of drug moieties per antibody) for each ADC was determined and was in the range of 1.4-2.0.

The resulting ADC structures and the terms used for them below are shown in FIG. 12.

Example 3

Efficacy of hu7C2 Antibody Drug Conjugates in MMTV-Her2 Fo5 Transgenic Mammary Tumor Transplant Xenograft Models CRL nu/nu mice (Charles River Laboratory) were implanted with ~2×2 mm fragments of MMTV-Her2 Fo5 transgenic breast tumors. When tumors reached a mean tumor volume of 100-250 $mm^3$, animals were grouped into 7 groups of 8-10 mice each. The mice received a single administration on day 1 of one of the following treatments, via intravenous tail vein injection: (1) vehicle (20 mM L-histidine, 240 mM sucrose, 0.02% Tween-20, pH 5.5), (2) thio-hu7C2-HC-A118C-disulfide-PBD, 0.3 mg/kg; (3) thio-hu7C2-HC-A118C-disulfide-PBD, 1 mg/kg; (4) thio-hu7C2-LC-K149C-disulfide-PBD, 0.3 mg/kg; (5) thio-hu7C2-LC-K149C-disulfide-PBD, 1 mg/kg; (6) thio-controlAb-HC-A118C-disulfide-PBD, 1 mg/kg; or (7) thio-controlAb-LC-K149C-disulfide-PBD, 1 mg/kg. Tumor and body weight measurements were taken at least once per week for the duration of the study. Mice were euthanized when tumors reached 1000-2000 $mm^3$ or if the mouse lost 20% or more of its body weight. Tumor volume was measured in two dimensions (length and width) using calipers and the tumor volume was calculated using the formula: Tumor size ($mm^3$)=(longer measurement×shorter measurement)×0.5.

Figure 4:
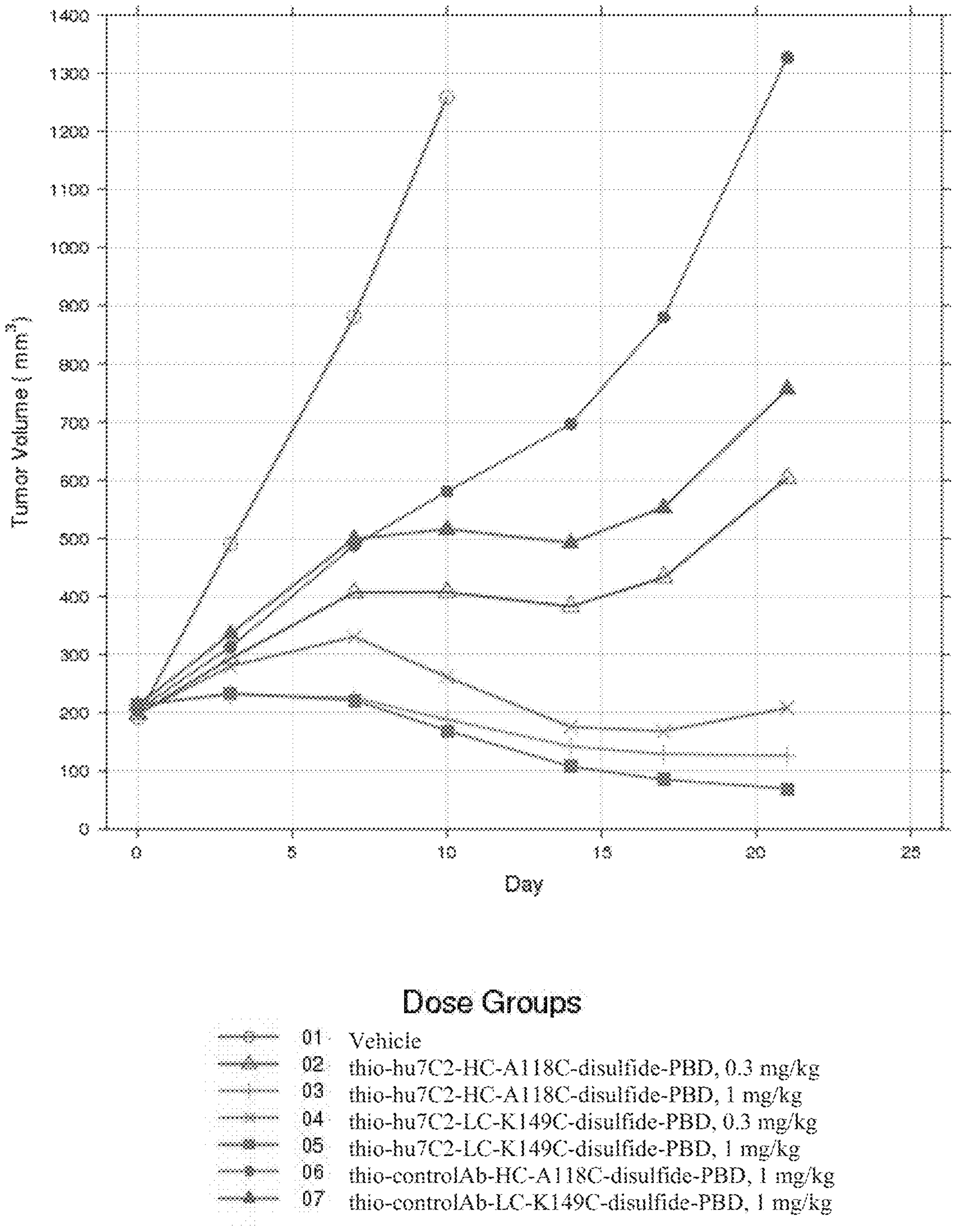
FIG. 4 shows change in tumor volume (mm3) over time upon treatment with hu7C2.v2.2. LA antibody-drug conjugates (ADCs), as described in Example 3.

The results of that experiment are shown in Table 5 and FIG. 4. The data in Table 5 is from day 21, except for the vehicle control group, which is from day 10. Each group contained 8 mice at the beginning of the study and 8 mice at day 21 (or 8 mice at day 10 for vehicle control group). AUC/day % TGI (tumor growth inhibition) is calculated using the following formula: % TGI=100×(1−AUCtreatment/Day÷AUCvehicle/Day). PR=partial response, which is defined as more than 50% but less than 100% reduction in tumor volume, compared with the starting tumor volume, on any day during the study. No animals showed a complete response in this experiment.

TABLE 5

Efficacy of hu7C2 ADCs in MMTV-Her2 Fo5 transgenic mammary tumor xenograft model

| Group | tumor volume, last day | AUC/day % TGI (lower, upper) | PR | % BW change, last day |
|---|---|---|---|---|
| (1) vehicle | 1258 | 0 (0, 0) | 0 | 12.65 |
| (2) thio-hu7C2-HC-A118C-disulfide-PBD, 0.3 mg/kg | 604 | 72 (51, 87) | 0 | 5.34 |
| (3) thio-hu7C2-HC-A118C-disulfide-PBD, 1 mg/kg | 127 | 98 (89, 108) | 2 | 2.81 |
| (4) thio-hu7C2-LC-K149C-disulfide-PBD, 0.3 mg/kg | 208 | 82 (67, 93) | 1 | 3.83 |
| (5) thio-hu7C2-LC-K149C-disulfide-PBD, 1 mg/kg | 70 | 99 (88, 107) | 8 | 1.90 |
| (6) thio-controlAb-HC-A118C-disulfide-PBD, 1 mg/kg | 1327 | 61 (35, 79) | 0 | 6.40 |
| (7) thio-controlAb-LC-K149C-disulfide-PBD, 1 mg/kg | 757 | 61 (37, 79) | 0 | 2.89 |

As shown in Table 5, thio-hu7C2-LC-K149C-disulfide-PBD showed 8 partial responses at 1 mg/kg and 1 partial response at 0.3 mg/kg. Thio-hu7C2-HC-A118C-disulfide-PBD showed 2 partial responses at 1 mg/kg and no partial responses at 0.3 mg/kg.

Example 4

Efficacy of hu7C2 Antibody Drug Conjugates in MMTV-Her2 Fo5 Transgenic Mammary Tumor Transplant Xenograft Models CRL nu/nu mice (Charles River Laboratory) were implanted with ~2×2 mm fragments of MMTV-Her2 Fo5 transgenic breast tumors. When tumors reached a mean tumor volume of 100-250 $mm^3$, animals were grouped into 9 groups of 8-10 mice each. The mice received a single administration on day 1 of one of the following treatments, via intravenous tail vein injection: (1) vehicle (20 mM L-histidine, 240 mM sucrose, 0.02% Tween-20, pH 5.5), (2) thio-hu7C2-LC-K149C-CBI dimer, 1 mg/kg; (3) thio-hu7C2-LC-K149C-CBI dimer, 3 mg/kg; (4) thio-hu7C2-LC-K149C-CBI dimer, 6 mg/kg; (5) thio-hu7C2-LC-K149C-disulfide-CBI-PBD, 1 mg/kg; (6) thio-hu7C2-LC-K149C-disulfide-CBI-PBD, 3 mg/kg; (7) thio-hu7C2-LC-K149C-disulfide-CBI-PBD, 6 mg/kg; (8) thio-controlAb-LC-K149C-CBI dimer, 6 mg/kg; or (9) thio-controlAb-LC-K149C-disulfide-CBI-PBD, 6 mg/kg. Tumor and body weight measurements were taken at least once per week for the duration of the study. Mice were euthanized when tumors reached 1000-2000 $mm^3$ or if the mouse lost 20% or more of its body weight. Tumor volume was measured in two dimensions (length and width) using calipers and the tumor volume was calculated using the formula: Tumor size ($mm^3$)=(longer measurement×shorter measurement)×0.5.

Figure 5:
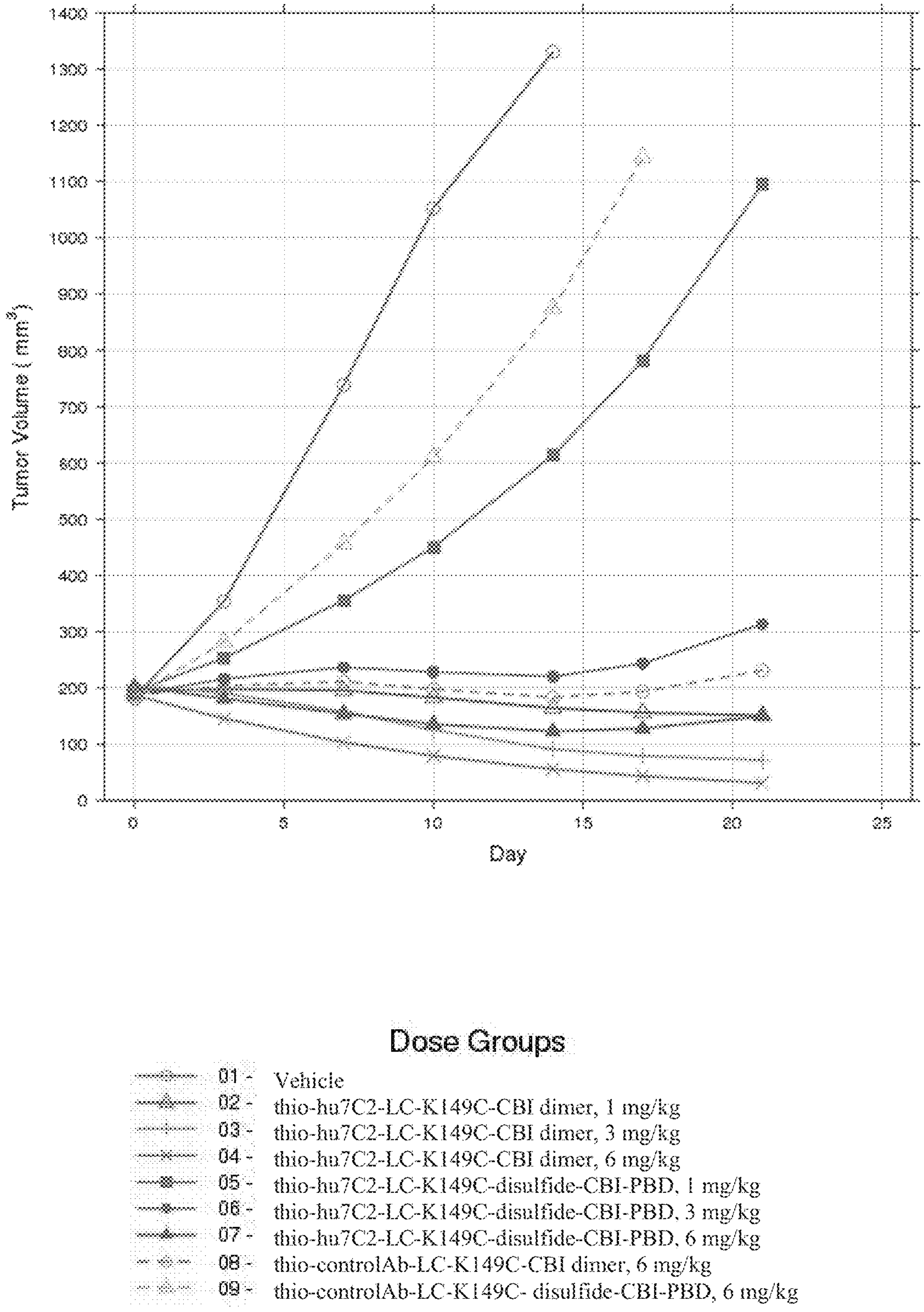
FIG. 5 shows change in tumor volume (mm3) over time upon treatment with hu7C2.v2.2. LA antibody-drug conjugates (ADCs), as described in Example 4.

The results of that experiment are shown in Table 6 and FIG. 5. The data in Table 6 is from day 21, except for the vehicle control group, which is from day 14. Each group contained 8 mice at the beginning of the study and 8 mice at day 21, except the vehicle control group, which had 8 mice at the beginning of the study and 7 mice at day 14. AUC/day % TGI (tumor growth inhibition) and PR were determined as described in the previous example. CR=complete response, which is defined as a 100% reduction in tumor volume (no measurable tumor), on any day during the study. The drug:antibody ratio (DAR) for each antibody-drug conjugate used in the experiment is shown in the second column.

TABLE 6

| Efficacy of hu7C2 ADCs in MMTV-Her2 Fo5 transgenic mammary tumor xenograft model | | | | | | |
|---|---|---|---|---|---|---|
| Group | DAR | tumor volume, last day | AUC/day % TGI (lower, upper) | PR | CR | % BW change, last day |
| (1) vehicle | | 1331 | 0 (0, 0) | 0 | 0 | 11.41 |
| (2) thio-hu7C2-LC-K149C-CBI dimer, 1 mg/kg | 2 | 151 | 101 (93, 109) | 1 | 0 | 3.77 |
| (3) thio-hu7C2-LC-K149C-CBI dimer, 3 mg/kg | 2 | 72 | 109 (103, 119) | 6 | 0 | 6.18 |
| (4) thio-hu7C2-LC-K149C-CBI dimer, 6 mg/kg | 2 | 32 | 114 (107, 124) | 5 | 2 | 0.07 |
| (5) thio-hu7C2-LC-K149C-disulfide-CBI-PBD, 1 mg/kg | 1.4 | 1095 | 69 (40, 86) | 0 | 0 | 6.84 |
| (6) thio-hu7C2-LC-K149C-disulfide-CBI-PBD, 3 mg/kg | 1.4 | 314 | 94 (83, 102) | 0 | 0 | 2.48 |
| (7) thio-hu7C2-LC-K149C-disulfide-CBI-PBD, 6 mg/kg | 1.4 | 150 | 108 (102, 117) | 1 | 0 | 4.01 |
| (8) thio-controlAb-LC-K149C-CBI dimer, 6 mg/kg | 2 | 231 | 98 (87, 106) | 1 | 0 | 4.17 |
| (9) thio-controlAb-LC-K149C- disulfide-CBI-PBD, 6 mg/kg | 1.4 | 1143 | 48 (8, 74) | 0 | 0 | 11.10 |

As shown in Table 6, thio-hu7C2-LC-K149C-CBI dimer showed 1 partial response at 1 mg/kg, 6 partial responses at 3 mg/kg, and 5 partial responses and 2 complete responses at 6 mg/kg. Thio-hu7C2-LC-K149C-disulfide-CBI-PBD showed 1 partial response at 6 mg/kg. In a second study in which the doses were reduced to 1 mg/kg, thio-hu7C2-LC-K149C-CBI dimer at 1 mg/kg caused tumor regressions while the thio-controlAb-LC-K149C-CBI dimer at 1 mg/kg caused % TGI of 60%. Without intending to be bound by any particular theory, it is believed that the activity of the control reflects non-targeted activity.

Example 5

Efficacy of hu7C2 Antibody Drug Conjugates in MMTV-Her2 Fo5 Transgenic Mammary Tumor Transplant Xenograft Models CRL nu/nu mice (Charles River Laboratory) were implanted with ~2×2 mm fragments of MMTV-Her2 Fo5 transgenic breast tumors. When tumors reached a mean tumor volume of 100-250 $mm^3$, animals were grouped into 7 groups of 8-10 mice each. The mice received a single administration on day 1 of one of the following treatments, via intravenous tail vein injection: (1) vehicle (20 mM L-histidine, 240 mM sucrose, 0.02% Tween-20, pH 5.5), (2) thio-hu7C2-LC-K149C-disulfide-PNU, 1 mg/kg; (3) thio-hu7C2-LC-K149C-disulfide-PNU, 3 mg/kg; (4) thio-controlAb-LC-K149C-disulfide-PNU, 1 mg/kg; (5) thio-controlAb-LC-K149C-disulfide-PNU, 3 mg/kg; (6) trastuzumab-MCC-DM1 (T-DM1, trastuzumab emtansine, ado-trastuzumab emtansine), 3 mg/kg; or (7) T-DM1, 10 mg/kg. Tumor and body weight measurements were taken at least once per week for the duration of the study. Mice were euthanized when tumors reached 1000-2000 $mm^3$ or if the mouse lost 20% or more of its body weight. Tumor volume was measured in two dimensions (length and width) using calipers and the tumor volume was calculated using the formula: Tumor size ($mm^3$)=(longer measurement×shorter measurement)×0.5.

Figure 6:
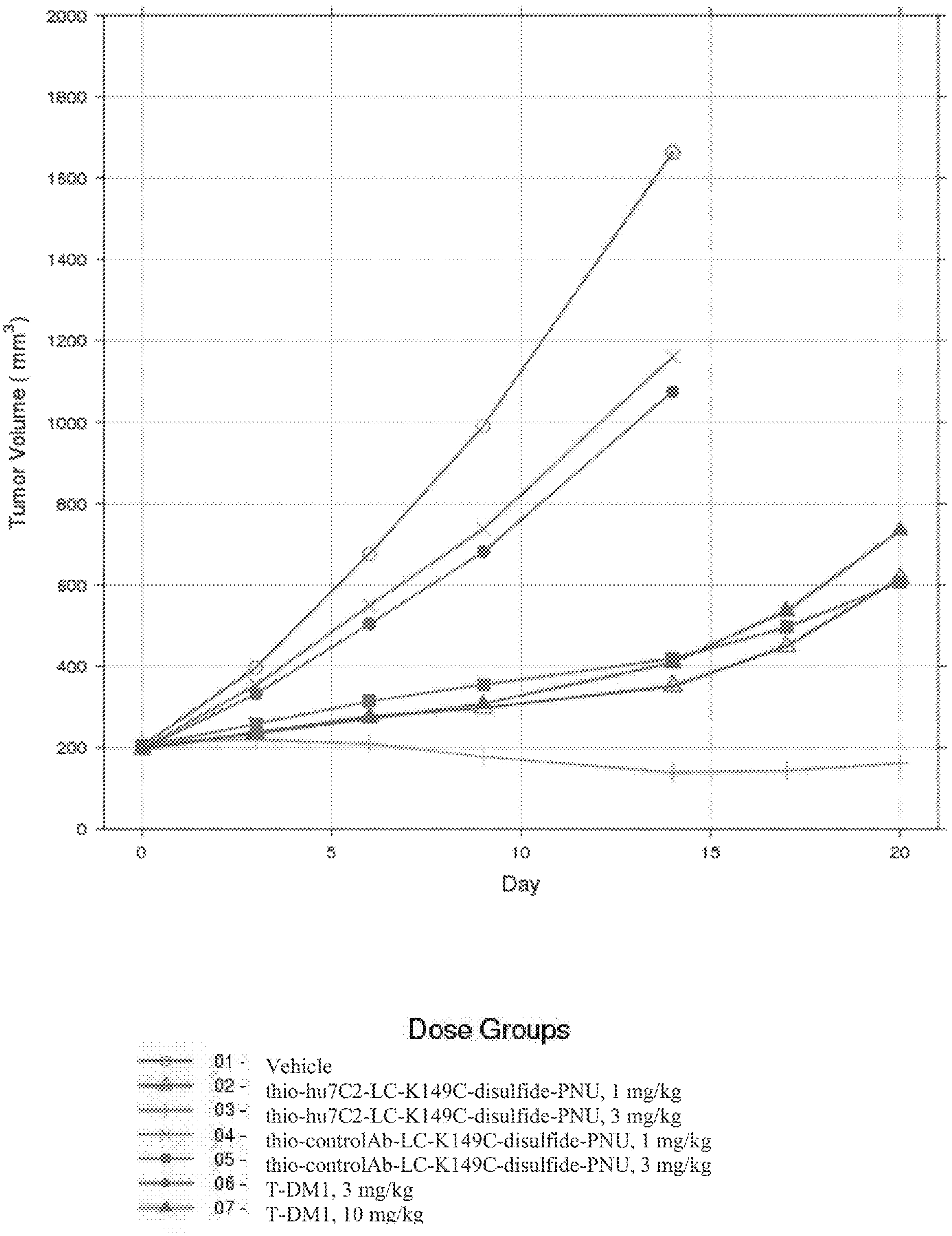
FIG. 6 shows change in tumor volume (mm3) over time upon treatment with hu7C2.v2.2. LA antibody-drug conjugates (ADCs), as described in Example 5.

The results of that experiment are shown in Table 7 and FIG. 6. The data in Table 7 is from day 20, except for the vehicle control group, thio-controlAb-LC-K149C-disulfide-PNU 1 mg/kg group, and T-DM1 3 mg/kg group, which are from day 14. Each group contained 8 mice at the beginning of the study and 8 mice at the end, except the vehicle control group, which had 8 mice at the beginning of the study and 7 mice at the end. AUC/day % TGI (tumor growth inhibition was determined as described in the previous examples. In this experiment, there were no partial or complete responses. The drug:antibody ratio (DAR) for each antibody-drug conjugate used in the experiment is shown in the second column.

TABLE 7

| Efficacy of hu7C2 ADCs in MMTV-Her2 Fo5 transgenic mammary tumor xenograft model | | | | |
|---|---|---|---|---|
| Group | DAR | tumor volume, last day | AUC/day % TGI (lower, upper) | % BW change, last day |
| (1) vehicle | | 1663 | 0 (0, 0) | 8.08 |
| (2) thio-hu7C2-LC-K149C-disulfide-PNU, 1 mg/kg | 1.9 | 616 | 87 (72, 95) | 0.52 |
| (3) thio-hu7C2-LC-K149C-disulfide-PNU, 3 mg/kg | 1.9 | 162 | 104 (99, 110) | 3.17 |
| (4) thio-controlAb-LC-K149C-disulfide-PNU, 1 mg/kg | 1.9 | 1160 | 31 (−21, 60) | 6.26 |
| (5) thio-controlAb-LC-K149C-disulfide-PNU, 3 mg/kg | 1.9 | 607 | 81 (61, 92) | 5.48 |
| (6) T-DM1, 3 mg/kg | 3.8 | 1075 | 38 (−5, 64) | 3.65 |
| (7) T-DM1, 10 mg/kg | 3.8 | 734 | 86 (73, 95) | 4.24 |

These data suggest that thio-hu7C2-LC-K149C-disulfide-PNU (3 mg/kg) has greater efficacy than T-DM1 or control immunoconjugate in this model.

Example 6

Efficacy of hu7C2 Antibody Drug Conjugates in MMTV-Her2 Fo5 Transgenic Mammary Tumor Transplant Xenograft Models CRL nu/nu mice (Charles River Laboratory) were implanted with ~2×2 mm fragments of MMTV-Her2 Fo5 transgenic breast tumors. When tumors reached a mean tumor volume of 100-250 $mm^3$, animals were grouped into 9 groups of 8-10 mice each. The mice received a single administration on day 1 of one of the following treatments, via intravenous tail vein injection: (1) vehicle (20 mM L-histidine, 240 mM sucrose, 0.02% Tween-20, pH 5.5), (2) thio-hu7C2-HC-A118C-maleimide-PNU, —1 mg/kg (drug dose matched to group IV); (3) thio-hu7C2-LC-K149C-maleimide-PNU, 0.3 mg/kg; (4) thio-hu7C2-LC-K149C-maleimide-PNU, 1 mg/kg; (5) thio-hu7C2-LC-K149C-maleimide-PNU, 3 mg/kg; (6) thio-controlAb-LC-K149C-maleimide-PNU, 3 mg/kg; (7) thio-hu7C2-LC-K149C-CBI dimer, 0.3 mg/kg; (8) thio-hu7C2-LC-K149C-CBI dimer, 1 mg/kg; or (9) thio-controlAb-LC-K149C-CBI dimer, 1 mg/kg. Tumor and body weight measurements were taken at least once per week for the duration of the study. Mice were euthanized when tumors reached 1000-2000 $mm^3$ or if the mouse lost 20% or more of its body weight. Tumor volume was measured in two dimensions (length and width) using calipers and the tumor volume was calculated using the formula: Tumor size ($mm^3$)=(longer measurement×shorter measurement)×0.5.

Figure 7:
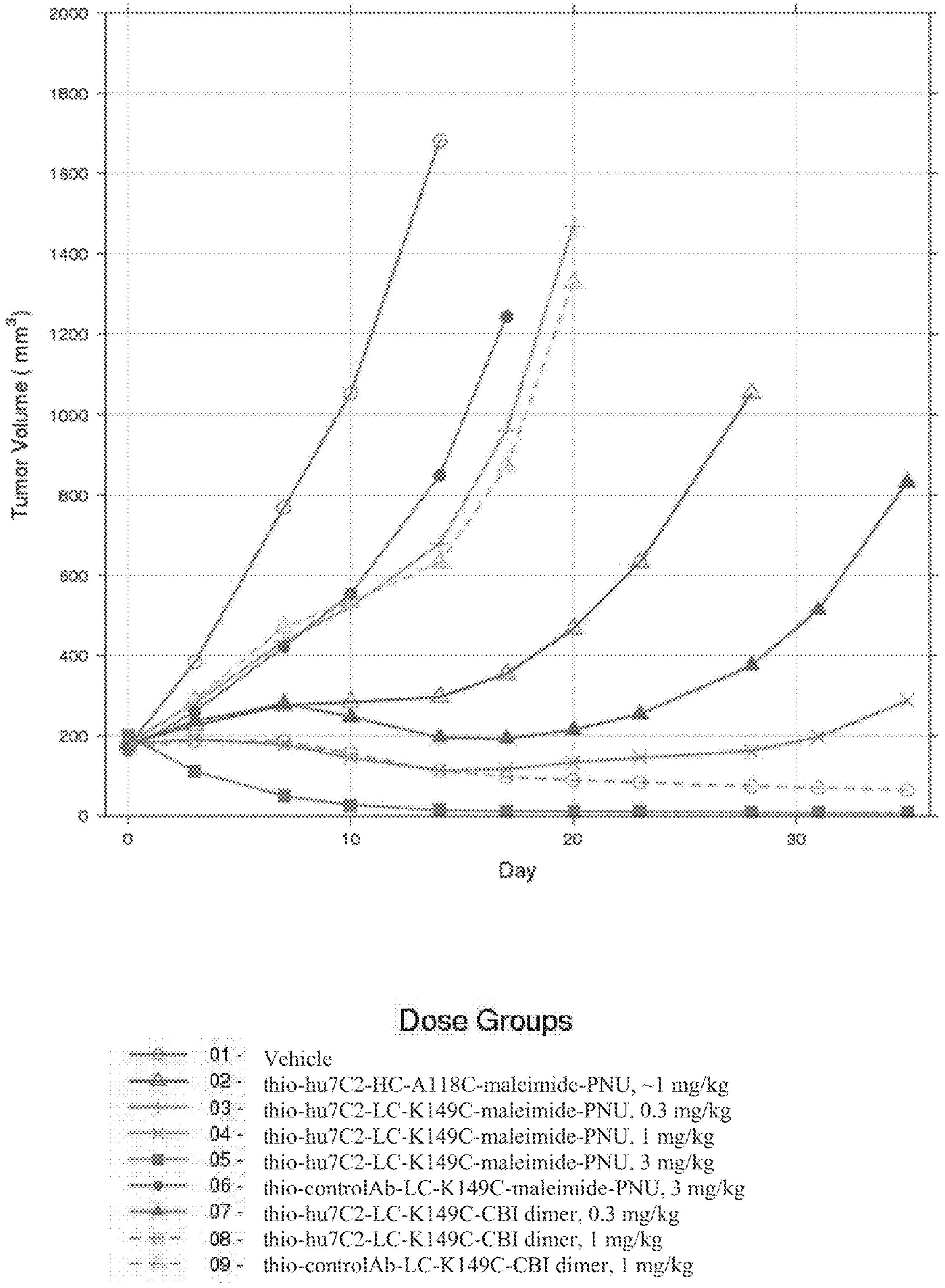
FIG. 7 shows change in tumor volume (mm3) over time upon treatment with hu7C2.v2.2. LA antibody-drug conjugates (ADCs), as described in Example 6.

The results of that experiment are shown in Table 8 and FIG. 7. The data in Table 8 is from the last day of the study for each group, indicated in the second column of the table. Each group contained 8 mice at the beginning of the study and 8 mice at the end, except group (9), which had 7 mice at the end of the study. AUC/day % TGI (tumor growth inhibition), PR, and CR were determined as described in the previous examples. The drug:antibody ratio (DAR) for each antibody-drug conjugate used in the experiment is shown in the second column.

TABLE 8

Efficacy of hu7C2 ADCs in MMTV-Her2 Fo5 transgenic mammary tumor xenograft model

| Group | DAR | last day | tumor volume, last day | AUC/day % TGI (lower, upper) | PR | CR | % BW change, last day |
|---|---|---|---|---|---|---|---|
| (1) vehicle | | 14 | 1681 | 0 (0, 0) | 0 | 0 | 9.98 |
| (2) thio-hu7C2-HC-A118C-maleimide-PNU, ~1 mg/kg | 1.73 | 28 | 1054 | 88 (69, 99) | 0 | 0 | 10.21 |
| (3) thio-hu7C2-LC-K149C-maleimide-PNU, 0.3 mg/kg | 1.8 | 20 | 1469 | 62 (25, 82) | 0 | 0 | 8.11 |
| (4) thio-hu7C2-LC-K149C-maleimide-PNU, 1 mg/kg | 1.8 | 35 | 288 | 103 (94, 111) | 3 | 0 | 8.73 |
| (5) thio-hu7C2-LC-K149C- maleimide-PNU, 3 mg/kg | 1.8 | 35 | 8 | 121 (112, 137) | 0 | 8 | 6.65 |
| (6) thio-controlAb-LC-K149C-maleimide-PNU, 3 mg/kg | 1.4-2 | 17 | 1244 | 56 (7, 79) | 0 | 0 | 5.40 |
| (7) thio-hu7C2-LC-K149C-CBI dimer, 0.3 mg/kg | 2 | 35 | 833 | 90 (74, 100) | 0 | 0 | 9.14 |
| (8) thio-hu7C2-LC-K149C-CBI dimer, 1 mg/kg | 2 | 35 | 65 | 100 (91, 109) | 5 | 0 | 7.14 |
| (9) thio-controlAb-LC-K149C-CBI dimer, 1 mg/kg | 2 | 20 | 1328 | 59 (11, 80) | 0 | 0 | 9.92 |

As shown in Table 8, thio-hu7C2-LC-K149C-maleimide-PNU showed 3 partial responses at 1 mg/kg and 8 complete responses at 3 mg/kg. Thio-hu7C2-LC-K149C-CBI dimer showed 5 partial responses at 1 mg/kg.

Example 7

Efficacy of hu7C2 Antibody Drug Conjugates in KPL4 Breast Cancer Cell Line Xenograft Model SCID beige mice (C.B-17 SCID.bg, Charles River Laboratories) were inoculated with 3 million cells per mouse suspended in HBSS/matrigel into the thoracic mammary fat pad in a volume of 0.2 ml. When tumors reached a mean tumor volume of 100-250 $mm^3$, animals were grouped into 9 groups of 8-10 mice each. The mice received a single administration on day 1 of one of the following treatments, via intravenous tail vein injection: (1) vehicle (20 mM L-histidine, 240 mM sucrose, 0.02% Tween-20, pH 5.5), (2) thio-hu7C2-LC-K149C-maleimide-PNU, 0.3 mg/kg; (3) thio-hu7C2-LC-K149C-maleimide-PNU, 1 mg/kg; (4) thio-hu7C2-LC-K149C-maleimide-PNU, 3 mg/kg; (5) thio-hu7C2-LC-K149C-disulfide-PNU, 0.3 mg/kg; (6) thio-hu7C2-LC-K149C-disulfide-PNU, 1 mg/kg; (7) thio-hu7C2-LC-K149C-disulfide-PNU, 3 mg/kg; (8) thio-controlAb-LC-K149C-maleimide-PNU, 3 mg/kg; (9) thio-controlAb-LC-K149C-disulfide-PNU, 3 mg/kg. Tumor and body weight measurements were taken at least once per week for the duration of the study. Mice were euthanized when tumors reached 1000-2000 $mm^3$ or if the mouse lost 20% or more of its body weight. Tumor volume was measured in two dimensions (length and width) using calipers and the tumor volume was calculated using the formula: Tumor size ($mm^3$)=(longer measurement×shorter measurement)×0.5.

Figure 8:
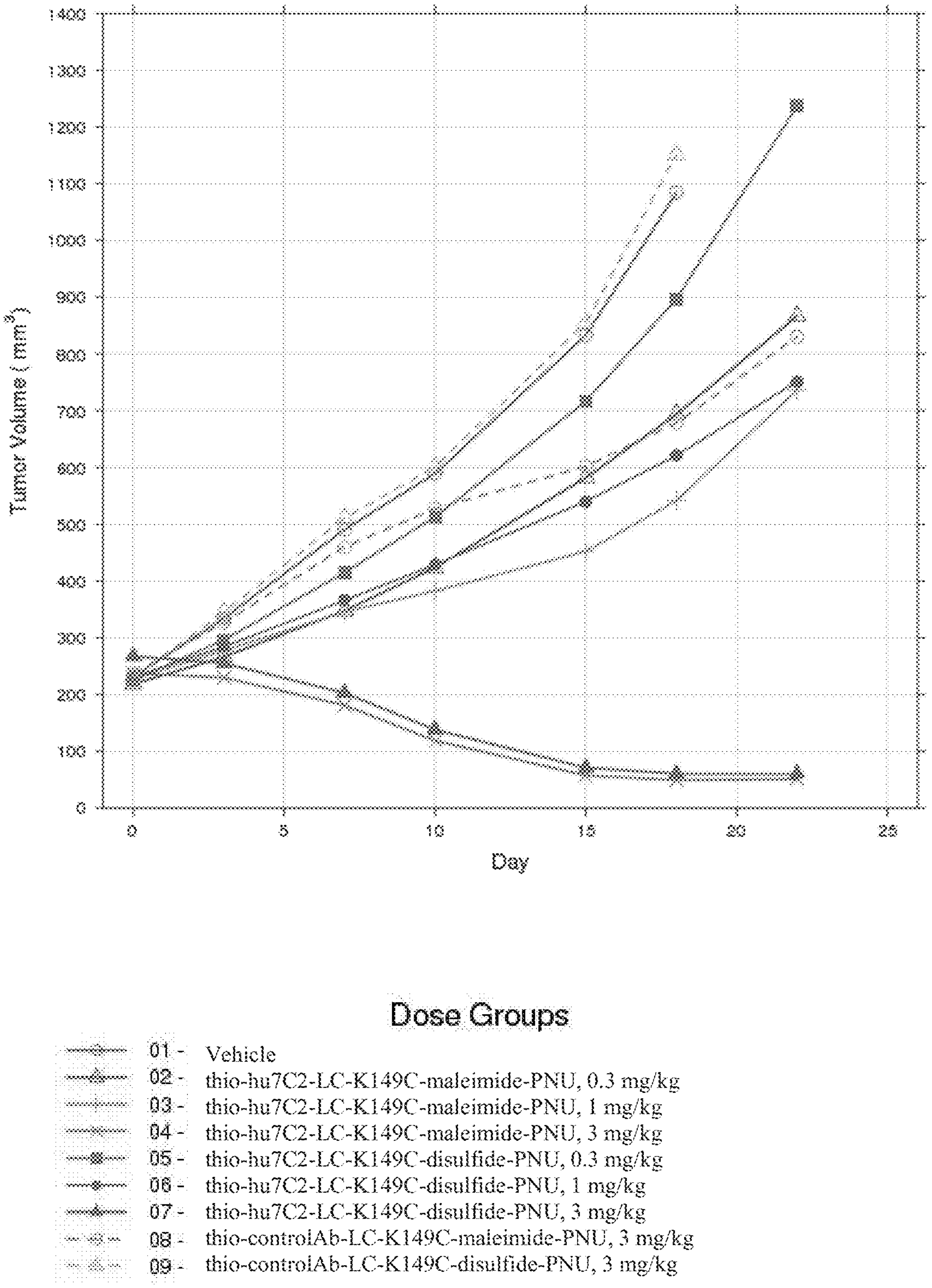
FIG. 8 shows change in tumor volume (mm3) over time upon treatment with hu7C2.v2.2. LA antibody-drug conjugates (ADCs), as described in Example 7.

The results of that experiment are shown in Table 9 and FIG. 8. The data in Table 9 is from day 22 for all groups except the vehicle control group and the thio-controlAb-LC-K149C-disulfide-PNU group, which are from day 18. Each group contained 8 mice at the beginning of the study and 8 mice at the end, except group (6), which had 7 mice at the end of the study. AUC/day % TGI (tumor growth inhibition), PR, and CR were determined as described in the previous examples. The drug:antibody ratio (DAR) for each antibody-drug conjugate used in the experiment is shown in the second column.

TABLE 9

Efficacy of hu7C2 ADCs in KPL4 breast cancer cell line xenograft model

| Group | DAR | tumor volume, last day | AUC/day % TGI (lower, upper) | PR | CR | % BW change, last day |
|---|---|---|---|---|---|---|
| (1) vehicle | | 1084 | 0 (0, 0) | 0 | 0 | −3.73 |
| (2) thio-hu7C2-LC-K149C-maleimide-PNU, 0.3 mg/kg | 1.8 | 867 | 43 (−18, 75) | 0 | 0 | −3.98 |
| (3) thio-hu7C2-LC-K149C-maleimide-PNU, 1 mg/kg | 1.8 | 736 | 59 (11, 83) | 0 | 0 | 0.01 |
| (4) thio-hu7C2-LC-K149C- maleimide-PNU, 3 mg/kg | 1.8 | 51 | 127 (115, 151) | 7 | 1 | 3.61 |
| (5) thio-hu7C2-LC-K149C-disulfide-PNU, 0.3 mg/kg | 1.9 | 1237 | 21 (−59, 65) | 0 | 0 | −4.67 |
| (6) thio-hu7C2-LC-K149C-disulfide-PNU, 1 mg/kg | 1.9 | 752 | 48 (−14, 78) | 0 | 0 | −4.65 |
| (7) thio-hu7C2-LC-K149C-disulfide-PNU, 3 mg/kg | 1.9 | 60 | 130 (114, 155) | 7 | 0 | 1.77 |
| (8) thio-controlAb-LC-K149C-maleimide-PNU, 3 mg/kg | 1.4-2 | 831 | 30 (−48, 66) | 0 | 0 | −9.49 |
| (9) thio-controlAb-LC-K149C-disulfide-PNU, 3 mg/kg | 1.9 | 1152 | −5 (−100, 50) | 0 | 0 | −6.46 |

As shown in Table 9, thio-hu7C2-LC-K149C-maleimide-PNU showed 7 partial responses and 1 complete response at 3 mg/kg. Thio-hu7C2-LC-K149C-disulfide-PNU showed 7 partial responses at 3 mg/kg.

Example 8

Efficacy of hu7C2 Antibody Drug Conjugates in MMTV-Her2 Fo5 Transgenic Mammary Tumor Transplant Xenograft Model CRL nu/nu mice (Charles River Laboratory) were implanted with ~2×2 mm fragments of MMTV-Her2 Fo5 transgenic breast tumors. When tumors reached a mean tumor volume of 100-250 $mm^3$, animals were grouped into 7 groups of 8-10 mice each. The mice received a single administration on day 0 of one of the following treatments, via intravenous tail vein injection: (1) vehicle (20 mM L-histidine, 240 mM sucrose, 0.02% Tween-20, pH 5.5), (2) thio-hu7C2-LC-K149C-disulfide-CBI-PBD, 2 mg/kg; (3) thio-hu7C2-LC-K149C-disulfide-CBI-PBD, 5 mg/kg; (4) thio-controlAb-LC-K149C-disulfide-CBI-PBD, 5 mg/kg; (5) thio-hu7C2-LC-K149C-disulfide-CBI-PBD (phosphate), 2 mg/kg; (6) thio-hu7C2-LC-K149C-disulfide-CBI-PBD (phosphate), 5 mg/kg; or (7) thio-controlAb-LC-K149C-disulfide-CBI-PBD (phosphate), 5 mg/kg. Tumor and body weight measurements were taken at least once per week for the duration of the study. Mice were euthanized when tumors reached 1000-2000 $mm^3$ or if the mouse lost 20% or more of its body weight. Tumor volume was measured in two dimensions (length and width) using calipers and the tumor volume was calculated using the formula: Tumor size ($mm^3$)=(longer measurement×shorter measurement)×0.5.

Figure 17:
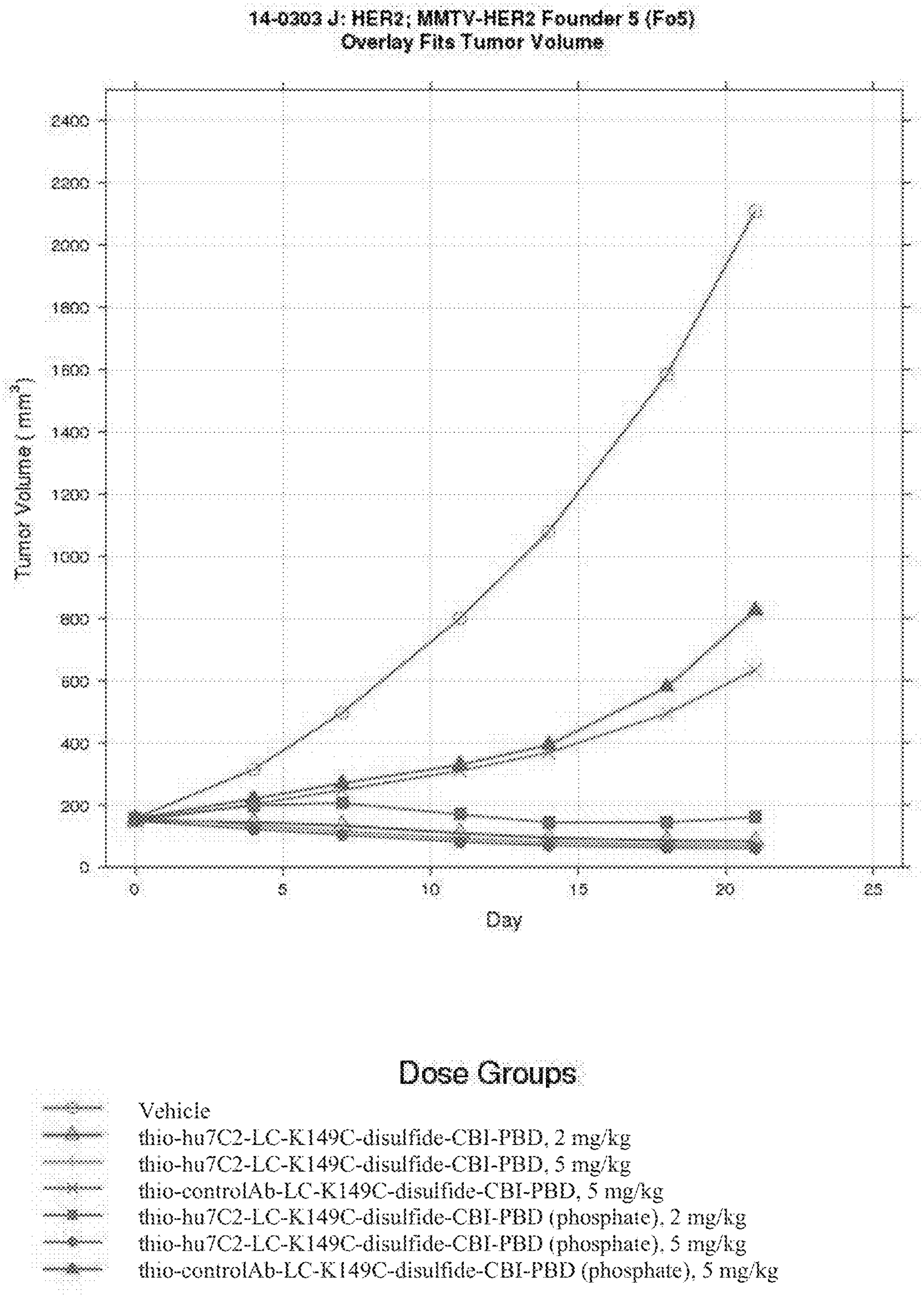
FIG. 17 shows change in tumor volume (mm3) over time upon treatment with hu7C2.v2.2. LA antibody-drug conjugates (ADCs), as described in Example 8.

The results of that experiment are shown in Table 10 and FIG. 17. The data in Table 10 is from day 21. Each group contained 7 mice at the beginning of the study and 7 mice at the end, except group (1), which had 5 mice at the end of the study, and group (4), which had 6 mice at the end of the study. AUC/day % TGI (tumor growth inhibition) and PR were determined as described in the previous examples. No mice showed a complete response in this experiment. The drug:antibody ratio (DAR) for each antibody-drug conjugate used in the experiment is shown in the second column.

TABLE 10

Efficacy of hu7C2 ADCs in MMTV-Her2 Fo5 transgenic mammary tumor xenograft model

| Group | DAR | tumor volume, last day | AUC/day % TGI (lower, upper) | PR | % BW change, last day |
|---|---|---|---|---|---|
| (1) vehicle | | 2109 | 0 (0, 0) | 0 | 5.36 |
| (2) thio-hu7C2-LC-K149C-disulfide-CBI-PBD, 2 mg/kg | 1.4 | 83 | 105 (100, 111) | 2 | 1.02 |

TABLE 10-continued

| Efficacy of hu7C2 ADCs in MMTV-Her2 Fo5 transgenic mammary tumor xenograft model | | | | | |
|---|---|---|---|---|---|
| Group | DAR | tumor volume, last day | AUC/day % TGI (lower, upper) | PR | % BW change, last day |
| (3) thio-hu7C2-LC-K149C-disulfide-CBI-PBD, 5 mg/kg | 1.4 | 71 | 108 (103, 106) | 4 | 0.81 |
| (4) thio-controlAb-LC-K149C-disulfide-CBI-PBD, 5 mg/kg | 1.4 | 635 | 75 (35, 92) | 0 | 0.82 |
| (5) thio-hu7C2-LC-K149C-disulfide-CBI-PBD (phosphate), 2 mg/kg | 1.4-2 | 161 | 98 (87, 104) | 1 | 0.66 |
| (6) thio-hu7C2-LC-K149C-disulfide-CBI-PBD (phosphate), 5 mg/kg | 1.4-2 | 61 | 108 (104, 116) | 7 | 2.55 |
| (7) thio-controlAb-LC-K149C-disulfide-CBI-PBD (phosphate), 5 mg/kg | 1.4-2 | 826 | 70 (29, 88) | 0 | 4.62 |

As shown in Table 10, thio-hu7C2-LC-K149C-disulfide-CBI-PBD showed 2 partial responses at 2 mg/kg and 4 partial responses at 5 mg/kg. Thio-hu7C2-LC-K149C-disulfide-CBI-PBD (phosphate) showed 1 partial response at 2 mg/kg and 7 partial responses at 5 mg/kg.

Example 9

Efficacy of hu7C2 Antibody Drug Conjugates in HCC1569X2 Transplant Xenograft Model The HCC1569 human breast cancer cell line was obtained from ATCC (American Type Culture Collection; Manassas, VA) and a sub-line HCC1569X2 was generated at Genentech for optimal growth in mice.

Female C.B-17 SCID-beige mice (Charles River Laboratory) were each inoculated in the thoracic mammary fat pad area with 5 million HCC1569X2 cells suspended in HBSS/matrigel (1:1 ratio). When the xenograft tumors reached an average tumor volume of 100-300 mm3 (Day 0), animals were randomized into 7 groups with 7 mice per group and received a single administration of one of the following treatments, via intravenous tail vein injection: (1) vehicle (20 mM L-histidine, 240 mM sucrose, 0.02% Tween-20, pH 5.5), (2) trastuzumab-MCC-DM1 (T-DM1, trastuzumab emtansine, ado-trastuzumab emtansine). 3 mg/kg; (3) thio-hu7C2-LC-K149C-disulfide-CBI-PBD, 0.5 mg/kg; (4) thio-hu7C2-LC-K149C-disulfide-CBI-PBD, 1 mg/kg; (5) thio-hu7C2-LC-K149C-disulfide-CBI-PBD, 2 mg/kg; (6) T-DM1, 3 mg/kg+thio-hu7C2-LC-K149C-disulfide-CBI-PBD, 0.5 mg/kg; or (7) T-DM1, 3 mg/kg+thio-hu7C2-LC-K149C-disulfide-CBI-PBD, 1 mg/kg. Tumors and body weights of mice were measured 1-2 times a week throughout the study. Mice were euthanized when body weight loss was >20% of their starting weight. All animals were euthanized before tumors reached 3000 $mm^3$ or showed signs of impending ulceration. Tumor volume was measured in two dimensions (length and width) using calipers and the tumor volume was calculated using the formula: Tumor size ($mm^3$)= (longer measurement×shorter measurement$^2$)×0.5.

Figure 18:
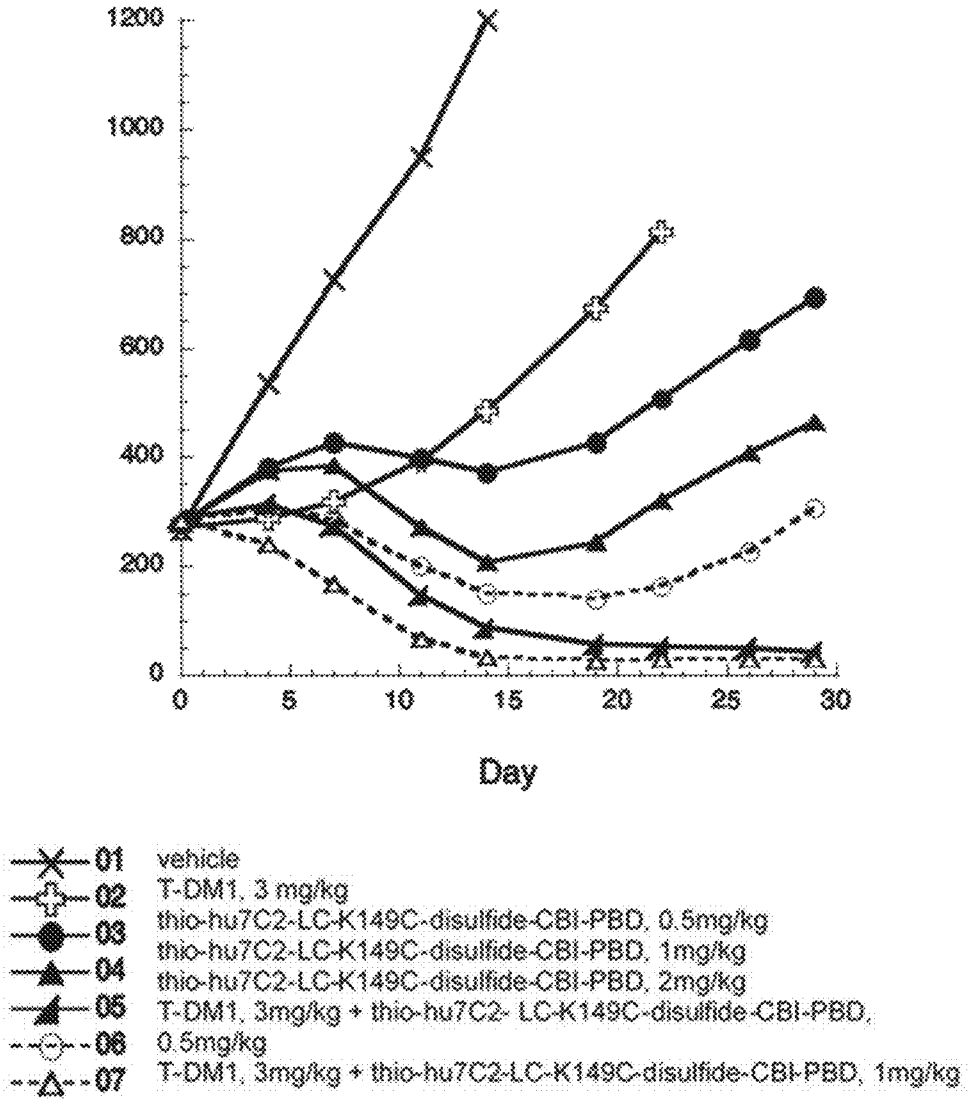
FIG. 18 shows change in tumor volume (mm3) over time upon treatment with hu7C2.v2.2. LA antibody-drug conjugates (ADCs), as described in Example 9.

The results of that experiment are shown in Table 11 and FIG. 18. The data in Table 11 is from day 14 with all groups having 7 mice.

TABLE 11

| Efficacy of hu7C2 Antibody Drug Conjugates in HCC1569X2 Transplant Xenograft Model. | | | | |
|---|---|---|---|---|
| Group | DAR | tumor volume, last day | AUC/day % TGI (lower,upper) | % BW change, last day |
| 01 - Vehicle | | 1200 | 0 (0, 0) | 5.15 |
| 02 - T-DM1, 3 mg/kg | 3.8 | 506 | 84 (42, 104) | 4.91 |
| 03 - thio-hu7C2-LC-K149C-disulfide-CBI-PBD, 0.5 mg/kg | 1.9 | 364 | 75 (28, 95) | 5.65 |
| 04 - thio-hu7C2-LC-K149C-disulfide-CBI-PBD, 1 mg/kg | 1.9 | 212 | 87 (53, 102) | 5.21 |
| 05 - thio-hu7C2-LC-K149C-disulfide-CBI-PBD, 2 mg/kg | 1.9 | 94 | 106 (91, 123) | 3.85 |
| 06 - T-DM1, 3 mg/kg + thio-hu7C2-LC-K149C-disulfide-CBI-PBD, 0.5 mg/kg | 3.8<br>1.9 | 145 | 101 (82, 118) | 4.2 |
| 07 - T-DM1, 3 mg/kg + thio-hu7C2-LC-K149C-disulfide-CBI-PBD, 1 mg/kg | 3.8<br>1.9 | 33 | 122 (110, 146) | 4.18 |

In this study, thio-hu7C2-LC-K149C-disulfide-CBI-PBD demonstrated dose-dependent inhibition of tumor growth, with tumor regression observed at 2 mg/kg dose. The combination of thio-hu7C2-LC-K149C-disulfide-CBI-PBD and T-DM1 resulted in greater efficacy than either agent alone and was well tolerated based on minimal changes in animal body weights compared with vehicle group.

Example 10

Crystal Structure of 7C2 Fab Bound to HER2

Methods

Expression, purification, and crystallization of the 7C2/HER2 complex—7C2 Fab was expressed in *E. coli* and purified using Protein G sepharose affinity resin (GE), SP sepharose cation exchange chromatography, and size exclusion chromatography (SEC). HER2 extracellular domain (ECD) was expressed in CHO cells and purified by affinity chromatography using trastuzumab antibody linked to controlled pore glass beads, followed by DEAE anion exchange and size exclusion chromatography.

The complex between Fab 7C2 and HER2 ECD was purified by SEC. The complex was deglycosylated using a combination of enzymes (Endo F1, F2, F3, Endo H and PNGase), followed by purification by SEC into 0.1M NaCl, 20 mM HEPES pH 7.2 and 2% glycerol. The complex was crystallized resulting in thick plates after one week in hanging drops using equal parts of protein at 10 mg/mL and reservoir (30% v/v PEG 550 monomethylether, 0.1M Sodium citrate tribasic dihydrate pH 5.0) and treated briefly with reservoir prior to immersion in liquid nitrogen.

The diffraction data for the complex extending to 2.7 Å resolution were collected at ~110 K at SSRL beam line 11-1. The diffraction images were integrated and scaled using the program HKL2000 and elements of the CCP4 suite. See Winn et al., 2011, *Acta Crystallogr D. Biol. Crystallogr.* 67: 235-42.

The structure was solved by molecular replacement (MR) using program Phaser. See McCoy et al., 2005, *Acta Crystallogr D. Biol. Crystallogr.* 61: 458-64. The MR search models include the HER2 ECD domain derived from a crystal structure of HER2/Herceptin Fab complex (PDB code: 1N8Z), Fab constant domain (PDB code: 1N8Z) and a predicted model for the variable domain generated by the program Modeller. See Fiser et al., 2003, *Methods Enzymol.,* 374: 461-91. The structure was refined with programs REF- MAC5 (Marshudov et al., 2011, *Acta Crystallogr D. Biol. Crystallogr.* 67: 355-67) and PHENIX.refine (Adams et al., 2010, *Acta Crystallogr D. Biol. Crystallogr.* 66 (pt. 2): 213-21) using the maximum likelihood target functions, anisotropic individual B-factors, and TLS refinement. The data and refinement statistics are summarized in Table 12.

TABLE 12

Statistics of x-ray diffraction data collection and structure refinement (values in parentheses are for last resolution shell)

| | |
|---|---|
| Data collection | SSRL 11-1 |
| Space group | $C222_1$ |
| Cell parameters (Å) | a = 136.8, b = 171.9, c = 162.5 |
| Resolution (Å) | 50-2.75 (2.85-2.75) |
| Rsym | 0.112 (0.689) |
| Number of observations | 319169 |
| Unique reflections | 49078 |
| Redundancy | 6.5 (5.5) |
| Completeness (%) | 98.8 (92.2) |
| <I>/<σI> | 20 (2.2) |
| Vm ($A^3$/Da) | 4.2 |
| Refinement | |
| Resolution (Å) | 48.33-2.75 |
| Number of reflections | 49053 |
| R, Rfree | 0.23, 0.25 |
| Number of residues | 1047 |
| Number of waters | 109 |
| Number of atoms | 8039 |
| RMSD bonds (Å) | 0.007 |
| RMSD angles (°) | 1.2 |
| Mean bonded ΔB ($Å^2$) | 5.5 |
| Ramachandran analysis (%) | 93/6/1 |
| Number of TLS groups | 3 |
| <B>[e] (Å) 7C2/HER2 | 88 |

Results

Figure 19B:
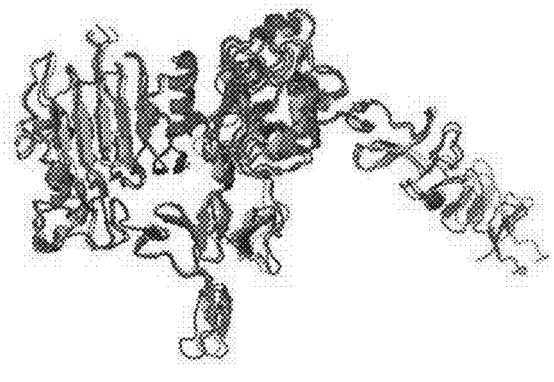
FIG. 19A-D show (A) crystal structure of the complex between HER2 ECD (surface shaded by domain and shown as a space-filling model) and 7C2 Fab. The 7C2 Fab binds to domain I of HER2, which is different from the binding epitopes of the trastuzumab Fab (Tmab, PDB code: 1N8Z) and the pertuzumab Fab (Pmab, PDB code: 1S78). (B) Superposition of the structures of HER2 ECD within the trastuzumab/HER2 complex, pertuzumab/HER2 complex, and 7C2/HER2 complex. (C) The 7C2/HER2 complex interface. The side chains of the residues involved in the 7C2/HER2 interaction are shown as sticks. Some of the potential intermolecular hydrogen bonds are shown as dashed lines. (D) The 7C2 binding epitope is partially overlapped with the chA21 single-chain Fv (scFv). Superposition of the structure of the chA21 scFv/HER2 complex (PDB code: 3H3B) with the 7C2/HER2 complex.

The crystal structure of the 7C2 Fab/HER2 complex was determined at 2.75 Å resolution. Each asymmetric unit cell contains one Fab/HER2 complex. The structure revealed that the 7C2 Fab binds to domain I of HER2 ECD (FIG. 19A). The binding epitope is distinct from those in the previously characterized complexes of HER2 ECD with Fab fragments of therapeutic antibodies trastuzumab (Tmab) or pertuzumab (Pmab), which are located at domains IV and II, respectively. See, e.g., Cho et al., 2003, *Nature,* 421: 756-60; Eigenbrot et al., 2010, *PNAS,* 107: 15039-44; and Franklin et al., 2004, *Caner Cell,* 5: 17-28. Indeed, an overlay of the 7C2 Fab/HER2 ECD complex structure with the structures of Tmab/HER2 ECD complex and Pmab/FIER2 ECD complex shows that the three Fabs have independent, non-overlapping epitopes and would not spatially interfere with each other binding to HER2 (FIG. 19A). A superposition of the HER2 ECD structures within the Tmab/FIER2 ECD complex, Pmab/FIER2 ECD complex and 7C2 Fab/FIER2 ECD complex showed a minimal structural differences (FIG. 19B). This observation suggested that the HER2 ECD is relatively rigid, which is consistent with previous reports in the literature. See, e.g., Cho et al., 2003, *Nature,* 421: 756-60; Eigenbrot et al., 2010, *PNAS,* 107: 15039-44; and Franklin et al., 2004, *Caner Cell,* 5: 17-28.

The 7C2 Fab binds to the loop 163-175 and the loop 185-189 within the HER2 domain I (i.e., amino acids 163-175 and 185-189 of mature HER2, e.g., SEQ ID NO: 39; domain I is shown in SEQ ID NO: 35). The binding buries ~1160 $Å^2$ of solvent accessible surface area on each side of the interface. There is an intricate network of hydrophobic, hydrogen bonding and ionic interactions. Certain residues that are involved in binding are labeled in FIG. 19C. The side chain of His171 makes contacts with the heavy chain residues His52 and Asp55. The HER2 residues Ser186, Ser187 and Glu188 form hydrogen bonding with the D102 from heavy chain and the two Tyr residues (Tyr36 and Tyr54) from the light chain.

Figure 19D:
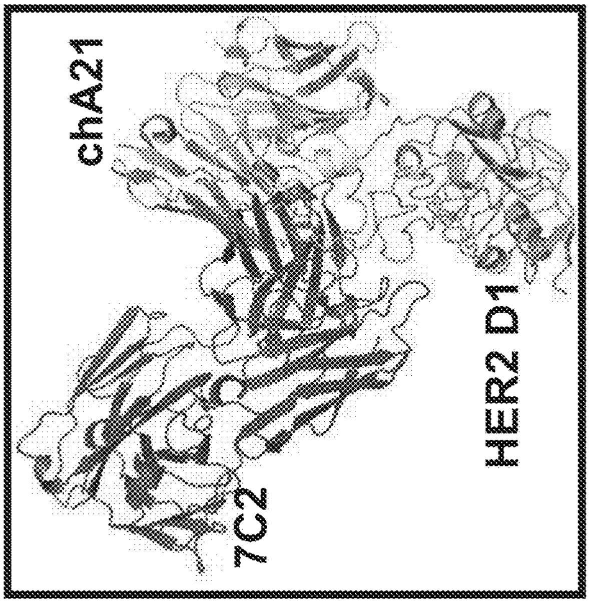
Figure 19A:
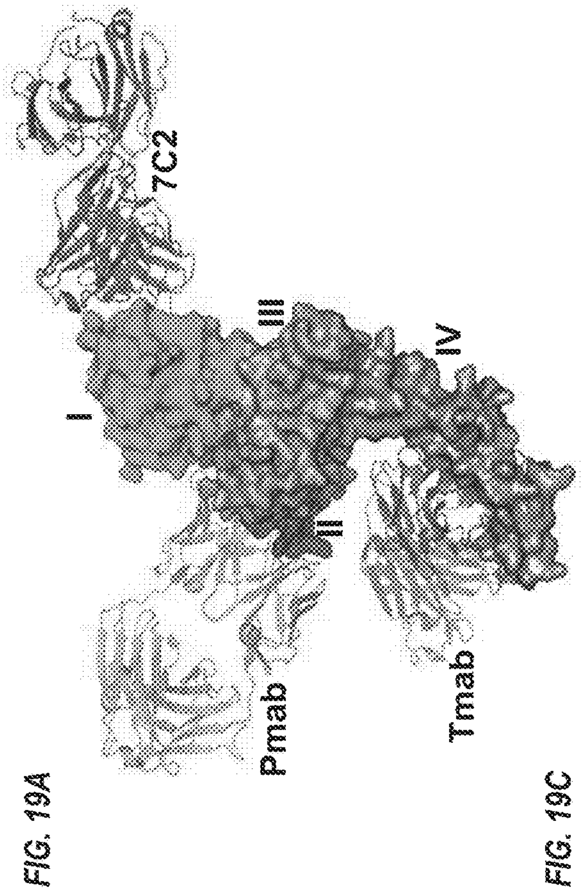
Figure 19C:
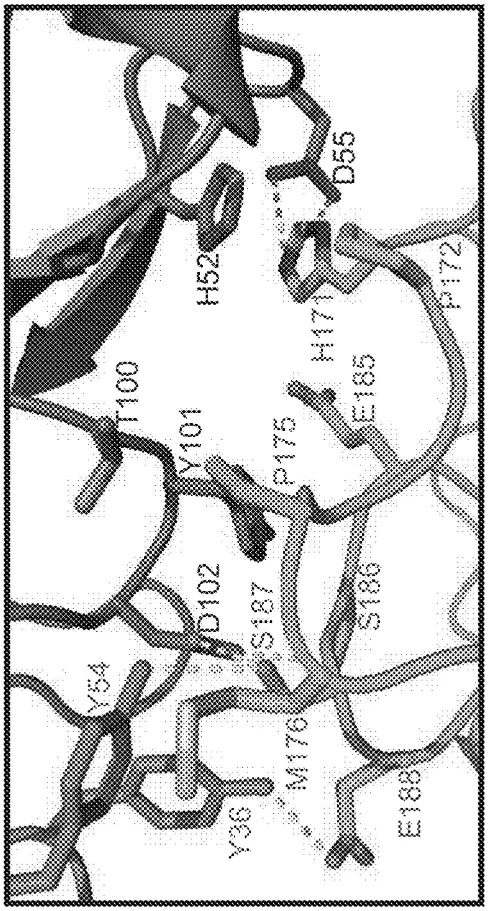

The 7C2 binding epitope partially overlaps with that from a previously reported anti-HER2 antibody, chA21 (FIG. 19D). See Zhou et al., 2011, *JBC,* 286: 31676-83. Both epitopes include a loop in domain I (residues 163-187). Interestingly, the residue His171 plays a role in the interaction with both antibodies. However, the chA21 binding epitope spans ~1820 $Å^2$ of solvent accessible surface area, which is ~660 $Å^2$ bigger than the 7C2 epitope and includes two additional N-terminal loops, residues 100-105 and residues 135-144.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

Table of Sequences

| NAME | SEQUENCE | SEQ ID NO |
|---|---|---|
| Human Her2 precursor (UniProtKB/ Swiss-Prot: P04626.1); aa 1-22 signal sequence; aa 23-1255 mature Her2 | MELAALCRWG LLLALLPPGA ASTQVCTGTD MKLRLPASPE THLDMLRHLY QGCQVVQGNL ELTYLPTNAS LSFLQDIQEV QGYVLIAHNQ VRQVPLQRLR IVRGTQLFED NYALAVLDNG DPLNNTTPVT GASPGGLREL QLRSLTEILK GGVLIQRNPQ LCYQDTILWK DIFHKNNQLA LTLIDTNRSR ACHPCSPMCK GSRCWGESSE DCQSLTRTVC AGGCARCKGP LPTDCCHEQC AAGCTGPKHS DCLACLHFNH SGICELHCPA LVTYNTDTFE SMPNPEGRYT FGASCVTACP YNYLSTDVGS CTLVCPLHNQ EVTAEDGTQR CEKCSKPCAR VCYGLGMEHL REVRAVTSAN IQEFAGCKKI FGSLAFLPES FDGDPASNTA PLQPEQLQVF ETLEEITGYL YISAWPDSLP DLSVFQNLQV IRGRILHNGA YSLTLQGLGI SWLGLRSLRE LGSGLALIHH NTHLCFVHTV PWDQLFRNPH QALLHTANRP EDECVGEGLA CHQLCARGHC WGPGPTQCVN CSQFLRGQEC VEECRVLQGL PREYVNARHC LPCHPECQPQ NGSVTCFGPE ADQCVACAHY KDPPFCVARC PSGVKPDLSY MPIWKFPDEE GACQPCPINC THSCVDLDDK GCPAEQRASP LTSIISAVVG ILLVVVLGVV FGILIKRRQQ KIRKYTMRRL LQETELVEPL TPSGAMPNQA QMRILKETEL RKVKVLGSGA FGTVYKGIWI PDGENVKIPV AIKVLRENTS PKANKEILDE AYVMAGVGSP YVSRLLGICL TSTVQLVTQL MPYGCLLDHV RENRGRLGSQ DLLNWCMQIA KGMSYLEDVR LVHRDLAARN VLVKSPNHVK ITDFGLARLL DIDETEYHAD GGKVPIKWMA LESILRRRFT HQSDVWSYGV TVWELMTFGA KPYDGIPARE IPDLLEKGER LPQPPICTID VYMIMVKCWM IDSECRPRFR ELVSEFSRMA RDPQRFVVIQ NEDLGPASPL | 1 |

-continued

Table of Sequences

| NAME | SEQUENCE | SEQ ID NO |
|---|---|---|
| | DSTFYRSLLE DDDMGDLVDA EEYLVPQQGF FCPDPAPGAG GMVHHRHRSS STRSGGGDLT LGLEPSEEEA PRSPLAPSEG AGSDVFDGDL GMGAAKGLQS LPTHDPSPLQ RYSEDPTVPL PSETDGYVAP LTCSPQPEYV NQPDVRPQPP SPREGPLPAA RPAGATLERP KTLSPGKNGV VKDVFAFGGA VENPEYLTPQ GGAAPQPHPP PAFSPAFDNL YYWDQDPPER GAPPSTFKGT PTAENPEYLG LDVPV | |
| mature human HER2 | TQVCTGTD MKLRLPASPE THLDMLRHLY QGCQVVQGNL ELTYLPTNAS LSFLQDIQEV QGYVLIAHNQ VRQVPLQRLR IVRGTQLFED NYALAVLDNG DPLNNTTPVT GASPGGLREL QLRSLTEILK GGVLIQRNPQ LCYQDTILWK DIFHKNNQLA LTLIDTNRSR ACHPCSPMCK GSRCWGESSE DCQSLTRTVC AGGCARCKGP LPTDCCHEQC AAGCTGPKHS DCLACLHFNH SGICELHCPA LVTYNTDTFE SMPNPEGRYT FGASCVTACP YNYLSTDVGS CTLVCPLHNQ EVTAEDGTQR CEKCSKPCAR VCYGLGMEHL REVRAVTSAN IQEFAGCKKI FGSLAFLPES FDGDPASNTA PLQPEQLQVF ETLEEITGYL YISAWPDSLP DLSVFQNLQV IRGRILHNGA YSLTLQGLGI SWLGLRSLRE LGSGLALIHH NTHLCFVHTV PWDQLFRNPH QALLHTANRP EDECVGEGLA CHQLCARGHC WGPGPTQCVN CSQFLRGQEC VEECRVLQGL PREYVNARHC LPCHPECQPQ NGSVTCFGPE ADQCVACAHY KDPPFCVARC PSGVKPDLSY MPIWKFPDEE GACQPCPINC THSCVDLDDK GCPAEQRASP LTSIISAVVG ILLVVVLGVV FGILIKRRQQ KIRKYTMRRL LQETELVEPL TPSGAMPNQA QMRILKETEL RKVKVLGSGA FGTVYKGIWI PDGENVKIPV AIKVLRENTS PKANKEILDE AYVMAGVGSP YVSRLLGICL TSTVQLVTQL MPYGCLLDHV RENRGRLGSQ DLLNWCMQIA KGMSYLEDVR LVHRDLAARN VLVKSPNHVK ITDFGLARLL DIDETEYHAD GGKVPIKWMA LESILRRRFT HQSDVWSYGV TVWELMTFGA KPYDGIPARE IPDLLEKGER LPQPPICTID VYMIMVKCWM IDSECRPRFR ELVSEFSRMA RDPQRFVVIQ NEDLGPASPL DSTFYRSLLE DDDMGDLVDA EEYLVPQQGF FCPDPAPGAG GMVHHRHRSS STRSGGGDLT LGLEPSEEEA PRSPLAPSEG AGSDVFDGDL GMGAAKGLQS LPTHDPSPLQ RYSEDPTVPL PSETDGYVAP LTCSPQPEYV NQPDVRPQPP SPREGPLPAA RPAGATLERP KTLSPGKNGV VKDVFAFGGA VENPEYLTPQ GGAAPQPHPP PAFSPAFDNL YYWDQDPPER GAPPSTFKGT PTAENPEYLG LDVPV | 39 |
| Murine 7C2.B9 (mu7C2) light chain variable region | DIVLTQSPAS LVVSLGQRAT ISCRASQSVS GSRFTYMHWY QQKPGQPPKL LIKYASILES GVPARFSGGG SGTDFTLNIH PVEEDDTATY YCQHSWEIPP WTFGGGTKLE IK | 2 |
| Mu7C2 heavy chain variable region | QVQLQQPGAE LVRPGASVKL SCKASGYSFT GYWMNWLKQR PGQGLEWIGM IHPSDSEIRA NQKFRDKATL TVDKSSTTAY MQLSSPTSED SAVYYCARGT YDGGFEYWGQ GTTLTVSS | 3 |
| Mu7C2 HVR-L1 | RASQSVSGSRFTYMH | 4 |
| Mu7C2 HVR-L2 | YASILES | 5 |
| Mu7C2 HVR-L3 | QHSWEIPPWT | 6 |
| Mu7C2 HVR-H1 | GYWMN | 7 |
| Mu7C2 HVR-H2 | MIHPSDSEIRANQKFRD | 8 |
| Mu7C2 HVR-H3 | GTYDGGFEY | 9 |
| Humanized 7C2.v2.2.LA ("hu7C2") light chain variable region | DIVMTQSPDS LAVSLGERAT INCRASQSVS GSRFTYMHWY QQKPGQPPKL LIKYASILES GVPDRFSGSG SGTDFTLTIS SLQAEDVAVY YCQHSWEIPP WTFGQGTKVE IK | 10 |
| Hu7C2 heavy chain variable region | EVQLVQSGAE VKKPGASVKV SCKASGYSFT GYWMNWVRQA PGQGLEWIGM IHPLDAEIRA NQKFRDRVTI TVDTSTSTAY LELSSLRSED TAVYYCARGT YDGGFEYWGQ GTLVTVSS | 11 |
| Hu7C2 HVR-L1 | RASQSVSGSRFTYMH | 12 |
| Hu7C2 HVR-L2 | YASILES | 13 |
| Hu7C2 HVR-L3 | QHSWEIPPWT | 14 |
| Hu7C2 HVR-H1 | GYWMN | 15 |
| Hu7C2 HVR-H2 (Hu7C2. | MIHPLDAEIRANQKFRD | 16 |

-continued

Table of Sequences

| NAME | SEQUENCE | SEQ ID NO |
|---|---|---|
| v2.1.S53L, S55A HVR-H2) | | |
| Hu7C2 HVR-H3 | GTYDGGFEY | 17 |
| Humanized 7C2.v2.2.LA (hu7C2) kappa light chain | DIVMTQSPDS LAVSLGERAT INCRASQSVS GSRFTYMHWY QQKPGQPPKL LIKYASILES GVPDRFSGSG SGTDFTLTIS SLQAEDVAVY YCQHSWEIPP WTFGQGTKVE IKRTVAAPSV FIFPPSDEQL KSGTASVVCL LNNFYPREAK VQWKVDNALQ SGNSQESVTE QDSKDSTYSL SSTLTLSKAD YEKHKVYACE VTHQGLSSPV TKSFNRGEC | 18 |
| Hu7C2IgG1 heavy chain | EVQLVQSGAE VKKPGASVKV SCKASGYSFT GYWMNWVRQA PGQGLEWIGM IHPLDAEIRA NQKFRDRVTI TVDTSTSTAY LELSSLRSED TAVYYCARGT YDGGFEYWGQ GTLVTVSSAS TKGPSVFPLA PSSKSTSGGT AALGCLVKDY FPEPVTVSWN SGALTSGVHT FPAVLQSSGL YSLSSVVTVP SSSLGTQTYI CNVNHKPSNT KVDKKVEPKS CDKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSREEMT KNQVSLTCLV KGFYPSDIAV EWESNGQPEN NYKTTPPVLD SDGSFFLYSK LTVDKSRWQQ GNVFSCSVMH EALHNHYTQK SLSLSPGK | 19 |
| Hu7C2. v2.1.S53M HVR-H2 | MIHPMDSEIRANQKFRD | 20 |
| Hu7C2. v2.1.S53L HVR-H2 | MIHPLDSEIRANQKFRD | 21 |
| Hu7C2. v2.1.E101K HVR-H3 | GTYDGGFKY | 22 |
| Humanized 7C2.v2.2.LA (hu7C2) K149C kappa light chain | DIVMTQSPDS LAVSLGERAT INCRASQSVS GSRFTYMHWY QQKPGQPPKL LIKYASILES GVPDRFSGSG SGTDFTLTIS SLQAEDVAVY YCQHSWEIPP WTFGQGTKVE IKRTVAAPSV FIFPPSDEQL KSGTASVVCL LNNFYPREAK VQWCVDNALQ SGNSQESVTE QDSKDSTYSL SSTLTLSKAD YEKHKVYACE VTHQGLSSPV TKSFNRGEC | 23 |
| Hu7C2A118C IgG1 heavy chain | EVQLVQSGAE VKKPGASVKV SCKASGYSFT GYWMNWVRQA PGQGLEWIGM IHPLDAEIRA NQKFRDRVTI TVDTSTSTAY LELSSLRSED TAVYYCARGT YDGGFEYWGQ GTLVTVSSCS TKGPSVFPLA PSSKSTSGGT AALGCLVKDY FPEPVTVSWN SGALTSGVHT FPAVLQSSGL YSLSSVVTVP SSSLGTQTYI CNVNHKPSNT KVDKKVEPKS CDKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSREEMT KNQVSLTCLV KGFYPSDIAV EWESNGQPEN NYKTTPPVLD SDGSFFLYSK LTVDKSRWQQ GNVFSCSVMH EALHNHYTQK SLSLSPGK | 24 |
| V205C cysteine engineered light chain constant region (Igκ) | TVAAPSVFIF PPSDEQLKSG TASVVCLLNN FYPREAKVQW KVDNALQSGN SQESVTEQDS KDSTYSLSST LTLSKADYEK HKVYACEVTH QGLSSPCTKS FNRGEC | 25 |
| A118C cysteine engineered heavy chain constant region (IgG1) | CSTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK | 26 |
| K149C cysteine engineered light chain constant region (Igκ) | TVAAPSVFIF PPSDEQLKSG TASVVCLLNN FYPREAKVQW CVDNALQSGN SQESVTEQDS KDSTYSLSST LTLSKADYEK HKVYACEVTH QGLSSPVTKS FNRGEC | 27 |
| S400C cysteine engineered heavy chain constant region (IgG1) | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC | 28 |

-continued

Table of Sequences

| NAME | SEQUENCE | SEQ ID NO |
|---|---|---|
| | LVKGFYPSDI AVEWESNGQP ENNYKTTPPV LDCDGSFFLY SKLTVDKSRW QQGNVFSCSV MHEALHNHYT QKSLSLSPGK | |

What is claimed is:

1. An isolated antibody that binds to HER2, wherein the antibody comprises (i)(a) HVR-H1 comprising the amino acid sequence of SEQ ID NO: 15; (b) HVR-H2 comprising the amino acid sequence of SEQ ID NO: 20 or 21; (c) HVR-H3 comprising the amino acid sequence of SEQ ID NO: 17; (d) HVR-L1 comprising the amino acid sequence of SEQ ID NO: 12; (e) HVR-L2 comprising the amino acid sequence of SEQ ID NO: 13; and (f) HVR-L3 comprising the amino acid sequence of SEQ ID NO: 14;

(ii)(a) HVR-H1 comprising the amino acid sequence of SEQ ID NO: 15; (b) HVR-H2 comprising the amino acid sequence of SEQ ID NO: 8; (c) HVR-H3 comprising the amino acid sequence of SEQ ID NO: 22; (d) HVR-L1 comprising the amino acid sequence of SEQ ID NO: 12; (e) HVR-L2 comprising the amino acid sequence of SEQ ID NO: 13; and (f) HVR-L3 comprising the amino acid sequence of SEQ ID NO: 14;

(iii) a light chain variable region comprising the sequence of SEQ ID NO: 10 and a heavy chain variable region comprising the sequence of SEQ ID NO: 11 with one of the following substitutions: (a) position 53 is serine, position 55 is serine, and position 101 is lysine; (b) position 53 is methionine and position 55 is serine; or (c) position 53 is leucine, wherein positions are numbered according to Kabat numbering; or (iv) a light chain variable region comprising the sequence of SEQ ID NO: 10 and a heavy chain variable region comprising the sequence of SEQ ID NO: 11 with one of the following substitutions (a) HVR-H2 (SEQ ID NO: 16) is substituted with SEQ ID NO: 8 and HVR-H3 (SEQ ID NO: 17) is substituted with SEQ ID NO: 22; (b) HVR-H2 (SEQ ID NO: 16) is substituted with SEQ ID NO: 20; or (c) HVR-H2 (SEQ ID NO: 16) is substituted with SEQ ID NO: 21.

2. The antibody of claim 1, wherein the antibody comprises (i) a light chain variable region comprising the sequence of SEQ ID NO: 10 and a heavy chain variable region comprising the sequence of SEQ ID NO: 11 with one of the following substitutions (a) position 53 is serine, position 55 is serine, and position 101 is lysine; (b); (b) position 53 is methionine and position 55 is serine; or (c) position 53 is leucine, wherein positions are numbered according to Kabat numbering; or (ii) a light chain variable region comprising the sequence of SEQ ID NO: 10 and a heavy chain variable region comprising the sequence of SEQ ID NO: 11 with one of the following substitutions (a) HVR-H2 (SEQ ID NO: 16) is substituted with SEQ ID NO: 8 and HVR-H3 (SEQ ID NO: 17) is substituted with SEQ ID NO: 22; (b) HVR-H2 (SEQ ID NO: 16) is substituted with SEQ ID NO: 20; or (c) HVR-H2 (SEQ ID NO: 16) is substituted with SEQ ID NO: 21.

3. The antibody of claim 1, which is a monoclonal, humanized, or chimeric antibody.

4. The antibody of claim 1, which is an antibody fragment that binds HER2.

5. The antibody of claim 1, wherein the antibody binds to extracellular domain I of HER2.

6. The antibody of claim 1, which is an IgG1, IgG2a or IgG2b antibody.

7. The antibody of claim 1, wherein the antibody comprises at least one mutation in the heavy chain constant region selected from A118C and S400C.

8. The antibody of claim 1, wherein the antibody comprises at least one mutation in the light chain constant region selected from K149C and V205C.

9. The antibody of claim 1, wherein the antibody comprises the heavy chain constant region of SEQ ID NO: 28 or SEQ ID NO: 19.

10. The antibody of claim 1, wherein the antibody comprises the light chain constant region of SEQ ID NO: 25 or SEQ ID NO: 23.

11. An isolated nucleic acid encoding the antibody of claim 1.

12. A host cell comprising the nucleic acid of claim 11.

13. A method of producing an antibody comprising culturing the host cell of claim 12 so that the antibody is produced.

14. An immunoconjugate comprising the antibody of claim 1 and a cytotoxic agent.

15. The antibody of claim 1, conjugated to a label.

* * * * *

SEQUENCE LISTING

<160> NUMBER OF SEQ ID NOS: 43

<210> SEQ ID NO 1
<211> LENGTH: 1255
<212> TYPE: PRT
<213> ORGANISM: Homo sapiens

<400> SEQUENCE: 1

```
Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300
```

```
Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
    690                 695                 700

Ala Met Pro Asn Gln Ala Gln Met Arg Ile Leu Lys Glu Thr Glu Leu
705                 710                 715                 720
```

-continued

```
Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
    770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
    850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
    930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu  Asp Ser Thr Phe Tyr  Arg Ser Leu
        995                 1000                1005

Leu Glu  Asp Asp Asp Met Gly  Asp Leu Val Asp Ala  Glu Glu Tyr
    1010                1015                1020

Leu Val  Pro Gln Gln Gly Phe  Phe Cys Pro Asp Pro  Ala Pro Gly
    1025                1030                1035

Ala Gly  Gly Met Val His His  Arg His Arg Ser Ser  Ser Thr Arg
    1040                1045                1050

Ser Gly  Gly Gly Asp Leu Thr  Leu Gly Leu Glu Pro  Ser Glu Glu
    1055                1060                1065

Glu Ala  Pro Arg Ser Pro Leu  Ala Pro Ser Glu Gly  Ala Gly Ser
    1070                1075                1080

Asp Val  Phe Asp Gly Asp Leu  Gly Met Gly Ala Ala  Lys Gly Leu
    1085                1090                1095

Gln Ser  Leu Pro Thr His Asp  Pro Ser Pro Leu Gln  Arg Tyr Ser
    1100                1105                1110

Glu Asp  Pro Thr Val Pro Leu  Pro Ser Glu Thr Asp  Gly Tyr Val
    1115                1120                1125

Ala Pro  Leu Thr Cys Ser Pro  Gln Pro Glu Tyr Val  Asn Gln Pro
```

```
    1130                1135                1140

Asp Val  Arg Pro Gln Pro Pro  Ser Pro Arg Glu Gly  Pro Leu Pro
    1145                1150                1155

Ala Ala  Arg Pro Ala Gly Ala  Thr Leu Glu Arg Pro  Lys Thr Leu
    1160                1165                1170

Ser Pro  Gly Lys Asn Gly Val  Val Lys Asp Val Phe  Ala Phe Gly
    1175                1180                1185

Gly Ala  Val Glu Asn Pro Glu  Tyr Leu Thr Pro Gln  Gly Gly Ala
    1190                1195                1200

Ala Pro  Gln Pro His Pro Pro  Pro Ala Phe Ser Pro  Ala Phe Asp
    1205                1210                1215

Asn Leu  Tyr Tyr Trp Asp Gln  Asp Pro Pro Glu Arg  Gly Ala Pro
    1220                1225                1230

Pro Ser  Thr Phe Lys Gly Thr  Pro Thr Ala Glu Asn  Pro Glu Tyr
    1235                1240                1245

Leu Gly  Leu Asp Val Pro Val
    1250                1255


<210> SEQ ID NO 2
<211> LENGTH: 112
<212> TYPE: PRT
<213> ORGANISM: Mus musculus

<400> SEQUENCE: 2

Asp Ile Val Leu Thr Gln Ser Pro Ala Ser Leu Val Val Ser Leu Gly
1               5                   10                  15

Gln Arg Ala Thr Ile Ser Cys Arg Ala Ser Gln Ser Val Ser Gly Ser
            20                  25                  30

Arg Phe Thr Tyr Met His Trp Tyr Gln Gln Lys Pro Gly Gln Pro Pro
        35                  40                  45

Lys Leu Leu Ile Lys Tyr Ala Ser Ile Leu Glu Ser Gly Val Pro Ala
    50                  55                  60

Arg Phe Ser Gly Gly Gly Ser Gly Thr Asp Phe Thr Leu Asn Ile His
65                  70                  75                  80

Pro Val Glu Glu Asp Asp Thr Ala Thr Tyr Tyr Cys Gln His Ser Trp
                85                  90                  95

Glu Ile Pro Pro Trp Thr Phe Gly Gly Gly Thr Lys Leu Glu Ile Lys
            100                 105                 110


<210> SEQ ID NO 3
<211> LENGTH: 118
<212> TYPE: PRT
<213> ORGANISM: Mus musculus

<400> SEQUENCE: 3

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Ser Phe Thr Gly Tyr
            20                  25                  30

Trp Met Asn Trp Leu Lys Gln Arg Pro Gly Gln Gly Leu Glu Trp Ile
        35                  40                  45

Gly Met Ile His Pro Ser Asp Ser Glu Ile Arg Ala Asn Gln Lys Phe
    50                  55                  60

Arg Asp Lys Ala Thr Leu Thr Val Asp Lys Ser Ser Thr Thr Ala Tyr
65                  70                  75                  80

Met Gln Leu Ser Ser Pro Thr Ser Glu Asp Ser Ala Val Tyr Tyr Cys
```

-continued

```
                85                  90                  95

Ala Arg Gly Thr Tyr Asp Gly Gly Phe Glu Tyr Trp Gly Gln Gly Thr
            100                 105                 110

Thr Leu Thr Val Ser Ser
        115


<210> SEQ ID NO 4
<211> LENGTH: 15
<212> TYPE: PRT
<213> ORGANISM: Mus musculus

<400> SEQUENCE: 4

Arg Ala Ser Gln Ser Val Ser Gly Ser Arg Phe Thr Tyr Met His
1               5                   10                  15


<210> SEQ ID NO 5
<211> LENGTH: 7
<212> TYPE: PRT
<213> ORGANISM: Mus musculus

<400> SEQUENCE: 5

Tyr Ala Ser Ile Leu Glu Ser
1               5


<210> SEQ ID NO 6
<211> LENGTH: 10
<212> TYPE: PRT
<213> ORGANISM: Mus musculus

<400> SEQUENCE: 6

Gln His Ser Trp Glu Ile Pro Pro Trp Thr
1               5                   10


<210> SEQ ID NO 7
<211> LENGTH: 5
<212> TYPE: PRT
<213> ORGANISM: Mus musculus

<400> SEQUENCE: 7

Gly Tyr Trp Met Asn
1               5


<210> SEQ ID NO 8
<211> LENGTH: 17
<212> TYPE: PRT
<213> ORGANISM: Mus musculus

<400> SEQUENCE: 8

Met Ile His Pro Ser Asp Ser Glu Ile Arg Ala Asn Gln Lys Phe Arg
1               5                   10                  15

Asp


<210> SEQ ID NO 9
<211> LENGTH: 9
<212> TYPE: PRT
<213> ORGANISM: Mus musculus

<400> SEQUENCE: 9

Gly Thr Tyr Asp Gly Gly Phe Glu Tyr
1               5


<210> SEQ ID NO 10
<211> LENGTH: 112
```

<212> TYPE: PRT
<213> ORGANISM: Artificial sequence
<220> FEATURE:
<223> OTHER INFORMATION: Synthetic polypeptide

<400> SEQUENCE: 10

```
Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Val Ser Gly Ser
            20                  25                  30

Arg Phe Thr Tyr Met His Trp Tyr Gln Gln Lys Pro Gly Gln Pro Pro
        35                  40                  45

Lys Leu Leu Ile Lys Tyr Ala Ser Ile Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
                85                  90                  95

Glu Ile Pro Pro Trp Thr Phe Gly Gln Gly Thr Lys Val Glu Ile Lys
            100                 105                 110
```

<210> SEQ ID NO 11
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 11

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Trp Met Asn Trp Val Arg Gln Ala Pro Gly Gln Gly Leu Glu Trp Ile
        35                  40                  45

Gly Met Ile His Pro Leu Asp Ala Glu Ile Arg Ala Asn Gln Lys Phe
    50                  55                  60

Arg Asp Arg Val Thr Ile Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Gly Thr Tyr Asp Gly Gly Phe Glu Tyr Trp Gly Gln Gly Thr
            100                 105                 110

Leu Val Thr Val Ser Ser
        115
```

<210> SEQ ID NO 12
<211> LENGTH: 15
<212> TYPE: PRT
<213> ORGANISM: Artificial sequence
<220> FEATURE:
<223> OTHER INFORMATION: Synthetic peptide

<400> SEQUENCE: 12

```
Arg Ala Ser Gln Ser Val Ser Gly Ser Arg Phe Thr Tyr Met His
1               5                   10                  15
```

<210> SEQ ID NO 13
<211> LENGTH: 7
<212> TYPE: PRT

<213> ORGANISM: Artificial sequence
<220> FEATURE:
<223> OTHER INFORMATION: Synthetic peptide

<400> SEQUENCE: 13

Tyr Ala Ser Ile Leu Glu Ser
1 5

<210> SEQ ID NO 14
<211> LENGTH: 10
<212> TYPE: PRT
<213> ORGANISM: Artificial sequence
<220> FEATURE:
<223> OTHER INFORMATION: Synthetic peptide

<400> SEQUENCE: 14

Gln His Ser Trp Glu Ile Pro Pro Trp Thr
1 5 10

<210> SEQ ID NO 15
<211> LENGTH: 5
<212> TYPE: PRT
<213> ORGANISM: Artificial sequence
<220> FEATURE:
<223> OTHER INFORMATION: Synthetic peptide

<400> SEQUENCE: 15

Gly Tyr Trp Met Asn
1 5

<210> SEQ ID NO 16
<211> LENGTH: 17
<212> TYPE: PRT
<213> ORGANISM: Artificial sequence
<220> FEATURE:
<223> OTHER INFORMATION: Synthetic peptide

<400> SEQUENCE: 16

Met Ile His Pro Leu Asp Ala Glu Ile Arg Ala Asn Gln Lys Phe Arg
1 5 10 15

Asp

<210> SEQ ID NO 17
<211> LENGTH: 9
<212> TYPE: PRT
<213> ORGANISM: Artificial sequence
<220> FEATURE:
<223> OTHER INFORMATION: Synthetic peptide

<400> SEQUENCE: 17

Gly Thr Tyr Asp Gly Gly Phe Glu Tyr
1 5

<210> SEQ ID NO 18
<211> LENGTH: 219
<212> TYPE: PRT
<213> ORGANISM: Artificial sequence
<220> FEATURE:
<223> OTHER INFORMATION: Synthetic polypeptide

<400> SEQUENCE: 18

Asp Ile Val Met Thr Gln Ser Pro Asp Ser Leu Ala Val Ser Leu Gly
1 5 10 15

Glu Arg Ala Thr Ile Asn Cys Arg Ala Ser Gln Ser Val Ser Gly Ser
20 25 30

```
Arg Phe Thr Tyr Met His Trp Tyr Gln Gln Lys Pro Gly Gln Pro Pro
        35                  40                  45

Lys Leu Leu Ile Lys Tyr Ala Ser Ile Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
                85                  90                  95

Glu Ile Pro Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 19
<211> LENGTH: 448
<212> TYPE: PRT
<213> ORGANISM: Artificial sequence
<220> FEATURE:
<223> OTHER INFORMATION: Synthetic polypeptide

<400> SEQUENCE: 19

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Trp Met Asn Trp Val Arg Gln Ala Pro Gly Gln Gly Leu Glu Trp Ile
        35                  40                  45

Gly Met Ile His Pro Leu Asp Ala Glu Ile Arg Ala Asn Gln Lys Phe
    50                  55                  60

Arg Asp Arg Val Thr Ile Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Gly Thr Tyr Asp Gly Gly Phe Glu Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

```
Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 20
<211> LENGTH: 17
<212> TYPE: PRT
<213> ORGANISM: Artificial sequence
<220> FEATURE:
<223> OTHER INFORMATION: Synthetic peptide

<400> SEQUENCE: 20

Met Ile His Pro Met Asp Ser Glu Ile Arg Ala Asn Gln Lys Phe Arg
1               5                   10                  15

Asp


<210> SEQ ID NO 21
<211> LENGTH: 17
<212> TYPE: PRT
<213> ORGANISM: Artificial sequence
<220> FEATURE:
<223> OTHER INFORMATION: Synthetic peptide

<400> SEQUENCE: 21

Met Ile His Pro Leu Asp Ser Glu Ile Arg Ala Asn Gln Lys Phe Arg
1               5                   10                  15
```

Asp

<210> SEQ ID NO 22
<211> LENGTH: 9
<212> TYPE: PRT
<213> ORGANISM: Artificial sequence
<220> FEATURE:
<223> OTHER INFORMATION: Synthetic peptide

<400> SEQUENCE: 22

Gly Thr Tyr Asp Gly Gly Phe Lys Tyr
1               5

<210> SEQ ID NO 23
<211> LENGTH: 219
<212> TYPE: PRT
<213> ORGANISM: Artificial sequence
<220> FEATURE:
<223> OTHER INFORMATION: Synthetic polypeptide

<400> SEQUENCE: 23

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Val Ser Gly Ser
            20                  25                  30

Arg Phe Thr Tyr Met His Trp Tyr Gln Gln Lys Pro Gly Gln Pro Pro
        35                  40                  45

Lys Leu Leu Ile Lys Tyr Ala Ser Ile Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
                85                  90                  95

Glu Ile Pro Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Cys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 24
<211> LENGTH: 448
<212> TYPE: PRT
<213> ORGANISM: Artificial sequence
<220> FEATURE:
<223> OTHER INFORMATION: Synthetic polypeptide

<400> SEQUENCE: 24

Glu Val Gln Leu Val Gln Ser Gly Ala Glu Val Lys Lys Pro Gly Ala
1               5                   10                  15

-continued

```
Ser Val Lys Val Ser Cys Lys Ala Ser Gly Tyr Ser Phe Thr Gly Tyr
            20                  25                  30

Trp Met Asn Trp Val Arg Gln Ala Pro Gly Gln Gly Leu Glu Trp Ile
        35                  40                  45

Gly Met Ile His Pro Leu Asp Ala Glu Ile Arg Ala Asn Gln Lys Phe
    50                  55                  60

Arg Asp Arg Val Thr Ile Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Gly Thr Tyr Asp Gly Gly Phe Glu Tyr Trp Gly Gln Gly Thr
            100                 105                 110

Leu Val Thr Val Ser Ser Cys Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430
```

```
Leu His Asn His Tyr Thr Gln Lys Ser Leu Ser Leu Ser Pro Gly Lys
        435                 440                 445


<210> SEQ ID NO 25
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 25

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Cys Thr Lys Ser Phe Asn Arg Gly Glu Cys
            100                 105


<210> SEQ ID NO 26
<211> LENGTH: 330
<212> TYPE: PRT
<213> ORGANISM: Artificial sequence
<220> FEATURE:
<223> OTHER INFORMATION: Synthetic polypeptide

<400> SEQUENCE: 26

Cys Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190
```

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 27
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 27

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Cys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 28
<211> LENGTH: 330
<212> TYPE: PRT
<213> ORGANISM: Artificial sequence
<220> FEATURE:
<223> OTHER INFORMATION: Synthetic polypeptide

<400> SEQUENCE: 28

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser 50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Asn Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Glu Glu
225 230 235 240

Met Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Cys Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly Lys
325 330

<210> SEQ ID NO 29
<211> LENGTH: 449
<212> TYPE: PRT
<213> ORGANISM: Artificial sequence
<220> FEATURE:
<223> OTHER INFORMATION: Synthetic polypeptide

<400> SEQUENCE: 29

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Arg Ile Tyr Pro Thr Asn Gly Tyr Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys

-continued

```
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly
```

<210> SEQ ID NO 30
<211> LENGTH: 214
<212> TYPE: PRT
<213> ORGANISM: Artificial sequence
<220> FEATURE:
<223> OTHER INFORMATION: Synthetic polypeptide

<400> SEQUENCE: 30

-continued

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 31
<211> LENGTH: 448
<212> TYPE: PRT
<213> ORGANISM: Artificial sequence
<220> FEATURE:
<223> OTHER INFORMATION: Synthetic polypeptide

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Glu Glu Met Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

<210> SEQ ID NO 32
<211> LENGTH: 214
<212> TYPE: PRT
<213> ORGANISM: Artificial sequence
<220> FEATURE:
<223> OTHER INFORMATION: Synthetic polypeptide

<400> SEQUENCE: 32

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Val Ser Ile Gly
20 25 30

Val Ala Trp Tyr Gln Gln Lys Pro Gly Lys Ala Pro Lys Leu Leu Ile
35 40 45

Tyr Ser Ala Ser Tyr Arg Tyr Thr Gly Val Pro Ser Arg Phe Ser Gly
50 55 60

-continued

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Tyr Ile Tyr Pro Tyr
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 33
<211> LENGTH: 449
<212> TYPE: PRT
<213> ORGANISM: Artificial sequence
<220> FEATURE:
<223> OTHER INFORMATION: Synthetic polypeptide

<400> SEQUENCE: 33

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Thr Asp Tyr
20 25 30

Thr Met Asp Trp Val Arg Gln Ala Pro Gly Lys Gly Leu Glu Trp Val
35 40 45

Ala Asp Val Asn Pro Asn Ser Gly Gly Ser Ile Tyr Asn Gln Arg Phe
50 55 60

Lys Gly Arg Phe Thr Leu Ser Val Asp Arg Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Asn Leu Gly Pro Ser Phe Tyr Phe Asp Tyr Trp Gly Gln Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

```
Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 34
<211> LENGTH: 217
<212> TYPE: PRT
<213> ORGANISM: Artificial sequence
<220> FEATURE:
<223> OTHER INFORMATION: Synthetic polypeptide

<400> SEQUENCE: 34

Val His Ser Asp Ile Gln Met Thr Gln Ser Pro Ser Ser Leu Ser Ala
1               5                   10                  15

Ser Val Gly Asp Arg Val Thr Ile Thr Cys Lys Ala Ser Gln Asp Val
            20                  25                  30

Ser Ile Gly Val Ala Trp Tyr Gln Gln Lys Pro Gly Lys Ala Pro Lys
        35                  40                  45

Leu Leu Ile Tyr Ser Ala Ser Tyr Arg Tyr Thr Gly Val Pro Ser Arg
    50                  55                  60

Phe Ser Gly Ser Gly Ser Gly Thr Asp Phe Thr Leu Thr Ile Ser Ser
65                  70                  75                  80

Leu Gln Pro Glu Asp Phe Ala Thr Tyr Tyr Cys Gln Gln Tyr Tyr Ile
                85                  90                  95

Tyr Pro Tyr Thr Phe Gly Gln Gly Thr Lys Val Glu Ile Lys Arg Thr
            100                 105                 110
```

-continued

```
Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215


<210> SEQ ID NO 35
<211> LENGTH: 195
<212> TYPE: PRT
<213> ORGANISM: Homo sapiens

<400> SEQUENCE: 35

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
            20                  25                  30

Val Val Gln Gly Asn Leu Glu Leu Thr Tyr Leu Pro Thr Asn Ala Ser
        35                  40                  45

Leu Ser Phe Leu Gln Asp Ile Gln Glu Val Gln Gly Tyr Val Leu Ile
    50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asn Asn Thr Thr Pro Val Thr Gly Ala Ser Pro
            100                 105                 110

Gly Gly Leu Arg Glu Leu Gln Leu Arg Ser Leu Thr Glu Ile Leu Lys
        115                 120                 125

Gly Gly Val Leu Ile Gln Arg Asn Pro Gln Leu Cys Tyr Gln Asp Thr
    130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
            180                 185                 190

Leu Thr Arg
        195


<210> SEQ ID NO 36
<211> LENGTH: 124
<212> TYPE: PRT
<213> ORGANISM: Homo sapiens

<400> SEQUENCE: 36

Thr Val Cys Ala Gly Gly Cys Ala Arg Cys Lys Gly Pro Leu Pro Thr
1               5                   10                  15
```

```
Asp Cys Cys His Glu Gln Cys Ala Ala Gly Cys Thr Gly Pro Lys His
            20                  25                  30

Ser Asp Cys Leu Ala Cys Leu His Phe Asn His Ser Gly Ile Cys Glu
        35                  40                  45

Leu His Cys Pro Ala Leu Val Thr Tyr Asn Thr Asp Thr Phe Glu Ser
    50                  55                  60

Met Pro Asn Pro Glu Gly Arg Tyr Thr Phe Gly Ala Ser Cys Val Thr
65                  70                  75                  80

Ala Cys Pro Tyr Asn Tyr Leu Ser Thr Asp Val Gly Ser Cys Thr Leu
                85                  90                  95

Val Cys Pro Leu His Asn Gln Glu Val Thr Ala Glu Asp Gly Thr Gln
            100                 105                 110

Arg Cys Glu Lys Cys Ser Lys Pro Cys Ala Arg Val
        115                 120


<210> SEQ ID NO 37
<211> LENGTH: 169
<212> TYPE: PRT
<213> ORGANISM: Homo sapiens

<400> SEQUENCE: 37

Cys Tyr Gly Leu Gly Met Glu His Leu Arg Glu Val Arg Ala Val Thr
1               5                   10                  15

Ser Ala Asn Ile Gln Glu Phe Ala Gly Cys Lys Lys Ile Phe Gly Ser
            20                  25                  30

Leu Ala Phe Leu Pro Glu Ser Phe Asp Gly Asp Pro Ala Ser Asn Thr
        35                  40                  45

Ala Pro Leu Gln Pro Glu Gln Leu Gln Val Phe Glu Thr Leu Glu Glu
    50                  55                  60

Ile Thr Gly Tyr Leu Tyr Ile Ser Ala Trp Pro Asp Ser Leu Pro Asp
65                  70                  75                  80

Leu Ser Val Phe Gln Asn Leu Gln Val Ile Arg Gly Arg Ile Leu His
                85                  90                  95

Asn Gly Ala Tyr Ser Leu Thr Leu Gln Gly Leu Gly Ile Ser Trp Leu
            100                 105                 110

Gly Leu Arg Ser Leu Arg Glu Leu Gly Ser Gly Leu Ala Leu Ile His
        115                 120                 125

His Asn Thr His Leu Cys Phe Val His Thr Val Pro Trp Asp Gln Leu
    130                 135                 140

Phe Arg Asn Pro His Gln Ala Leu Leu His Thr Ala Asn Arg Pro Glu
145                 150                 155                 160

Asp Glu Cys Val Gly Glu Gly Leu Ala
                165


<210> SEQ ID NO 38
<211> LENGTH: 142
<212> TYPE: PRT
<213> ORGANISM: Homo sapiens

<400> SEQUENCE: 38

Cys His Gln Leu Cys Ala Arg Gly His Cys Trp Gly Pro Gly Pro Thr
1               5                   10                  15

Gln Cys Val Asn Cys Ser Gln Phe Leu Arg Gly Gln Glu Cys Val Glu
            20                  25                  30

Glu Cys Arg Val Leu Gln Gly Leu Pro Arg Glu Tyr Val Asn Ala Arg
        35                  40                  45
```

```
His Cys Leu Pro Cys His Pro Glu Cys Gln Pro Gln Asn Gly Ser Val
    50                  55                  60

Thr Cys Phe Gly Pro Glu Ala Asp Gln Cys Val Ala Cys Ala His Tyr
65                  70                  75                  80

Lys Asp Pro Pro Phe Cys Val Ala Arg Cys Pro Ser Gly Val Lys Pro
                85                  90                  95

Asp Leu Ser Tyr Met Pro Ile Trp Lys Phe Pro Asp Glu Glu Gly Ala
            100                 105                 110

Cys Gln Pro Cys Pro Ile Asn Cys Thr His Ser Cys Val Asp Leu Asp
        115                 120                 125

Asp Lys Gly Cys Pro Ala Glu Gln Arg Ala Ser Pro Leu Thr
    130                 135                 140


<210> SEQ ID NO 39
<211> LENGTH: 1233
<212> TYPE: PRT
<213> ORGANISM: Homo sapiens

<400> SEQUENCE: 39

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
            20                  25                  30

Val Val Gln Gly Asn Leu Glu Leu Thr Tyr Leu Pro Thr Asn Ala Ser
        35                  40                  45

Leu Ser Phe Leu Gln Asp Ile Gln Glu Val Gln Gly Tyr Val Leu Ile
    50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asn Asn Thr Thr Pro Val Thr Gly Ala Ser Pro
            100                 105                 110

Gly Gly Leu Arg Glu Leu Gln Leu Arg Ser Leu Thr Glu Ile Leu Lys
        115                 120                 125

Gly Gly Val Leu Ile Gln Arg Asn Pro Gln Leu Cys Tyr Gln Asp Thr
    130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
            180                 185                 190

Leu Thr Arg Thr Val Cys Ala Gly Gly Cys Ala Arg Cys Lys Gly Pro
        195                 200                 205

Leu Pro Thr Asp Cys Cys His Glu Gln Cys Ala Ala Gly Cys Thr Gly
    210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255

Phe Glu Ser Met Pro Asn Pro Glu Gly Arg Tyr Thr Phe Gly Ala Ser
            260                 265                 270

Cys Val Thr Ala Cys Pro Tyr Asn Tyr Leu Ser Thr Asp Val Gly Ser
        275                 280                 285
```

-continued

```
Cys Thr Leu Val Cys Pro Leu His Asn Gln Glu Val Thr Ala Glu Asp
    290                 295                 300

Gly Thr Gln Arg Cys Glu Lys Cys Ser Lys Pro Cys Ala Arg Val Cys
305                 310                 315                 320

Tyr Gly Leu Gly Met Glu His Leu Arg Glu Val Arg Ala Val Thr Ser
                325                 330                 335

Ala Asn Ile Gln Glu Phe Ala Gly Cys Lys Lys Ile Phe Gly Ser Leu
            340                 345                 350

Ala Phe Leu Pro Glu Ser Phe Asp Gly Asp Pro Ala Ser Asn Thr Ala
        355                 360                 365

Pro Leu Gln Pro Glu Gln Leu Gln Val Phe Glu Thr Leu Glu Glu Ile
    370                 375                 380

Thr Gly Tyr Leu Tyr Ile Ser Ala Trp Pro Asp Ser Leu Pro Asp Leu
385                 390                 395                 400

Ser Val Phe Gln Asn Leu Gln Val Ile Arg Gly Arg Ile Leu His Asn
                405                 410                 415

Gly Ala Tyr Ser Leu Thr Leu Gln Gly Leu Gly Ile Ser Trp Leu Gly
            420                 425                 430

Leu Arg Ser Leu Arg Glu Leu Gly Ser Gly Leu Ala Leu Ile His His
        435                 440                 445

Asn Thr His Leu Cys Phe Val His Thr Val Pro Trp Asp Gln Leu Phe
    450                 455                 460

Arg Asn Pro His Gln Ala Leu Leu His Thr Ala Asn Arg Pro Glu Asp
465                 470                 475                 480

Glu Cys Val Gly Glu Gly Leu Ala Cys His Gln Leu Cys Ala Arg Gly
                485                 490                 495

His Cys Trp Gly Pro Gly Pro Thr Gln Cys Val Asn Cys Ser Gln Phe
            500                 505                 510

Leu Arg Gly Gln Glu Cys Val Glu Glu Cys Arg Val Leu Gln Gly Leu
        515                 520                 525

Pro Arg Glu Tyr Val Asn Ala Arg His Cys Leu Pro Cys His Pro Glu
    530                 535                 540

Cys Gln Pro Gln Asn Gly Ser Val Thr Cys Phe Gly Pro Glu Ala Asp
545                 550                 555                 560

Gln Cys Val Ala Cys Ala His Tyr Lys Asp Pro Pro Phe Cys Val Ala
                565                 570                 575

Arg Cys Pro Ser Gly Val Lys Pro Asp Leu Ser Tyr Met Pro Ile Trp
            580                 585                 590

Lys Phe Pro Asp Glu Glu Gly Ala Cys Gln Pro Cys Pro Ile Asn Cys
        595                 600                 605

Thr His Ser Cys Val Asp Leu Asp Asp Lys Gly Cys Pro Ala Glu Gln
    610                 615                 620

Arg Ala Ser Pro Leu Thr Ser Ile Ile Ser Ala Val Val Gly Ile Leu
625                 630                 635                 640

Leu Val Val Val Leu Gly Val Val Phe Gly Ile Leu Ile Lys Arg Arg
                645                 650                 655

Gln Gln Lys Ile Arg Lys Tyr Thr Met Arg Arg Leu Leu Gln Glu Thr
            660                 665                 670

Glu Leu Val Glu Pro Leu Thr Pro Ser Gly Ala Met Pro Asn Gln Ala
        675                 680                 685

Gln Met Arg Ile Leu Lys Glu Thr Glu Leu Arg Lys Val Lys Val Leu
    690                 695                 700
```

-continued

```
Gly Ser Gly Ala Phe Gly Thr Val Tyr Lys Gly Ile Trp Ile Pro Asp
705                 710                 715                 720

Gly Glu Asn Val Lys Ile Pro Val Ala Ile Lys Val Leu Arg Glu Asn
                725                 730                 735

Thr Ser Pro Lys Ala Asn Lys Glu Ile Leu Asp Glu Ala Tyr Val Met
            740                 745                 750

Ala Gly Val Gly Ser Pro Tyr Val Ser Arg Leu Leu Gly Ile Cys Leu
        755                 760                 765

Thr Ser Thr Val Gln Leu Val Thr Gln Leu Met Pro Tyr Gly Cys Leu
    770                 775                 780

Leu Asp His Val Arg Glu Asn Arg Gly Arg Leu Gly Ser Gln Asp Leu
785                 790                 795                 800

Leu Asn Trp Cys Met Gln Ile Ala Lys Gly Met Ser Tyr Leu Glu Asp
                805                 810                 815

Val Arg Leu Val His Arg Asp Leu Ala Ala Arg Asn Val Leu Val Lys
            820                 825                 830

Ser Pro Asn His Val Lys Ile Thr Asp Phe Gly Leu Ala Arg Leu Leu
        835                 840                 845

Asp Ile Asp Glu Thr Glu Tyr His Ala Asp Gly Gly Lys Val Pro Ile
    850                 855                 860

Lys Trp Met Ala Leu Glu Ser Ile Leu Arg Arg Arg Phe Thr His Gln
865                 870                 875                 880

Ser Asp Val Trp Ser Tyr Gly Val Thr Val Trp Glu Leu Met Thr Phe
                885                 890                 895

Gly Ala Lys Pro Tyr Asp Gly Ile Pro Ala Arg Glu Ile Pro Asp Leu
            900                 905                 910

Leu Glu Lys Gly Glu Arg Leu Pro Gln Pro Pro Ile Cys Thr Ile Asp
        915                 920                 925

Val Tyr Met Ile Met Val Lys Cys Trp Met Ile Asp Ser Glu Cys Arg
    930                 935                 940

Pro Arg Phe Arg Glu Leu Val Ser Glu Phe Ser Arg Met Ala Arg Asp
945                 950                 955                 960

Pro Gln Arg Phe Val Val Ile Gln Asn Glu Asp Leu Gly Pro Ala Ser
                965                 970                 975

Pro Leu Asp Ser Thr Phe Tyr Arg Ser Leu Leu Glu Asp Asp Asp Met
            980                 985                 990

Gly Asp Leu Val Asp Ala Glu Glu  Tyr Leu Val Pro Gln  Gln Gly Phe
        995                 1000                 1005

Phe Cys  Pro Asp Pro Ala Pro  Gly Ala Gly Gly Met  Val His His
    1010                 1015                 1020

Arg His  Arg Ser Ser Ser Thr  Arg Ser Gly Gly Gly  Asp Leu Thr
    1025                 1030                 1035

Leu Gly  Leu Glu Pro Ser Glu  Glu Glu Ala Pro Arg  Ser Pro Leu
    1040                 1045                 1050

Ala Pro  Ser Glu Gly Ala Gly  Ser Asp Val Phe Asp  Gly Asp Leu
    1055                 1060                 1065

Gly Met  Gly Ala Ala Lys Gly  Leu Gln Ser Leu Pro  Thr His Asp
    1070                 1075                 1080

Pro Ser  Pro Leu Gln Arg Tyr  Ser Glu Asp Pro Thr  Val Pro Leu
    1085                 1090                 1095

Pro Ser  Glu Thr Asp Gly Tyr  Val Ala Pro Leu Thr  Cys Ser Pro
    1100                 1105                 1110

Gln Pro  Glu Tyr Val Asn Gln  Pro Asp Val Arg Pro  Gln Pro Pro
```

```
    1115                1120                1125

Ser Pro  Arg Glu Gly Pro Leu  Pro Ala Ala Arg Pro  Ala Gly Ala
    1130                1135                1140

Thr Leu  Glu Arg Pro Lys Thr  Leu Ser Pro Gly Lys  Asn Gly Val
    1145                1150                1155

Val Lys  Asp Val Phe Ala Phe  Gly Gly Ala Val Glu  Asn Pro Glu
    1160                1165                1170

Tyr Leu  Thr Pro Gln Gly Gly  Ala Ala Pro Gln Pro  His Pro Pro
    1175                1180                1185

Pro Ala  Phe Ser Pro Ala Phe  Asp Asn Leu Tyr Tyr  Trp Asp Gln
    1190                1195                1200

Asp Pro  Pro Glu Arg Gly Ala  Pro Pro Ser Thr Phe  Lys Gly Thr
    1205                1210                1215

Pro Thr  Ala Glu Asn Pro Glu  Tyr Leu Gly Leu Asp  Val Pro Val
    1220                1225                1230


<210> SEQ ID NO 40
<211> LENGTH: 117
<212> TYPE: PRT
<213> ORGANISM: Homo sapiens

<400> SEQUENCE: 40

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Trp Ile Asn Pro Gly Ser Gly Asn Thr Asn Tyr Ala Gln Lys Phe
    50                  55                  60

Gln Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Thr Ala Ala Tyr Phe Asp Tyr Trp Gly Gln Gly Thr Leu
            100                 105                 110

Val Thr Val Ser Ser
        115


<210> SEQ ID NO 41
<211> LENGTH: 114
<212> TYPE: PRT
<213> ORGANISM: Homo sapiens

<400> SEQUENCE: 41

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
```

-continued 85 90 95

Tyr Tyr Ser Thr Pro Phe Thr Phe Gly Gln Gly Thr Lys Val Glu Ile
100 105 110

Lys Arg

<210> SEQ ID NO 42
<211> LENGTH: 113
<212> TYPE: PRT
<213> ORGANISM: Mus musculus

<400> SEQUENCE: 42

Asp Ile Val Leu Thr Gln Ser Pro Ala Ser Leu Val Val Ser Leu Gly
1 5 10 15

Gln Arg Ala Thr Ile Ser Cys Arg Ala Ser Gln Ser Val Ser Gly Ser
20 25 30

Arg Phe Thr Tyr Met His Trp Tyr Gln Gln Lys Pro Gly Gln Pro Pro
35 40 45

Lys Leu Leu Ile Lys Tyr Ala Ser Ile Leu Glu Ser Gly Val Pro Ala
50 55 60

Arg Phe Ser Gly Gly Gly Ser Gly Thr Asp Phe Thr Leu Asn Ile His
65 70 75 80

Pro Val Glu Glu Asp Asp Thr Ala Thr Tyr Tyr Cys Gln His Ser Trp
85 90 95

Glu Ile Pro Pro Trp Thr Phe Gly Gly Gly Thr Lys Leu Glu Ile Lys
100 105 110

Arg

<210> SEQ ID NO 43
<211> LENGTH: 113
<212> TYPE: PRT
<213> ORGANISM: Artificial sequence
<220> FEATURE:
<223> OTHER INFORMATION: Synthetic polypeptide

<400> SEQUENCE: 43

Asp Ile Val Met Thr Gln Ser Pro Asp Ser Leu Ala Val Ser Leu Gly
1 5 10 15

Glu Arg Ala Thr Ile Asn Cys Arg Ala Ser Gln Ser Val Ser Gly Ser
20 25 30

Arg Phe Thr Tyr Met His Trp Tyr Gln Gln Lys Pro Gly Gln Pro Pro
35 40 45

Lys Leu Leu Ile Lys Tyr Ala Ser Ile Leu Glu Ser Gly Val Pro Asp
50 55 60

Arg Phe Ser Gly Ser Gly Ser Gly Thr Asp Phe Thr Leu Thr Ile Ser
65 70 75 80

Ser Leu Gln Ala Glu Asp Val Ala Val Tyr Tyr Cys Gln His Ser Trp
85 90 95

Glu Ile Pro Pro Trp Thr Phe Gly Gln Gly Thr Lys Val Glu Ile Lys
100 105 110

Arg